United States Patent [19]
Groneberg et al.

[11] Patent Number: 6,057,369
[45] Date of Patent: May 2, 2000

[54] SUBSTITUTED (ARYL, HETEROARYL, ARYLMETHYL OR HETEROARYLMETHYL) HYDROXAMIC ACID COMPOUNDS

[75] Inventors: Robert D. Groneberg, Collegeville; Kent W. Neuenschwander, Schwensville, both of Pa.; Stevan W. Djuric, Libertyville, Ill.; Gerald M. McGeehan, Chester Springs, Pa.; Christopher J. Burns, Rosemont, Pa.; Steven M. Condon, Chester Springs, Pa.; Matthew M. Morrissette, Pottstown, Pa.; Joseph M. Salvino, Schwenksville, Pa.; Anthony C. Scotese, King of Prussia, Pa.; John W. Ullrich, Schwenksville, Pa.

[73] Assignee: Rhone-Poulenc Rorer Pharmaceuticals Inc., Collegeville, Pa.

[21] Appl. No.: 08/928,943

[22] Filed: Sep. 12, 1997

Related U.S. Application Data

[63] Continuation of application No. PCT/US97/00264, Jan. 2, 1997
[60] Provisional application No. 60/009,484, Jan. 2, 1996, abandoned.

[51] Int. Cl.$^7$ .................................................. A01N 37/28
[52] U.S. Cl. ........................... 514/575; 562/621; 562/623
[58] Field of Search .................................. 562/621, 623; 514/575

[56] References Cited

U.S. PATENT DOCUMENTS

| | | |
|---|---|---|
| 5,240,958 | 8/1993 | Campion et al. ....................... 514/445 |
| 5,525,629 | 6/1996 | Crimmin et al. ....................... 514/542 |
| 5,691,382 | 11/1997 | Crimmin et al. ....................... 514/575 |
| 5,696,082 | 12/1997 | Crimmin et al. ........................... 514/8 |

FOREIGN PATENT DOCUMENTS

| | | |
|---|---|---|
| 0606046 | 7/1994 | European Pat. Off. . |
| 0 780 386 | 6/1997 | European Pat. Off. . |
| 7-196598 | 8/1995 | Japan . |

OTHER PUBLICATIONS

Decicco et al., Amide Surrogates of Matrix Metalloproteinase Inhibitors: Urea and Sulfonamide Mimics, Bioorganic & Med.Chem.Letters, vol. 17, No. 18, pp. 2331–2336, 1997.
Potapov et al., Acylation of hydroxylamine by 2–methyl–3–phenylpropanoic acid, Vestn. Mosk. Univ., Ser. 2: Khim. 1983, 24(4), 391–3 (Russ.) (Abstract).
Derwent Patent Preview, WO9839316–A1, Barta et al. Sep. 11, 1998.
Derwent Patent Preview, WO9834915–A1, Robinson, Aug. 13, 1998.
Derwent Patent Preview, WO9839315–A1, Becker et al. Sep. 11, 1998.
Derwent Patent Preview, WO9839313–A1, Getman et al., Sep. 11, 1998.
Derwent Patent Preview, WO98329326–A1, Freskos et al., Sep. 11, 1998.
Derwent Patent Preview, WO9838163–A1, Venkatesan et al., Sep. 3, 1998.
Derwent Patent Preview, WO9837877–A1, Venkatesan et al., Sep. 3, 1998.

*Primary Examiner*—Brian M. Burn
*Assistant Examiner*—Brian J. Davis
*Attorney, Agent, or Firm*—Raymond S. Parker, III

[57] ABSTRACT

This invention is directed to compounds of formula I:

$$\text{HO}\diagdown\underset{H}{N}\diagdown\overset{O}{\underset{\|}{C}}\diagdown(C)_p\underset{R_1\ R_2}{\overset{R_3\ R_4}{\diagup\diagdown\diagup}}C\diagdown(S(O)_n)_q\text{—}(C)_m\underset{R_5\ R_6}{\overset{}{\diagup\diagdown}}\text{—Ar} \quad (I)$$

wherein the variables are as described herein. Compounds within the scope of the present invention possess useful properties, more particularly pharmaceutical properties. They are especially useful for inhibiting the production or physiological effects of TNF in the treatment of a patient suffering from a disease state associated with a physiologically detrimental excess of tumor necrosis factor (TNF). Compounds within the scope of the present invention also inhibit cyclic AMP phosphodiesterase, and are useful in treating a disease state associated with pathological conditions that are modulated by inhibiting cyclic AMP phosphodiesterase, such disease states including inflammatory and autoimmune diseases, in particular type IV cyclic AMP phosphodiesterase. Compounds within the scope of the present invention may also inhibit an MMP, and are useful in treating a disease state associated with pathological conditions that are modulated by inhibiting MMPs, such disease states involve tissue breakdown and those associated with a physiologically detrimental excess of TNF. The present invention is therefore also directed to the pharmaceutical use of the compounds, pharmaceutical compositions containing the compounds, intermediates leading thereto and methods for the preparation of the compounds and their intermediates.

93 Claims, No Drawings

SUBSTITUTED (ARYL, HETEROARYL, ARYLMETHYL OR HETEROARYLMETHYL) HYDROXAMIC ACID COMPOUNDS

This application is a continuation of international patent application No. PCT/US97/00264, filed Jan. 2, 1997, which designated the United States, which, in turn, is a continuation-in-part patent application of U.S. patent application Ser. No. 60/009,484, filed Jan. 2, 1996, now abandoned.

FIELD OF THE INVENTION

This invention is directed to (aryl, heteroaryl, arylmethyl or heteroarylmethyl)] hydroxamic acid compounds, their preparation, pharmaceutical compositions containing these compounds, and their pharmaceutical use in the treatment of disease states associated with proteins that mediate cellular activity which are capable of being modulated by inhibiting a matrix metalloproteinase (MMP), tumor necrosis factor (TNF) or cyclic AMP phosphodiesterase, or proteins associated therewith that mediate cellular activity. This invention is also directed to intermediates useful in preparing the (aryl, heteroaryl, aralkyl or heteroaralkyl) hydroxamic acid compounds.

Disease states associated with abnormally high physiological levels of cytokines such as TNF are treatable according to the invention. TNF is an important pro-inflammatory cytokine which causes hemorrhagic necrosis of tumors and possesses other important biological activities. TNF is released by activated macrophages, activated T-lymphocytes, natural killer cells, mast cells and basophils, fibroblasts, endothelial cells and brain astrocytes among other cells.

The principal in vivo actions of TNF can be broadly classified as inflammatory and catabolic. It has been implicated as a mediator of endotoxic shock, inflammation of joints and of the airways, immune deficiency states, allograft rejection, and in the cachexia associated with malignant disease and some parasitic infections. In view of the association of high serum levels of TNF with poor prognosis in sepsis, graft versus host disease and acute respiratory distress syndrome, and its role in many other immunologic processes, this factor is regarded as an important mediator of general inflammation.

TNF primes or activates neutrophils, eosinophils, fibroblasts and endothelial cells to release tissue damaging mediators. TNF also activates monocytes, macrophages and T-lymphocytes to cause the production of colony stimulating factors and other pro-inflammatory cytokines such $IL_1$, $IL_6$, $IL_8$ and GM-CSF, which in some case mediate the end effects of TNF. The ability of TNF to activate T-lymphocytes, monocytes, macrophages and related cells has been implicated in the progression of Human Immunodeficiency Virus (HIV) infection. In order for these cells to become infected with HIV and for HIV replication to take place the cells must be maintained in an activated state. Cytokines such as TNF have been shown to activate HIV replication in monocytes and macrophages. Features of endotoxic shock such as fever, metabolic acidosis, hypotension and intravascular coagulation are thought to be mediated through the actions of TNF on the hypothalamus and in reducing the anti-coagulant activity of vascular endothelial cells. The cachexia associated with certain disease states is mediated through indirect effects on protein catabolism. TNF also promotes bone resorption and acute phase protein synthesis.

The discussion herein related to disease states associated with TNF include those disease states related to the production of TNF itself, and disease states associated with other cytokines, such as but not limited to IL-1, or IL-6, that are modulated by associated with TNF. For example, a IL-1 associated disease state, where IL-1 production or action is exacerbated or secreted in response to TNF, would therefore be considered a disease state associated with TNF. TNF-α and TNF-β are also herein referred to collectively as "TNF" unless specifically delineated otherwise, since there is a close structural homology between TNF-α (cachectin) and TNF-β (lymphotoxin) and each of them has a capacity to induce similar biologic responses and bind to the same cellular receptor.

Disease states associated with pathological conditions that are modulated by inhibiting enzymes, which are associated with secondary cellular messengers, such as cyclic AMP phosphodiesterase are also treatable according to the invention. Cyclic AMP phosphodiesterase is an important enzyme which regulates cyclic AMP levels and in turn thereby regulates other important biological reactions. The ability to regulate cyclic AMP phosphodiesterase, including type IV cyclic AMP phosphodiesterase, therefore, has been implicated as being capable of treating assorted biological conditions. In particular, inhibitors of type IV cyclic AMP phosphodiesterase have been implicated as being bronchodilators and asthma-prophylactic agents and as agents for inhibiting eosinophil accumulation and of the function of eosinophils, and for treating other diseases and conditions characterized by, or having an etiology involving, morbid eosinophil accumulation. Inhibitors of cyclic AMP phosphodiesterase are also implicated in treating inflammatory diseases, proliferative skin diseases and conditions associated with cerebral metabolic inhibition.

Disease states associated with the activity of matrix metalloproteinases (MMPs), especially collagenase, stromelysin and gelatinase, or as described by Schwartz M A, Van Wart H E, *Prog. Med. Chem.*, 29, 271–334 (1992) are treatable according to the invention. Thus, the present invention provides compounds of formula I, and compositions containing compounds of formula I, which are of use in a method for treating a patient suffering from, or subject to, conditions which can be ameliorated or prevented by the administration of an inhibitor of an MMP. For example, compounds within the present invention are useful in inhibiting connective tissue breakdown and in the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumor metastasis, invasion and growth. Compounds within the scope of the invention as MMP inhibitors may also inhibit the production of TNF (Mohler et al., *Nature*, 370, 218–220 (1994); Gearing A J H et al., *Nature*, 370, 555–557 (1994); McGeehan G M et al., *Nature*, 370, 558–561 (1994)), and, thus are useful in the treatment or prophylaxis of conditions wherein the inhibition of the production or action of TNF are thought to be potentially useful for the treatment or prophylaxis of disease states associated with detrimental amounts of TNF, as described above.

Reported Developments

EP patent application publication No. 606046-A1 pertains to a compound of formula

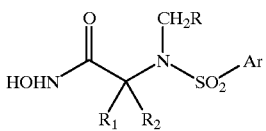

is a matrix metalloproteinase inhibitor which is useful for treating rheumatoid arthritis, tissue ulceration, bone disease, tumor metastasis and HIV infection. The reference does not disclose or suggest that the compound inhibits TNF.

Japanese patent application publication No. JP07196598-A disclose that a compound of formula

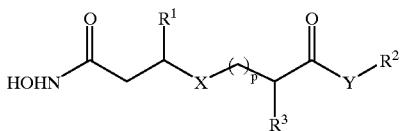

wherein $R^1$ represents an alkyl group; $R^2$ represents a hydrogen atom, a lower alkyl group or benzyl group; $R^3$ represents a hydrogen atom or lower alkyl group; X may represent a sulfur atom, sulfinyl group or a sulfonyl group; Y represents an oxygen atom or NH; and n represents an integer from 1–3, and is a collagenase inhibitor which is useful for treating and preventing rheumatoid arthritis, osteoarthritis, neoplastic infiltration and bone resorption. The reference does not disclose or suggest that the compound inhibits TNF.

SUMMARY OF THE INVENTION

This invention is directed to a compound of formula I:

(I)

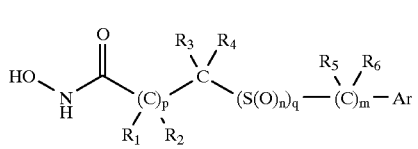

wherein $R_1$ is hydrogen, optionally substituted alkyl, optionally substituted alkenyl, optionally substituted cycloalkyl, optionally substituted cycloalkenyl, optionally substituted aryl, optionally substituted heteroaryl, optionally substituted aralkyl, optionally substituted heteroaralkyl, optionally substituted aralkyloxyalkyl, optionally substituted aryloxyalkyl, hydroxy, optionally substituted alkoxy, optionally substituted aryloxy, optionally substituted aralkyloxy, $Y^3Y^4N-$, $Y^1Y^2NCO$-alkyl, aryl-$SO_2Y^1N$-alkyl, arylsulfanylalkyl, arylsulfinylalkyl, arylsulfonylalkyl, cyclocarbamoylalkyl or imidealkyl;

$R_2$, $R_4$, $R_5$, $R_6$ are independently hydrogen or optionally substituted alkyl, or $R_2$ and $R_4$ taken together with the carbon atoms through which $R_2$ and $R_4$ are linked form optionally substituted cycloalkyl or optionally substituted cycloalkenyl, or $R_1$ and $R_2$ taken together with the carbon atoms through which $R_1$ and $R_2$ are linked form optionally substituted cycloalkyl;

$R_3$ is optionally substituted alkyl, optionally substituted alkenyl, optionally substituted cycloalkyl, optionally substituted cycloalkenyl, optionally substituted aryl, optionally substituted heteroaryl, optionally substituted aralkyl, optionally substituted aralkenyl, optionally substituted aralkynyl, optionally substituted heteroaralkyl, optionally substituted heteroaralkenyl, optionally substituted heteroaralkynyl, optionally substituted alkyloxyalkyl, optionally substituted aryloxyalkyl, optionally substituted heteroaryloxyalkyl, optionally substituted aryloxyalkenyl, optionally substituted heteroaryloxyalkenyl, optionally substituted aralkyloxyalkyl, optionally substituted aralkyloxyalkenyl, optionally substituted heteroaralkyloxyalkyl, optionally substituted heteroaralkyloxyalkenyl, optionally substituted cycloalkyloxy, optionally substituted cycloalkyloxyalkyl, optionally substituted heterocyclyl, optionally substituted heterocyclyloxyalkyl or optionally substituted heterocyclyloxy, $Y^3Y^4$Nalkyl, $Y^1Y^2NCO_2$alkyl, $Y^1Y^2NCO$-alkyl, imidealkyl, or $R_3$ and $R_4$ taken together with the carbon to which $R_3$ and $R_4$ are attached form an optionally substituted cycloalkyl, or one of $R_1$ and $R_2$ and one of $R_3$ and $R_4$ taken together with the carbons through which the one of $R_1$ and $R_2$ and one of $R_3$ and $R_4$ are linked form a bond or optionally substituted cycloalkyl or optionally substituted cycloalkenyl;

Ar is optionally substituted aryl or optionally substituted heteroaryl;

$Y^1$ and $Y^2$ are independently hydrogen, optionally substituted alkyl, optionally substituted aryl or optionally substituted aralkyl, or $Y^1$ and $Y^2$ taken together with the nitrogen atom to which $Y^1$ and $Y^2$ are attached form an optionally substituted heterocyclyl;

$Y^3$ and $Y^4$ are independently $Y^1$ and $Y^2$, or optionally substituted acyl, optionally substituted aroyl, optionally substituted aralkyloxycarbonyl, optionally substituted heteroaralkyloxycarbonyl or optionally substituted alkoxycarbonyl;

n is 0, 1 or 2;

m is 0 or 1;

p is 0 or 1; and q is 0 or 1, or an n-oxide thereof, solvate thereof, hydrate thereof or pharmaceutically acceptable salt thereof.

Compounds within the scope of the present invention possess useful properties, more particularly pharmaceutical properties. They are especially useful for inhibiting the production or physiological effects of TNF in the treatment of a patient suffering from a disease state associated with a physiologically detrimental excess of tumor necrosis factor (TNF). Compounds within the scope of the present invention also inhibit cyclic AMP phosphodiesterase, and are useful in treating a disease state associated with pathological conditions that are modulated by inhibiting cyclic AMP phosphodiesterase, such disease states including inflammatory and autoimmune diseases, in particular type IV cyclic AMP phosphodiesterase. Compounds within the scope of the present invention also inhibit matrix metalloproteinases, and are useful in treating a disease state associated with pathological conditions that are modulated by inhibiting MMPs, such disease states involve tissue breakdown and those associated with a physiologically detrimental excess of TNF. The present invention is therefore also directed to the pharmaceutical use of the compounds, pharmaceutical compositions containing the compounds, intermediates leading thereto and methods for the preparation of the compounds and their intermediates.

DETAILED DESCRIPTION OF THE INVENTION

As used above, and throughout the description of the invention, the following terms, unless otherwise indicated, shall be understood to have the following meanings:

Definitions

"Patient" includes both human and other mammals.

"Alkyl" means an aliphatic hydrocarbon group which may be straight or branched having about 1 to about 15 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl group may be substituted by one or more hydroxy, halo, cycloalkyl, cycloalkenyl or heterocyclyl. Exemplary alkyl groups include methyl, fluoromethyl, difluoromethyl, trifluoromethyl, cyclopropylmethyl, cyclopentylmethyl, ethyl, n-propyl, i-propyl, n-butyl, t-butyl, n-pentyl, 3-pentyl, heptyl, octyl, nonyl, decyl and dodecyl.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group may be substituted by one or more halo or cycloalkyl. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Cycloalkyl" means a non-aromatic mono- or multicyclic ring system of about 3 to about 10 carbon atoms. Preferred monocyclic cycloalkyl rings include cyclopentyl, fluorocyclopentyl, cyclohexyl and cycloheptyl; more preferred is cyclopentyl. The cycloalkyl group may be substituted by one or more halo, methylene ($H_2C=$), alkyl, aralkyl, heteroaralkyl, fused aryl or fused heteroaryl. Exemplary multicyclic cycloalkyl rings include 1-decalin, adamant-(1- or 2-)yl and norbornyl.

"Cycloalkenyl" means a non-aromatic monocyclic or multicyclic ring system containing a carbon-carbon double bond and having about 3 to about 10 carbon atoms. Preferred monocyclic cycloalkenyl rings include cyclopentenyl, cyclohexenyl or cycloheptenyl; more preferred is cyclopentenyl. A preferred multicyclic cycloalkenyl ring is norbornylenyl. The cycloalkenyl group may be substituted by one or more halo, methylene ($H_2C=$), alkyl, aralkyl or heteroaralkyl.

"Aryl" means aromatic carbocyclic radical containing about 6 to about 10 carbon atoms. Exemplary aryl include phenyl or naphthyl, or phenyl or naphthyl substituted with one or more aryl group substituents which may be the same or different, where "aryl group substituent" includes hydrogen, alkyl, aryl, aralkyl, hydroxy, alkoxy, aryloxy, aralkoxy, carboxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, alkylsulfinyl, arylsulfinyl, alkylthio, arylthio, aralkylthio, oxyalkylenyloxy, $Y^1Y^2N-$, $Y^1Y^2NCO-$ or $Y^1Y^2NSO_2-$, where $Y^1$ and $Y^2$ are independently hydrogen, alkyl, aryl, and aralkyl. Preferred aryl group substituents include hydrogen, alkyl, hydroxy, acyl, aroyl, halo, nitro, cyano, alkoxycarbonyl, acylamino, alkylthio, $Y^1Y^2N-$, $Y^1Y^2NCO-$ or $Y^1Y^2NSO_2-$, where $Y^1$ and $Y^2$ are independently hydrogen and alkyl.

"Heteroaryl" means about a 5- to about a 10- membered aromatic monocyclic or multicyclic hydrocarbon ring system in which one or more of the carbon atoms in the ring system is/are element(s) other than carbon, for example nitrogen, oxygen or sulfur. The "heteroaryl" may also be substituted by one or more aryl group substituents. Exemplary heteroaryl groups include pyrazinyl, furanyl, thienyl, pyridyl, pyrimidinyl, isoxazolyl, isothiazolyl, quinolinyl, and isoquinolinyl. Preferred heteroaryl groups include pyrazinyl, thienyl, pyridyl, pyrimidinyl, isoxazolyl and isothiazolyl.

"Heterocyclyl" means an about 4 to about 10 member monocyclic or multicyclic ring system wherein one or more of the atoms in the ring system is an element other than carbon chosen amongst nitrogen, oxygen or sulfur. The heterocyclyl may be optionally substituted by one or more alkyl group substituents. Exemplary heterocyclyl moieties include quinuclidine, pentamethylenesulfide, tetrahydropyranyl, tetrahydrothiophenyl, pyrrolidinyl or tetrahydrofuranyl.

"Aralkyl" means an aryl-alkyl- group in which the aryl and alkyl are as previously described. Preferred aralkyls contain a lower alkyl moiety. Exemplary aralkyl groups include benzyl, 2-phenethyl and naphthlenemethyl.

"Aralkenyl" means an aryl-alkenyl- group in which the aryl and alkenyl are as previously described. Preferred aralkenyls contain a lower alkenyl moiety. Exemplary aralkenyl groups include styryl and phenylallyl.

"Aralkynyl" means an aryl-alkynyl- group in which the aryl and alkynyl are as previously described. Preferred aralkynyls contain a lower alkynyl moiety. An exemplary aralkynyl group is phenylacetylenyl.

"Heteroaralkyl" means an heteroaryl-alkyl- group in which the heteroaryl and alkyl are as previously described. Preferred heteroaralkyls contain a lower alkyl moiety. An exemplary heteroaralkyl group is 4-pyridylmethyl.

"Heteroaralkenyl" means an heteroaryl-alkenyl- group in which the heteroaryl and alkenyl are as previously described. Preferred heteroaralkenyls contain a lower alkenyl moiety. An exemplary aralkenyl group is 4-pyridylvinyl.

"Heteroaralkynyl" means an heteroaryl-alkynyl- group in which the heteroaryl and alkynyl are as previously described. Preferred heteroaralkynyls contain a lower alkynyl moiety. An exemplary heteroaralkynyl group is 4-pyridylethynyl.

"Heterocyclylalkyl" means an heterocyclyl-alkyl- group in which the heterocyclyl and alkyl are as previously described. Preferred heterocyclylalkyls contain a lower alkyl moiety. An exemplary heteroaralkyl group is tetrahydropyranylmethyl.

"Heterocyclylalkyloxyalkyl" means an heterocyclyl-alkyl-O-alkyl- group in which the heterocyclyl and alkyls groups independently are as previously described. An exemplary heteroaralkyl group is tetrahydropyranylmethyloxymethyl.

"Hydroxy substituted alkyl" means a HO-alkyl- group in which alkyl is as previously defined. Preferred hydroxyalkyls contain lower alkyl. Exemplary hydroxyalkyl groups include hydroxymethyl and 2-hydroxyethyl.

"Acyl" means an H—CO— or alkyl-CO— group in which the alkyl group is as previously described. Preferred acyls contain a lower alkyl. Exemplary acyl groups include formyl, acetyl, propanoyl, 2-methylpropanoyl, butanoyl and palmitoyl.

"Aroyl" means an aryl-CO— group in which the alkyl group is as previously described. Exemplary groups include benzoyl and 1- and 2-naphthoyl.

"Alkoxy" means an alkyl-O— group in which the alkyl group is as previously described. Exemplary alkoxy groups include methoxy, ethoxy, n-propoxy, i-propoxy, n-butoxy and heptoxy.

"Cycloalkyloxy" means an cycloalkyl-O— group in which the cycloalkyl group is as previously described. Exemplary cycloalkyloxy groups include cyclopentyloxy and cyclohexyloxy.

"Alkoxyalkyl" means an alkyl-O-alkyl- group in which the alkyl groups are independently as previously described. Exemplary alkoxy groups include methoxyethyl, ethoxymethyl, n-butoxymethyl and cyclopentylmethyloxyethyl.

"Aryloxy" means an aryl-O— group in which the aryl group is as previously described. Exemplary aryloxy groups include phenoxy and naphthoxy.

"Aralkyloxy" means an aralkyl-O— group in which the aralkyl group is as previously described. Exemplary aralkyloxy groups include benzyloxy and 1- or 2-naphthalenemethoxy.

"Aralkyloxyalkyl" means an aralkyl-O-alkyl group in which the aralkyl and alkyl groups are as previously described. An exemplary aralkyloxyalkyl group is benzyloxyethyl.

"Aralkyloxyalkenyl" means an aralkyl-O-alkenyl group in which the aralkyl and alkenyl groups are as previously described. An exemplary aralkyloxyalkenyl group is 3-benzyloxyallyl.

"Aryloxyalkyl" means an aryl-O-alkyl- group in which the aryl or alkyl groups are as previously described. An exemplary aryloxyalkyl groups is phenoxypropyl.

"Aryloxyalkenyl" means an aryl-O-alkenyl- group in which the aryl or alkenyl groups are as previously described. An exemplary aryloxyalkenyl groups is phenoxyallyl.

"Heteroaralkyloxy" means an heteroaralkyl-O— group in which the heteroaralkyl group is as previously described. An exemplary heteroaralkyloxy group is 4-pyridylmethyloxy.

"Heteroaralkyloxyalkyl" means an heteroaralkyl-O-alkyl group in which the heteroaralkyl and alkyl groups are as previously described. An exemplary heteroaralkyloxy group is 4-pyridylmethyloxyethyl.

"Heteroaralkyloxyalkenyl" means an heteroaralkyl-O-alkenyl group in which the heteroaralkyl and alkenyl groups are as previously described. An exemplary heteroaralkyloxyalkenyl group is 4-pyridylmethyloxyallyl.

"Alkylthio" means an alkyl-S— group in which the alkyl group is as previously described. Exemplary alkylthio groups include methylthio, ethylthio, i-propylthio and heptylthio.

"Arylthio" means an aryl-S— group in which the aryl group is as previously described. Exemplary arylthio groups include phenylthio and naphthylthio.

"Aralkylthio" means an aralkyl-S— group in which the aralkyl group is as previously described. An exemplary aralkylthio group is benzylthio.

"Oxyalkylenyloxy" means a —O-lower alkyl-O— group in which the lower alkyl group is as previously described. An exemplary alkylenedioxy group is —O—CH$_2$—O—.

"Cyclocarbamoylalkyl" means a compound of formulae

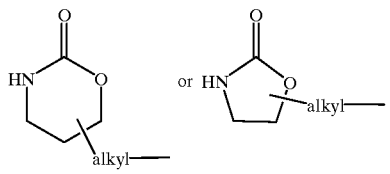

in which the cyclocarbamoyl group consists of the oxooxazaheterocyclyl ring moiety, and the alkyl group is as previously described. The alkyl moiety may be attached to the carbamoyl through either a carbon atom or the nitrogen atom of the carbamoyl moiety. An exemplary cyclocarbamoylalkyl group is N-oxazolidinylpropyl.

"Imidealkyl" means a compound of formulae

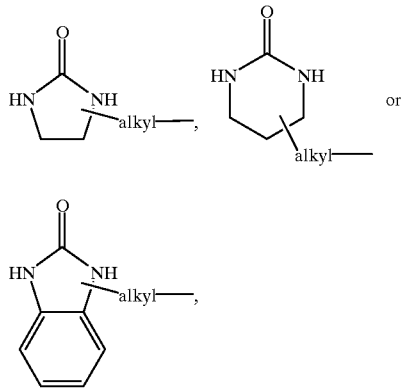

in which the imide group consists of the oxodiazaheterocyclyl ring moiety, and the alkyl group is as previously described. The alkyl moiety may be attached to the carbamoyl through either a carbon atom or nitrogen atom of the carbamoyl moiety. An exemplary imidealkyl group is n-phthalimidepropyl.

"$Y^1Y^2N$—" means a substituted or unsubstituted amino group, wherein $Y^1$ and $Y^2$ are as previously described. Exemplary groups include amino ($H_2N$—), methylamino, ethylmethylamino, dimethylamino and diethylamino.

"Alkoxycarbonyl" means an alkyl-O—CO— group. Exemplary alkoxycarbonyl groups include methoxy- and ethoxycarbonyl.

"Aryloxycarbonyl" means an aryl-O—CO— group. Exemplary aryloxycarbonyl groups include phenoxy- and naphthoxycarbonyl.

"Aralkoxycarbonyl" means an aralkyl-O—CO— group. An exemplary aralkoxycarbonyl group is benzyloxycarbonyl.

"$Y^1Y^2NCO$—" means a substituted or unsubstituted carbamoyl group, wherein $Y^1$ and $Y^2$ are as previously described. Exemplary groups are carbamoyl ($H_2NCO$—) and dimethylaminocarbamoyl ($Me_2NCO$—).

"$Y^1Y^2NSO_2$—" means a substituted or unsubstituted sulfamoyl group, wherein $Y^1$ and $Y^2$ are as previously described. Exemplary groups are aminosulfamoyl ($H_2NSO_2$—) and dimethylaminosulfamoyl ($Me_2NSO_2$—).

"Acylamino" is an acyl-NH— group wherein acyl is as defined herein.

"Aroylamino" is an aroyl-NH— group wherein aroyl is as defined herein.

"Alkylsulfonyl" means an alkyl-SO$_2$— group. Preferred groups are those in which the alkyl group is lower alkyl.

"Alkylsulfinyl" means an alkyl-SO— group. Preferred groups are those in which the alkyl group is lower alkyl.

"Arylsulfonyl" means an aryl-SO$_2$— group.

"Arylsulfinyl" means an aryl-SO— group.

"Halo" means fluoro, chloro, bromo, or iodo. Preferred are fluoro, chloro or bromo, and more preferred are fluoro or chloro.

Preferred Embodiments

A preferred compound aspect of the invention is the compound of formula I wherein $R_1$ is hydrogen, optionally substituted alkyl, optionally substituted alkenyl, optionally substituted cycloalkyl, hydroxy, $Y^1Y^2N$—, arylsulfanylalkyl, arylsulfinylalkyl or arylsulfonylalkyl;

$R_2$, $R_4$, $R_5$, $R_6$ are independently hydrogen or optionally substituted alkyl, or $R_4$ is optionally substituted aryl or optionally substituted heteroaryl, or $R_2$ and $R_4$ taken together with the carbon atoms through which $R_2$ and $R_4$ are linked form optionally substituted cycloalkyl or optionally substituted cycloalkenyl, or $R_1$ and $R_2$ taken together with the carbon atoms through which $R_1$ and $R_2$ are linked form optionally substituted cycloalkyl;

$R_3$ is optionally substituted alkyl, optionally substituted aryl, optionally substituted heteroaryl, optionally substituted aralkyl, optionally substituted heteroaralkyl, $Y^3Y^4N$alkyl, $Y^1Y^2NCO_2$alkyl, $Y^1Y^2NCO$-alkyl, imidealkyl, or $R_3$ and $R_4$ taken together with the carbon to which $R_3$ and $R_4$ are attached form an optionally substituted cycloalkyl, or one of $R_1$ and $R_2$ and one of $R_3$ and $R_4$ taken together with the carbons through which the one of $R_1$ and $R_2$ and one of $R_3$ and $R_4$ are linked form a bond or optionally substituted cycloalkyl or optionally substituted cycloalkenyl;

Ar is optionally substituted aryl or optionally substituted heteroaryl;

$Y^1$ and $Y^2$ are independently hydrogen, optionally substituted alkyl or optionally substituted aryl, or $Y^1$ and $Y^2$ taken together with the nitrogen atom to which $Y^1$ and $Y^2$ are attached form an optionally substituted heterocyclyl, and $Y^3$ and $Y^4$ are independently $Y^1$ or $Y^2$, or optionally substituted aroyl or optionally substituted aralkyloxycarbonyl.

Another preferred compound aspect of the invention is the compound wherein $R_1$ is optionally substituted alkyl, optionally substituted alkenyl, optionally substituted aralkyl or optionally substituted heteroaralkyl.

Another preferred compound aspect of the invention is the compound wherein $R_1$ is optionally substituted alkyl.

Another preferred compound aspect of the invention is the compound wherein $R_1$ is hydroxy.

Another preferred compound aspect of the invention is the compound wherein $R_1$ is optionally substituted alkyl.

Another preferred compound aspect of the invention is the compound wherein $R_1$ is $Y^1Y^2N$— and $Y^1$ or $Y^2$ are hydrogen.

Another preferred compound aspect of the invention is the compound wherein $R_2$ is hydrogen.

Another preferred compound aspect of the invention is the compound wherein $R_1$ and $R_2$ are optionally substituted alkyl.

Another preferred compound aspect of the invention is the compound wherein $R_3$ is optionally substituted aryl, optionally substituted heteroaryl, optionally substituted aralkyl, optionally substituted heteroaralkyl or $Y^3Y^4N$alkyl.

Another preferred compound aspect of the invention is the compound wherein $R_3$ is optionally substituted aralkyl.

Another preferred compound aspect of the invention is the compound wherein $R_4$ is hydrogen or optionally substituted alkyl.

Another preferred compound aspect of the invention is the compound wherein $R_4$ is optionally substituted alkyl.

Another preferred compound aspect of the invention is the compound wherein $R_3$ and $R_4$ taken together with the carbon atom to which $R_3$ and $R_4$ are attached form optionally substituted cycloalkyl.

Another preferred compound aspect of the invention is the compound wherein Ar is optionally substituted aryl; more preferred is 4-methoxyphenyl or 3,4-dimethoxyphenyl.

Another preferred compound aspect of the invention is the compound wherein n is 0 or 2.

Another preferred compound aspect of the invention is the compound wherein m is 0.

Another preferred compound aspect of the invention is the compound wherein q is 1.

Preferred compounds for use according to the invention are selected from the following species:

A 7-Phenyl-3-phenylsulfonylheptanoic acid hydroxyamide;
B 7-Phenyl-3-phenylsulfanylheptanoic acid hydroxyamide;
C 3-(4-Acetoamidophenylsulfonyl)-7-phenylheptanoic acid hydroxyamide;
D 3-(4-Acetoamidophenylsulfanyl)-7-phenylheptanoic acid hydroxyamide;
E 3-(2-Naphthalenylsulfonyl)-7-phenylheptanoic acid hydroxyamide;
F 3-(2-Naphthalenylsulfanyl)-7-phenylheptanoic acid hydroxyamide;
G 3-(4-Methoxyphenylsulfonyl)-7-phenylheptanoic acid hydroxyamide;
H 3-(4-Methoxyphenylsulfanyl)-7-phenylheptanoic acid hydroxyamide;
I 3-(Benzylsulfonyl)-7-phenylheptanoic acid hydroxyamide;
J 3-(Benzylsulfanyl)-7-phenylheptanoic acid hydroxyamide;
K N-hydroxy-3-(4-methoxybenzenesulfonyl)-4-phenylbutyramide;
L N-hydroxy-3-(4-methoxybenzenesulfanyl)-4-phenylbutyramide;
M N-hydroxy-3-(4-methoxybenzenesulfonyl)-3-phenylpropionamide;
N N-hydroxy-3-(4-methoxybenzenesulfanyl)-3-phenylpropionamide;
O 3-(4-Methoxybenzenesulfonyl)-5-phenylpentanoic acid hydroxyamide;
P 3-(4-Methoxybenzenesulfanyl)-5-phenylpentanoic acid hydroxyamide;
Q 3-(4-Methoxybenzenesulfonyl)-6-phenylhexanoic acid hydroxamide;
R 3-(4-Methoxybenzenesulfanyl)-6-phenylhexanoic acid hydroxamide;
S 3-(4-Methoxybenzenesulfonyl)-3-methyl-7-phenylheptanoic acid hydroxamide
T 3-(4-Methoxybenzenesulfanyl)-3-methyl-7-phenylheptanoic acid hydroxamide
U (±)-N-Hydroxy-3-(4-methoxyphenyl)sulfanyl-4-(4-biphenyl)butyramide;
V (±)-N-Hydroxy-3-(4-methoxyphenyl)sulfanyl-4-(4-phenyloxyphenyl)butyramide;
W (±)-N-Hydroxy-3-(4-methoxyphenyl)sulfanyl-4-(4-benzyloxyphenyl)butyramide;
X (±)-N-Hydroxy-3-(4-methoxyphenyl)sulfanyl-4-(4-n-butyloxyphenyl)butyramide;
Y (±)-N-Hydroxy-3-(4-methoxyphenyl)sulfonyl-4-(4-biphenyl)butyramide;
Z (±)-N-Hydroxy-3-(4-methoxyphenyl)sulfonyl-4-(4-phenyloxyphenyl)butyramide;

AA (±)-N-Hydroxy-3-(4-methoxyphenyl)sulfonyl-4-(4-benzyloxyphenyl)butyramide;
AB (±)-N-Hydroxy-3-(4-methoxyphenyl)sulfonyl-4-(4-n-butyloxyphenyl)butyramide;
AC 3-(4-Methoxybenzenesulfonyl)-3-ethyl-7-phenylheptanoic acid hydroxamide;
AD 3-(4-Methoxybenzenesulfonyl)-3,7-diphenylheptanoic acid hydroxamide;
AE N-Hydroxy-3-(4-methoxybenzenesulfonyl)-3-methylbutyramide;
AF N-Hydroxy-2-[1-(4-methoxybenzenesulfonyl)cyclopentyl]acetamide;
AG N-Hydroxy-2-[1-(4-methoxybenzenesulfonyl)-4-phenylcyclohexyl]acetamide;
AH (2R*,3R*)-2-Amino-3-(4-methoxybenzene)sulfonyl-7-phenylheptanoic acid hydroxy amide;
AI N-Hydroxy-2-[(3,4-dimethoxyphenyl)sulfonyl]-6-phenylhexanamide;
AJ (E)-N-Hydroxy-3-[(3,4-dimethoxyphenyl)thio]-7-phenyl-2-heptenamide;
AK (E)-N-Hydroxy-3-[(3,4-dimethoxyphenyl)sulfonyl]-7-phenyl-2-heptenamide;
AL (Z)-N-Hydroxy-3-[(3,4-dimethoxyphenyl)thio]-7-phenyl-2-heptenamide;
AM N-hydroxy-3-(4-methoxyphenyl)thio-2-(1-propane-3-yl)-7-phenylheptanamide;
AN N-Hydroxy-2-(1-propane-3-yl)-3-(4-methoxyphenyl)sulfonyl-7-phenylheptanamide;
AO N-Hydroxy-2-[(3,4-dimethoxyphenyl)thio]-3-(3-phenylpropyl-1-yl)-1-cyclopentenecarboxamide;
AP N-Hydroxy-2-[(3,4-dimethoxyphenyl)sulfonyl]-3-(3-phenylpropyl-1-yl)-1-cyclopentenecarboxamide;
AQ N-Hydroxy-3-(3,4-dimethoxyphenyl-7-phenyl-2-heptenamide;
AR N-Hydroxy-3-(3,4-dimethoxyphenyl-7-phenylheptanamide;
AS (−)-(2S, 3R)-N-Hydroxy-2-(2-benzenesulfonylethyl)-3-(3,4-dimethoxyphenylsulfonyl)-7-phenylheptanamide;
AT (+)-(2S, 3R)-N-Hydroxy-2-(2-benzenesulfonylethyl)-3-(3,4-dimethoxyphenylsulfonyl)-7-phenylheptanamide;
AU (−)-N-Hydroxy-2-(2-benzenesulfonylethyl)-3-(3,4-dimethoxyphenylsulfanyl)-7-phenylheptanamide;
AV (+)-N-Hydroxy-2-(2-benzenesulfonylethyl)-3-(3,4-dimethoxyphenylsulfanyl)-7-phenylheptanamide;
AW N-Hydroxy-3-(3,4-dimethoxybenzenesulfonyl)-4-phenylbutyramide;
AX N-Hydroxy-3-(3,4-dimethoxyphenylsulfanyl)-4-phenylbutyramide;
AY N-Hydroxy-3-(3,4-dimethoxybenzenesulfonyl)-3-phenylproprionamide;
AZ N-Hydroxy-3-(3,4-dimethoxyphenylsulfanyl)-3-phenylpropionamide;
BA 3-(3,4-Dimethoxyphenylsulfanyl)-5-phenylpentanoic acid hydroxamide;
BB 3-(3,4-Dimethoxyphenylsulfonyl)-5-phenylpentanoic acid hydroxamide;
BC 3-(3,4-Dimethoxybenzenesulfonyl)-6-phenylhexanoic acid hydroxamide;
BD 3-(3,4-Dimethoxyphenylsulfanyl)-6-phenylhexanoic acid hydroxamide;
BE 3-(3,4-Dimethoxybenzenesulfonyl)-6-phenylhexanoic acid hydroxamide;
BF 3-(R*)-(3,4-Dimethoxybenzenesulfonyl)-2-(S*)-isopropyl-7-phenylheptanoic acid hydroxamide;
BG 3-(3,4-Dimethoxybenzenesulfanyl)-2-isopropyl-7-phenylheptanoic acid hydroxamide;
BH (+)-(2R,3R)-3-(3,4-Dimethoxyphenylsulfanyl)-2-methyl-7-phenylheptanoic acid hydroxyamide;
BI (+)-(2R,3R)-3-(3,4-Dimethoxyphenylsulfonyl)-2-methyl-7-phenylheptanoic acid hydroxyamide;
BJ (+)-(2R,3S)-3-(3,4-Dimethoxyphenylsulfanyl)-2-methyl-7-phenylheptanoic acid hydroxyamide;
BK (+)-(2R,3S)-3-(3,4-Dimethoxyphenylsulfonyl)-2-methyl-7-phenylheptanoic acid hydroxyamide;
BL 1-[1-(3,4-Dimethoxyphenylsulfonyl)-5-phenylpentyl]cyclopentane-carboxylic acid hydroxyamide;
BM 1-[1-(3,4-Dimethoxyphenylsulfanyl)-5-phenylpentyl]cyclopentane-carboxylic acid hydroxyamide;
BN 3-(3,4-Dimethoxybenzenesulfonyl)-2,2-dimethyl-7-phenylheptanoic acid hydroxyamide;
BO 3-(4-Methoxybenzenesulfonyl)-2,2-dimethyl-7-phenylheptanoic acid hydroxyamide;
BP 3-(4-Methoxybenzenesulfinyl)-7-phenylheptanoic acid hydroxamide;
BQ (±)-N-Hydroxy-3-(3,4-Dimethoxyphenyl)sulfonyl-7-phenylheptanamide;
BR (±)-N-Hydroxy-3-(3,4-methylenedioxyphenyl)sulfonyl-7-phenylheptanamide;
BS (±)-N-Hydroxy-3-(3,4-dimethoxyphenyl)sulfinyl-7-phenylheptanamide;
BT (±)-N-Hydroxy-3-(3,4-Dimethoxyphenyl)sulfanyl-7-phenylheptanamide;
BU (±)-N-hydroxy-3-(3,4-methylenedioxyphenyl)sulfanyl-7-phenylheptanamide;
BV (−)-N-Hydroxy-3-(3,4-dimethoxyphenyl)sulfonyl-7-phenylheptanamide;
BW (+)-N-hydroxy-3-(3,4-dimethoxyphenyl)sulfonyl-7-phenylheptanamide;
BX (±)-(2R*,3R*)-3-(4-Methoxybenzenesulfonyl)-7-phenyl-2-(2-phenoxyethyl)heptanoic acid hydroxyamide;
BY (±)-(2R*,3R*)-3-(4-Methoxybenzenesulfonyl)-7-phenyl-2-(2-phenylsulfanylethyl)heptanoic acid hydroxyamide;
BZ (2R*, 3R*)-3-(4-Methoxybenzenesulfonyl)-7-phenyl-2-(2-phenylsulfanylethyl)heptanoic acid hydroxyamide;
CA (±)-(2R*,3S*)-3-(4-Methoxybenzenesulfonyl)-7-phenyl-2-(benzenesulfonylmethyl)heptanoic acid hydroxyamide;
CB (±)-(2R*,3S*)-3-(4-methoxybenzenesulfonyl)-7-phenyl-2-(phenylsulfanylmethyl)heptanoic acid hydroxyamide;
CC (±) 2-Hydroxy-3-(4-methoxybenzenesulfonyl)-2-methyl-7-phenylheptanoic acid hydroxyamide;
CD (±)-3-(4-Methoxyphenylsulfanyl)-2-methyl-7-phenylheptanoic acid hydroxyamide;
CE (±)-3-(4-Methoxybenzenesulfonyl)-2-methyl-7-phenylheptanoic acid hydroxyamide;
CF 3-(3,4-Dimethoxybenzenesulfonyl)-5-methylhexanoic acid hydroxyamide;
CG 5-(4-Butoxyphenyl)-3-(3,4-dimethoxybenzenesulfonyl)-pentanoic acid hydroxyamide;
CH 3-(3,4-Dimethoxybenzenesulfonyl)hexanoic acid hydroxyamide;
CI 3-(3,4-Dimethoxybenzenesulfonyl)-4-methylpentanoic acid hydroxyamide;
CJ 3-(3,4-Dimethoxybenzenesulfonyl)-5-methylhexanoic acid hydroxyamide;
CK 3-(3-Benzyloxyphenyl)-3-(3,4-dimethoxybenzenesulfonyl)-N-hydroxypropionamide;
CL 3-(2-Benzyloxyphenyl)-3-(3,4-dimethoxybenzenesulfonyl)-N-hydroxypropionamide;
CM 3-(3-Benzyloxy-4-methoxyphenyl)-3-(3,4-dimethoxybenzenesulfonyl)-N-hydroxypropionamide;
CN 3-(3,4-Dimethoxybenzenesulfonyl)-N-hydroxy-3-(3-phenoxyphenyl)-propionamide;

CO 3-(3-(4-Chlorophenoxy)phenyl)-3-(3,4-dimethoxybenzenesulfonyl)-N-hydroxypropionamide;
CP 3-(3,4-Dimethoxybenzenesulfonyl)-N-hydroxy-3-(3-(4-methoxyphenoxy)phenyl)propionamide;
CQ N-[2-(3,4-Dimethoxybenzenesulfonyl)-3-hydroxycarbamoyl-propyl]-N methylbenzamide;
CR N-[2-(3,4-Dimethoxybenzenesulfonyl)-3-hydroxycarbamoyl-butyl]-N methylbenzamide;
CS Methyl-phenyl-carbamic acid 3-(3,4-dimethoxybenzenesulfonyl)-4-hydroxycarbamoyl-butyl ester;
CT [3-(3,4-Dimethoxybenzenesulfonyl)-4-hydroxycarbamoylbutyl]methylcarbamic acid benzyl ester;
CU 3-(3,4-Dimethoxybenzenesulfonyl)hexanedioic acid-1-hydroxyamide-6-(methylphenylamide);
CV 3-(3,4-Dimethoxybenzenesulfonyl)heptanedioic acid-1-hydroxyamide-7-(methylphenylamide);
CW 3-(3,4-Dimethoxybenzenesulfonyl)-6-(1,3-dioxo-1,3-dihydroisoindol-2-yl)hexanoic acid hydroxyamide;
CX 7-(3,4-Dihydro-2H-quinolin-1-yl)-3-(3,4-dimethoxybenzenesulfonyl)-7-oxoheptanoic acid hydroxyamide;
CY 7-(3,4-Dihydro-2H-quinolin-1-yl)-3-(3,4-dimethoxybenzenesulfonyl)-6-oxohexanoic acid hydroxyamide;
CZ 7-Benzo(1,3)dioxol-5-yl-3-(3,4-dimethoxybenzenesulfonyl)heptanoic acid hydroxyamide;
DA 3-(3,4-Dimethoxybenzenesulfonyl)-3-(thien-3-yl)-N-hydroxypropionamide;
DB 3-(3,4-Dimethoxybenzenesulfonyl)-5-phenylpentanoic acid hydroxyamide;
DC 3-(3,4-Dimethoxybenzenesulfonyl)-5-(3-phenoxyphenyl)pentanoic acid hydroxyamide;
DD 5-(4-Benzyloxyphenyl)-3-(3,4-dimethoxybenzenesulfonyl)pentanoic acid hydroxyamide;
DE 2-{(3,4-Dimethoxybenzenesulfonyl)-[4-(4-fluorobenzyloxyphenyl]methyl}-4-methylpentanoic acid hydroxyamide;
DF 3-(3,4-dimethoxybenzenesulfonyl)-7-phenyl-2-(4-phenylbutyl)heptanoic acid hydroxyamide;
DG 2-[1-(3-(3,4-dimethoxybenzenesulfonyl)-5-phenylpentyl]-N 1-hydroxy-N 4-methyl-N 4-phenylsuccinamide;
DH 3-(3,4-dimethoxybenzenesulfonyl)-7-phenyl-2-(3-phenylpropyl)heptanoic acid hydroxyamide;
DI 3-(3,4-dimethoxybenzenesulfonyl)-2-isopropyl-7-phenylheptanoic acid hydroxyamide;
DJ 3-(3,4-dimethoxybenzenesulfonyl)-2-isobutyl-7-phenylheptanoic acid hydroxyamide;
DK 3-(3,4-dimethoxybenzenesulfonyl)-7-phenyl-2-propylheptanoic acid hydroxyamide;
DL 3-(3,4-dimethoxybenzenesulfonyl)-7-phenyl-2-(4-phenylbutyl)heptanoic acid hydroxyamide;
DM 3-(3,4-dimethoxybenzenesulfonyl)-2-[2-(2-methoxyethoxy)ethyl]-7-phenylheptanoic acid hydroxyamide;
DN 3-(3,4-dimethoxybenzenesulfonyl)-2-benzenesulfonylethyl-7-phenylheptanoic acid hydroxyamide;
DO 3-(3,4-dimethoxybenzenesulfonyl)-7-phenyl-2-(5-phenylpentyl)heptanoic acid hydroxyamide;
DP 4-Benzenesulfonyl-2-{(3,4-dimethoxybenzenesulfonyl)-[4-(4-fluorobenzyloxy) phenyl]methyl}-N-hydroxy-butyramide;
DQ 2-{(3,4-dimethoxybenzenesulfonyl)-[4-(4-fluorobenzyloxy)phenyl]methyl}-N-hydroxy-4-phenyl-butyramide;
DR 2-{(3,4-dimethoxybenzenesulfonyl)-[4-(4-fluorobenzyloxy)phenyl]methyl}-N-hydroxy-4-(2-methoxyethoxy)butyramide;
DS 2-{(3,4-dimethoxybenzenesulfonyl)-[4-(4-fluorobenzyloxy)phenyl]methyl}-N-hydroxy-butyramide;
DT 2-{(3,4-dimethoxybenzenesulfonyl)-[4-(4-fluorobenzyloxy)phenyl]methyl}-pentanoic acid hydroxyamide;
DU 2-{(3,4-dimethoxybenzenesulfonyl)-[4-(4-fluorobenzyloxy)phenyl]methyl}-4-methylpentanoic acid hydroxyamide;
DV 2-{(3,4-dimethoxybenzenesulfonyl)-[4-(4-fluorobenzyloxy)phenyl]methyl}-N-hydroxy-3-methylbutyramide;
DW 2-{(3,4-dimethoxybenzenesulfonyl)-[4-(4-fluorobenzyloxy)phenyl]methyl}-7-phenylheptanoic acid hydroxyamide;
DX 2-{(3,4-dimethoxybenzenesulfonyl)-[4-(4-fluorobenzyloxy)phenyl]methyl}-5-phenylpentanoic acid hydroxyamide;
DY 2-{(3,4-dimethoxybenzenesulfonyl)-[4-(4-fluorobenzyloxy)phenyl]methyl}-N 1-hydroxy-N 4-methyl-N 4-phenyl-succinimide;
DZ 2-{(3,4-dimethoxybenzenesulfonyl)-[4-(4-fluorobenzyloxy)phenyl]methyl}-6-phenylhexanoic acid hydroxyamide;
EA 2-[Biphenyl-4-yl-(3,4-dimethoxybenzenesulfonyl)methyl]-4-methylpentanoic acid hydroxyamide;
EB 2-[(3,4-Dimethoxybenzenesulfonyl)-(4-phenoxyphenyl)methyl]-N-hydroxy-4-(2-methoxyethoxy)butyramide;
EC 2-[(3,4-Dimethoxybenzenesulfonyl)-(4-phenoxyphenyl)methyl]-N-hydroxy-butyramide;
ED 4-Benzenesulfonyl-2-[biphenyl-4-yl-(3,4-dimethoxybenzenesulfonyl)methyl]-N-hydroxybutyramide;
EE 2-[Biphenyl-4-yl-(3,4-dimethoxybenzenesulfonyl)methyl]-N-hydroxy-4-phenylbutyramide;
EF 2-[Biphenyl-4-yl-(3,4-dimethoxybenzenesulfonyl)methyl]-N-hydroxy-4-(2-methoxyethoxy)butyramide;
EG 2-[Biphenyl-4-yl-(3,4-dimethoxybenzenesulfonyl)methyl]-N-hydroxybutyramide;
EH 2-[Biphenyl-4-yl-(3,4-dimethoxybenzenesulfonyl)methyl]-4-methylpentanoic acid hydroxyamide;
EI 2-[Biphenyl-4-yl-(3,4-dimethoxybenzenesulfonyl)methyl]-N-hydroxy-3-methyl-butyramide;
EJ 2-[Biphenyl-4-yl-(3,4-dimethoxybenzenesulfonyl)methyl]-7-phenylheptanoic acid hydroxyamide;
EK 2-[Biphenyl-4-yl-(3,4-dimethoxybenzenesulfonyl)methyl]-5-phenylpentanoic acid hydroxyamide;
EL 2-[(3,4-Dimethoxybenzenesulfonyl)-(4-phenoxyphenyl)methyl]-N-hydroxy-3-methylbutyramide;
EM 2-[(3,4-Dimethoxybenzenesulfonyl)-(4-phenoxyphenyl)methyl]-7-phenylheptanoic acid hydroxyamide;
EN 3-(3,4-Dimethoxybenzenesulfonyl)-2-ethylhexanoic acid hydroxyamide;
EO 3-(3,4-Dimethoxybenzenesulfonyl)-2-(3-phenyl-propyl)hexanoic acid hydroxyamide;
EP 2-[(3-Benzyloxyphenyl)-(3,4-dimethoxybenzenesulfonyl)methyl]-5-phenylpentanoic acid hydroxyamide;
EQ 3-(4-Methoxybenzenesulfonyl)-3-(4-ethoxyphenyl) propionic acid hydroxyamide;

ER 3-(4-methoxybenzenesulfonyl)-3-(4-biphenyl)propionic acid hydroxy amide);

ES 3-(4-methoxybenzenesulfonyl)-3-(4-phenoxyphenyl) propionic acid hydroxy amide;

ET 3-(4-methoxybenzenesulfonyl)-3-(4-benzyloxyphenyl) propionic acid hydroxy amide;

EU 3-(4-methoxybenzenesulfonyl)-3-(4-fluorobenzyloxyphenyl)propionic acid hydroxy amide; and EV 3-(4-methoxybenzenesulfonyl)-3-(4-(3-trifluoromethylphenoxy)phenylpropionic acid hydroxy amide;

EW (+)-3-(4-methoxyphenylsulfonyl)-7-phenylheptanoic acid hydroxamide;

EX (−)-3-(4-methoxyphenylsulfonyl)-7-phenylheptanoic acid hydroxamide;

EY (−)-(2S,3S)-3-(3,4-Dimethoxybenzenesulfanyl)-2-methyl-7-phenylheptanoic acid hydroxyamide;

EZ (−)-(2S,3S)-3-(3,4-Dimethoxybenzenesulfonyl)-2-methyl-7-phenylheptanoic acid hydroxyamide;

FA (−)-(2S,3R)-3-(3,4-dimethoxyphenylsulfanyl)-2-methyl-7-phenylheptanoic acid hydroxyamide; and FB (−)-(2S,3R)-3-(3,4-dimethoxybenzenesulfonyl)-2-methyl-7-phenylheptanoic acid hydroxyamide.

More preferred compounds include G, Z, AA, AE–AG, AI, AP, AU, BF, BH–BK, BN–BO, BQ, BS, BV–BW, CA, CZ, DI, DM–DN, ES–EU, EW–EZ, and FA–FB.

The letters A to FB are allocated to compounds for easy reference in this specification.

Compounds of formula I may be prepared by the application or adaptation of known methods, by which is meant methods used heretofore or described in the literature.

General methods for preparing compounds according to the invention may also be prepared as described in the Schemes that follow. The variables in the Schemes are as described above, unless otherwise noted.

One procedure for preparing compounds according to the invention, particularly α,α-disubstituted analogs, is shown in Scheme A.

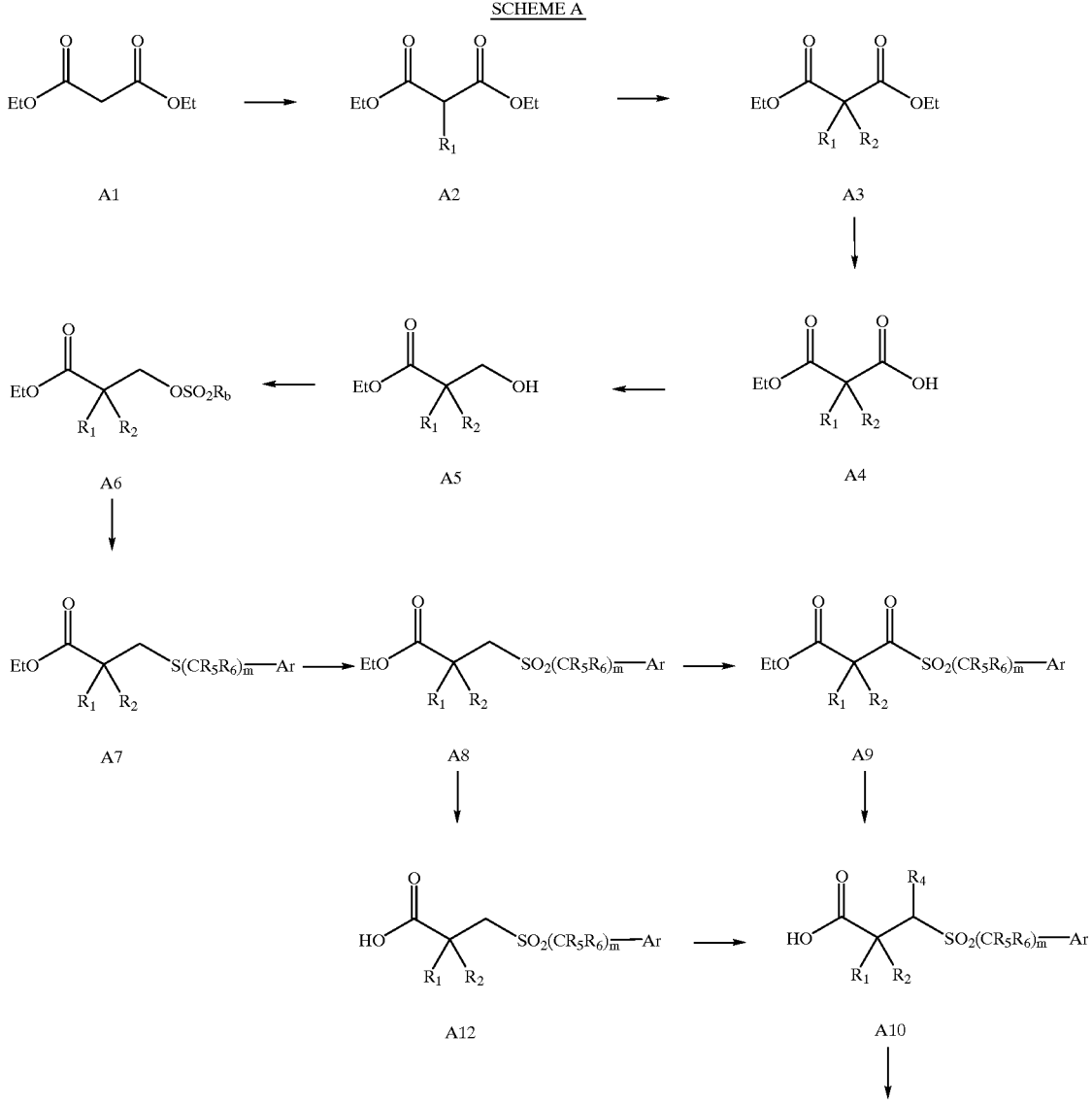

SCHEME A

-continued

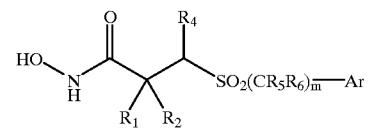

A11

For example, a dialkyl malonate such as diethyl (A1) or dimethyl may be monoalkylated using an appropriate alkyl halide ($R_1$—Cl, $R_1$—I, $R_1$—Br, preferably $R_1$—I, $R_1$—Br) and a suitable base such as a carbonate (such as sodium or calcium carbonate), hydroxide (such as sodium or potassium hydroxide) or alkoxide (such as sodium methoxide or ethoxide) in a polar solvent such as ethanol at about 20 to about 90° C. to give A2.

A2 may then be alkylated using another appropriate alkyl halide ($R_2$—Cl, $R_2$—I, $R_2$—Br, preferably $R_2$—I, $R_2$—Br), and similar reaction conditions as in the first alkylation to provide A3.

A3 is then deprotected to the corresponding mono acid (A4) by using one equivalent of hydroxide (such as sodium or potassium hydroxide) in an aqueous alcohol or tetrahydrofuran solvent at about 20 to about 90° C.

The acid moiety of A4 is then reduced selectively using diborane in an organic solvent such as tetrahydrofuran at about 0 to about 40° C. to give the alcohol (A5).

A5 is then be converted to the corresponding sulfonate ester (A6) using a sulfonyl chloride ($ClSO_2R_b$) such as p-toluenesulfonyl chloride, methanesulfonyl chloride or trifluoromethane sulfonyl chloride and a suitable base such as pyridine or triethylamine in an organic solvent.

The sulfonate ester is then be reacted with a thiol in the presence of a trialkylamine base or hydroxide to give a sulfide (A7).

The sulfide is then oxidized to a sulfone (A8) using a minimum of two equivalents of an oxidant such as oxone, m-chloroperbenzoic acid or hydrogen peroxide.

When A8 is α,α-disubstituted then the sulfone may then be alkylated with an alkyl iodide or bromide using a base such as lithium diisopropylamine, lithium bis(trimethylsilyl)amine, sodium bis(trimethylsilyl)amine or n-butyllithium in a solvent such as tetrahydrofuran, hexamethylphosphoramide, diethyl ether, dimethoxyethane or a combination thereof at about −75 to about 20° C. to give A9.

A8 and A9 are then converted to the corresponding acids respectively A12 and A10 using hydroxide in an aqueous alcohol or tetrahydrofuran solvent at about 20 to about 90° C.

A10 is then reacted using standard peptide coupling procedures with an O-protected hydroxylamine such as O-trimethylsilyl hydroxylamine, O-t-butyldimethylsilyl hydroxylamine, O-tetrahydropyranyl hydroxylamine followed by acid treatment to yield the hydroxamic acid A11.

An alternative sequence for preparing A10 involves alkylating A12 with an alkyl iodide or bromide using two equivalents of a base such as lithium diisopropylamine, lithium bis(trimethylsilyl)amine, sodium bis(trimethylsilyl) amine or butyllithium in a solvent such as tetrahydrofuran, hexamethylphosphoramide, diethyl ether, dimethoxyethane or a combination thereof at about 75 to about 20° C. to give A10.

An alternative sequence for preparing A3, particularly where $R_1$ aryl or heteroaryl, is from A13 by treatment with a suitable base such as trityl sodium, lithium diisopropylamine, lithium bis(trimethylsilyl)amine or sodium bis(trimethylsilyl)amine followed by a chloroformate at about −78 to about 25° C.

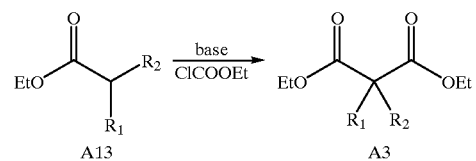

An alternative sequence for preparing A4 involves a mixed ester malonate such as benzyl ethyl malonate (A14). Sequential alkylation using alkyl halide ($R_1$—I, $R_1$—Br) followed by ($R_2$—I, $R_2$—Br) and a suitable base such as carbonate, sodium hydride, hydroxide or alkoxide in a polar solvent such as ethanol at about 20 to about 90° C. can yield A15. Deprotection of the benzylester to the mono acid A4 may be accomplished using catalytic hydrogenation.

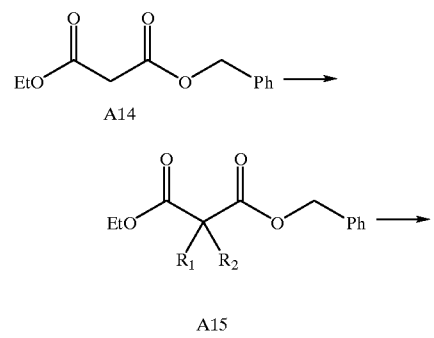

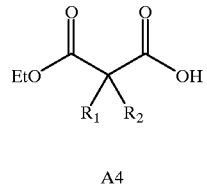

A4

Another procedure for preparing compounds according to the invention is shown in Scheme B.

SCHEME B
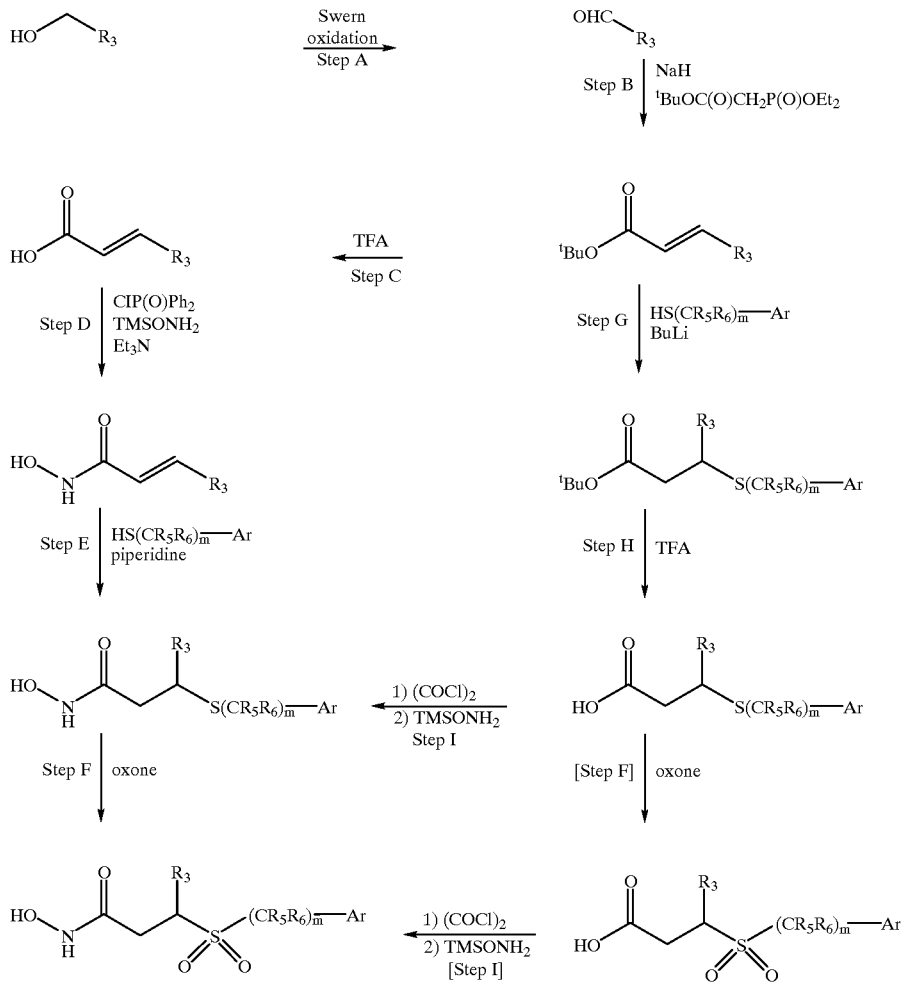
Another procedure for preparing compounds according to the invention is shown in Scheme C.
SCHEME C
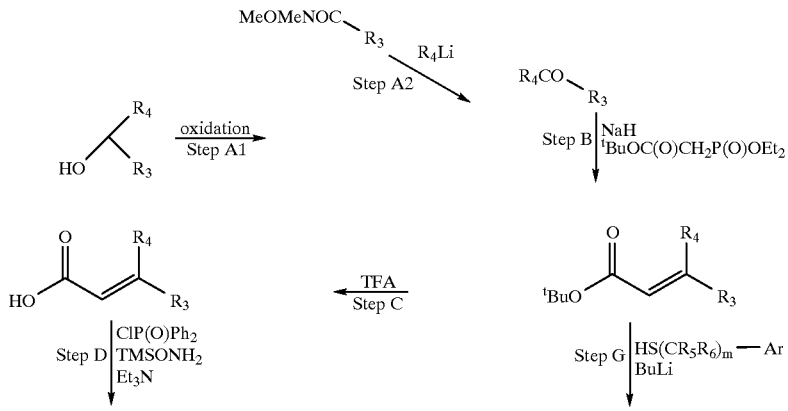

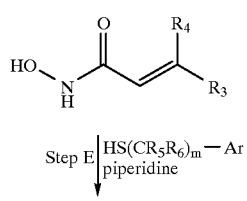
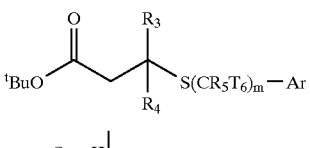
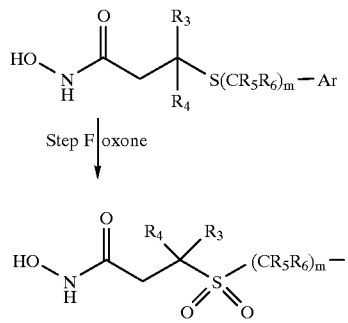

Following the procedures shown in Scheme B or C, except that the t-butyl diethylphosphonoacetate is substituted by a substituted t-butyl dialkylphosphonoacetate in step B, then a trisubstituted or tetrasubstituted olefin is produced respectively as shown in Scheme D. Those olefins may then be transformed according to the remaining procedures in Schemes B or C to an α-substituted hydroxamic acid.

Scheme D

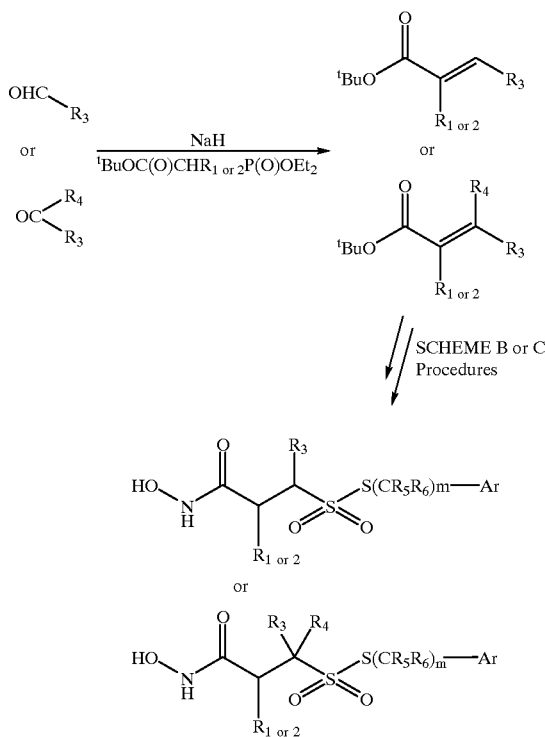

An example according to Scheme D, step B may use t-butyl diethylphosphonopropionate to prepare a hydroxyamide using the remaining steps as outlined in Scheme A. In addition, a number of substituted t-butyl dialkylphosphonoacetates can be prepared by alkylation of t-butyl diethylphosphonoacetate with an appropriate alkyl halide in the presence of a base such as sodium hydride, lithium diisopropylamine or sodium bis(trimethylsilyl)amine in a solvent such as tetrahydrofuran.

These phosphonoacetates can then be substituted in step B of Scheme D.

An alternative preparation of trisubstituted olefins is via an aldol reaction followed by elimination of the alcohol. Reaction of a t-butyl ester with an aldehyde in the presence of an appropriate base such as lithium diisopropylamine, lithium bis(trimethylsilyl)amine, sodium bis(trimethylsilyl)amine or butylithium in a solvent such as tetrahydrofuran, hexamethylphosphoramide, diethyl ether, dimethoxyethane or a combination thereof at about −75 to about 20° C. may provide the aldol adduct which may be treated with a sulfonyl halide such as methanesulfonyl chloride and a trialkylamine base such as triethylamine to provide a sulfonate ester which may be directly eliminated with an additional base such as 1,8-diazabicyclo-[5.4.0]undec-7-ene to give the trisubstituted olefin. This olefin may then be used in Scheme B to yield hydroxamic acids.

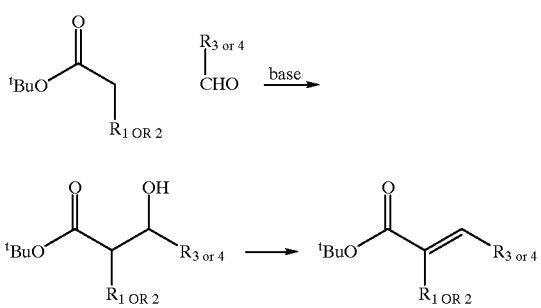
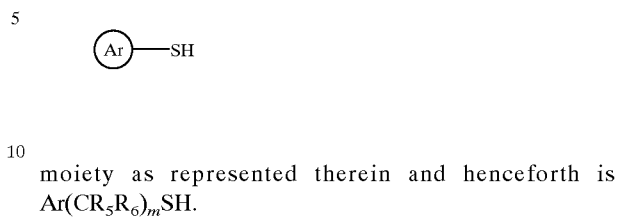
Scheme E shows another means for preparing compounds according to the invention starting with an alkyl dialkylphosphonoacetate and aldehyde/ketone. The moiety as represented therein and henceforth is $Ar(CR_5R_6)_mSH$.
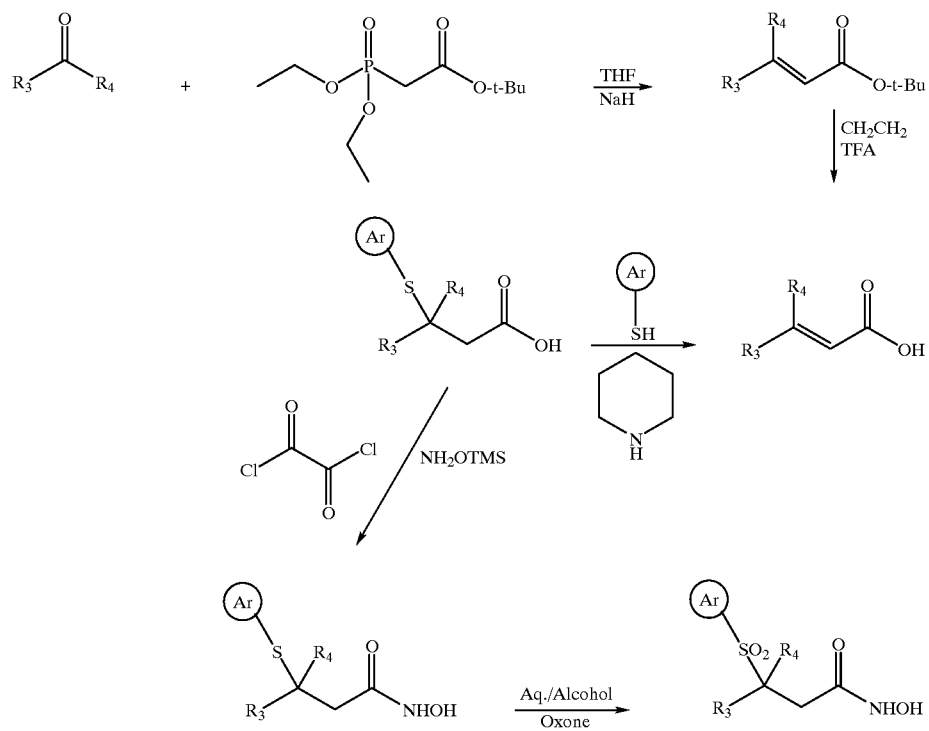
Scheme E Scheme F shows another means for preparing β,β' disubstituted and β,β' spiro compounds according to the invention starting with an alkyl dialkylphosphonoacetate and aldehyde/ketone.
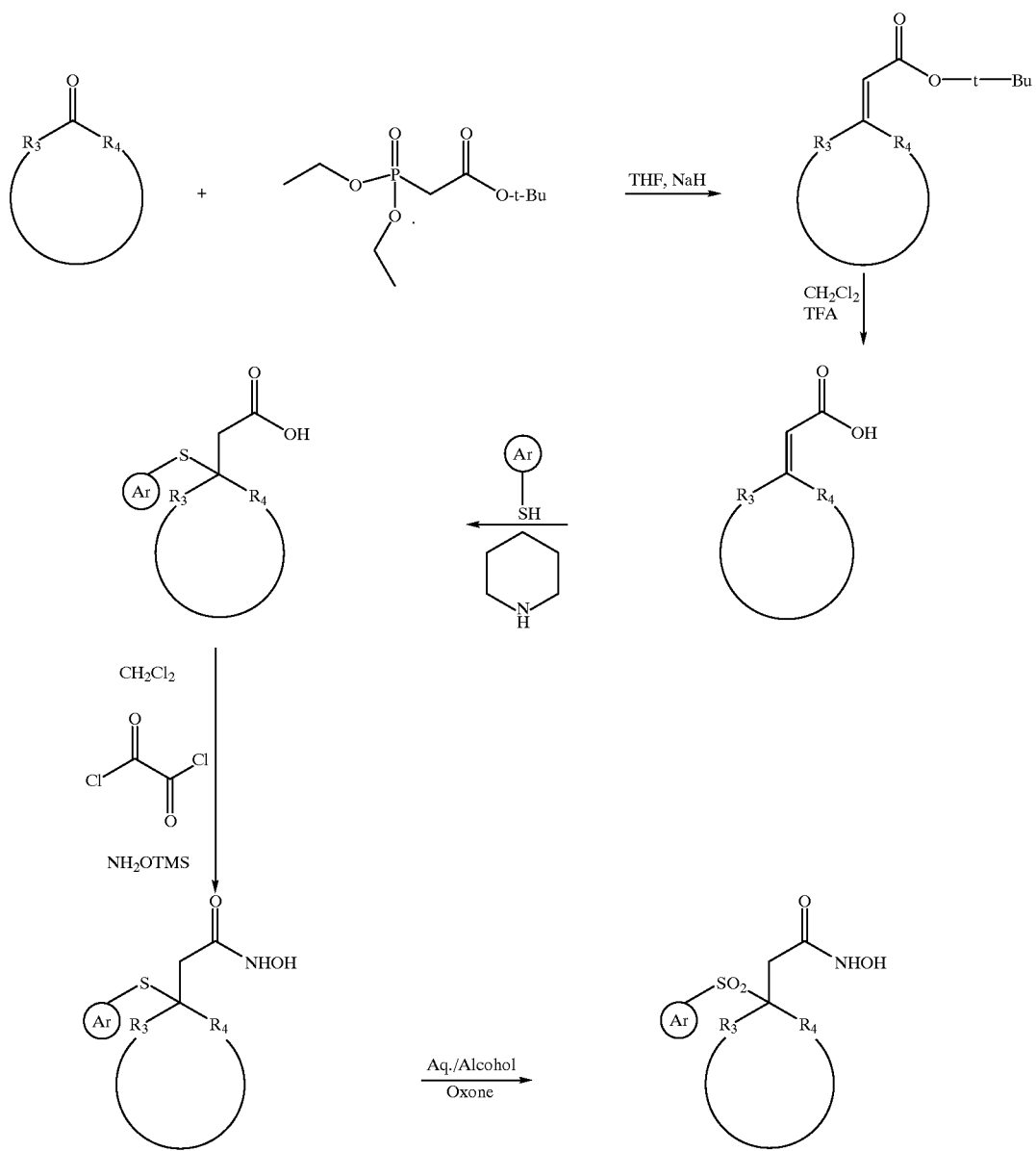
Scheme F
Scheme G shows a means for preparing ketone starting materials useful in the Schemes herein.

Scheme G
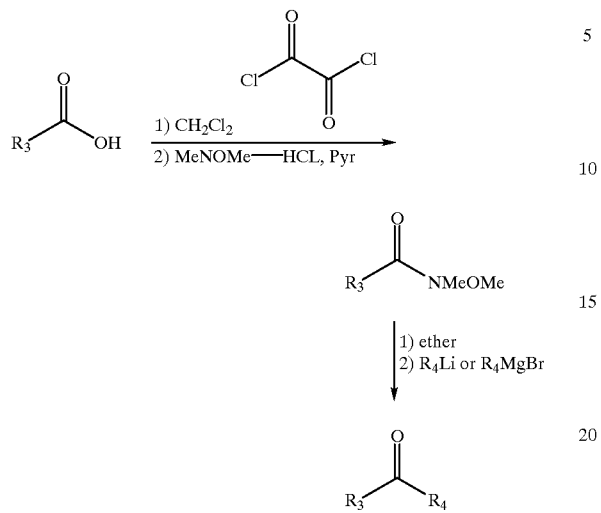
Scheme H shows alternative means for preparing hydroxamic acid compounds within the scope of the invention.
Scheme H
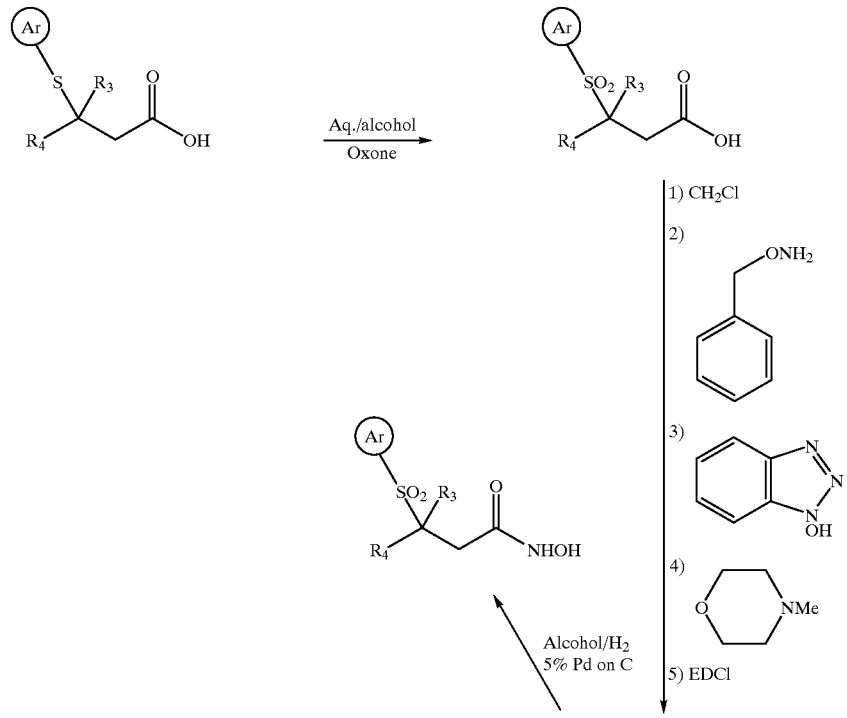

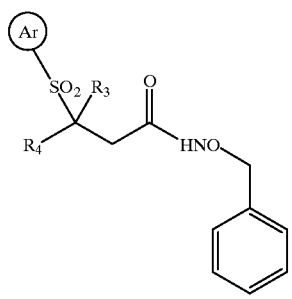
Scheme I shows alternative means for preparing hydroxamic acid compounds within the scope of the invention.
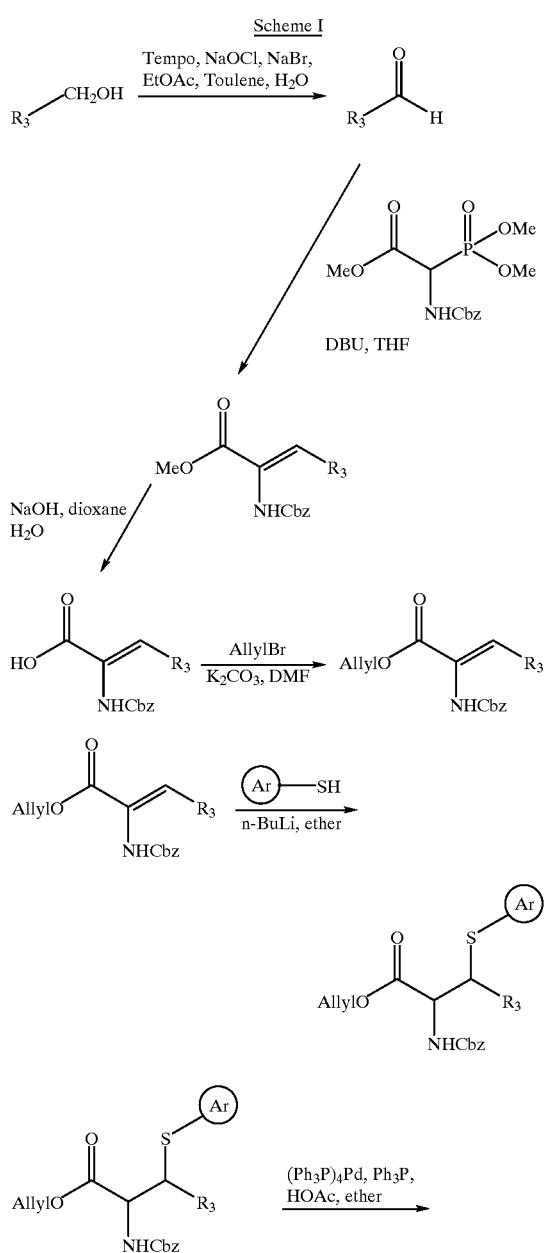
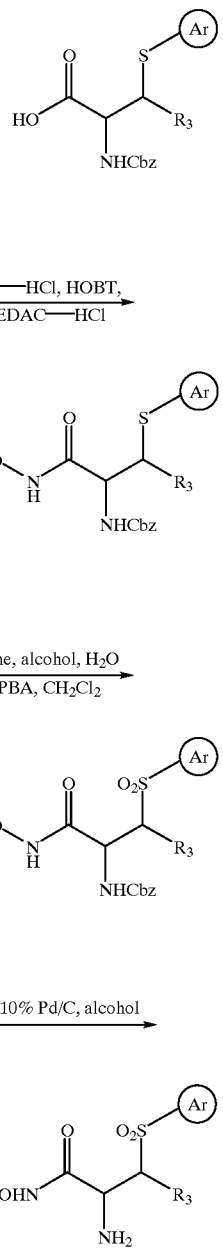
Scheme J shows alternative means for preparing hydroxamic acid compounds within the scope of the invention. $X_1$ as used hereinbelow represents halo, preferably Cl, Br or I.

Scheme J

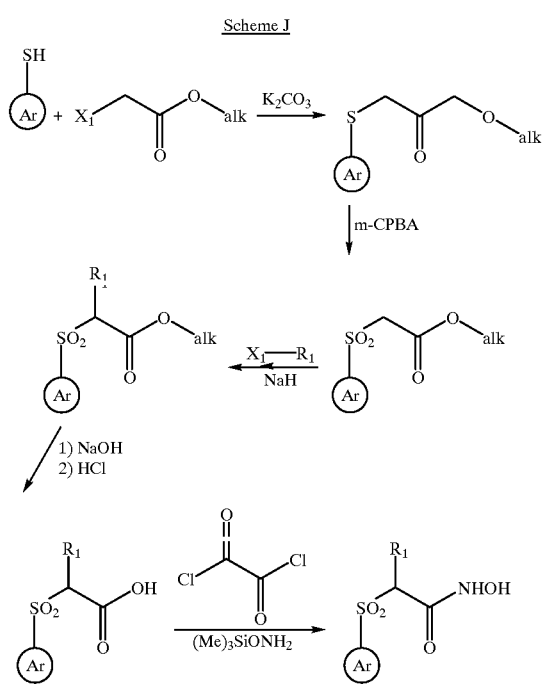

Scheme K shows alternative means for preparing hydroxamic acid compounds within the scope of the invention.

Scheme K

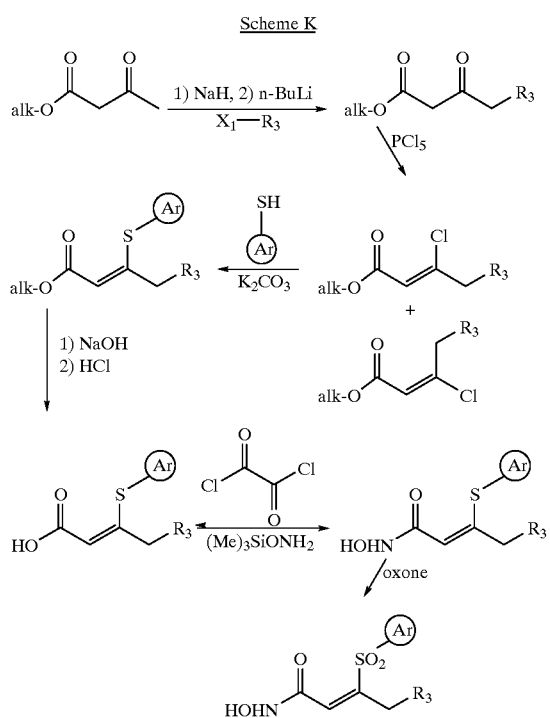

Scheme L shows alternative means for preparing hydroxamic acid compounds within the scope of the invention.

Scheme L

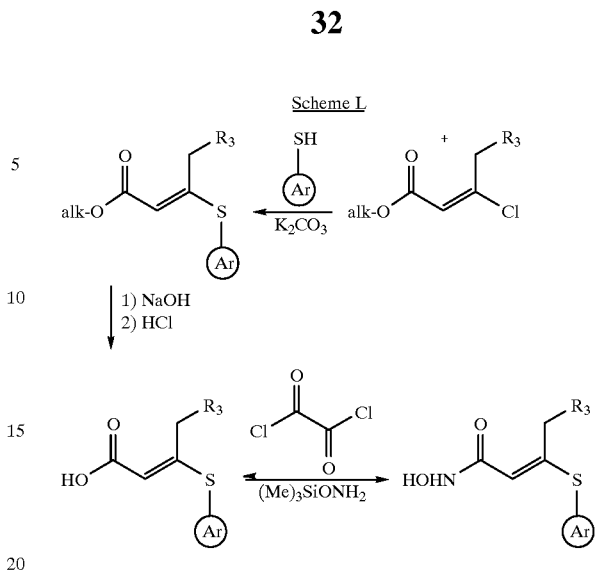

Scheme M shows alternative means for preparing hydroxamic acid compounds within the scope of the invention.

Scheme M

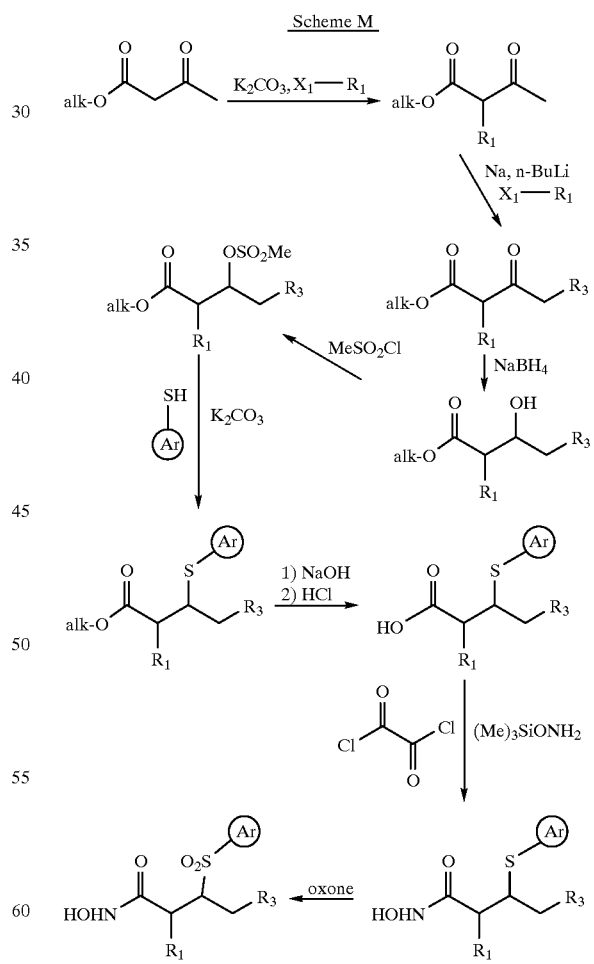

Scheme N shows alternative means for preparing hydroxamic acid compounds within the scope of the invention.

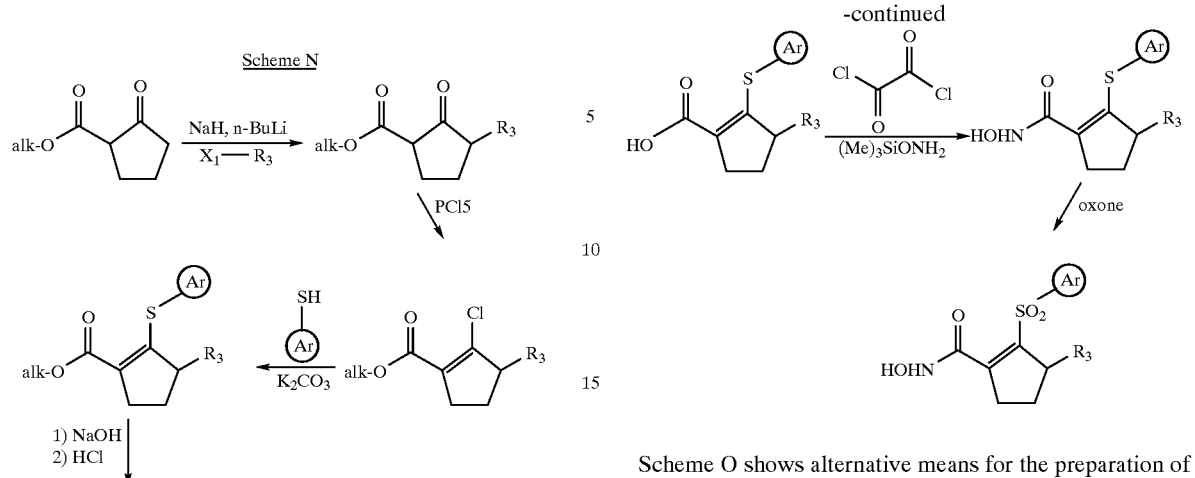
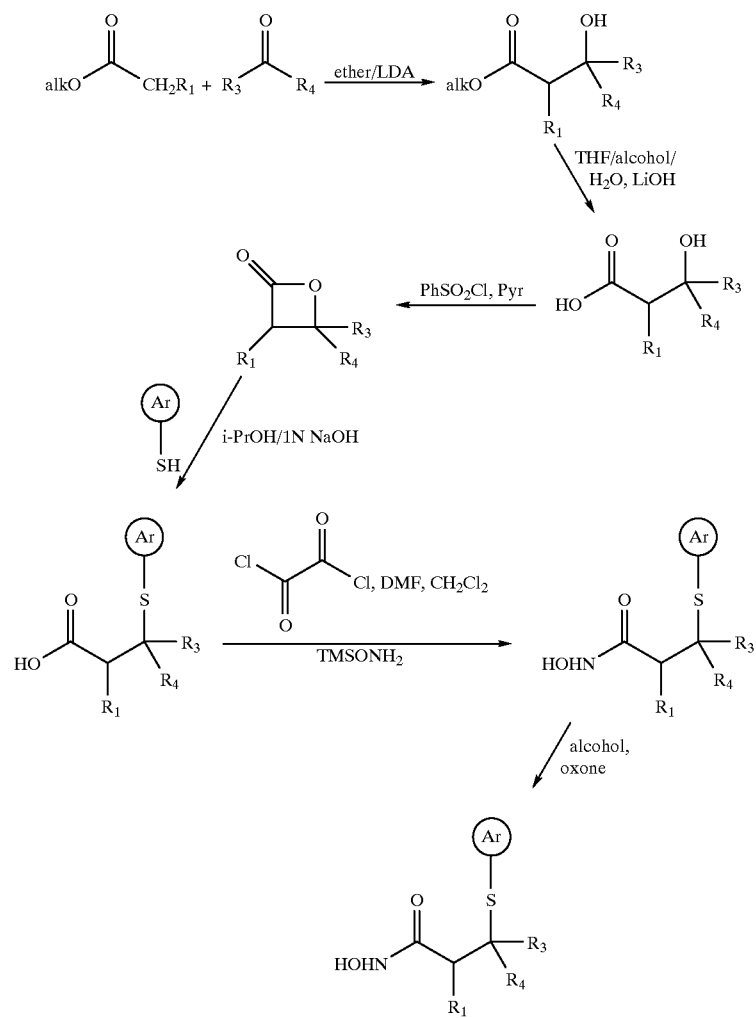
Scheme O shows alternative means for the preparation of hydroxamic acid compounds within the scope of the invention.

Scheme P shows alternative means for the preparation of hydroxamic acid compounds within the scope of the invention, particularly where $R_1$ and $R_2$ taken together with the carbon atoms through which $R_1$ and $R_2$ are linked form optionally substituted cycloalkyl.

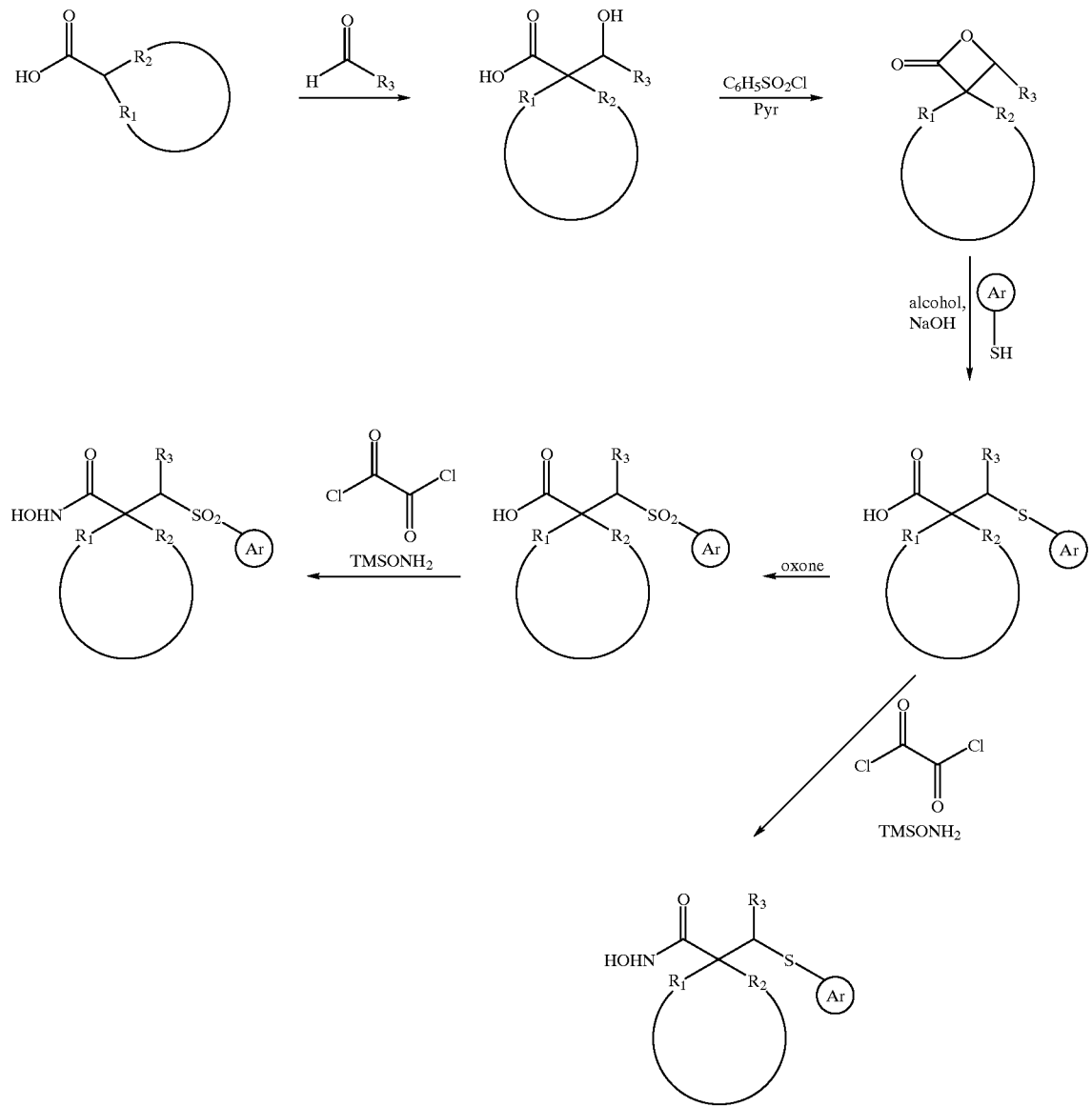

Scheme P

Scheme Q shows alternative means for the preparation of hydroxamic acid compounds within the scope of the invention.

Scheme Q
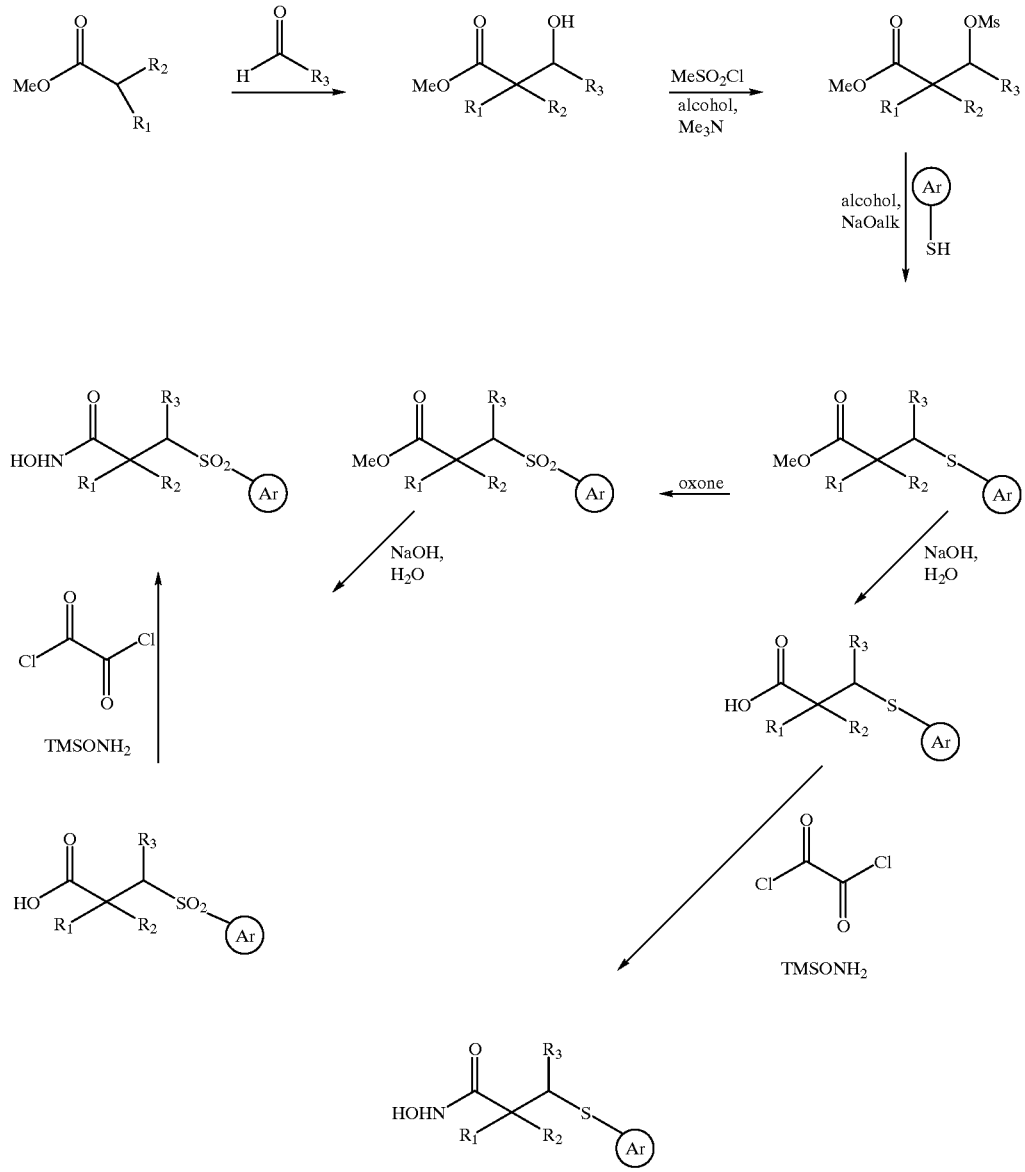
Scheme R shows alternative means for preparing hydroxamic acid compounds within the scope of the invention, particularly wherein m is 0. The (Ar₁) moiety as represented therein and henceforth is Ar.

Scheme R
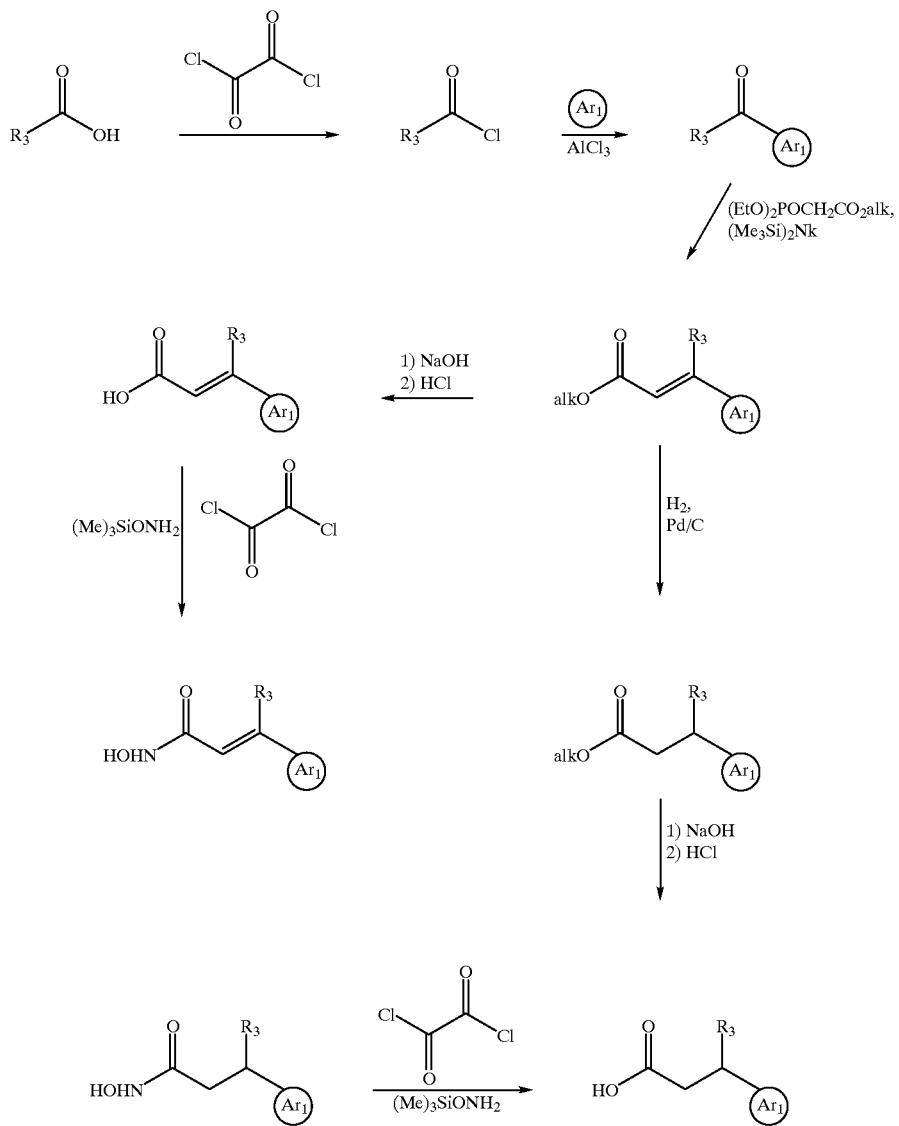
Scheme S shows alternative means for preparing hydroxamic acid compounds within the scope of the invention, which may be resolved using resolution methods.

Scheme S
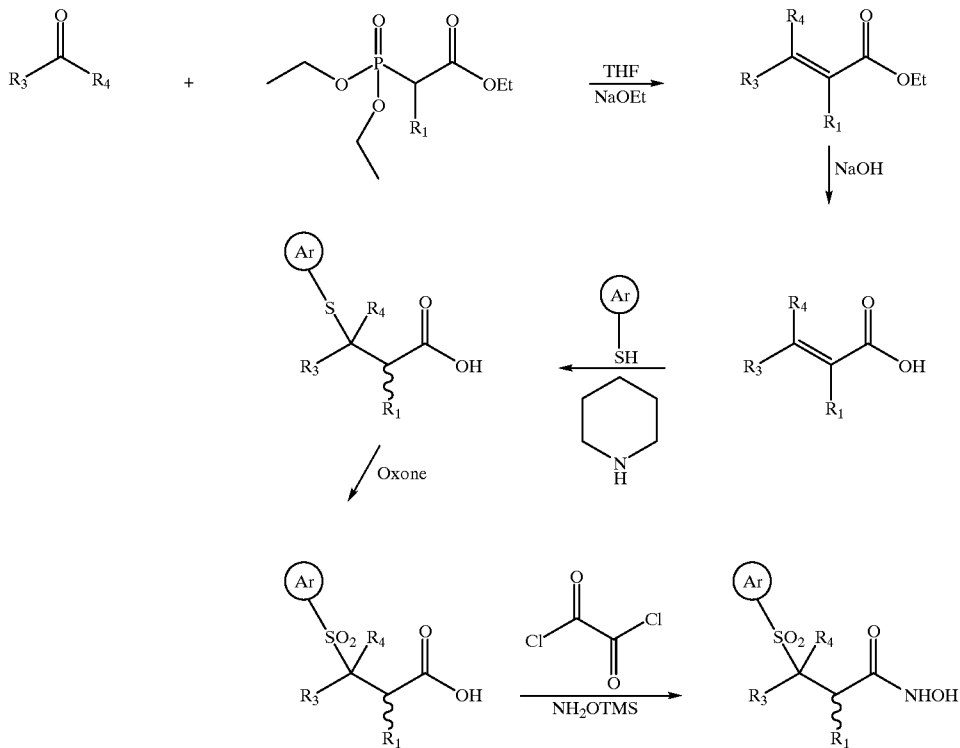
Scheme T shows a means for preparing stereoisomerically hydroxamic acid compounds within the scope of the invention.
Scheme T
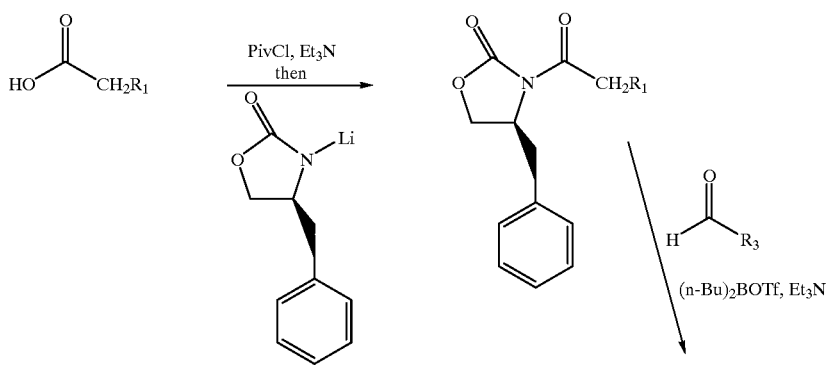

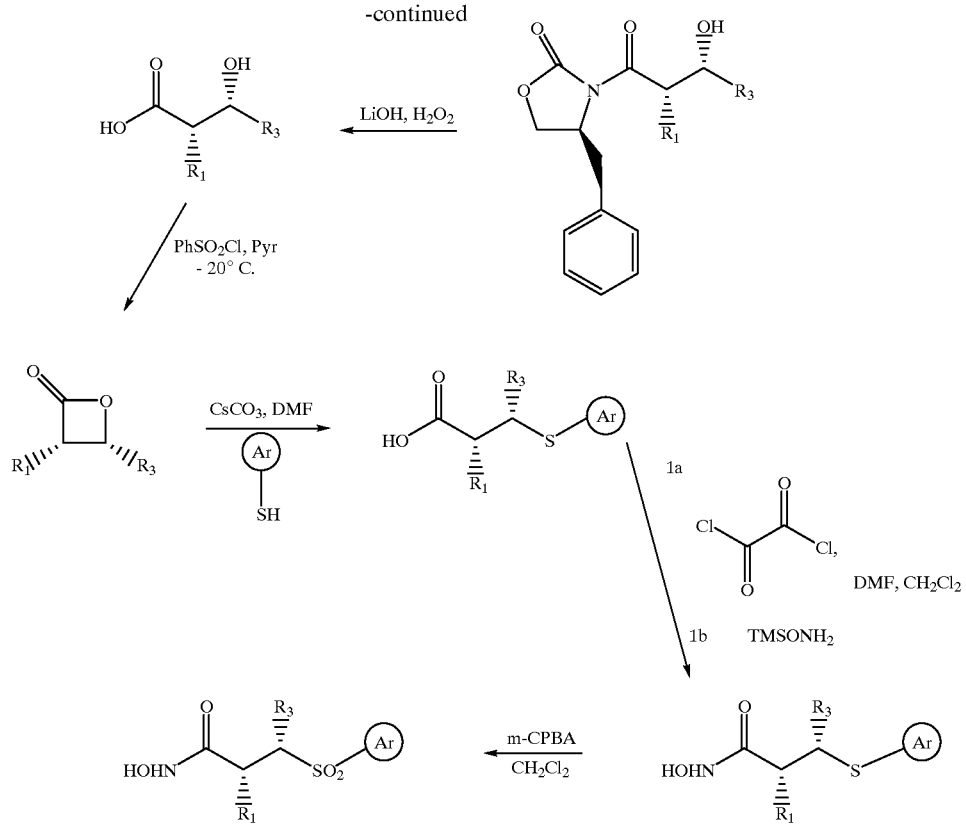
Scheme U shows alternative means for preparing stereoisomerically hydroxamic acid compounds within the scope of the invention.
Scheme U
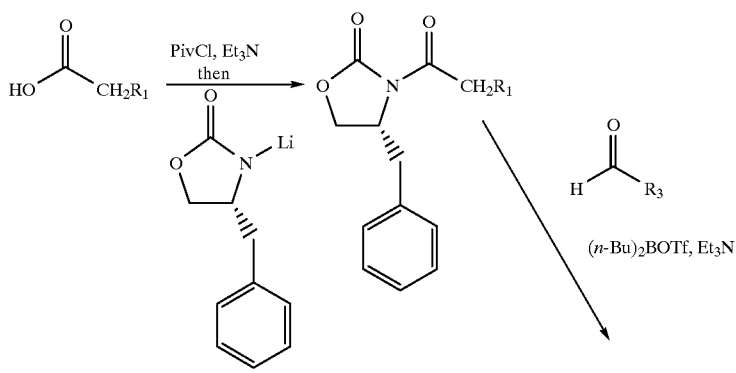

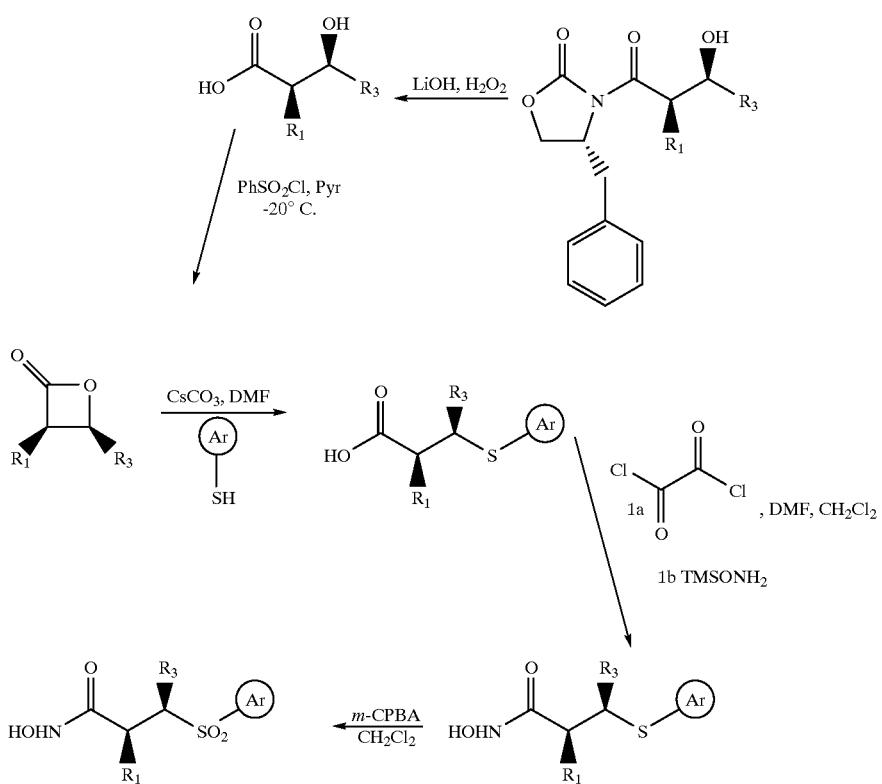

Scheme V shows alternative means for preparing stereoisomerically acid compounds which can be converted to steroisomeric hydroxamic compounds within the scope of the invention.

Scheme V

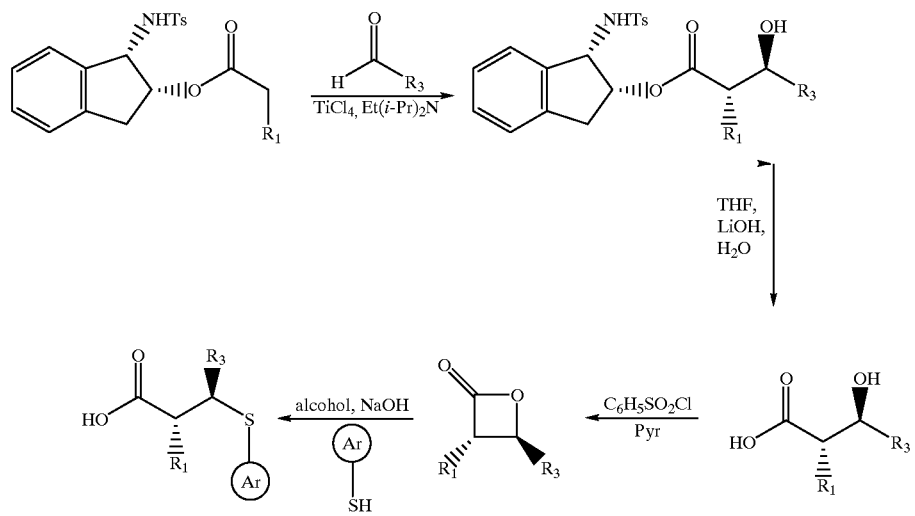

Scheme W shows alternative means for preparing stereoisomerically acid compounds which can be converted to steroisomeric hydroxamic acid compounds within the scope of the invention.

Scheme W
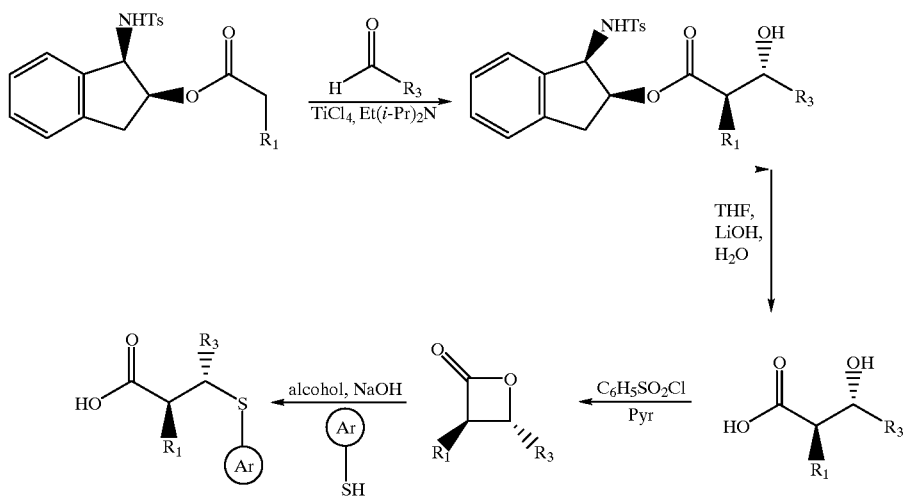
Scheme X shows alternative means for preparing stereoisomerically hydroxamic acid compounds within the scope of the invention.
Scheme X
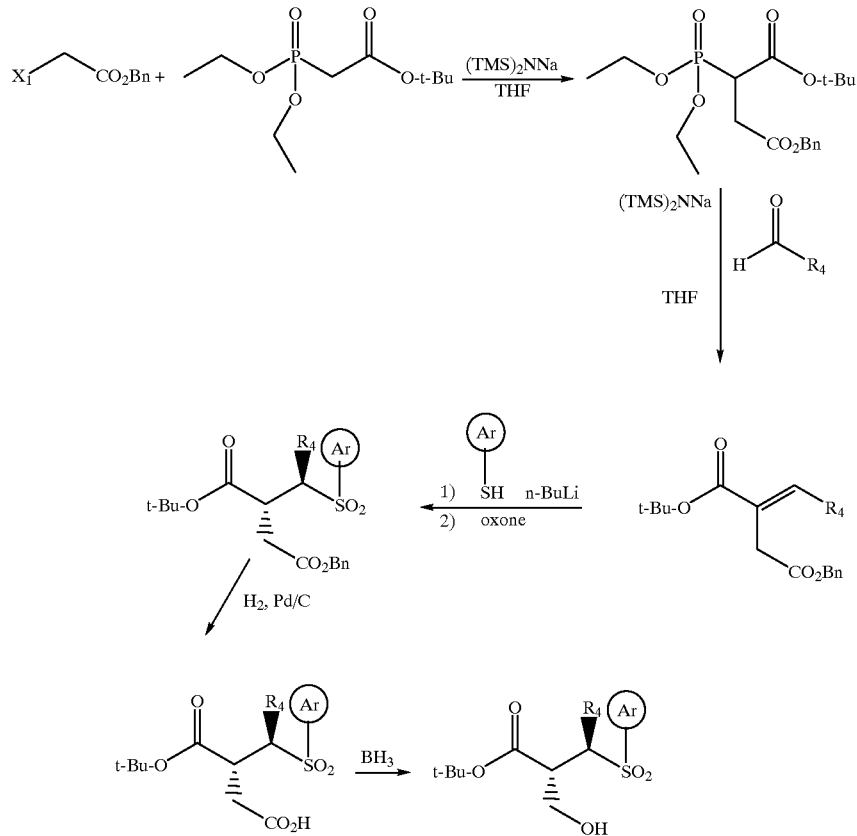

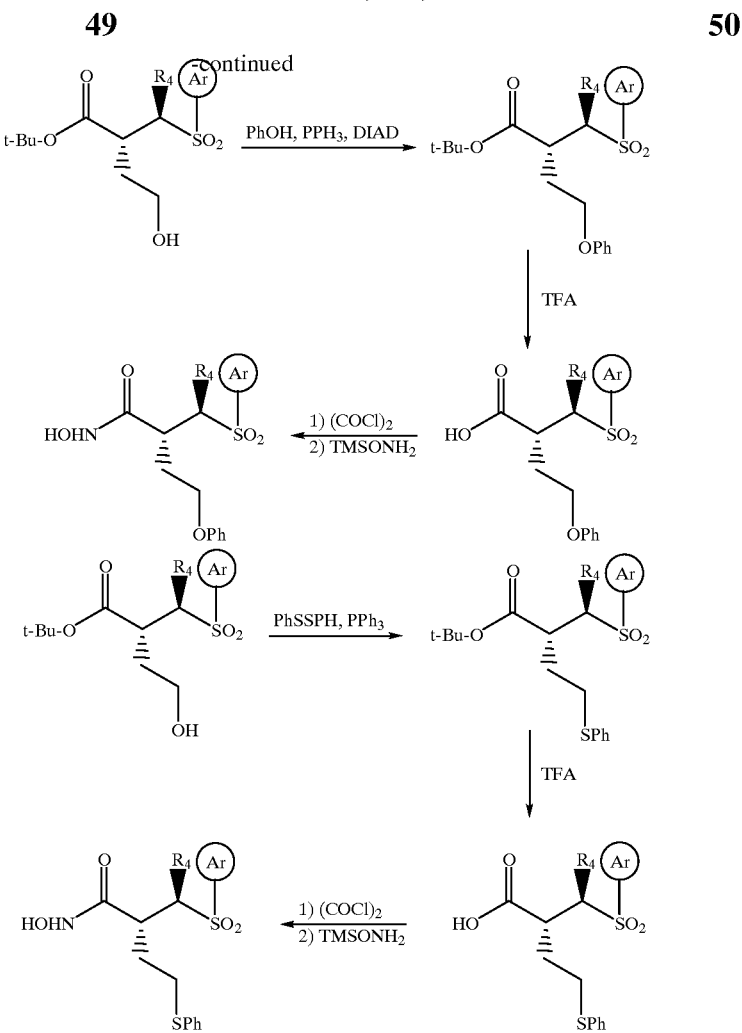
Scheme Y shows alternative means for preparing stereoisomerically hydroxamic acid compounds within the scope of the invention.
Scheme Y
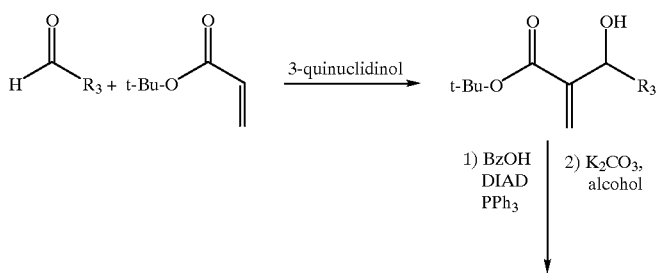

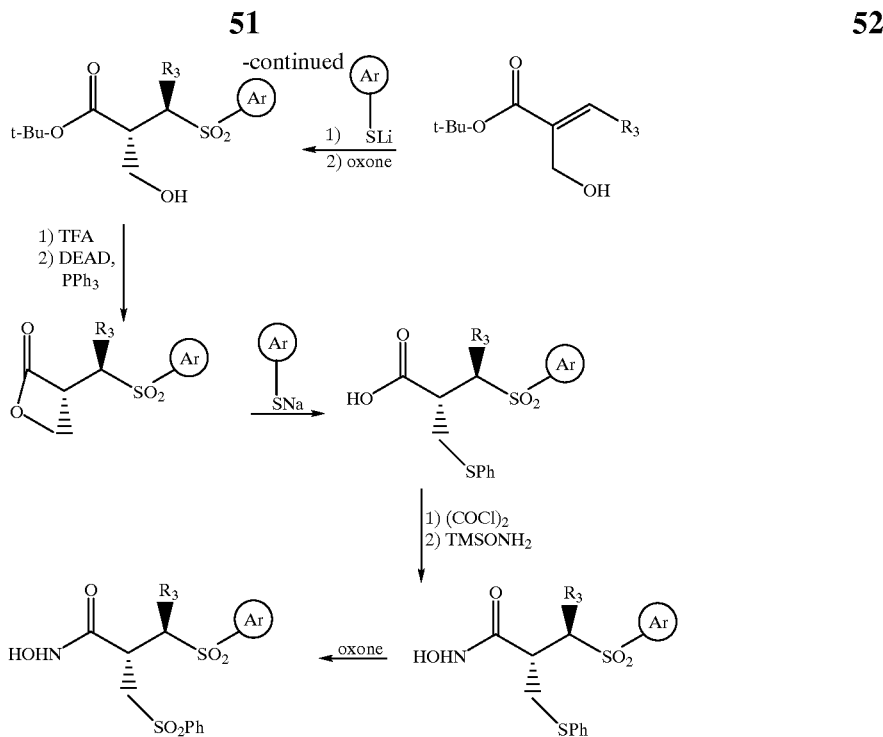
Scheme Z shows alternative means for preparing stereoisomerically hydroxamic acid compounds within the scope of the invention.
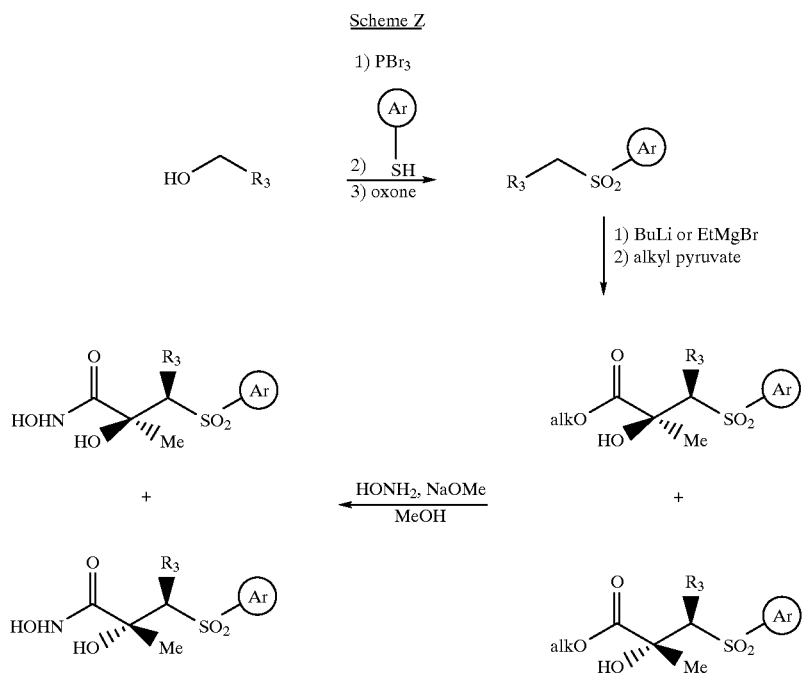
Scheme AA shows alternate means for preparing hydroxamic acid compounds within the scope of the invention employing a solid phase.

Scheme AA[a]

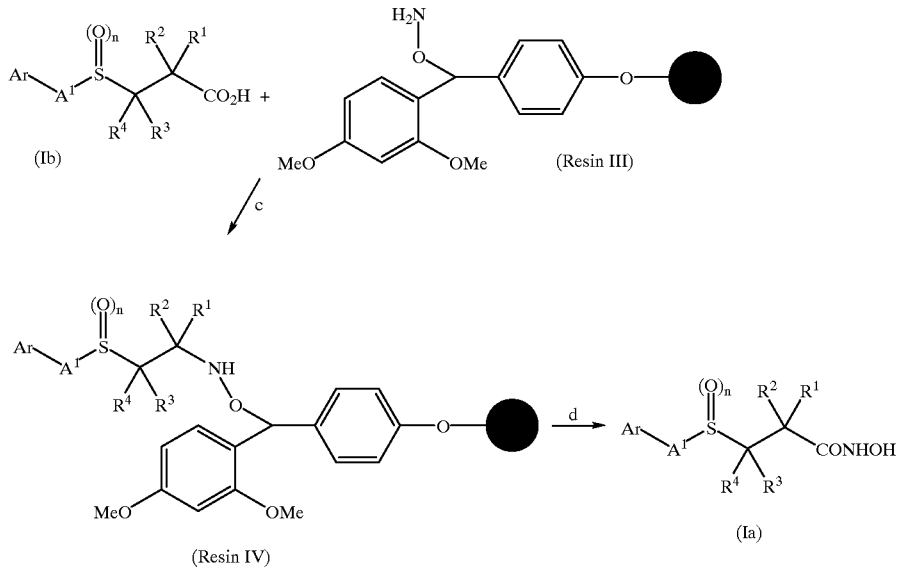

[a]Reagents and Conditions: c) 3-(4-methyoxyphenylsulfonyl) propionic acid (5 equiv.); 1-(3-dimethylaminopropyl)-3-ethyl carbodiimide hydrochloride (EDCl 5 equiv.); DMF; 25° C.; 12 hours. d) 50% TFA in $CH_2Cl_2$ (100 equiv.); 30 minutes.

Resin III may then be coupled, as in Scheme AA, Step c, with an acid of formula (Ib), wherein $A^1$ is $(R^5R^6C)_m$ and Ar, n, $R^1$, $R^2$, $R^3$ and $R^4$ are as hereinbefore defined, to give the hydroxamate ester resin (Resin IV). The coupling reaction may conveniently be carried out in the presence of a carbodiimide, such as EDCl, in an inert solvent such as dimethylformamide and at about room temperature. Resin IV may then be treated with an acid, such as trifluoroacetic acid, in an inert solvent such as dichloromethane to liberate the hydroxamic acid of formula (Ia).

Scheme AB also shows an alternative means for preparing hydroxamic acid compounds within the scope of the invention employing a solid phase.

Scheme AB[a]

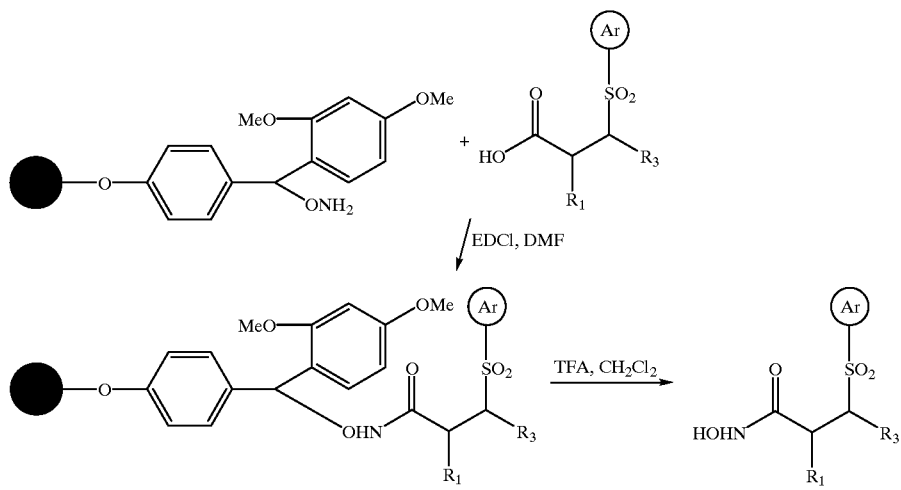

A resin such as Resin V may be used to prepare a compound of formula (Ib), wherein Ar, $A^1$, n, $R^1$, $R^2$, $R^3$ and $R^4$ are as hereinbefore defined, as shown in Scheme AC.

Scheme AC

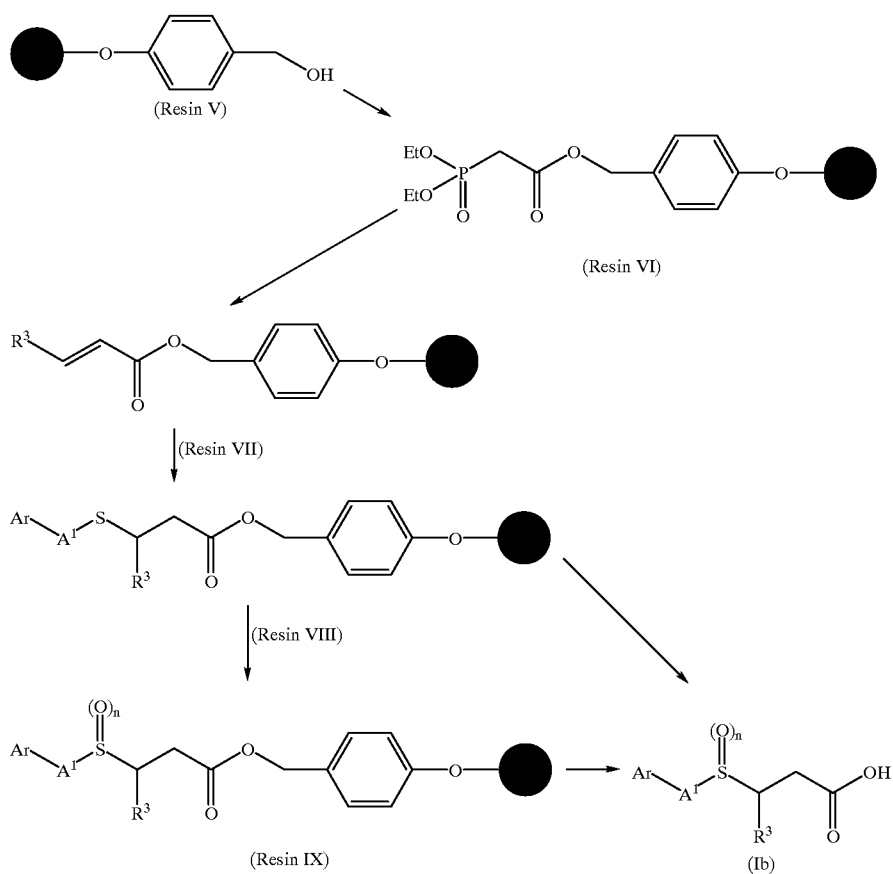

For example Wang resin (Resin V) is treated, in Scheme AC, Step 1, with diethylphosphonoacetic acid in an inert solvent such as dimethylformamide in the presence of 2,6-dichlorobenzoyl chloride and pyridine at about room temperature to give the esterified resin (Resin VI).

The diethylphosphonoacetoxy-resin (Resin VI) is treated, in Scheme AC, Step 2, with a base such as potassium bis(trimethylsilyl) amide in an inert solvent such as toluene, at about 0° C., followed by reaction with an aldehyde of formula (II):

$$R^3—CHO \quad (II)$$

wherein $R^3$ is as defined above, at about room temperature to give the alkenoate resin (Resin VII).

Resin VII may then be reacted, as in Scheme AC, Step 3, with a thiol of formula (III):

$$Ar—A^1—SH \quad (III)$$

wherein Ar and $A^1$ are as defined above, to give the alkanoate resin (Resin VIII). The Michael addition may be conveniently carried out under mild basic conditions, for example in the presence of lithium hydroxide and at about room temperature.

Resin VIII may then be hydrolyzed by treatment with an acid, such as trifluoroacetic acid, in an inert solvent such as dichloromethane, to liberate acids of formula (Ib).

Resin VIII may also be treated with an oxidizing agent such as m-chloro-perbenzoic acid in an inert solvent, such as dioxane, and at a temperature at about room temperature to give Resin IX.

Resin IX may then be hydrolyzed by treatment with an acid, such as trifluoracetic acid, in an inert solvent such as dichloromethane, to liberate acids of formula (Ib).

Resin V may also be converted to a hydroxylamine drivatized resin which may also be used in the preparation of compounds within the scope of the invention. The hydroxylamine drivatized resin is more acid stable and is synthesized as in Scheme AD.

Scheme AD[a]

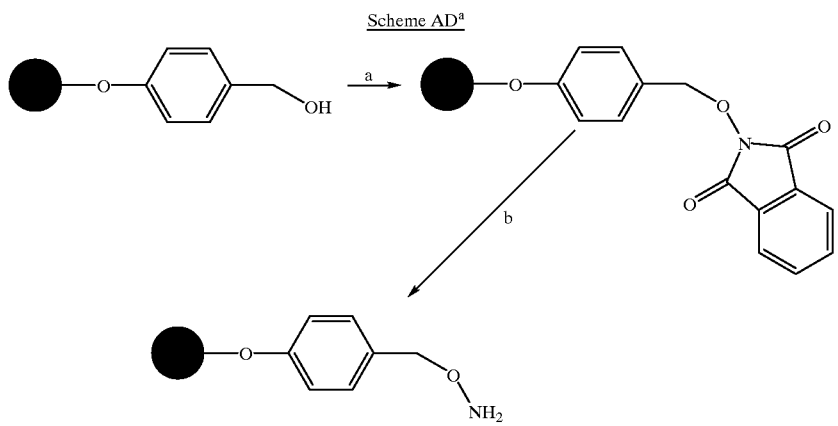

[a]Reagents and conditions: a) N-hydroxyphthalimide (5 equiv.); triphenylphosphine (3 equiv.); DIAD (3 equiv.); THF; 0° C. to 25° C.; 12 hours, b) 40% aq. methylamine (115 equiv.); THF; 40° C.; 2 hours.

N-hydroxyphthalimide is coupled to the resin using Mitsunobu conditions (Mitsunobu, O., *Synthesis* 1981, 1). The phthalimido protection is removed by methylaminolysis in THF at 40° C. in about 2 hours or hydrazinolysis of the resin swelled in t-butanol or THF/t-butanol. The use of the methylamine to cleave the phthalimide protection offers a significant advantage over the commonly used hydrazinolysis procedure (Wolf, S. and Hasan, S. K. *Can. J. Chem.* 48, 3572 (1970).

Scheme AE shows a means for preparing hydroxamic acid compounds within the scope of the invention. Carboxylic acids are readily coupled to the resin using procedures similar to those used in solid phase peptide synthesis. Thus, EDCl efficiently couples a carboxylic acid of formula Ib, for example wherein $R_1$ and $R_2$ are hydrogen, dissolved in DMF to the resin. The resulting O-resin bound -hydroxamic acid is then released from the solid support by reaction with 10% TFA in DCM for ten minutes. The Rink handle (H. Rink, *Tet. Lett.*, 28, 3787–3790, 1987) has the advantage of being cleaved under mild acidolysis for short periods of time (i.e. 10% TFA in DCM for 10–15 minutes).

Scheme AE

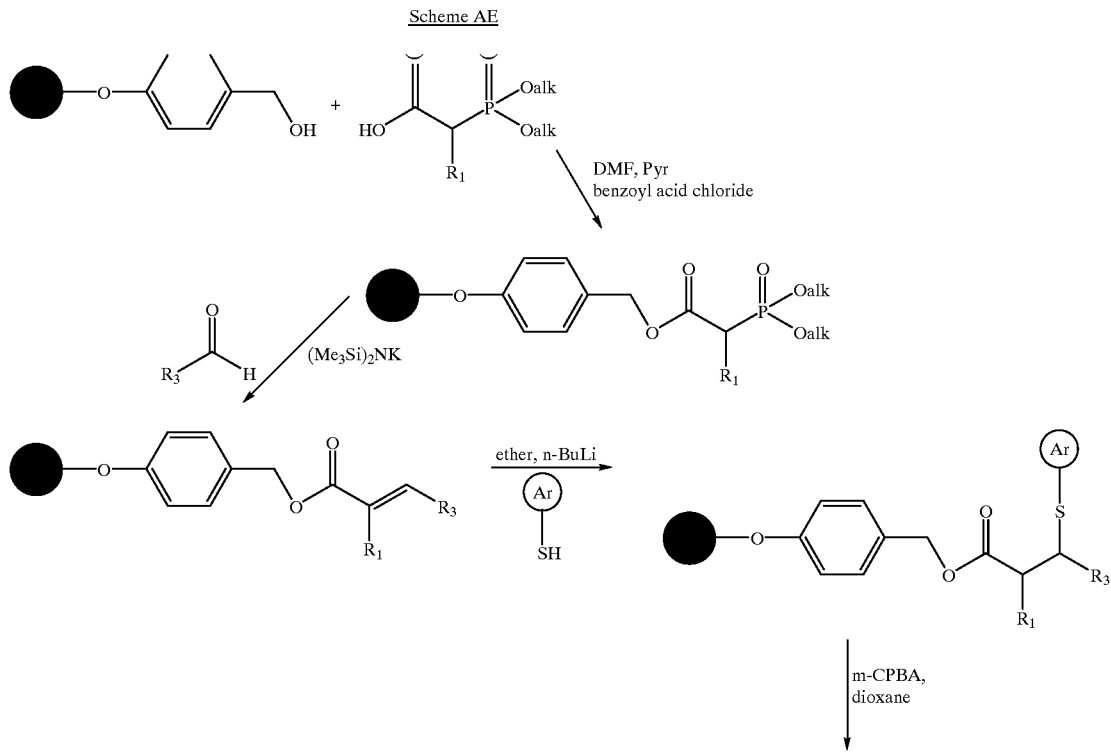

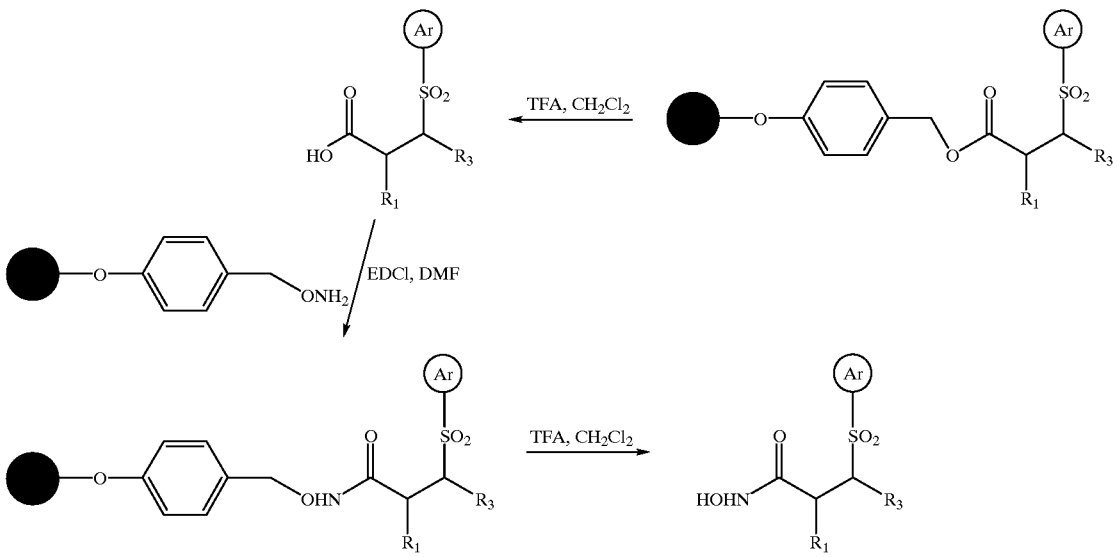

However, due to the cost of the resin it is desirable to synthesize the corresponding functional resin on the Wang solid support ((a) S. S. Wang, *J. Am. Chem. Soc.*, 95, 1328 (1973); b) G. Lu, S. Mojsov, J. P. Tam, and R. B. Merrifield, *J. Org. Chem.*, 46, 3433 (1981)).

Scheme AF shows a means for preparing Ar moiety starting material useful in the Schemes herein.

Scheme AF

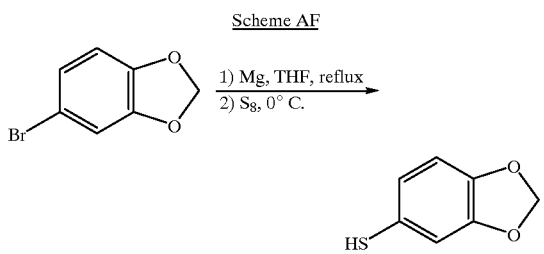

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on TNF inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-β-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on TNF inherent in the free acid are not vitiated by side effects ascribable to the cations.

Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, n-methyl-glucamine, lysine, arginine, ornithine, choline, N,N'-dibenzylethylenediamine, chloroprocaine, diethanolamine, procaine, n-benzylphenethylamine, diethylamine, piperazine, tris (hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

Compounds of the present invention may contain asymmetric centers. These asymmetric centers may independently be in either the R or S configuration. It will also be apparent to those skilled in the art that certain compounds of formula I may exhibit geometrical isomerism. Geometrical isomers include the cis and trans forms of compounds of the invention having alkenyl moieties. The present invention comprises the individual geometrical isomers and stereoisomers and mixtures thereof.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The starting materials and intermediates are prepared by the application or adaptation of known methods, for example methods as described in the Reference Examples or their obvious chemical equivalents, or by methods described according to the invention herein.

The present invention is further exemplified but not limited by the following illustrative examples which illustrate the preparation of the compounds according to the invention.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad.

EXAMPLE 1

7-Phenyl-3-phenylsulfonylheptanoic Acid Hydroxyamide

Step A

5-Phenylpentanal

Method 1

To a mechanically stirred solution of oxalyl chloride (21.6 g; 170 mmol) in dry $CH_2Cl_2$ (400 mL) at −78° C. is added DMSO (22.3 g; 360 mmol) dropwise over 45 minutes. After stirring 15 minutes 5-phenylpentanol (25 g; 150 mmol) is added and the internal temperature is allowed to warm to −55° C. After stirring at this temperature for 30 minutes the reaction is cooled to −78° C. and triethylamine (104 mL; 750 mmol) is added slowly over 20 minutes. After stirring 15 minutes the reaction bath is removed and the temperature is allowed to warm to 20° C. over 40 minutes. The reaction mixture is then washed with 500 mL water. The water layer is then back-extracted with $CH_2Cl_2$ (2×50 mL). The combined organic fractions are washed with 300 mL 2 N HCl, 100 mL water, 200 mL $NaHCO_3$, 100 mL brine and dried ($MgSO_4$). The solution is concentrated in vacuo to obtain 5-phenylpentanal (25 g) which is used directly in Step B.

Method 2

A solution containing 5-phenylpentanol (10 g, 60 mmol), sodium bromide (6.45 g, 63 mmol) and TEMPO (95 mg, 0.6 mmol) in a 7:7:1 mixture of EtOAc, toluene and water (258 mL) is cooled to 0° C. With vigorous stirring, an aqueous NaOCl solution (0.35 M, 571 mL, 200 mmol) saturated with $NaHCO_3$ (43.85 g, 520 mmol) is added in five portions separated by 10 minutes intervals. TLC analysis following the final addition indicated complete reaction. Ethanol (20 mL) is added and the mixture is partitioned between water (500 mL) and EtOAc (500 mL). Aqueous layer is extracted with EtOAc (2×500 mL) and combined organic phases are washed successively with 5% aqueous $Na_2S_2O_3$ (500 mL), water (200 mL) and brine (200 mL) then dried over $MgSO_4$ and concentrated to afford 5-phenylpentanal as an orange oil which is used without further purification assuming 100% yield. TLC analysis [pet-ether/EtOAc, 9:1, $R_f$ (alcohol)= 0.20, $R_f$ (aldehyde)=0.60]. $^1H$ NMR (300 MHz, $CDCl_3$) δ 1.65 (m, 4H), 2.35 (m, 2H), 2.60 (t, 2H), 7.10–7.30 (m, 5H), 9.75 (s, 1H) ppm.

Step B t-butyl 7-phenyl-hept-2-enoate t-butyl diethylphosphonoacetate (18 g; 70 mmol) is dissolved in dry THF (250 mL) and cooled to −40° C. NaH (60% in oil; 2.8 g; 70 mmol) is added and the reaction is warmed to 0° C. Gas evolution is controlled with cooling and then stirred at 20° C. for 30 minutes. 5-Phenylpentanal (11.3 g; 70 mmol) is added and the reaction stirred 20 minutes. The reaction is concentrated to half volume and petroleum ether (500 mL) is added. The reaction is washed with 100 mL water, 100 mL 0.5 N HCl, $NaHCO_3$, brine and dried ($MgSO_4$). The solution is concentrated in vacuo to obtain t-butyl 7-phenylhept-2-enoate which is used directly in Step C.

Step C

7-Phenyl-hept-2-enoic acid t-butyl 7-phenylhept-2-enoate (19 g; 70 mmol) is dissolved in dry $CH_2Cl_2$ (120 mL) and trifluoroacetic acid (25 mL) is added slowly. After 5 hours the reaction is concentrated in vacuo and purified by column chromatography using $CH_2Cl_2$ to obtain 7-phenylhept-2-enoic acid (7 g; 34 mmol). $^1H$ NMR (300 MHz, $CDCl_3$) δ 12-10 (br, 1H), 7.30–7.24 (m, 2H), 7.20–7.12 (m, 3H), 7.06 (dd, J=15.7, 7 Hz, 1H), 5.80 (d, J=15.7 Hz, 1H), 2.62 (t, J=7.5 HZ, 2H), 2.25 (q, J=7 HZ, 2H), 1.70–1.61 (m, 2H), 1.56–1.46 (m, 2H).

Step D

7-Phenylhept-2-enoic acid hydroxyamide

7-Phenylhept-2-enoic acid (7 g; 34 mmol) is dissolved in dry THF and cooled to 0° C. Diphenylphosphinic chloride (ClP(O)Ph$_2$) (7.1 mL; 37 mmol) is added followed by dropwise addition of triethylamine (4.7 mL; 34 mmol). After 45 min at 0° C., a mixture of O-(trimethylsilyl) hydroxylamine (TMSONH$_2$) (4.3 g; 37 mmol) and triethylamine (4.7 mL; 34 mmol) is added dropwise at 0° C. The bath is removed and the reaction is allowed to stir at 20° C. for 2 hours. The reaction is then filtered and the solid is extracted with EtOAc (500 mL). The EtOAc is washed with 60 mL 1 N HCl, 50 mL brine and dried (MgSO$_4$). The resulting solution is concentrated in vacuo to yield a white solid which is purified by tituration with Et$_2$O to obtain 7-phenylhept-2-enoic acid hydroxyamide (3.9 g; 18 mmol). MS (EI) m/e 219 (M+). Anal. ($C_{13}H_{17}NO_2$) C, H, N.

Step E

7-Phenyl-3-phenylsulfanylheptanoic acid hydroxyamide

7-Phenyl-hept-2-enoic acid hydroxyamide (0.3 g; 1.4 mmol) is combined with thiophenol (0.26 g; 2.4 mmol) and piperidine (0.04 g; 0.5 mmol) in 1,4-dioxane (6 mL) and heated to 85° C. for 4 hours. After cooling, the reaction is concentrated in vacuo and purified by column chromatography using 5% MeOH/$CH_2Cl_2$ to obtain 7-phenyl-3-phenylsulfanylheptanoic acid hydroxyamide.

Step F

7-Phenyl-3-phenylsulfonylheptanoic acid hydroxyamide

A solution of 7-phenyl-3-phenylsulfanylheptanoic acid hydroxyamide (0.39 g; 1.2 mmol) in MeOH (8 mL) is cooled to 0° C. and a solution of oxone (1.1 g; 1.8 mmol) in water (8 mL) is added dropwise over 10 minutes. The bath is removed and the reaction is allowed to warm to 20° C. and stir for 16 hours. The mixture is then partitioned between 70 mL of $CH_2Cl_2$ and 50 mL of water, the aqueous layer is back-extracted (2×20 mL), the organic fractions are combined, washed with brine and dried (MgSO$_4$). The solution is concentrated in vacuo and purified by reverse-phase HPLC using $CH_3CN$/0.1% TFA to provide pure 7-phenyl-3-phenylsulfonylheptanoic acid hydroxyamide. $^1H$ NMR (300 MHz, $CD_3OD$) δ 7.88 (d, J=7 Hz, 2H), 7.74–7.58 (m, 3H), 7.24–7.08 (m, 5H), 3.66–3.61 (m, 1H), 2.64 (dd, J=15.2, 4.8 Hz, 1H), 2.50 (t, J=7.1 Hz, 2H), 2.26 (dd, J=15.2, 8.4 Hz, 1H), 1.89–1.79 (m, 1H), 1.50–1.27 (m, 5H); MS (FAB) m/e 384 (M+H)$^+$. Anal. ($C_{19}H_{23}NO_4S$) C, H, N.

Alternatively, The product of Step E may be prepared by the following reaction Steps G–I.

Step G t-butyl 7-phenyl-3-phenylsulfanylheptanoate t-butyl 7-phenylhept-2-enoate (2 g; 7.7 mmol) and thiophenol (1.2 g; 11 mmol) are dissolved in THF (25 mL) and cooled to 0° C. n-BuLi (2.5 M in hexane; 0.3 mL; 0.7 mmol) is added dropwise and the reaction is allowed to warm and stir at 20° C. for 3 hours. The reaction is concentrated in vacuo and purified by column chromatography using 5% Et$_2$O/petroleum ether to obtain t-butyl 7-phenyl-3-phenylsulfanylheptanoate.

Step H

7-Phenyl-3-phenylsulfanylheptanoic acid

To a solution of t-butyl 7-phenyl-3-phenylsulfanylheptanoate (1.8 g; 6.5 mmol) in $CH_2Cl_2$ (20 mL) is slowly added trifluoroacetic acid (6 mL). The reaction is stirred 5 hours and concentrated in vacuo to yield 7-phenyl-3-phenylsulfanylheptanoic acid which is used directly in Step I.

Step I

7-Phenyl-3-phenylsulfanylheptanoic acid hydroxyamide

7-Phenyl-3-phenylsulfanylheptanoic acid (2 g; 6.5 mmol) is dissolved in $CH_2Cl_2$ (20 mL) and cooled to 0° C. Oxalyl chloride (1.1 mL, 13 mmol) is added dropwise, the bath removed and the reaction allowed to warm and stir at 20° C. for 2 hours. The reaction is then concentrated in vacuo and azeotroped with $CH_2Cl_2$. The resulting oil is dissolved in $CH_2Cl_2$ (20 mL), cooled to 0° C. and O-(trimethylsilyl) hydroxylamine (1.7 g, 16 mmol) is added dropwise. The bath is removed and the reaction is allowed to warm to 20° C. The reaction is then partitioned between $CH_2Cl_2$ (100 mL) and 1 N HCl (50 mL), the organic layer is then separated and washed with water (40 mL), dried (MgSO$_4$) and concentrated in vacuo to yield 7-phenyl-3-phenylsulfanylheptanoic acid hydroxyamide.

EXAMPLE 2

3-(4-Acetoamidophenylsulfonyl)-7-phenylheptanoic Acid Hydroxyamide

When thiophenol in Example 1, Step E is replaced with 4-acetoamidothiophenol, then 3-(4-Acetoamidophenylsulfanyl)-7-phenylheptanoic acid hydroxyamide is prepared, which when reacted subsequently as in Example 1, Step F, then the title compound is prepared having the following characteristics:

m.p. 165–169° C.; $^1H$ NMR (300 MHz, $CD_3OD$) δ 7.85–7.78 (m, 4H), 7.24–7.19 (m, 2H), 7.14–7.08 (m, 3H), 3.63–3.55 (m, 1H), 2.64 (dd, J=15.1, 4.9 Hz, 1H), 2.50 (t, J=7.1 Hz, 2H), 2.24 (dd, J=15.1, 8.3 Hz, 1H), 2.17 (s, 3H), 1.89–1.79 (m,1H), 1.52–1.29 (m, 5H); MS (FAB) m/e 419 (M+H)$^+$; Anal. ($C_{21}H_{26}N_2O_5S$) C, H, N.

EXAMPLE 3

3-(2-Naphthalenylsulfonyl)-7-phenylheptanoic Acid Hydroxyamide

When thiophenol in Example 1, Step E is replaced with 2-Naphthalenethiol, then 3-(2-Naphthalenylsulfanyl)-7-phenylheptanoic acid hydroxyamide is prepared, which when reacted subsequently as in Example 1, Step F, then the title compound is prepared having the following characteristics:

M.P. 60–64° C.; $^1H$ NMR (300 MHz, $CD_3OD$) δ 8.51 (s, 1H), 8.12–8.01 (m, 3H), 7.85 (dd, J=8.6, 1.8 Hz, 1H), 7.76–7.64 (m, 2H), 7.18–7.05 (m, 3H), 6.98 (d, J=6.7 Hz, 1H), 3.76–3.71 (m, 1H), 2.73 (dd, J=15.1, 4.9 Hz, 1H), 2.45–2.40 (m, 2H), 2.30 (dd, J=15.1, 8.3 Hz, 1H), 1.91–1.85 (m,$_1$H), 1.61–1.30 (m, 5H); MS (FAB) m/e 411 (M+H)$^+$; Anal. ($C_{23}H_{25}NO_4S$) C, H, N.

EXAMPLE 4

3-(4-Methoxyphenylsulfonyl)-7-phenylheptanoic Acid Hydroxyamide

When thiophenol in Example 1, Step E is replaced with 4-Methoxybenzenethiol, then 3-(4-

Methoxyphenylsulfanyl)-7-phenylheptanoic acid hydroxyamide is prepared, which when reacted subsequently as in Example 1, Step F, then the title compound is prepared having the following characteristics:

1H NMR (300 MHz, CDCl$_3$) δ 7.79 (d, J=8.7 Hz,1H), 7.25 (t, J=7.5 Hz, 2H), 7.17 (d, J=6.7 Hz, 1H), 7.10 (d, J=7.5 Hz, 2H), 3.89 (s, 3H), 3.57–3.50 (bm, 1H), 2.79–2.70 (bm, 1H), 2.52 (t, J=7.1 Hz, 2H), 2.48–2.37 (bm, 1H), 1.81–1.70 (bm,1H), 1.59–1.22 (bm, 5H); MS (FAB) m/e 391 (M+H)$^+$; Anal. (C$_{20}$H$_{25}$NO$_5$S) C, H, N.

EXAMPLE 5

3-(Benzylsulfonyl)-7-phenylheptanoic Acid Hydroxyamide

When thiophenol in Example 1, Step E is replaced with benzyl mercaptan, then 3-(Benzylsulfanyl)-7-phenylheptanoic acid hydroxyamide is prepared, which when reacted subsequently as in Example 1, Step F, then the title compound is prepared having the following characteristics:

1H NMR (300 MHz, CD$_3$OD) δ 7.45–7.42 (m, 2H), 7.39–7.36 (m, 3H), 7.24–7.22 (m, 2H), 7.16–7.11 (m, 3H), 4.42 (d, J=13.8 Hz, 1H), 4.37 (d, J=13.8 Hz, 1H), 3.55 (m, 1H), 2.75 (dd, J=15.4, 5.6 Hz, 1H), 2.58 (t, J=7.4 Hz, 2H), 2.35 (dd, J=15.4, 7.4 Hz, 1H), 2.01–1.89 (m, 1H), 1.68–1.33 (m, 5H); MS (FAB) m/e 376 (M+H)$^+$; Anal. (C$_{20}$H$_{25}$NO$_4$S) C, H, N.

EXAMPLE 6

N-hydroxy-3-(4-methoxybenzenesulfonyl)-4-phenylbutyramide

Step A t-butyl 4-phenylbut-2-enoate

To a solution of 12.15 mL (45.78 mmol) of t-butyldiethylphosphonoacetate in 100 mL of THF under argon at 25° C. is added 1.83 g (45.78 mmol) of 60% NaH in oil dispersion. The reaction mixture is stirred at 25° C. for 45 minutes at which time 5.41 mL (41.62 mmol) of phenylacetaldehyde is added. After 30 minutes at 25° C. the reaction is partitioned between 1 N HCl and ethyl ether. The organic layer is dried over anhydrous MgSO$_4$ and concentrated in vacuo. Purification by flash silica gel chromatography affords 6.3 g (69%) of t-butyl 4-phenylbut-2-enoate as a yellow oil.

Step B 4-phenylbut-2-enoic acid

A solution of 6.3 g (28.86 mmol) of t-butyl 4-phenylbut-2-enoate in 100 mL of CH$_2$Cl$_2$ and 30 mL of trifluoroacetic acid is stirred at 25° C. for 18 hours. The reaction is concentrated in vacuo to afford 4.67 g (99.85%) of 4-phenylbut-2-enoic acid as a yellow crystalline solid.

Step C 3-(4-methoxyphenylsulfanyl)-4-phenylbutyric acid

A mixture of 2 g (12.53 mmol) of 4-phenylbut-2-enoic acid, 1.8 mL (14.8 mmol) of 4-methoxybenzenethiol, and 0.4 mL (3.7 mmol) of piperidine is heated at 110° C. in a bomb for 18 hours. The reaction is partitioned between ethyl ether and 1N HCl. The organic layer is dried over anhydrous MgSO$_4$ and concentrated in vacuo. Purification by flash silica gel chromatography affords 3.07 g (82%) of 3-(4-methoxyphenylsulfanyl)-4-phenylbutyric acid as a white crystalline solid.

Step D

N-hydroxy-3-(4-methoxyphenylsulfanyl)-4-phenylbutyramide

To a solution of 1 g (3.31 mmol) of 3-(4-methoxyphenylsulfanyl)-4-phenylbutyric acid in 30 mL of CH$_2$Cl$_2$ at 25° C. under argon is added 0.2 mL of DMF followed by 4.1 mL (8.27 mmol) of 2 M solution of oxalyl chloride in CH$_2$Cl$_2$. After stirring at 25° C. for 1.5 hours, 2.1 mL (16.53 mmol) of O-trimethylsilylhydroxylamine is added and this is then stirred at 25° C. for 18 hours. The reaction is partitioned between CH$_2$Cl$_2$ and 1 N HCl. The organic layer is dried over anhydrous Na$_2$SO$_4$ and concentrated in vacuo. Purification by flash silica gel chromatography affords 0.86 g (82%) of N-hydroxy-3-(4-methoxyphenylsulfanyl)-4-phenylbutyramide as a yellow crystalline solid.

Step E

N-hydroxy-3-(4-methoxyphenylsulfonyl)-4-phenylbutyramide

To a solution of 0.86 g (2.71 mmol) of the N-hydroxy-3-(4-methoxyphenylsulfanyl)-4-phenylbutyramide in 50 mL of methanol at 0° C. is dropped in a solution of 2.5 g (4.1 mmol) of oxone dissolved in 15 mL of water. After stirring for 18 hours at 25° C. the reaction is concentrated in vacuo, then partitioned between ethyl acetate and water. The organic layer is dried over anhydrous Na$_2$SO$_4$then concentrated in vacuo. Purification by flash silica gel chromatography and crystallization from CH$_2$Cl$_2$/hexanes affords 0.38 g (40%) of N-hydroxy-3-(4-methoxyphenylsulfonyl)-4-phenylbutyramide in the form of a white crystalline solid, m.p. 118–120° C. $^1$H NMR (DMSO-d$_6$) δ 2.05–2.15 (m, 1H), 2.4–2.55 (m, 1H), 2.6–2.75 (m, 1H), 3.0–3.1 (m, 1H), 3.8–3.95 (m, 1H), 3.85 (s, 3H), 7.05–7.3 (m, 7H), 7.7–7.85 (d, 2H), 8.8 (s, 1H), 10.5 (s, 1H).

EXAMPLE 7

N-hydroxy-3-(4-methoxybenzenesulfonyl)-3-phenylpropionamide

The preparation of the titled compound is carried out according to Example 6, steps 3 through 5, using cinnamic acid instead of 4-phenylbut-2-enoic acid to give N-hydroxy-3-(4-methoxybenzenesulfanyl)-3-phenylpropionamide, which then is converted to 0.744 g of N-hydroxy-3-(4-methoxybenzenesulfonyl)-3-phenylpropionamide in the form of a white crystalline solid, m.p. 157–159° C. $^1$H NMR (DMSO-d$_6$) δ 2.7–2.9 (m, 2H), 3.85 (s, 3H), 4.7–4.8 (m, 1H), 7.0–7.1 (d, 2H), 7.1–7.2 (d, 2H), 7.2–7.35 (m, 3H), 7.45–7.55 (d, 2H), 8.8 (s, 1H), 10.5 (s, 1H).

EXAMPLE 8

3-(4-Methoxybenzenesulfonyl)-5-phenylpentanoic Acid Hydroxyamide

The preparation of the titled compound is carried out according to Example 6, steps 1 through 5, using hydrocinnamaldehyde instead of phenylacetaldehyde as the starting aldehyde, to give 3-(4-methoxybenzenesulfanyl)-5-phenylpentanoic acid hydroxyamide, which is then converted to 0.694 g of 3-(4-methoxybenzenesulfonyl)-5-phenylpentanoic acid hydroxyamide in the form of an off-white crystalline solid, m.p. 65–68° C. $^1$H NMR (DMSO-d$_6$) d 1.6–1.8 (m, 1H), 1.85–2.1 (m, 1H), 2.2–2.35 (m, 1H), 2.45–2.8 (m, 3H), 3.45–3.6 (m, 1H), 3.85 (s, 3H), 7.05–7.35 (m, 7H), 7.7–7.85 (d, 2H), 8.95 (s, 1H), 10.6 (s, 1H).

EXAMPLE 9

3-(4-Methoxybenzenesulfonyl)-6-phenylhexanoic Acid Hydroxamide

The preparation of the titled compound is carried out according to Example 6, steps 1 through 5, using 4-phenylbutrylaldehyde as the starting aldehyde which is prepared by the following procedure:

Oxidation of 4-phenylbutanol

To a solution of 20 mL (39.94 mmol, 1.2 eq) of oxalyl chloride in 100 mL of $CH_2Cl_2$ at −78° C. under argon is added dropwise 5.7 mL (79.88 mmol) of DMSO. After stirring for 1 hour at −78° C., 5 g (33.28 mmol) of 4-phenylbutanol dissolved in 20 mL of $CH_2Cl_2$ is added dropwise. After the reaction mixture is stirred for 2 hour at −78° C., 23.2 mL (166.42 mmol) of triethylamine is added dropwise. The reaction mixture is then stirred at −78° C. for 0.5 hours, 0° C. for 1 hour, and 25° C. for 1 hour. The reaction is partitioned between $CH_2Cl_2$ and 1 N HCl. The organic layer is washed well with water, dried over anhydrous $MgSO_4$ and concentrated in vacuo to afford 5 g (100%) of 4-phenylbutrylaldehyde in the form of a yellow oil.

Following Steps 1 through 5 yields 3-(4-Methoxybenzenesulfanyl)-6-phenylhexanoic acid which is then converted to 1.23 g of 3-(4-methoxybenzene-sulfonyl)-6-phenylhexanoic acid hydroxamide in the form of a white foam, m.p. 43–46° C. $^1$H NMR (DMSO-$d_6$) δ 1.3–1.85 (m, 4H), 2.05–2.2 (m, 1H), 2.4–2.65 (m, 3H), 3.45–3.6 (m, 1H), 3.9 (s, 3H), 7.05–7.35 (m, 7H), 7.65–7.8 (d, 2H), 8.85 (s, 1H), 10.55 (s, 1H).

EXAMPLE 10

3-(4-Methoxybenzenesulfonyl)-3-methyl-7-phenylheptanoic Acid Hydroxamide

The preparation of the titled compound is carried out according to Example 6, steps 1 through 5, using methyl 5-phenylbutyl ketone in place of the starting aldehyde. The ketone is prepared by the following procedure:

To a solution of 2 g (11.22 mmol) of 5-phenylvaleric acid in 75 mL of $CH_2Cl_2$ at 0° C. under argon is added 2 drops of DMF followed by 7 mL (14.03 mmol) of oxalyl chloride. This stirred at 25° C. for 1 hour, then 1.4 g (14.03 mmol) of N,O-dimethylhydroxylamine hydrochloride and 2.7 mL (33.66 mmol, 3 eq) of pyridine are added sequentially and stirred for 72 hours at 25° C. The reaction is partitioned between $CH_2Cl_2$ and 1 N HCl. The organic layer is dried over anhydrous $Na_2SO_4$ and concentrated in vacuo to give 2.5 g (100%) of 5-phenylpentanoic acid-methoxy-methyl-amide in the form of a yellow oil.

To a solution of 2.5 g (11.30 mmol) of 5-phenylpentanoic acid-methoxymethyl-amide from above in 50 mL of THF at −78° C. under argon is added 9 mL (12.43 mmol, 1.1 eq) of 1.4 M MeLi in diethyl ether. This stirred at for 0.5 hours at −78° C. and is quenched by addition of 1 N HCl. The reaction is partitioned between diethyl ether and water. The organic layer is dried over anhydrous $MgSO_4$ and concentrated in vacuo to give 2 g (100%) of methyl 5-phenylbutyl ketone in the form of a red-brown liquid.

Following Steps 1 through 5 yields 3-(4-methoxybenzenesulfanyl)-3-methyl-7-phenylheptanoic acid hydroxamide which is then converted to 0.946 g of 3-(4-methoxy-benzenesulfonyl)-3-methyl-7-phenylheptanoic acid hydroxamide in the form of a white solid, m.p. 52–55° C. $^1$H NMR (CDCl$_3$) δ 1.35 (s, 3H), 1.45–1.7 (m, 4H), 1.7–1.95 (m, 2H), 2.5–2.75 (m, 4H), 3.9 (s, 3H), 6.95–7.05 (d, 2H), 7.1–7.25 (m, 3H), 7.25–7.35 (m, 2H), 7.65–7.8 (d, 2H), 7.6–8.1 (bs, 1H), 9.35 (s, 1H).

EXAMPLE 11

Preparation of (E)-t-Butyl 4-Aryl-2-butenoates for Effecting Variations in the $R_3$ Position of Compounds According to the Invention

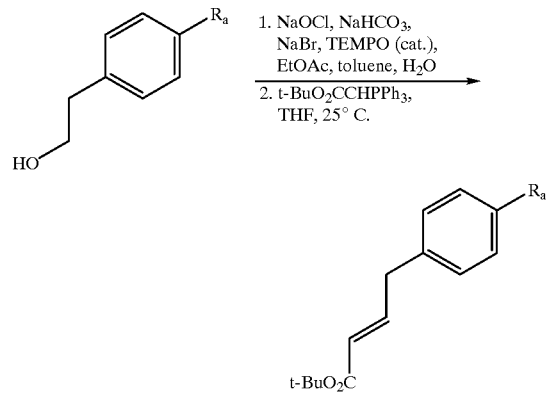

Step A

Preparation of Phenylacetaldehydes

2-Phenethyl alcohols ($R_a$=Phenyl, O-Phenyl, O-Benzyl, O-n-Butyl) are oxidized following a modification of the procedure described by Leanna et al. (Tetrahedron Lett. 33, 5029 (1992)) and is described below for the preparation of 4-biphenylacetaldehyde, i.e., where $R_a$ is Phenyl.

A solution containing 2-(4-biphenyl)ethyl alcohol (1 g, 5.04 mmol), NaBr (0.53 g, 5.19 mmol), and TEMPO (8 mg, 0.05 mmol) in a 7:7:1 mixture of EtOAc, toluene, and water (30 mL) is cooled to 0° C. With vigorous stirring, an aqueous NaOCl solution (0.35 M, 47 mL, 16.6 mmol) saturated with NaHCO$_3$ (3.7 g, 44 mmol) is added in four portions separated by 15 minutes intervals. Following the final addition, the reaction is complete by TLC analysis. The white, heterogeneous reaction mixture is warmed to ambient temperature and diluted with diethyl ether and water. The layers are separated and the organic phase is washed successively with aqueous Na$_2$S$_2$O$_3$ and brine, dried over anhydrous MgSO$_4$, filtered and concentrated. The crude aldehyde is homogeneous by TLC analysis (hexane/ethyl acetate, 2:1, $R_f$ (alcohol)=0.35, $R_f$ (aldehyde)=0.55) and used directly without further purification.

Step B

Preparation of (E)-t-butyl 4-Phenyl-2-butenoates

To a solution containing the crude aldehyde of Step B in anhydrous THF (30 mL) is added (t-butoxycarbonylmethylene)triphenylphosphorane (1.9 g, 5.04 mmol). After 15 min, an additional portion of the Wittig reagent is added (0.6 g, 1.5 mmol) to drive the reaction to completion. The reaction mixture is concentrated in vacuo and the crude ester is purified by flash silica gel chromatography (hexane/ethyl acetate, 19:1) to provide 1.26 g (85%) of t-butyl 4-(4-biphenyl)-2-butenoate as a colorless oil which is homogeneous by TLC analysis (hexane/ethyl acetate, 2:1, $R_f$ (ester)=0.85). $^1$H NMR (300 MHz, CDCl$_3$) δ 1.48 (s, 9H), 3.52 (d, 2H), 5.75 (d, 1H), 7.02 (dt, 1H), 7.21–7.62 (m, 9H) ppm.

EXAMPLE 12

Preparation of (±)-t-Butyl 3-(4-Methoxyphenyl)sulfanyl-4-arylbutanoates for Effecting Variations in the $R_3$ Position of Compounds According to the Invention

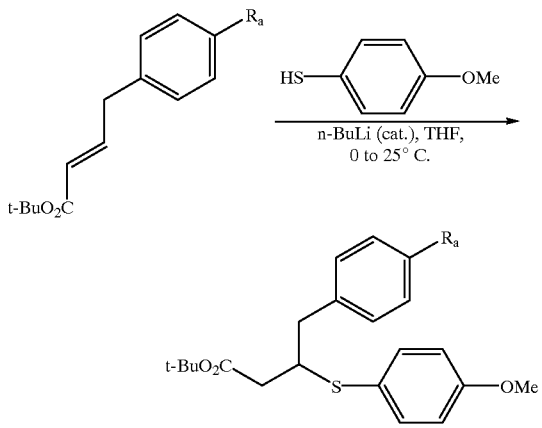

The conjugate addition of 4-methoxybenzenethiol to several (E)-t-butyl 4-aryl-2-butenoates ($R_a$=Phenyl, O-Phenyl, O-Benzyl, O-n-Butyl) is performed following a modification of the procedure described by Naito et al. (J. Org. Chem. 56, 6556 (1991)) and is described below for the preparation of (±)-t-butyl 3-(4-methoxyphenyl)sulfanyl-4-(4-benzyloxy)butanoate.

To a solution containing 4-methoxybenzenethiol (1.14 g, 8.32 mmol) in anhydrous THF (5 mL) at 0° C. is added n-BuLi (1.1 M in hexanes, 75 mL, 0.08 mmol). After 15 minutes, a solution containing (E)-t-butyl 4-(4-benzyloxy)-2-butenoate (0.54 g, 1.66 mmol) in anhydrous THF (3 mL) is added and the reaction mixture is allowed to warm to ambient temperature. After 16 hours, the reaction mixture is diluted with diethyl ether and water. The layers are separated and the organic phase is washed successively with aqueous $Na_2CO_3$ and brine, dried over anhydrous $MgSO_4$, filtered and concentrated. The crude (±)-t-butyl 3-(4-methoxyphenyl)sulfinyl-4-(4-benzyloxy)butanoate (0.61 g, 79%) is used without further purification. TLC analysis (hexane/diethyl ether, 10:1, $R_f$ (butenoate)=0.60, $R_f$ (butanoate)=0.25). $^1$H NMR (300 MHz, $CDCl_3$) δ 1.45 (s, 9H), 2.36 (m, 2H), 2.79 (ABq, 2H), 3.44 (quint., 1H), 3.80 (s, 3H), 5.03 (s, 3H), 6.80–7.45 (m, 13H) ppm.

EXAMPLE 13

Preparation of (±)-3-(4-Methoxyphenyl)sulfanyl-4-arylbutanoic Acids for Effecting Variations in the R3 Position of Compounds According to the Invention

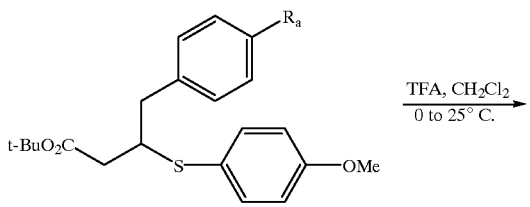

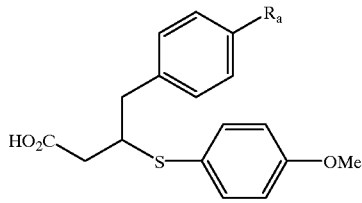

The general procedure for deesterifying a series of (±)-t-butyl 3-(4-methoxyphenyl)sulfinyl-4-arylbutanoates ($R_a$=Phenyl, O-Phenyl, O-Benzyl, O-n-Butyl) is performed using TFA in $CH_2Cl_2$ and is described below for the preparation of (±)-3-(4-methoxyphenyl)sulfinyl-4-(4-benzyloxy)butanoic acid.

A solution containing (±)-t-butyl 3-(4-methoxyphenyl)sulfinyl-4-(4-benzyloxy)butanoate (0.61 g, 1.31 mmol) in $CH_2Cl_2$ (12 mL) is cooled to 0° C. Trifluoroacetic acid (3 mL) is added in one portion and the reaction mixture is allowed to warm to ambient temperature. After 16 hours, the reaction mixture is concentrated in vacuo. The crude (±)-3-(4-methoxyphenyl)sulfinyl-4-(4-benzyloxy)butanoic acid (0.53 g, 100%) is used without further purification. TLC analysis (hexane/ethyl acetate, 1:1, $R_f$ (ester)=0.95, $R_f$ (acid)=0.30). 1H NMR (300 MHz, CDCl3) δ 2.52 (m, 2H), 2.83 (ABq, 2H), 3.48 (quint., 1H), 3.79 (s, 3H), 5.01 (s, 2H), 6.80–7.45 (m, 13H), 7.98 (br s, 1H) ppm.

EXAMPLE 14

Preparation of (±)-N-hydroxy-3-(4-methoxyphenyl)sulfanyl-4-arylbutyramides for Effecting Variations in the R3 Position of Compounds According to the Invention

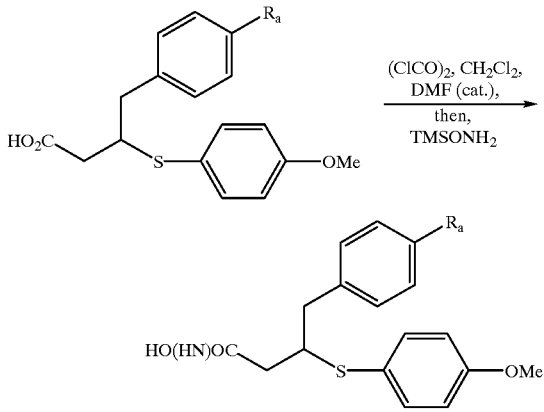

The transformation of a series of (±)-3-(4-methoxyphenyl)sulfanyl-4-arylbutanoic acids ($R_a$=Phenyl, O-Phenyl, O-Benzyl, O-n-Butyl) to the corresponding hydroxamic acids is accomplished using the general procedure described below for the preparation of (±)-N-hydroxy-3-(4-methoxyphenyl)sulfanyl-4-(4-biphenyl)butyramide.

To a solution containing (±)-3-(4-methoxyphenyl)sulfanyl-4-(4-biphenyl)butanoic acid (0.82 g, 2.17 mmol) and DMF (0.17 mL, 2.17 mmol) in anhydrous $CH_2Cl_2$ (50 mL) is added oxalyl chloride (0.69 g, 5.43 mmol) via a syringe. After 1 hour, $TMSONH_2$ (1.14 g, 10.8 mmol) is added in one portion. The reaction mixture is diluted with dichloromethane and water. The layers are separated and the organic phase is washed successively with 1 M HCl, water and brine, dried over anhydrous MgSO$_4$, filtered and concentrated. The crude (±)-N-hydroxy-3-(4-methoxyphenyl)sulfanyl-4-(4-biphenyl)butyramide (0.51 g, 60%) is used without further purification. TLC analysis (ethyl acetate, 1:1, R$_f$ (acid)=0.20, R$_f$ (hydroxamic acid)=0.20). $^1$H NMR (300 MHz, CDCl$_3$) δ 2.38 (ABq, 2H), 2.90 (m, 2H), 3.59 (m, 1H), 3.74 (s, 3H), 6.81 (d, 2H), 7.18–7.57 (m, 11H), 8.01 (s, 1H) ppm.

EXAMPLE 15

Preparation of (±)-N-hydroxy-3-(4-methoxyphenyl)sulfonyl-4-arylbutyramides for Effecting Variations in the R3 Position of Compounds According to the Invention

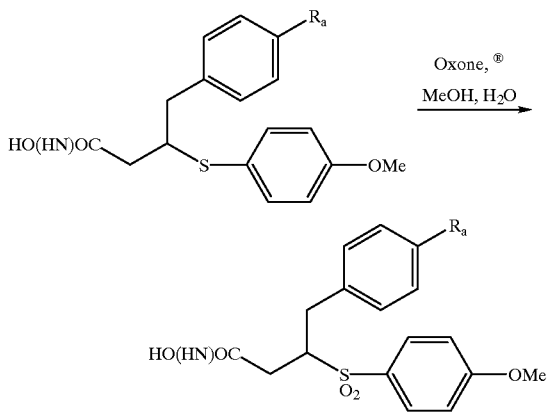

The oxidation of a series of (±)-N-hydroxy-3-(4-methoxyphenyl)sulfanyl-4-arylbutyramides (R$_a$=Phenyl, O-Phenyl, O-Benzyl, O-n-Butyl) is accomplished using either oxone or m-CPBA following the general procedures described below for the preparation of (±)-N-hydroxy-3-(4-methoxyphenyl)sulfonyl-4-(4-n-butoxyphenyl)butyramide and (±)-N-hydroxy-3-(4-methoxyphenyl)sulfonyl-4-(4-phenoxyphenyl)butyramide, respectively.

1. Oxidation with oxone
(±)-N-hydroxy-3-(4-methoxyphenyl)sulfonyl-4-(4-n-butoxyphenyl)butyramide To a solution containing (±)-N-hydroxy-3-(4-methoxyphenyl)sulfanyl-4-(4-n-butoxyphenyl)butyramide (540 mg, 1.38 mmol) in MeOH (25 mL) at 0° C. is added a solution of oxone (1.27 g, 2.07 mmol) in water (20 mL). The heterogeneous mixture is allowed to warm to ambient temperature. After 16 hours, the mixture is diluted with diethyl ether and water and the layers are separated. The organic phase is washed successively with aqueous Na$_2$S$_2$O$_3$ and brine, dried over anhydrous Na$_2$SO$_4$, filtered and concentrated. The crude sulfone is purified by flash silica gel chromatography (CH$_2$Cl$_2$ to 10% MeOH/CH$_2$Cl$_2$) to provide 270 mg (47%) of (±)-N-hydroxy-3-(4-methoxyphenyl)sulfonyl-4-(4-n-butoxyphenyl)butyramide as a clear, glassy solid which is homogeneous by TLC analysis (ethyl acetate, R$_f$ (sulfide)=0.80, R$_f$ (sulfone)=0.74). m.p. 55–60° C. $^1$H NMR (300 MHz, d6-DMSO) δ 0.89 (t, 3H), 1.39 (m, 2H), 1.60 (m, 2H), 2.22 (ABq, 2H), 2.72 (ABq, 2H), 3.81 (s, 3H), 3.82 (m, 1H), 6.70 (d, 2H), 6.95 (d, 2H), 7.08 (d, 2H), 7.72 (d, 2H), 8.76 (s, 1H), 10.5 (s, 1H) ppm; mass spectrum (FAB), m/z 422 (M+H)$^+$.
(±)-N-hydroxy-3-(4-methoxyphenyl)sulfonyl-4-(4-benzyloxyphenyl)butyramide Applying the prior procedure using oxone yields the titled compound that is characterized as follows: White, amorphous powder. m.p. 128–130° C. TLC analysis (hexane/ethyl acetate, 1:2, R$_f$ (sulfide)=0.45, R$_f$ (sulfone)=0.33). $^1$H NMR (300 MHz, d6-DMSO) δ 2.24 (ABq, 2H), 2.75 (ABq, 2H), 3.80 (m, 1H), 3.81 (s, 3H), 4.99 (s, 2H), 6.80 (d, 2H), 6.99 (d, 2H), 7.08 (d, 2H), 7.22–7.42 (m, 5H), 7.71 (d, 2H), 8.76 (s, 1H), 10.44 (s, 1H) ppm; mass spectrum (FAB), m/z 456 (M+H)$^+$.

2. Oxidation with m-CPBA
(±)-N-hydroxy-3-(4-methoxyphenyl)sulfonyl-4-(4-phenoxyphenyl)butyramide To a solution containing (±)-N-hydroxy-3-(4-methoxyphenyl)sulfanyl-4-(4-phenoxyphenyl)butyramide (0.84 g, 2.05 mmol) in anhydrous CH$_2$Cl$_2$ (20 mL) at 0° C. is added m-CPBA (1.70 g, 10.2 mmol). The reaction mixture is warmed to ambient temperature and stirred for an additional 3 hours. The heterogeneous mixture is diluted with diethyl ether and water and the layers are separated. The organic phase is washed successively with aqueous NaHSO$_3$, aqueous NaHCO$_3$ and brine, dried over anhydrous Na$_2$SO$_4$, filtered and concentrated. The crude sulfone is purified by flash silica gel chromatography (CH$_2$Cl$_2$ to 5% MeOH/CH$_2$Cl$_2$) to provide 190 mg (21%) of (±)-N-hydroxy-3-(4-methoxyphenyl)sulfonyl-4-(4-phenoxyphenyl)butyramide as a glassy, white solid which is homogeneous by TLC analysis (hexane/ethyl acetate, 1:2, R$_f$ (sulfide)=0.50, R$_f$ (sulfone)=0.40). m.p. 65–70° C. $^1$H NMR (300 MHz, d6-DMSO) δ 2.34 (ABq, 2H), 2.83 (ABq, 2H), 3.80 (s, 3H), 3.87 (m, 1H), 6.78 (d, 2H), 6.92 (d, 2H), 7.08 (m, 5H), 7.31 (d, 2H), 7.72 (d, 2H), 8.78 (s, 1H), 10.47 (s, 1H) ppm; mass spectrum (FAB), m/z 442 (M+H)$^+$.
(±)-N-Hydroxy-3-(4-methoxyphenyl)sulfonyl-4-(4-biphenyl)butyramide Applying the prior procedure using m-CPBA yields the titled compound that is characterized as follows: Clear, viscous glass. TLC analysis (5% MeOH/CH$_2$Cl$_2$, Rf(sulfide)=0.50, Rf(sulfone)=0.45). $^1$H NMR (300 MHz, d6-DMSO) δ 2.30 (ABq, 2H), 2.84 (ABq, 2H), 3.76 (s, 3H), 3.90 (m, 1H), 7.02–7.78 (m, 13H), 8.76 (s, 1H), 10.49 (s, 1H) ppm; mass spectrum (FAB), m/z 426 (M+H)$^+$.

EXAMPLE 15

3-(4-Methoxybenzenesulfonyl)-3-ethyl-7-phenylheptanoic Acid Hydroxamide

The preparation of the titled compound is carried out according to Example 6, however the starting ketone (ethyl 5-phenylbutyl ketone) is made according to Scheme G.

To a solution of 1.5 g (6.78 mmol) of N-methyl-N-methoxy-5-phenylpentanamide in 20 mL of THF at −78° C. under argon is added 13.56 mL (13.56 mmol, 2 eq) of 1 M EtMgBr in THF. This stirred at for 0.25 hours at −78° C., 0.75 hours at 0° C., and is quenched by addition of 1 N HCl. The reaction is partitioned between diethyl ether and water. The organic layer is dried over anhydrous MgSO$_4$ and concentrated in vacuo to give 1.3 g (100%) of ethyl-5-phenylbutylketone in the form of a yellow oil.

The ethyl 5-phenylbutyl ketone is then reacted according to Example 6, steps A–C to form 3-(4-methoxyphenylsulfanyl)-3-ethyl-7-phenylheptanoic acid.

To a solution of 0.95 g (2.45 mmol) of the 3-(4-methoxyphenylsulfanyl)-3-ethyl-7-phenylheptanoic acid in 50 mL of MeOH at 0° C. is dropped in a solution of 2.26 g (3.68 mmol, 1.5 eq) of oxone dissolved in 15 mL of water. After stirring for 18 hours at 25° C. the reaction is concentrated in vacuo, then partitioned between ethyl acetate and water. The organic layer is dried over anhydrous Na$_2$SO$_4$ then concentrated in vacuo. Crystallization by treatment with hexanes afforded 1 g (100%) of 3-(4-methoxyphenylsulfonyl)-3-ethyl-7-phenylheptanoic acid as a white powder.

To a solution of 0.4 g (0.99 mmol) of 3-(4-methoxyphenylsulfonyl)-3-ethyl-7-phenylheptanoic acid in 50 mL of methylene chloride is added 0.47 g (2.96 mmol, 3 eq) of O-benzyl-hydroxylamine hydrochloride, 0.13 g (0.247 mmol) of HOBT, 0.54 mL (4.94 mmol, 5 eq) of n-Methylmorpholine (NMM), and 0.25 g (1.28 mmol, 1.3 eq) of EDCl. After stirring for 18 hours at 25° C. the reaction is partitioned between methylene chloride and 1 N HCl. The organic layer is dried over anhydrous Na$_2$SO$_4$ then concentrated in vacuo. Purification by flash silica gel chromatography afforded 0.463 g (92%) of N-benzyloxy-3-(4-methoxyphenylsulfonyl)-3-ethyl-7-phenylheptanamide in the form of a colorless oil.

A solution of 0.463 g (0.91 mmol) of N-benzyloxy-3-(4-methoxyphenylsulfonyl)-3-ethyl-7-phenylheptanamide in 75 mL of EtOH is shaken for 3 days under 50 psi of H$_2$ with 0.2 g of 10% Pd on carbon. The mixture is filtered and concentrated in vacuo. Purification by flash silica gel chromatography afforded 0.1 g (26%) of 3-(4-methoxybenzenesulfonyl)-3-ethyl-7-phenylheptanoic acid hydroxamide in the form of a white foam, m.p. 44–46° C. $^1$H NMR (DMSO-d$_6$) δ (TMS)0.97 (t, 3H), 1.45–1.9 (m, 8H), 2.4 (s, 2H), 2.55 (m, 2H), 3.87 (s, 3H), 7.1–7.25(m, 5H), 7.28 (d, 2H), 7.65 (d, 2H), 8.83 (s,1H), 10.6 (s,1H).

EXAMPLE 16

3-(4-Methoxybenzenesulfonyl)-3,7-diphenylheptanoic Acid Hydroxamide

The preparation of the titled compound is carried out according to Example 6, however the starting ketone (phenyl 5-phenylbutyl ketone) is made according to Scheme G.

To a solution of 1.5 g (6.78 mmol) of N-methyl-N-methoxy-5-phenylpentanamide in 20 mL of THF at −78° C. under argon is added 7.5 mL (13.56 mmol, 2 eq) of 1.8 M PhLi in THF. This is stirred at for 0.5 hours at −78° C. and is quenched by addition of 1 N HCl. The reaction is partitioned between diethyl ether and water. The organic layer is dried over anhydrous MgSO$_4$ and concentrated in vacuo. Purification by flash silica gel chromatography afforded 1.3 g (80%) of phenyl 5-phenylbutyl ketone in the form of a yellow oil.

The phenyl 5-phenylbutyl ketone is then reacted according to Example 6, Steps A–E to afford 0.051 g (48%) of 3-(4-Methoxybenzenesulfonyl)-3,7-diphenylheptanoic acid hydroxamide in the form of a beige powder, m.p. 75–78° C. $^1$H NMR (DMSO-d$_6$) δ (TMS) 1.4–1.7 (m, 4H), 2.4–2.55 (m, 2H), 2.6 (t, 2H), 3.82 (s, 3H), 6.93 (d, 2H), 7.0 (d, 2H), 7.1–7.35 (m, 10H) 8.78 (s, 1H), 10.65 (s, 1H).

EXAMPLE 17

N-hydroxy-3-(4-methoxybenzenesulfonyl)-3-methylbutyramide

The titled compound is prepared as in Example 6, Steps C–D using the commercially available 3,3-dimethylacrylic acid in place of 4-phenylbut-2-enoic acid. The product is crystallized from ethyl acetate and ether to afford 0.275 g (61%) of N-hydroxy-3-(4-methoxybenzenesulfonyl)-3-methylbutyramide in the form of a white powder, m.p. 153°154° C. $^1$H NMR (DMSO-d$_6$) δ (TMS)1.25(s, 6H), 2.25(s, 2H), 3.87(s, 3H), 7.18(d, 2H), 7.73(d, 2H), 8.85(s, 1H), 10.6(s, 1H)

EXAMPLE 18

N-hydroxy-2-[1-(4-methoxybenzenesulfonyl)cyclopentyl]acetamide

The titled compound is prepared according to Example 6, Steps A–E except using cyclopentanone in place of phenylacetaldehyde to afford 0.435 g (74%) of N-hydroxy-2-[1-(4-methoxy-benzenesulfonyl)cyclopentyl]acetamide in the form of a white powder, m.p. 148–150° C. The product is recrystallized from ether and hexanes. $^1$H NMR (DMSO-d$_6$) δ (TMS) 1.5(m, 4H), 2.0(m, 2H), 2.15(m, 2H), 2.3(s, 2H), 3.85(s, 3H), 7.18(d, 2H), 7.78(d, 2H), 8.85(s, 1H), 10.65(s, 1H)

EXAMPLE 18

N-hydroxy-2-[1-(4-methoxybenzenesulfonyl)-4-phenylcyclohexyl]-acetamide

The titled compound is prepared according to Example 6, Steps A–E except using 4-phenylcyclohexanone in place of phenylacetaldehyde to afford 0.396 g (23%) of N-hydroxy-2-[1-(4-methoxybenzenesulfonyl)cyclopentyl]acetamide in the form of a white powder, m.p. 210° C. The product is purified by flash silica gel chromatography and crystallized from ethyl acetate and methano. $^1$H NMR (DMSO-d$_6$) δ (TMS)1.72(m, 6H), 2.1(m, 2H), 2.37(m, 1H), 2.53(s, 2H), 3.85(s, 3H), 7.15(d, 2H), 7.25(m, 5H)7.78(d, 2H), 8.75(s, 1H), 10.55(s, 1H)

EXAMPLE 19

(2R*,3R*)-2-amino-3-(4-methoxybenzene)sulfonyl-7-phenylheptanoic Acid Hydroxy Amide The titled compound is prepared according to the following steps:

Step A (Z)-Allyl 2-benzyloxycarbonylamino-7-phenyl-2-heptenoate:

To a solution of 5-phenylpentanol (5 g, 30.4 mmol), NaBr (3.2 g, 31.3 mmol), and TEMPO® (48 mg, 0.3 mmol) in EtOAc (60 mL), toluene (60 mL), and water (9 mL), cooled to 0° C., is added portionwise (50 mL) over 30 minutes a solution containing NaOCl (0.35 M in H$_2$O, 287 mL, 100.4 mmol) and NaHCO$_3$ (22.2 g, 264.8 mmol). The reaction is quenched by the addition of EtOH (10 mL). The biphasic mixture is separated and the organic phase is washed with aqueous Na$_2$S$_2$O$_3$ (2×100 mL), brine (100 mL), dried over anhydrous MgSO$_4$, filtered and concentrated to afford crude 5-phenylpentanal which is homogeneous by TLC analysis [hexane/EtOAc, 4:1, R$_f$(5-phenylpentanol)=0.30; R$_f$(5-phenylpentanal)=0.65] and used without further purification.

The crude aldehyde in anhydrous THF (20 mL) is added at 0° C. to a solution containing n-(benzyloxycarbonyl)-α-phosphonoglycine trimethyl ester (12.1 g, 36.5 mmol), and DBU (6.1 g, 39.5 mmol) in anhydrous THF (200 mL). After 30 minutes, the reaction mixture is diluted with EtOAc (200 mL) and water (200 mL); dilute aqueous HCl (1 M, 50 mL) is added and the layers are separated. The organic phase is washed with 1 M HCl (50 mL), water (50 mL), brine (50 mL), dried over anhydrous MgSO$_4$, filtered and concentrated to afford crude (Z)-methyl 2-benzyloxycarbonylamino-7-phenyl-2-heptenoate which is homogeneous by TLC analysis [hexane/EtOAc, 4:1, $R_f$(methyl 2-benzyloxycarbonylamino-7-phenyl-2-heptenoate)=0.45] and used without further purification. $^1$H NMR (300 MHz, CDCl$_3$) δ 1.49 (m, 2H), 1.66 (m, 2H), 2.22 (q, 2H), 2.60 (t, 2H), 3.74 (s, 3H), 5.13 (s, 2H), 6.19 (br s, 1H), 6.62 (t, 1H), 7.12–7.40 (m, 10H) ppm.

To a solution containing crude ester in 1,4-dioxane (100 mL) is added aqueous NaOH (1 M, 50 mL) at ambient temperature. After 16 hours, an additional portion of aqueous NaOH (1 M, 50 mL) is added and stirring is continued for 2 hours until TLC analysis revealed complete consumption of ester. The reaction mixture is diluted with diethyl ether (200 mL) and water (200 mL) and the layers are separated. The aqueous phase is acidified with concentrated HCl (10 mL) and extracted with diethyl ether (2×100 mL). The combined organic extracts are washed with water (50 mL), brine (50 mL), dried over anhydrous Na$_2$SO$_4$, filtered and concentrated to afford crude (Z)-2-benzyloxycarbonylamino-7-phenyl-2-heptenoic acid which is homogeneous by TLC analysis [hexane/EtOAc, 4:1, $R_f$(2-benzyloxycarbonylamino-7-phenyl-2-heptenoic acid)=0.01] and used without further purification. $^1$H NMR (300 MHz, CDCl$_3$) δ 1.50 (m, 2H), 1.64 (m, 2H), 2.26 (q, 2H), 2.60 (t, 2H), 5.13 (s, 2H), 6.22 (br s, 1H), 6.79 (t, 1H), 7.10–7.38 (m, 10H) ppm.

Allyl bromide (3.6 g, 30.4 mmol) is added at ambient temperature to a vigorously stirred mixture of crude acid and K$_2$CO$_3$ (8.6 g, 62 mmol) in anhydrous DMF (60 mL). After 2 hours, the reaction mixture is diluted with diethyl ether (200 mL) and water (100 mL) and the layers are separated. The organic phase is washed with water (5×100 mL), brine (50 mL), dried over anhydrous Na$_2$SO$_4$, filtered and concentrated. The crude ester is chromatographed on silica gel (hexane/EtOAc, 19:1) to provide 9.5 g (79%, 3 steps) of (Z)-allyl 2-benzyloxycarbonylamino-7-phenyl-2-heptenoate as a clear colorless oil which is homogeneous by TLC analysis [hexane/EtOAc, 4:1, $R_f$(allyl 2-benzyloxycarbonylamino-7-phenyl-2-heptenoate)=0.40]. $^1$H NMR (300 MHz, CDCl$_3$) δ 1.48 (m, 2H), 1.62 (m, 2H), 2.21 (q, 2H), 2.58 (t, 2H), 4.61 (d, 2H), 5.07 (s, 2H), 5.20 (d, 1H), 5.28 (d, 1H), 5.87 (m, 1H), 6.26 (br s, 1H), 6.63 (t, 1H), 7.10–7.34 (m, 10H) ppm.

Step B (2R*,3R*)-Allyl 2-benzyloxycarbonylamino-3-(4-methoxyphenyl)sulfanyl-7-phenyl heptanoate:

n-Butyllithium (1.1 M in hexanes, 1.1 mL, 1.21 mmol) is added at 0° C. to a solution containing 4-methoxybenzenethiol (17.1 g, 121 mmol) in anhydrous THF (200 mL). After 15 minutes, a solution containing (Z)-allyl 2-benzyloxycarbonylamino-7-phenyl-2-heptenoate (9.5 g, 24.2 mmol) in anhydrous THF (40 mL) is added. The reaction mixture is warmed slowly to ambient temperature. After 16 hours, the reaction mixture is concentrated (~30% v/v) and the residue is dissolved in diethyl ether (300 mL). The ether solution is washed with 5% aqueous Na$_2$CO$_3$ (5×50 mL), brine (50 mL), dried over anhydrous Na$_2$SO$_4$, filtered and concentrated. The crude sulfide is chromatographed on silica gel (hexane/EtOAc, 19:1 to 9:1) to provide 12.5 g (96%) of (2R*,3R*)-allyl 2-benzyloxycarbonylamino-3-(4-methoxybenzene)sulfanyl-7-phenyl heptanoate as a clear colorless oil which is homogeneous by TLC analysis [hexane/EtOAc, 4:1, $R_f$(allyl 2-benzyloxycarbonylamino-3-(4-methoxybenzene)sulfanyl-7-phenylheptanoate)=0.42]. $^1$H NMR (300 MHz, CDCl$_3$) δ 1.64 (m, 6H), 2.62 (m, 2H), 3.54 (m,1H), 3.79 (s, 3H), 4.07 (dd, 1H), 4.37 (dd,1H), 4.70 (dd, 1H), 5.15 (s, 2H), 5.23 (m, 1H), 5.62–5.80 (m, 2H), 6.82 (m, 2H), 7.22 (m, 2H), 7.28–7.47 (m, 10H) ppm; mass spectrum (FAB) m/z 534 (M+H)$^+$.

Step C (2R*,3R*)-2-Benzyloxycarbonylamino-3-(4-methoxybenzene)sulfanyl-7-phenylheptanoic acid:

A solution containing (2R*,3R*)-allyl 2-benzyloxycarbonylamino-3-(4-methoxybenzene)sulfanyl-7-phenylheptanoate (12.5 g, 23.4 mmol), Ph$_3$P (6 g, 23.4 mmol), (Ph$_3$P)$_4$Pd (2 g, 2.34 mmol), and glacial HOAc (4 mL) in anhydrous THF (200 mL) is stirred for 4 hours at ambient temperature. The reaction mixture is concentrated then dissolved in EtOAc (200 mL). The EtOAc solution is washed with dilute aqueous NaOH (3×50 mL), 1 M aqueous HCl (50 mL), brine (50 mL), dried over anhydrous Na$_2$SO$_4$, filtered and concentrated. The crude acid is chromatographed on silica gel (CH$_2$Cl$_2$ to 10% MeOH/CH$_2$Cl$_2$) to afford 11.4 g (99%) of (2R*,3R*)-2-benzyloxycarbonylamino-3-(4-methoxybenzene)sulfanyl-7-phenylheptanoic acid as a hygroscopic, white foam which is homogeneous by TLC analysis [5% MeOH/CH$_2$Cl$_2$, $R_f$(allyl 2-benzyloxycarbonylamino-3-(4-methoxybenzene)sulfanyl-7-phenylheptanoate)=0.85; $R_f$(2-benzyloxycarbonylamino-3-(4-methoxybenzene)sulfanyl-7-phenylheptanoic acid)=0.45].$^1$H NMR (300 MHz, CDCl$_3$) δ 1.63 (m, 6H), 2.60 (m, 2H), 3.47 (m, 1H), 3.71 (s, 3H), 4.59 (m, 1H), 5.10 (s, 2H), 5.56 (d, 1H), 6.72 (d, 2H), 7.10–7.40 (m, 12H) ppm; mass spectrum (FAB) m/z 494 (M+H)$^+$.

Step D (2R*,3R*)-N-Benzyloxy-2-benzyloxycarbonylamino-3-(4-methoxybenzene)sulfanyl-7-phenylheptanamide:

A solution containing (2R*,3R*)-2-benzyloxycarbonylamino-3-(4-methoxybenzene)sulfanyl-7-phenylheptanoic acid (3.1 g, 6.28 mmol), HOBT (0.85 g, 6.28 mmol), O-benzyl-hydroxylamine HCl (3 g, 18.8 mmol), n-methylmorpholine (3.1 g, 31.4 mmol), and EDAC.HCl (1.6 g, 8.16 mmol) in anhydrous CH$_2$Cl$_2$ (70 mL) is stirred at ambient temperature for 16 hours. The reaction mixture is concentrated and the residue is dissolved in EtOAc (100 mL). The EtOAc solution is washed with 0.5 M aqueous HCl (3×30 mL), brine (30 mL), dried over anhydrous MgSO$_4$, filtered and concentrated. The crude amide is chromatographed on silica gel (hexane/EtOAc, 4:1 to 2:1) to provide 3 g (79%) of (2R*,3R*)-N-benzyloxy-2-benzyloxycarbonylamino-3-(4-methoxybenzene) sulfanyl-7-phenylheptanamide as a white foam which is homogeneous by TLC analysis [hexane/EtOAc, 1:1, $R_f$(2-benzyloxycarbonylamino-3-(4-methoxybenzene)sulfanyl-7-phenylheptanoic acid)=0.01; $R_f$(N-benzyloxy-2-benzyloxycarbonylamino-3-(4-methoxybenzene)sulfanyl-7-phenylheptanamide)=0.75]. $^1$H NMR (300 MHz, CDCl$_3$) δ 1.38–1.74 (m, 6H), 2.57 (m, 2H), 3.40 (m, 1H), 3.76 (s, 3H), 4.07 (m, 1H), 4.84 (m, 2H), 5.05 (m, 2H), 5.79 (m, 1H), 6.77 (d, 2H), 7.13–7.36 (m, 17H), 9.07 (br s, 1H) ppm.

Step E (2R*,3R*)-N-Benzyloxy-2-benzyloxycarbonylamino-3-(4-methoxybenzene)sulfonyl-7-phenylheptanamide:

To a solution at 0° C. containing (2R*,3R*)-N-benzyloxy-2-benzyloxycarbonylamino-3-(4-methoxybenzene)sulfanyl-7-phenylheptanamide (3 g, 5.01 mmol) in MeOH (200 mL) is added oxone (6.2 g, 10 mmol) in water (200 mL). The white, biphasic mixture is slowly warmed to ambient temperature. After 16 hours, the reaction mixture is concentrated in vacuo to remove MeOH then diluted with water (100 mL)

and washed with CH$_2$Cl$_2$ (2×100 mL). The combined organic extracts are washed with aqueous NaHSO$_3$ (3×50 mL), brine (50 mL), dried over anhydrous Na$_2$SO$_4$, filtered and concentrated. The crude sulfoxides are chromatographed on silica gel (hexane/EtOAc, 4:1) to provide 1.8 g (58%) of a diastereomeric mixture of sulfoxides which appeared homogeneous by TLC analysis [hexane/EtOAc, 1:1, R$_f$(sulfoxides)=0.55].

At 0° C., m-CPBA, practical grade, (1 g, 5.85 mmol) is added to a solution containing the previously prepared mixture of sulfoxides (1.8 g, 2.92 mmol) in CH$_2$Cl$_2$ (60 mL). The reaction mixture is warmed to ambient temperature. After 1 hour, the reaction mixture is concentrated in vacuo and the residue is dissolved in diethyl ether (100 mL). The ether solution is washed with aqueous Na$_2$S$_2$O$_3$ (3×20 mL), aqueous NaHCO$_3$ (3×20 mL), brine (20 mL), dried over anhydrous Na$_2$SO$_4$, filtered and concentrated. The crude sulfone is chromatographed on silica gel (hexane/EtOAc, 4:1) to provide 1.8 g (97%) of (2R*,3R*)-N-benzyloxy-2-benzyloxycarbonylamino-3-(4-methoxybenzene)sulfonyl-7-phenyl heptanamide as an off-white solid which is homogeneous by TLC analysis [hexane/EtOAc, 1:1, R$_f$(N-benzyloxy-2-benzyloxycarbonylamino-3-(4-methoxybenzene) sulfonyl-7-phenylheptanamide)=0.72].
$^1$H NMR (300 MHz, CDCl$_3$) δ 1.24–1.58 (m, 4H), 1.70 (m, 2H), 2.46 (m, 2H), 3.85 (s, 3H), 3.98 (m, 1H), 4.72 (m, 1H), 4.91 (dd, 2H), 5.09 (s, 3H), 5.99 (d, 1H), 6.96 (d, 2H), 7.04 (d, 2H), 7.12–7.44 (m, 13H), 7.77 (d, 2H), 9.01 (br s, 1H) ppm; mass spectrum (FAB) m/z 631 (M+H)$^+$.

Step F (2R*,3R*)-2-amino-3-(4-methoxybenzene)sulfonyl-7-phenylheptanoic acid hydroxy amide:

A solution containing (2R*,3R*)-N-benzyloxy-2-benzyloxycarbonylamino-3-(4-methoxybenzene)sulfonyl-7-phenylheptanamide (10 g, 15.8 mmol), and 10% palladium-on-carbon (500 mg) in MeOH (250 mL) is shaken under an atmosphere of hydrogen (60 PSI) for 8 hours at ambient temperature. The reaction mixture is filtered through a pad of Celite and the solids are washed with MeOH (3×50 mL). The clear filtrate is concentrated in vacuo to provide the crude product which is recrystallized from aqueous MeOH to afford 4.6 g (71%) of (2R*,3R*)-2-amino-3-(4-methoxybenzene)sulfonyl-7-phenylheptanoic acid hydroxyamide as an off-white solid which is homogeneous by TLC analysis [n-BuOH/HOAc/water, 4:1:1, R$_f$(N-benzyloxy-2-benzyloxycarbonylamino-3-(4-methoxybenzene)sulfonyl-7-phenylheptanamide)=0.99; R$_f$(2-amino-3-(4-methoxybenzene) sulfonyl-7-phenylheptanoic acid hydroxyamide)=0.62]. m.p. 103–106° C. $^1$H NMR (300 MHz, CDCl$_3$) δ 1.14–1.42 (m, 2H), 1.43–1.63 (m, 2H), 1.81 (m, 2H), 2.47 (t, 2H), 3.68 (br s, 1H), 3.84 (s, 4H), 6.97 (d, 2H), 7.03 (d, 2H), 7.14–7.25 (m, 3H), 7.77 (d, 2H) ppm. Anal. Calcd for C$_{20}$H$_{26}$N$_2$O$_5$S: C, 59.1; H, 6.45; N, 6.89. Found: C, 57.6; H, 6.53; N, 6.51.

EXAMPLE 20

N-hydroxy-2-[(3,4-dimethoxyphenyl)sulfonyl]-6-phenylhexanamide

The titled compound is prepared according to the following steps:

Step A

Methyl 2-(3,4-dimethylphenylthio)acetate

A mixture of 3,4-dimethoxythiophenol (3 g, 17.6 mmol), methyl bromoacetate (1.67 mL, 17.6 mmol) and potassium carbonate (2.4 g, 17.6 mmol) in acetone (40 mL) is heated under reflux for 4 hours. The mixture is filtered and the filtrate is added to water and is extracted with ether. The ether layer is washed with water and is dried over MgSO$_4$ and the solvent is removed in vacuo. The residue is chromatographed on silica gel (7:3 hexane:ethyl acetate) to afford 1 as an oil (2.6 g, 65%): $^1$H-NMR (330 MHz, CDCl$_3$) δ (TMS) 3.57 (s, 2H), 3.72 (s, 3H), 3.88 (s, 6H), 6.79 (d, 1H), 7.00–7.10 (m, 2H).

Step B

Methyl (3,4-dimethoxyphenylsulfonyl)acetate

To a solution of methyl 2-(3,4-dimethylphenylthio) acetate (2.6 g, 11.5 mmol) in dichloromethane (70 mL) is added 50% m-chloroperoxybenzoic acid (11.8 g, 34.5 mmol) in portions over 5 minutes. The mixture is stirred at room temperature for 2 hours and is filtered. The filtrate is extracted with aqueous sodium metabisulfite and then with aqueous sodium bicarbonate. The organic layer is washed with water and dried over MgSO$_4$ and the solvent is removed in vacuo. The residue is dissolved in hot ethyl acetate and the solution is diluted with hexane to precipitate methyl (3,4-dimethoxyphenylsulfonyl)acetate (1.6 g, 52%), m.p. 81–3° C.: $^1$H-NMR (300 MHz, CDCl$_3$) δ (TMS) 3.72 (s, 3H), 3.94 (d, 6H), 4.12 (s, 2H), 6.98 (d, 1H), 7.39 (s, 1H), 7.58 (d, 1H).

Step C

Methyl 2-[(3,4-dimethoxyphenyl)sulfonyl]-6-phenylhexanoate

To a suspension of 60% NaH (0.23 g, 5.84 mmol) in anhydrous DMF (15 mL) is added a solution of methyl (3,4-dimethoxyphenylsulfonyl)acetate in 20 mL of DMF (1.6 g, 5.84 mmol) dropwise over 10 minutes. The mixture is stirred at room temperature for 20 minutes. 1-Bromo-4-phenylbutane (1.6 g, 5.84 mmol) is added and the mixture is stirred at room temperature for 24 hours. The mixture is added to 5% HCl and is extracted with ether. The organic layer is washed with water and is dried over MgSO$_4$. The solvent is removed in vacuo and the residue is chromatographed on silica gel (7:3 hexane:ethyl acetate) to afford methyl 2-[(3,4-dimethoxyphenyl)sulfonyl]-6-phenylhexanoate (1.3 g, 55%): $^1$H-NMR (300 MHz, CDCl$_3$) δ (TMS) 1.30–1.42 (m, 2H), 1.52–1.68 (m, 2H), 1.95–2.12 (m, 2H), 2.48–2.68 (m, 2H), 3.64 (s, 3H). 3.92 (d, 7H), 6.95 (d, 1H), 7.07–7.18 (m, 2H). 7.20–7.30 (m. 4H), 7.44 (d, 1H); MS (EI) m/e 406 (M$^+$).

Step D

2-[(3,4-Dimethoxyphenyl)sulfonyl]-6-phenylhexanoic acid

A solution of methyl 2-[(3,4-dimethoxyphenyl)sulfonyl]-6-phenylhexanoate (1.3 g, 3.2 mmol) and 10% sodium hydroxide (15 mL) in ethanol (15 mL) is heated under reflux for 20 minutes. The solution is cooled and is added to aqueous HCl and is extracted with ether. The organic layer is washed with water and is dried over MgSO$_4$. The solvent is removed in vacuo and the residue is dissolved in ethyl acetate and the solution is diluted with hexane to precipitate 2-[(3,4-dimethoxyphenyl)sulfonyl]-6-phenylhexanoic acid (0.5 g, 40%): m.p. 114–16° C. Anal. (C$_{20}$H$_{24}$O$_6$S) C, H: $^1$H-NMR (300 MHz, CDCl$_3$) δ (TMS) 1.28–1.48 (m, 2H), 1.54–1.70 (m, 2H), 1.87–2.05 (m, 2H), 2.48–2.64 (m, 2H), 3.88 (d, 7H), 6.97 (d, 1H), 7.12–7.20 (m, 2H), 7.20–7.30 (m, 4H), 7.40–7.50 (m, 1H).

Step E

N-hydroxy-2-[(3,4-dimethoxyphenyl)sulfonyl]-6-phenylhexanamide

To a solution of 2-[(3,4-dimethoxyphenyl)sulfonyl]-6-phenylhexanoic acid (0.3 g, 0.76 mmol) in dichloromethane (10 mL) is added 1M oxalyl chloride (1.5 mL, 1.5 mmol). The solution is stirred at room temperature for 1 hour. Several more mL of oxalyl chloride were added and the solution is stirred at room temperature overnight. The solvent is removed in vacuo and the residue is dissolved in dichloromethane and O-(trimethylsilyl)hydroxylamine (2 mL) is added. The mixture is stirred at room temperature over 30 minutes. The mixture is poured into 5% HCl and is extracted with dichloromethane. The organic layer is washed with water and is dried over $MgSO_4$. The solvent is removed in vacuo and the residue is dissolved in ethyl acetate and the solution is diluted with hexane to precipitate N-hydroxy-2-[(3,4-dimethoxyphenyl)sulfonyl]-6-phenylhexanamide (0.3 g, 100% ): m.p. 180–8°. Anal. ($C_{20}H_{25}NO_6S$) C, H, N: $^1$H-NMR (300 MHz, $CDCl_3$-DMSO-$d^6$) δ (TMS) 1.18–1.45 (m, 2H), 1.50–1.68 (m, 2H), 1.72–2.02 (m, 2H), 2.42–2.60 (m, 2H), 3.69–3.80 (m, 1H), 3.90 (d, 6H), 6.96 (d, 1H), 7.08–7.18 (m, 2H), 7.18–7.28 (m, 2H), 7.40–7.52 (m, 3H).

EXAMPLE 21

(E)-N-hydroxy-3-[(3,4-dimethoxyphenyl)thio]-7-phenyl-2-heptenamide

The titled compound is prepared according to the following steps:

Step A

Methyl 3-keto-7-phenylheptenoate

To a suspension of 60% NaH (2.76 g, 69 mmol) in anhydrous DMF (50 mL) at 0° C. is added a solution of methyl acetoacetate (8 g) in DMF (50 mL) dropwise over 10 minutes. The mixture is cooled to –25° C. and 2.5M n-butyllithium (27.6 mL, 69 mmol) is added dropwise over 5 minutes. The mixture is stirred for 5 minutes and 1-bromo-3-phenylpropane (10.48 mL, 69 mmol) is added dropwise over 5 minutes. The cooling bath is removed and the mixture is stirred at room temperature for 2 hours. The mixture is poured into water and is extracted with ether. The organic layer is washed with water and is dried over $MgSO_4$. The solvent is removed in vacuo and the residue is chromatographed on silica gel (6:1 hexane:ethyl acetate) to produce methyl 3-keto-7-phenylheptenoate as an oil (8 g, 50% ): $^1$H-NMR (300 MHz, $CDCl_3$) δ (TMS) 1.50–1.68 (m, 4H), 2.42–2.62 (m, 4H), 3.40 (s, 2H), 3.70 (s, 3H), 7.10–7.18 (m, 2H), 7.18–7.30 (m, 3H).

Step B

Methyl (E) and (Z)-3-chloro-7-phenyl-2-heptenoate

A mixture of methyl 3-keto-7-phenylheptenoate (8 g, 34 mmol) and phosphorus pentachloride (14.1 g, 68 mmol) in hexane (60 mL) is heated under reflux for 2 hours. The solution is cooled in ice and methanol (5 mL) is added slowly. The mixture is stirred at room temperature for 10 minutes and is added to water and is extracted with hexane. The organic layer is dried over $MgSO_4$ and the solvent is removed in vacuo. The residue is dissolved in dichloromethane (70 mL) and 17 mL of 2 M oxalyl chloride is added. The solution is stirred for 2 hours and the solvent is removed in vacuo. The residue is dissolved in dichloromethane and some methanol is added. After stirring for 30 minutes the solvent is removed in vacuo. The residue is chromatographed on silica gel (20:1 hexane:ethyl acetate) to give methyl (E)-3-chloro-7-phenyl-2-heptenoate (2.1 g, 25%) as the first component off the column and methyl (Z)-3-chloro-7-phenyl-2-heptenoate (1.4 g, 17%) as the second component off the column: methyl (E)-3-chloro-7-phenyl-2-heptenoate, $^1$H-NMR (300 MHz, $CDCl_3$) δ (TMS) 1.58–1.69 (m, 4H), 2.57–2.60 (m, 2H), 2.92–3.04 (m, 2H), 3.68 (s, 3H), 6.06 (s, 1H), 7.12–7.22 (m, 3H), 7.22–7.45 (m, 2H); methyl (Z)-3-chloro-7-phenyl-2-heptenoate, $^1$H-NMR (300 MHz, $CDCl_3$) δ (TMS) 1.58–1.78 (m, 4H), 2.38–2.50 (m, 2H), 2.57–2.62 (m, 2H), 3.72 (s, 3H), 6.00 (s, 1H), 7.12–7.27 (m, 3H), 7.27–7.38(m, 2H).

Step C

Methyl (E)-3-[(3,4-dimethoxyphenyl)thio]-7-phenyl-2-heptenoate

A mixture of methyl (E)-3-chloro-7-phenyl-2-heptenoate (1.3 g, 5.1 mmol), 3,4-dimethoxythiophenol (0.86 g, 5.1 mmol) and potassium carbonate (0.7 g, 5.1 mmol) in methanol (50 mL) is heated under reflux for 3 hours. The mixture is filtered and the filtrate is poured into water and is extracted with ether. The organic layer is washed with water and is dried over $MgSO_4$. The solvent is removed in vacuo and the residue is chromatographed (4:1 hexane:ethyl acetate) to obtain methyl (E)-3-[(3,4-dimethoxyphenyl)thio]-7-phenyl-2-heptenoate (0.6 g, 31% ). A small amount is recrystallized from hexane to give m.p. 53–5° C. Anal.($C_{22}H_{26}O_4S$) C, H: $^1$H-NMR (300 MHz, $CDCl_3$) δ (TMS) 1.68–1.82 (m, 4H), 2.60–2.70 (m, 2H) 2.80–2.92 (m, 2H), 3.57 (s, 3H), 3.86 (s,3H), 3.90 (s, 3H), 5.12 (s, 1H), 6.82–6.92 (m, 2H), 6.98–7.08 (m, 1H), 7.13–7.31 (m, 5H); MS (EI) m/e 386 ($M^+$).

Step D (E)-[3,4-Dimethoxyphenyl)thio]-7-phenyl-2-heptenoic acid

A solution of methyl (E)-3-[(3,4-dimethoxyphenyl)thio]-7-phenyl-2-heptenoate (1.3 g, 3.3 mmol) and 10% sodium hydroxide (10 mL) in ethanol (15 mL) is heated under reflux for 2 hours. A little water is added to precipitate a solid which is air dried. The solid is dissolved in ethyl acetate and the solution is diluted to the cloudy point with hexane to precipitate (E)-[3,4-dimethoxyphenyl)thio]-7-phenyl-2-heptenoic acid (0.4 g, 37% ), m.p. 138–40° C. Anal. ($C_{21}H_{24}O_4S$) C, H: $^1$H-NMR (300 MHz, $CDCl_3$) δ (TMS) 1.62–1.78 (m, 4H), 2.53–2.67 (m, 2H), 2.80–2.90 (m, 2H), 3.86 (s, 3H), 3.96 (s, 3H), 5.12 (s, 1H), 6.84–6.92 (m, 2H), 7.00–7.08 (m, 1H), 7.12–7.31 (m, 5H).

Step F (E)-N-hydroxy-3-[(3,4-dimethoxyphenyl)thio]-7-phenyl-2-heptenamide

To a solution of (E)-[3,4-dimethoxyphenyl)thio]-7-phenyl-2-heptenoic acid (0.4 g, 1.1 mmol) in dichloromethane (20 mL) is added a few mL of 2 M oxalyl chloride. The solution is stirred at room temperature for 2 hours. The solvent is removed in vacuo and the residue is dissolved in dichloromethane and O-(trimethylsilyl) hydroxylamine (2 mL) is added. The mixture is stirred for 1 hour and is poured into aqueous HCl and is extracted with dichloromethane. The organic layer is removed in vacuo and the residue is dissolved in ethyl acetate and the solution is diluted to the cloudy point with hexane to precipitate (E)-N-hydroxy-3-[(3,4-dimethoxyphenyl)thio]-7-phenyl-2-heptenamide (0.3 g, 75%), m.p. 165–7° C. Anal. ($C_{21}H_{25}NO_4S.\frac{1}{4}H_2O$) C, H, N: $^1$H-NMR (300 MHz, $CDCl_3$) δ (TMS) 1.68–1.80 (m, 4H), 2.58–2.62 (m, 2H), 2.88–3.00 (m, 2H), 3.86 (s, 3H), 3.91 (s, 3H), 4.88 (s, 1H), 6.82–6.92 (m, 2H), 7.00–7.08 (m, 1H), 7.11–7.30 (m, 5H); MS (FAB) m/e 387 $(M+H)^+$.

EXAMPLE 22

(E)-N-hydroxy-3-[(3,4-dimethoxyphenyl)sulfonyl]-7-phenyl-2-heptenamide

To a solution of (E)-N-hydroxy-3-[(3,4-dimethoxyphenyl)thio]-7-phenyl-2-heptenamide (0.3 g, 0.77 mmol) in methanol (20 mL) is added 1 g (1.6 mmol) of oxone dissolved in 10 mL of water. The mixture is stirred at room temperature for 18 hours. The mixture is poured into water and is extracted with ethyl acetate. The organic layer is dried over $MgSO_4$. The solvent is removed in vacuo and the residue is dissolved in ethyl acetate. The solution is diluted to the cloudy point with hexane to precipitate (E)-N-hydroxy-3-[(3,4-dimethoxyphenyl)sulfonyl]-7-phenyl-2-heptenamide (0.16 g, 50%), m.p. 123–6° C. Anal. ($C_{21}H_{25}NO_6S$) C, H, N: $^1$H-NMR (300 MHz, $CDCl_3$-DMSO-$d^6$) δ (TMS) 1.36–1.60 (m, 4H), 2.42–2.55 (m, 2H), 2.69–2.82 (m, 2H), 3.88 (s, 3H), 3.93 (s, 3H), 6.89–7.20 (m, 7H), 7.40–7.50 (m, 1H); MS (FAB) m/e 419 (M+H)$^+$.

EXAMPLE 23

(Z)-N-hydroxy-3-[(3,4-dimethoxyphenyl)thio]-7-phenyl-2-heptenamide

The titled compound is prepared according to the following steps:

Step A

Methyl (Z)-3-[(3,4-dimethoxyphenyl)thio]-7-phenyl-2-heptenoate

A mixture of methyl (Z)-3-chloro-7-phenyl-2-heptenoate (0.7 g, 2.77 mmol), 3,4-dimethoxythiophenol (0.47 g, 2.77 mmol) and potassium carbonate (0.38 g, 2.77 mmol) in methanol (30 mL) is heated under reflux for 3 hours. The mixture is added to aqueous HCl and is extracted with ether. The organic layer is washed with water and is dried over $MgSO_4$. The solvent is removed in vacuo and the residue is chromatographed on silica gel (4:1 hexane:ethyl acetate) to produce methyl (Z)-3-[(3,4-dimethoxyphenyl)thio]-7-phenyl-2-heptenoate as an oil (0.8 g, 75% ): $^1$H-NMR (300 MHz, $CDCl_3$) δ (TMS) 1.30–1.53 (m, 3H), 1.62–1.76 (m, 1H), 2.03–2.18 (m, 2H), 2.38–2.48 (m, 1H), 2.64–2.74 (m, 1H), 3.72 (s, 3H), 3.78–3.90 (m, 6H), 5.78 (s, 1H), 6.72–6.82 (m, 1H), 6.92–7.00 (m, 1H), 7.05–7.10 (m, 1H), 7.20–7.38 (m, 5H).

Step B (Z)-3-[3,4-Dimethoxyphenyl)thio]-7-phenyl-2-heptenoic acid

A solution of methyl (Z)-3-[(3,4-dimethoxyphenyl)thio]-7-phenyl-2-heptenoate (0.9 g, 2.3 mmol) and a few mL of 2 N sodium hydroxide in ethanol (15 mL) is heated under reflux for 3 hours. The mixture is poured into aqueous HCl and is extracted with ether. The organic layer is washed with water and is dried over $MgSO_4$. The solvent is removed in vacuo and the residue is dissolved in ethyl acetate. The solution is diluted to the cloudy point with hexane to precipitate (Z)-3-[3,4-dimethoxyphenyl)thio]-7-phenyl-2-heptenoic acid (0.13 g, 15% ), m.p. 128–30° C. Anal. ($C_{21}H_{24}O_4S$) C, H: $^1$H-NMR (300 MHz, $CDCl_3$) δ (TMS) 1.32–1.48 (m, 4H), 2.08–2.18 (m, 2H), 2.40–2.50 (m, 2H), 3.80 (s, 3H), 3.88 (s, 3H), 5.82 (s, 1H), 6.78 (d, 1H), 6.98 (s, 1 H), 6.98–7.10 (m, 3H), 7.10–7.28 (m, 3H).

Step C (Z)-N-hydroxy-3-[(3,4-dimethoxyphenyl)thio]-7-phenyl-2-heptenamide

To a solution of (Z)-3-[3,4-dimethoxyphenyl)thio]-7-phenyl-2-heptenoic acid (0.3 g, 0.8 mmol) in dichloromethane (20 mL) is added a few mL of 2 M oxalyl chloride. The solution is stirred at room temperature for 20 minutes. The solvent is removed in vacuo and the residue is dissolved in dichloromethane. To this solution is added O-(trimethylsilyl)-hydroxylamine (1 mL). The mixture is stirred at room temperature for 40 minutes and is added to aqueous HCl. The mixture is extracted with ether. The organic layer is washed with water and is dried over $MgSO_4$. The solvent is removed in vacuo. The residue is dissolved in ethyl acetate and the solution is diluted to the cloudy point with hexane to provide some of the (E) form. Further dilution of the filtrate with hexane produces (Z)-N-hydroxy-3-[(3,4-dimethoxyphenyl)thio]-7-phenyl-2-heptenamide (0.078 g, 26% ), m.p. 148–50° C. Anal. ($C_{21}H_{25}NO_4S$) C, H, N: $^1$H-NMR (300 MHz, $CDCl_3$) δ (TMS) 1.35–1.50 (m, 4H), 2.04–2.18 (m, 2H), 2.42–2.52 (m, 2H), 3.80 (s, 3H), 3.90 (s, 3H), 5.68 (s, 1H), 6.78 (d, 1H), 6.96 )s, 1H), 6.98–7.11 (m, 3H), 7.11–7.30 (m, 3H).

EXAMPLE 24

N-hydroxy-3-(4-methoxyphenyl)thio-2-(1-propane-3-yl)-7-phenylheptanamide

The titled compound is prepared according to the following steps:

Step

A Methyl 3-oxo-2-(1-propen-3-yl)butanoate

A mixture of methyl acetoacetate (11.6 g, 100 mmol), allyl bromide (12.1 g, 100 mmol) and potassium carbonate (13.8 g, 100 mmol) in acetone (70 mL) is heated under reflux for 18 hours. The mixture is filtered and the filtrate is evaporated. The residue is chromatographed on silica gel (15:1 hexane:ethyl acetate) to give methyl 3-oxo-2-(1-propen-3-yl)butanoate (8.8 g, 47%): $^1$H-NMR (300 MHz, $CDCl_3$) δ (TMS) 2.22 (s, 3H), 2.58 (t, 2H), 3.54 (t, 1H), 3.72 (s, 3H), 4.90–5.12(m, 2H), 5.60–5.82 (m, 1H).

Step B

Methyl 3-oxo-2-(1-propane-3-yl)-7-phenylheptanoate

To a suspension of 60% sodium hydride (2 g, 51.2 mmol) in anhydrous THF (70 mL) is added methyl 3-oxo-2-(1-propen-3-yl)butanoate (8 g, 51.2 mmol) in THF (20 mL) dropwise over 10 minutes. The mixture is cooled to −25° C. and 2.5 M n-butyllithium (20.4 mL, 51.2 mmol) is added dropwise over 5 minutes. The mixture is stirred for 5 minutes and 1-bromo-3-phenylpropane (7.78 mL, 51.2 mmol) in THF (10 mL) is added dropwise over 5 minutes. The mixture is stirred at room temperature for 2 hours. The mixture is poured into 5% aqueous HCl and is extracted with ether. The organic layer is washed with water and is dried over $MgSO_4$. The solvent is removed in vacuo and the residue is chromatographed on silica gel (9:1 hexane:ethyl acetate) to provide methyl 3-oxo-2-(1-propane-3-yl)-7-phenylheptanoate (7.4 g, 53% ): $^1$H-NMR (300 MHz, $CDCl_3$) δ (TMS) 1.53–1.68 (m, 4H), 2.08–2.20 (m, 1H), 2.42–2.62 (m, 4H), 3.48 (t, 1H), 3.52 (t, 1H), 3.68 (s, 3H), 4.94–5.18 (m, 2H), 5.62–5.70 (m, 1H), 7.08–7.30 (m, 5H).

Step C

Methyl 3-hydroxy-2-(1-propen-3-yl)-7-phenylheptanoate

To a solution of methyl 3-oxo-2-(1-propane-3-yl)-7-phenylheptanoate (7.4 g, 26.98 mmol) in methanol (30 mL) is added sodium borohydride (1.2 g, 32 mmol) in portions over 5 minutes. The mixture is stirred at room temperature for 30 minutes. The mixture is poured into 5% aqueous HCl and is extracted with ether. The organic layer is washed with water and is dried over $MgSO_4$. The solvent is removed in vacuo to provide methyl 3-hydroxy-2-(1-propen-3-yl)-7-phenylheptanoate as an oil (6.5 g, 91% ): $^1$H-NMR (300 MHz, $CDCl_3$) δ (TMS) 1.42–1.72 (m, 4H), 2.08–2.22 (m, 1H), 2.30–2.62 (m, 4H), 2.78 (t, 1H), 3.48 (t, 1H), 3.66 (s, 3H), 3.72–3.98 (m, 1H), 4.90–5.12 (m, 2H), 5.60–5.88 (m, 1H), 7.07–7.30 (m, 5H); MS (FAB) m/e 276 (M+H)$^+$.

Step D

Methyl 3-methanesulfonyloxy-2-(1-propane-3-yl)-7-phenylheptanoate

To a solution of methyl 3-hydroxy-2-(1-propen-3-yl)-7-phenylheptanoate (6.5 g, 23.5 mmol) in dichloromethane (70 mL) is added triethylamine (4.7 g, 47 mmol). To this mixture is added methanesulfonyl chloride (1.96 mL, 25.5 mmol) dropwise over 5 minutes. A few mg of DMAP is added and the mixture is stirred at room temperature for 1 hour. The mixture is poured into 5% HCl and is extracted with ether. The organic layer is washed with water and is dried over $MgSO_4$. The solvent is removed in vacuo to provide methyl 3-methanesulfonyloxy-2-(1-propane-3-yl)-7-phenylheptanoate as an oil (7.1 g, 85%): $^1$H-NMR (300 MHz, $CDCl_3$) δ (TMS) 1.38–1.80 (m, 4H), 2.08–2.18 (m, 1H), 2.32–2.48 (m, 2H), 2.48–2.68 (m, 2H), 2.70–2.90 (m, 1H), 2.90–3.00 (m, 3H), 3.48 (t, 1H), 3.65 (s, 3H), 4.82–4.92 (m, 1H), 4.92–5.12 (m, 2H), 5.60–5.82 (m, 1H), 7.10–7.35 (m, 5H); MS (FAB) m/e 354 $(M+H)^+$.

Step E

Methyl 3-(4-methoxyphenyl)thio-2-(1-propane-3-yl)-7-phenylheptanoate

A mixture of methyl 3-methanesulfonyloxy-2-(1-propane-3-yl)-7-phenylheptanoate (7.1 g, 20 mmol), 4-methoxythiophenol (2.8 g, 20 mmol) and potassium carbonate (2.76 g, 20 mmol) in methanol (70 mL) is heated under reflux for 4 hours. The mixture is filtered and the filtrate is added to aqueous HCl and is extracted with ether. The ether layer is extracted with 5% sodium hydroxide. The organic layer is washed with water and is dried over $MgSO_4$. The solvent is removed in vacuo and the residue is chromatographed on silica gel (20:1 hexane:ethyl acetate) to afford methyl 3-(4-methoxyphenyl)thio-2-(1-propane-3-yl)-7-phenylheptanoate (1 g, 12.5%): $^1$H-NMR (300 MHz, $CDCl_3$) δ (TMS) 1.5840–1.70 (m, 4H), 2.48–2.75 (m, 2H), 3.00 (m, 1H), 3.58 (s, 1H), 3.78 (s, 6H), 4.13 (s, 1H), 4.90–5.08 (m, 2H), 5.60–5.80 (m, 1H), 6.80 (m, 3H), 7.10–7.48 (m, 6H); MS (FAB) m/e 398 $(M^+)$.

Step F 3-(4-Methoxyphenyl)thio-2-(1-propane-3-yl)-7-phenylheptanoic acid

A mixture of methyl 3-(4-methoxyphenyl)thio-2-(1-propane-3-yl)-7-phenylheptanoate (1 g, 2.5 mmol) in ethanol (15 mL) containing 1 N sodium hydroxide (10 mL) is heated under reflux for 3 hours. The mixture is cooled and is added to 5% HCl and is extracted with ether. The organic layer is washed with water and is dried over $MgSO_4$. The solvent is removed in vacuo and the residue is chromatographed on silica gel (1:1 hexane:ethyl acetate) to give 3-(4-Methoxyphenyl)thio-2-(1-propane-3-yl)-7-phenylheptanoic acid as an oil (0.2 g, 21%): $^1$H-NMR (300 MHz, $CDCl_3$) δ (TMS) 1.35–1.65 (m, 4H), 1.70–1.90 (m, 1H), 2.02–2.36 (m, 1H), 2.45–2.62 (m, 2H), 2.68–2.87 (m, 1H), 3.02–3.32 (m, 2H), 3.62–3.92 (m, 4H), 4.87–5.09 (m, 2H), 5.42–5.68 (m, 1H), 6.7862–6.90(m, 3H), 7.02–7.42 (m, 6H); MS (FAB) m/e 384 $(M+H)^+$.

Step G

N-hydroxy-3-(4-methoxyphenyl)thio-2-(1-propane-3-yl)-7-phenylheptanamide

To a solution of 3-(4-Methoxyphenyl)thio-2-(1-propane-3-yl)-7-phenylheptanoic acid (0.2 g, 0.52 mmol) in dichloromethane (20 mL) is added a few mL of 1 M oxalyl chloride. The mixture is stirred at room temperature for 2 hours. The solution is evaporated and the residue is dissolved in dichloromethane (15 mL). To this solution is added 2 mL of O-(trimethylsilyl)hydroxylamine. The mixture is stirred at room temperature for 1 hour. The mixture is poured into 5% aqueous HCl and is extracted with dichloromethane. The organic layer is washed with water and is dried over $MgSO_4$. The solvent is removed in vacuo to give 0.2 g of N-hydroxy-3-(4-methoxyphenyl)thio-2-(1-propane-3-yl)-7-phenylheptanamide as an oil which is used in the next step without purification (100%); MS (FAB) m/e 399 $(M^+)$.

EXAMPLE 25

N-hydroxy-2-(1-propane-3-yl)-3-(4-methoxyphenyl) sulfonyl-7-phenylheptanamide

To a solution of N-hydroxy-3-(4-methoxyphenyl)thio-2-(1-propane-3-yl)-7-phenylheptanamide (0.2 g, 0.5 mmol) in methanol (10 mL) is added a solution of oxone (0.3 g, 0.5 mmol) in 5 mL of water. The mixture is stirred at room temperature for 18 hours. The mixture is poured into water and is extracted with ethyl acetate. The organic layer is washed with water and is dried over $MgSO_4$. The solvent is removed in vacuo and the residue is chromatographed on silica gel (4:1 hexane:ethyl acetate and then 100% methanol). The methanol residue is further purified by reverse phase HPLC (55–60% acetonitrile:0.1% TFA) to give N-hydroxy-2-(1-propane-3-yl)-3-(4-methoxyphenyl) sulfonyl-7-phenylheptanamide (0.02 g, 10%) as a foam; MS (FAB) m/e 431 $(M+H)^+$.

To a solution of N-hydroxy-3-(4-methoxyphenyl)thio-2-(1-propane-3-yl)-7-phenylheptanamide (0.9 g, 2.2 mmol) in methanol (30 mL) is added a solution of oxone (2.77 g, 4.4 mmol) in 20 mL of water slowly over 5 minutes. The mixture is stirred at room temperature for 18 hours. The mixture is poured into water and is extracted with ethyl acetate. The organic layer is washed with water and is dried over $MgSO_4$. The solvent is removed in vacuo and the residue is chromatographed by chiral HPLC to provide four fractions—0.01 g, 0.02 g, 0.033 g and 0.08 g.

EXAMPLE 26

N-hydroxy-2-[(3,4-dimethoxyphenyl)thio]-3-(3-phenylpropyl-1-yl)-1-cyclopentenecarboxamide The titled compound is prepared according to the following steps:

Step A

Methyl 2-oxo-3-(3-phenylpropyl-1-yl)cyclopentanecarboxylate

To a suspension of 60% NaH (1.2 g, 30 mmol) in anhydrous THF (30 mL) in an ice bath is added a solution of methyl 2-oxocyclopentanecarboxylate (4.26 g, 30 mmol) in 10 mL of THF dropwise over 5 minutes. The mixture is stirred at room temperature for 20 minutes. The mixture is cooled to −25° C. and 2.5 M n-butyllithium is added over 5 minutes (12 mL, 30 mmol). After stirring for 5 minutes, 1-bromo-3-phenylpropane (4.6 mL, 30 mmol) is added. The mixture is stirred at room temperature for 3 hours. The mixture is poured into water and is extracted with ether. The organic layer is washed with water and is dried over $MgSO_4$. The solvent is removed in vacuo and the residue is chromatographed on silica gel (6:1 hexane:ethyl acetate) to afford methyl 2-oxo-3-(3-phenylpropyl-1-yl)cyclopentanecarboxylate (1 g, 13%): $^1$H-NMR (300 MHz, $CDCl_3$) δ (TMS) 1.22–1.50 (m, 2H), 1.62–1.90 (m, 4H), 2.12– 2.38 (m, 4H), 2.58–2.69 (m, 2H), 3.75 (s, 3H), 7.10–7.32 (m, 5H); MS (EI) m/e 260 $(M^+)$.

Step B

Methyl 2-chloro-3-(3-phenylpropyl-1-yl)-1-cyclopentenecarboxylate

To a mixture of methyl 2-oxo-3-(3-phenylpropyl-1-yl)cyclopentanecarboxylate (1 g, 3.8 mmol) in hexane (40 mL) is added phosphorus pentachloride (1.5 g, 7.6 mmol). The mixture is heated under reflux for 2.5 hours. The solution is cooled in ice and methanol (few mL) is added. The mixture is stirred at room temperature for 15 minutes. The mixture is poured into water and is extracted with hexane. The organic layer is washed with water and is dried over $MgSO_4$. The organic layer is removed in vacuo and the residue is dissolved in dichloromethane. To this solution is added 2 M oxalyl chloride (few mL). The mixture is stirred at room temperature for 2 hours. The solvent is removed in vacuo and the residue is dissolved in dichloromethane and methanol (few mL) is added. The solution is stirred at room temperature for 15 minutes. The solvent is removed in vacuo and the residue is chromatographed on silica gel (20:1 hexane:ethyl acetate) to give methyl 2-chloro-3-(3-phenylpropyl-1-yl)-1-cyclopentenecarboxylate (0.2 g, 20%): $^1$H-NMR (300 MHz, $CDCl_3$) δ (TMS) 1.50–1.70 (m, 4H), 1.78–1.92 (m, 1H), 2.07–2.19 (m, 1H), 2.53–2.71 (m, 4H), 2.78–2.92 (m, 1H), 3.78 (s, 3H), 7.17–7.32 (m, 5H); MS (EI) m/e 278 ($M^+$).

Step C

Methyl 2-[(3,4-dimethoxyphenyl)thio]-3-(3-phenylpropyl-1-yl)-1-cyclopentenecarboxylate A mixture of Methyl 2-chloro-3-(3-phenylpropyl-1-yl)-1-cyclopentenecarboxylate (0.2 g, 0.72 mmol), 3,4-dimethoxythiophenol (0.12 g, 0.72 mmol) and potassium carbonate (0.1 g, 0.72 mmol) in methanol (20 mL) is heated under reflux for 6 hours. After standing at room temperature for 2 days, the mixture is heated under reflux for another 4 hours. The mixture is poured into water and is extracted with ether. The organic layer is washed with water and is dried over $MgSO_4$. The solvent is removed in vacuo and the residue is chromatographed on silica gel (4:1 hexane:ethyl acetate) to provide methyl 2-[(3,4-dimethoxyphenyl)thio]-3-(3-phenylpropyl-1-yl)-1-cyclopentenecarboxylate (0.17 g, 58%): $^1$H-NMR (300 MHz, $CDCl_3$) δ (TMS) 1.10–1.70 (m, 5H), 1.88–1.98 (m, 1H), 2.31–2.40 (t, 3H), 2.58–2.70 (t, 3H), 3.78 (s, 3H), 3.84 (s, 3H), 3.90 (s, 3H), 6.68–6.75 (d, 1H), 6.95–7.09 (m, 4H), 7.17–7.30 (m, 3H); MS (EI) m/e 412 ($M^+$).

Step D

2-[(3,4-Dimethoxyphenyl)thio]-3-(3-phenylpropyl-1-yl)-1-cyclopentenecarboxylic acid A mixture of methyl 2-[(3,4-dimethoxyphenyl)thio]-3-(3-phenylpropyl-1-yl)-1-cyclopentenecarboxylate (0.5 g, 1.2 mmol) and 10% sodium hydroxide (5 mL) in ethanol (10 mL) is heated under reflux for 4 hours. The mixture is cooled and is poured into aqueous HCl. The mixture is extracted with ether. The organic layer is washed with water and is dried over $MgSO_4$. The solvent is removed in vacuo to provide 2-[(3,4-dimethoxyphenyl)thio]-3-(3-phenylpropyl-1-yl)-1-cyclopentenecarboxylic acid (0.4 g, 85%): m.p. 146–8° C. Anal. ($C_{23}H_{26}O_4S$) C,H,N: $^1$H-NMR (300 MHz, $CDCl_3$) δ (TMS) 1.10–1.70 (m, 5H), 1.83–2.02 (m, 1H), 2.32–2.41 (t, 2H), 2.60–2.72 (m, 3H), 3.84 (s, 3H), 3.90 (s, 3H), 6.69–6.75 (d, 1H), 6.94–7.00 (m, 2H), 7.00–7.10 (d, 2H), 7.18–7.32 (m, 3H); MS (EI) m/e 398 ($M^+$).

Step E

N-hydroxy-2-[(3,4-dimethoxyphenyl)thio]-3-(3-phenylpropyl-1 -yl)-1-cyclopentenecarboxamide To a solution of 2-[(3,4-dimethoxyphenyl)thio]-3-(3-phenylpropyl-1-yl)-1-cyclopentenecarboxylic acid (0.6 g, 1.5 mmol) in dichloromethane (20 mL) is added 2 M oxalyl chloride (1.5 mL, 3 mmol). The mixture is stirred at room temperature for 15 minutes. The solvent is removed in vacuo and the residue is dissolved in dichloromethane and O-(trimethylsilyl)hydroxylamine (0.3 mL, 3 mmol) is added. The mixture is stirred at room temperature for 30 minutes. The mixture is poured into 5% HCl and is extracted with dichloromethane. The organic layer is washed with water and is dried over $MgSO_4$. The solvent is removed in vacuo and the residue is chromatographed on silica gel (100% ethyl acetate). The product is dissolved in the minimum amount of ethyl acetate and the solution is diluted to the cloudy point with hexane to precipitate N-hydroxy-2-[(3,4-dimethoxyphenyl)thio]-3-(3-phenylpropyl-1-yl)-1-cyclopentenecarboxamide on standing at room temperature overnight (0.1 g, 16%): m.p. 44–6° C. Anal. ($C_{23}H_{27}NO_4S·¼H_2O$) C,H,N: $^1$H-NMR (300 MHz, $CDCl_3$) δ (TMS) 1.42–1.78 (m, 5H), 1.90–2.08 (m, 1H), 2.38–2.50 (m, 2H), 2.59–2.78 (m, 3H), 3.82 (s, 3H), 3.90 (s, 3H), 6.72–6.79 (d, 1H), 6.88–6.98 (m, 2H), 6.98–7.10 (d, 2H), 7.10–7.30 (m, 3H), 9.02 (s, 1H); MS (Ion Spray) m/e 413 $(M+H)^+$.

EXAMPLE 27

N-hydroxy-2-[(3,4-dimethoxyphenyl)sulfonyl]-3-(3-phenylpropyl-1-yl)-1-cyclopentenecarboxamide To a solution of N-hydroxy-2-[(3,4-dimethoxyphenyl)thio]-3-(3-phenylpropyl-1-yl)-1-cyclopentenecarboxamide (0.2 g, 0.4 mmol) in methanol (15 mL) is added 0.5 g (0.8 mmol) of oxone dissolved in 5 mL of water. The mixture is stirred at room temperature for 18 hours. The mixture is poured into water and is extracted with ethyl acetate. The organic layer is washed with water and is dried over $MgSO_4$. The solvent is removed in vacuo and the residue is chromatographed on silica gel (100% ethyl acetate and then 100% methanol). The methanol is removed in vacuo and the residue is triturated with ether (50 mL) and is filtered. The filtrate is removed in vacuo and the residue is dissolved in methanol and the solution is diluted with water and is lyophilized to afford N-hydroxy-2-[(3,4-dimethoxyphenyl)sulfonyl]-3-(3-phenylpropyl-1-yl)-1-cyclopentenecarboxamide (0.02 g, 11%): m.p. 70–3° C. Anal. ($C_{23}H_{27}NO_6S·¼H_2O$) C,H,N: $^1$H-NMR (300 MHz, $CDCl_3$) δ (TMS) 1.22–1.90 (m, 6H), 2.40–2.60 (m, 2H), 2.75–2.88 (m, 2H), 3.08–3.12 (m, 1H), 3.95 (s, 3H), 3.98 (s, 3H), 6.88–6.98 (d, 1H), 7.08–7.32 (m, 5H); MS (Fab) m/e 446 $(M+H)^+$.

EXAMPLE 28

N-hydroxy-3-(3,4-dimethoxyphenyl-7-phenyl-2-heptenamide

The titled compound is prepared according to the following steps:

Step A 1-(3,4-Dimethoxyphenyl)-1-oxo-5-phenylpentane

To a solution of 5-phenylvaleric acid (10 g, 56.1 mmol) in dichloromethane (70 mL) is added 2 M oxalyl chloride (33.5 mL, 67 mmol). The mixture is stirred at room temperature for 18 hours. The solvent is removed in vacuo. The residue is dissolved in dichloromethane (60 mL) and veratrole (11.6 g, 84 mmol) is added. The mixture is cooled in ice and aluminum chloride (7.4 g, 56.1 mmol) is added in portions over 10 minutes. The mixture is stirred for 3 hours warming to room temperature. The mixture is added to aqueous HCl and is extracted with dichloromethane. The organic layer is washed with water and is dried over MgSO$_4$. The solvent is removed in vacuo and the residue is chromatographed on silica gel (7:3 hexane:ethyl acetate) to give 1-(3,4-dimethoxyphenyl)-1-oxo-5-phenylpentane (5.5 g 33%), m.p. 56–8° C. $^1$H-NMR (300 MHz, CDCl$_3$) δ (TMS) 1.68–1.82 (m, 4H), 2.52–2.61 (t, 2H), 2.88–2.98 (t, 2H), 3.95 (s, 6H), 6.82–6.92 (m, 2H), 7.10–7.30 (m, 4H), 7.48–7.60 (m, 2H); MS (EI) m/e 298 (M$^+$).

Step B

Ethyl 3-(3,4-dimethoxyphenyl)-7-phenyl-2-heptenoate

To a solution of triethyl phosphonoacetate (0.38 g, 1.68 mmol) in anhydrous THF (15 mL) cooled in an ice bath is added 0.5 M potassium bis(trimethylsilyl)amide (3.36 mL, 1.68 mmol) dropwise over 3 minutes. The mixture is stirred for 20 minutes and a solution of 1-(3,4-dimethoxyphenyl)-1-oxo-5-phenylpentane (0.5 g, 1.68 mmol) in THF (10 mL) is added dropwise over 3 minutes. The mixture is heated under reflux for 3 days. The mixture is added to a saturated ammonium chloride solution and is extracted with ether. The organic layer is washed with water and is dried over MgSO$_4$. The solvent is removed in vacuo and the residue is chromatographed on silica gel (4:1 hexane:ethyl acetate) to produce ethyl 3-(3,4-dimethoxyphenyl)-7-phenyl-2-heptenoate (0.1 g, 16%) $^1$H-NMR (300 MHz, CDCl$_3$) δ (TMS) 1.29–1.36 (t, 3H), 1.42–1.58 (m, 2H), 1.62–1.75 (m, 2H), 2.53–2.62 (t, 2H), 3.08–3.19 (t, 2H), 3.89 (s, 6H), 4.16–4.26 (q, 2H), 6.02 (s, 1H), 6.82–6.88 (d, 1H), 6.90–7.10 (d, 1H), 7.00–7.10 (m, 1H), 7.10–7.20 (m, 3H), 7.20–7.30 (m, 2H); MS (EI) m/e 368 (M$^+$).

Step C 3-(3,4-Dimethoxyphenyl)-7-phenyl-2-heptenoic acid

A mixture containing ethyl 3-(3,4-dimethoxyphenyl)-7-phenyl-2-heptenoate (0.9 g, 2.4 mmol) and 10% sodium hydroxide (10 mL) in ethanol (20 mL) is heated under reflux for 1 hour. The mixture is cooled and is added to aqueous HCl and is extracted with ether. The organic layer is washed with water and is dried over MgSO$_4$. The solvent is removed in vacuo to provide 3-(3,4-Dimethoxyphenyl)-7-phenyl-2-heptenoic acid as an oil (0.7 g, 87%) $^1$H-NMR (300 MHz, CDCl$_3$) δ (TMS) 1.48–1.60 (m, 2H), 1.60–1.80 (m, 2H), 2.58–2.69 (t, 2H), 3.10–3.20 (t, 2H), 3.90 (s, 6H), 6.08 (s, 1H), 6.80–6.90 (d, 1H), 6.90–6.98 (s, 1H), 6.98–7.09 (d, 1H), 7.09–7.32 (m, 5H); MS (EI) m/e 340 (M$^+$).

Step D

N-hydroxy-3-(3,4-dimethoxyphenyl-7-phenyl-2-heptenamide

To a solution of 33 (0.7 g, 2.1 mmol) in dichloromethane (20 mL) is added 2 M oxalyl chloride (3 mL, 6 mmol). The mixture is stirred at room temperature for 15 minutes. The solvent is removed in vacuo and the residue is dissolved in dichloromethane. To this solution is added O-(trimethylsilyl)hydroxylamine (0.5 mL, 3.6 mmol). The mixture is stirred at room temperature for 30 minutes. The mixture is added to aqueous HCl and is extracted with dichloromethane. The organic layer is washed with water and is dried over MgSO$_4$. The solvent is removed in vacuo and the residue is chromatographed on silica gel (1:1 hexane:ethyl acetate and then 100% ethyl acetate). The product residue is dissolved in ether (1 mL) and is evaporated to give N-hydroxy-3-(3,4-dimethoxyphenyl-7-phenyl-2-heptenamide as a hygroscopic foam (0.08 g, 11%). $^1$H-NMR (300 MHz, CDCl$_3$) δ (TMS) 1.42–1.78 (m, 4H), 2.51–2.63 (t, 2H), 3.08–3.22 (t, 2H), 4.01 (s, 6H), 5.78 (s, 1H), 6.80–6.92 (m, 2H), 6.92–7.08 (m, 1H), 7.10–7.32 (m, 5H); MS (ion Spray) m/e 356 (M+H)$^+$.

EXAMPLE 28

N-hydroxy-3-(3,4-dimethoxyphenyl-7-phenylheptanamide

The titled compound is prepared according to the following steps:

Step A

Ethyl 3-(3,4-dimethoxyphenyl)-7-phenylheptanoate

A solution of ethyl 3-(3,4-dimethoxyphenyl)-7-phenyl-2-heptenoate (0.4 g, 1.1 mmol) in ethanol (20 mL) containing 10% Pd/C (few mg) is stirred under a balloon of hydrogen for 4 hours at room temperature. The catalyst is filtered and the solvent is removed in vacuo to produce ethyl 3-(3,4-dimethoxyphenyl)-7-phenylheptanoate (0.3 g, 73%) as an oil. $^1$H-NMR (300 MHz, CDCl$_3$) δ (TMS) 1.11–1.20 (t, 3H), 1.20–1.65 (m, 6H), 2.45–2.59 (m, 4H), 2.92–3.10 (m, 1H), 3.82 (s, 6H), 4.00–4.08 (q, 2H), 6.62–6.82 (m, 3H), 7.02–7.28 (m, 5H); MS (EI) m/e 370 (M$^+$).

Step B 3-(3,4-Dimethoxyphenyl)-7-phenylheptanoic acid

A solution of ethyl 3-(3,4-dimethoxyphenyl)-7-phenylheptanoate (0.3 g, 0.8 mmol) and 10% sodium hydroxide (5 mL) in ethanol (10 mL) is heated under reflux for 30 minutes. The mixture is cooled and is added to aqueous HCl and is extracted with ether. The organic layer is washed with water and is dried over MgSO$_4$. The solvent is removed in vacuo to afford 3-(3,4-dimethoxyphenyl)-7-phenylheptanoic acid (0.25 g, 92%); MS (EI) m/e 342 (M$^+$).

Step C

N-hydroxy-3-(3,4-dimethoxyphenyl-7-phenylheptanamide

To a solution of 3-(3,4-dimethoxyphenyl)-7-phenylheptanoic acid (0.25 g, 0.7 mmol) in dichloromethane (20 mL) is added 2 M oxalyl chloride (few mL). The solution is stirred at room temperature for 30 minutes. The solvent is removed in vacuo and the residue is dissolved in dichloromethane. To this solution is added O-(trimethylsilyl)hydroxylamine (0.2 mL). The mixture is stirred at room temperature for 1 hour. The mixture is poured into aqueous HCl and is extracted with dichloromethane. The organic layer is washed with water and is dried over MgSO$_4$. The solvent is removed in vacuo and the residue is chromatographed on silica gel (100% ethyl acetate and then 100% methanol). The product residue is triturated with ethyl acetate and is filtered. The evaporated filtrate is dissolved in methanol and is diluted with water. The solution is lyophilized to produce N-hydroxy-3-(3,4-dimethoxyphenyl-7-phenylheptanamide (0.03 g, 11%) $^1$H-NMR (300 MHz, CDCl$_3$) δ (TMS) 1.10–1.78 (m, 6H), 2.18–2.64 (m, 4H), 2.94–3.08 (m,1H), 3.88 (s, 6H), 6.60–6.82 (m, 3H), 7.04–7.28 (m, 5H); MS (EI) m/e 357 (M$^+$).

EXAMPLE 29

(+)- and (−)-(2S, 3R)-N-hydroxy-2-(2-benzenesulfonylethyl)-3-(3,4-dimethoxyphenylsulfonyl)-7-phenylheptanamide The titled compounds are prepared according to the following steps:

Step A

4-Phenylsulfanylbutanoic acid

To a suspension of sodium hydride (60% in mineral oil, 10.4 g, 0.26 mol) in anhydrous THF (400 mL) at ambient temperature is added thiophenol (26 g, 0.23 mol) dropwise via syringe. The resulting white suspension is stirred for 30 minutes under a nitrogen atmosphere then γ-butyrolactone (22.4 g, 0.26 mol) is added. The mixture is warmed to gentle reflux and stirred for 6 hours after which it became a solid mass and is allowed to cool to room temperature and stand overnight. The mixture is dissolved in water (1200 mL) containing 1 N NaOH (100 mL) and is extracted with diethyl ether (2×500 mL). The aqueous layer is acidified with 1N HCl and extracted with diethyl ether (3×500 mL). The organic extracts are washed with brine (300 mL) then dried over $MgSO_4$, filtered and concentrated to afford a white solid which is chromatographed on silica gel (pet-ether/EtOAc, 19:1→9:1) to afford 4-phenylsulfanylbutanoic acid (36.6 g, 79%) as a white solid. TLC analysis [pet-ether/EtOAc, 1:1, $R_f$ (thiophenol)=0.90, $R_f$ (acid)=0.50]. m.p. 73–74° C.; $^1H$ NMR (300 MHz, $CDCl_3$) δ 1.95 (quint, J=7.1 Hz, 2H), 2.52 (t, J=7.2 Hz, 2H), 2.97 (t, J=7.1 Hz, 2H), 7.1–7.3 (m, 5H) ppm. Mass spectrum (EI) m/z 196 $(M)^+$.

Step B

4-Phenylsulfonylbutanoic acid.

To a solution containing 4-phenylsulfanylbutanoic acid (16 g, 81.5 mmol) in methanol (300 mL) at 0° C. is added a solution of oxone (72.5 g, 122 mmol) in water (300 mL). The reaction mixture is allowed to slowly warm to ambient temperature. After 6 hours, the heterogeneous mixture is concentrated in vacuo to remove methanol and the concentrate is dissolved in water (300 mL). The aqueous solution is saturated with sodium chloride then extracted with diethyl ether (2×200 mL) and ethyl acetate (200 mL). The combined organic extracts are washed with $Na_2S_2O_3$ (100 mL), brine (100 mL), dried over anhydrous $Na_2SO_4$, filtered and concentrated to provide a mixture of 4-phenylsulfonyl-butanoic acid and methyl 4-phenylsulfonylbutanoate.

The crude product mixture is dissolved in 1:1:1 MeOH/THF/water (150 mL). At ambient temperature, LiOH monohydrate (3.8 g, 89.6 mmol) is added in one portion. After 16 hours, the reaction mixture is concentrated in vacuo then diluted with water (100 mL). The yellow solution is treated with decolorizing carbon (2 g) and filtered through a pad of Celite. The solids are washed with water (3×50 mL) and the pale yellow filtrate is washed with diethyl ether (2×50 mL). The aqueous solution is acidified with concentrated HCl (20 mL) and extracted with diethyl ether (2×100 mL). The combined organic extracts are washed with brine (50 mL), dried over anhydrous $Na_2SO_4$, filtered and concentrated. The crude acid is purified by silica gel chromatography ($CH_2Cl_2$→5% $MeOH/CH_2Cl_2$) to afford 4-phenylsulfonylbutanoic acid (16.1 g, 87%) as a white solid which is homogeneous by TLC analysis (hexane/ethyl acetate, 1:1, $R_f$ (sulfide)=0.45, $R_f$ (sulfone)=0.15). m.p. 94–95° C.; $^1H$ NMR (300 MHz, $CDCl_3$) δ 2.01 (dt, J=7.5, 7.1 Hz, 2H), 2.50 (t, J=7.1 Hz, 2H), 3.17 (t, J=7.5 Hz, 2H), 7.53–7.92 (m, 5H) ppm. Mass spectrum (EI) m/z 229 $(M+H)^+$.

Step C (+)-4-Benzyl-3-(4-phenylsulfanylbutanoyl)oxazolidin-2-one

To a solution containing (S)-(–)-4-benzyl-2-oxazolidinone (4.9 g, 28 mmol) in anhydrous THF (50 mL) at –78° C. is added n-butyllithium (2.5 M in hexane, 11.2 mL, 28 mmol) dropwise over 10 minutes and the resulting deep yellow solution is stirred at –78° C. under nitrogen atmosphere for 1 hour. In a separate flask, a solution of 4-phenylsulfanylbutanoic acid (5 g, 25.5 mmol) in anhydrous THF (50 mL) is cooled to 0° C. and trimethylacetyl chloride (3.5 mL, 28 mmol) is added. Triethylamine (4.3 mL, 30.6 mmol) is then added dropwise and the resulting white slurry is stirred at 0° C. for 1 hour. The anion solution is added via cannula to the mixed anhydride slurry and the resulting pale yellow, heterogeneous mixture is stirred at 0° C. for 30 minutes then quenched with saturated aqueous ammonium chloride solution.

The mixture is combined with the quenched product of a reaction performed on identical scale and concentrated to 50% volume in vacuo. The residue is partitioned between water (200 mL) and ethyl acetate (200 mL) and the aqueous layer is extracted with ethyl acetate (2×200 mL). The combined organic extracts are washed successively with 5% $NaHCO_3$ (3×100 mL), water (100 mL) and brine (100 mL) then dried over $MgSO_4$, filtered and concentrated to afford a pale yellow oil which crystallized upon standing. The crude product is triturated with diethyl ether to afford 4-benzyl-3-(4-phenylsulfanylbutanoyl)oxazolidin-2-one (12.5 g, 69%) as a white solid. TLC analysis [pet-ether/EtOAc, 2:1, $R_f$ (acid)=0.30, $R_f$ (oxazolidinone)=0.65]. m.p. 84–85° C.; $[α]^{23}_D$+47.8° (c 0.5, $CHCl_3$); $^1H$ NMR (300 MHz, $CDCl_3$) δ 2.03 (quint. J=7.1 Hz, 2H), 2.75 (dd, J=13.4, 9.6 Hz, 1H), 3.02 (t, J=7.1 Hz, 2H), 3.09 (dt, J=7.1, 2.4 Hz, 2H), 3.27 (dd, J=13.4, 3.4 Hz, 1H), 4.17 (m, 2H), 4.65 (m, 1H), 7.1–7.4 (m, 10H) ppm. Mass spectrum (EI) m/z 355 $(M)^+$.

Step D (–)-4-Benzyl-3-(4-phenylsulfonylbutanoyl)-oxazolidin-2-one

A solution containing 4-phenylsulfonylbutanoic acid (5 g, 21.9 mmol) in anhydrous THF (50 mL) is cooled to –78° C. Trimethylacetyl chloride (2.9 g, 24.1 mmol) is then added followed by the addition of triethylamine (2.66 g, 26.3 mmol). The heterogeneous mixture is stirred 1 hour at –78° C.

In a separate flask, a solution containing (R)-(+)-4-benzyl-2-oxazolidinone (4.27 g, 24.1 mmol) in anhydrous THF (50 mL) is cooled to –78° C. followed by the addition of n-BuLi (1 M in hexanes, 15 mL, 24.1 mmol) via syringe. After 1 hour at –78° C., the pre-formed mixed anhydride solution is added via cannula and the reaction mixture is maintained at –78° C. for an additional hour. The reaction is quenched with saturated aqueous $NH_4Cl$ (100 mL) and warmed to ambient temperature. The THF is removed in vacuo and the aqueous layer is partitioned between water (100 mL) and $CH_2Cl_2$ (100 mL). The layers are separated and the organic phase is washed with 5% $NaHCO_3$ (2×50 mL), brine (50 mL), dried over anhydrous $Na_2SO_4$, filtered and concentrated. The crude product is triturated in diethyl ether (200 mL) and the white solid (5.9 g, 69%) is collected on a Buchner funnel then washed with fresh diethyl ether (3×50 mL) and dried. TLC analysis, hexane/ethyl acetate, 1:1, $R_f$ (acid)=0.15, $R_f$ (2-oxazolidinone)=0.25, $R_f$ (product)=0.47. m.p. 110–111° C.; $[α]^{23}_D$–33.8° (c 1.4, $CHCl_3$); $^1H$ NMR (300 MHz, $CDCl_3$) δ 2.08 (m, 1H), 2.73 (dd, J=13.3, 9.5 Hz, 1H), 3.04 (dt, J=7.0, 2.5 Hz, 2H), 3.22 (m, 3H), 4.16 (m, 2H), 4.61 (m, 1H), 7.14–7.94 (m, 10H) ppm. Mass spectrum (EI) m/z 387 $(M)^+$.

Step E (+)-4-Benzyl-3-[3-hydroxy-7-phenyl-2-(2-phenylsulfanylethyl)heptanoyl]-oxazolidin-2-one To a solution containing (+)-4-benzyl-3-(4-phenylsulfanylbutanoyl)oxazolidin-2-one (2 g, 5.63 mmol) in anhydrous $CH_2Cl_2$ (30 mL) under nitrogen atmosphere at 0° C. is added di-n-butyl boron triflate (1 M in $CH_2Cl_2$, 6.6 mL, 6.59 mmol). To the resulting brown solution is added triethylamine (1 mL, 7.38 mmol). The pale yellow solution is cooled to −78° C. and a solution of 5-phenyl-1-pentanal (1 g, 6.25 mmol) in CH$_2$Cl$_2$ (5 mL) is added via syringe. The mixture is stirred at −78° C. for 1 hour and at 0° C. for 45 minutes then is quenched by the dropwise addition of 3:1 methanol/pH 7 phosphate buffer (40 mL) followed by 2:1 methanol/30% H$_2$O$_2$ (30 mL). The biphasic mixture is stirred at 0° C. for 1 hour then is combined with an identical reaction performed on 1.3 g-scale and evaporated to 50% volume in vacuo. The residue is partitioned between 5% NaHCO$_3$ (200 mL) and diethyl ether (200 mL) and the layers are separated. The aqueous phase is extracted with diethyl ether (200 mL). The combined organic extracts are washed successively with 5% NaHCO$_3$ (3×100 mL), 5% Na$_2$S$_2$O$_3$ (3×100 mL), water (100 mL), brine (100 mL), dried over anhydrous MgSO$_4$, filtered and concentrated to afford a yellow oil which is chromatographed on silica gel (pet-ether/EtOAc 9:1→4:1) to provide (+)-4-benzyl-3-[3-hydroxy-7-phenyl-2-(2-phenylsulfanylethyl)heptanoyl]-oxazolidin-2-one (2 g, 43%) as a colorless oil. TLC analysis [pet-ether/EtOAc, 4:1, R$_f$ (oxazolidinone)=0.50, R$_f$ (aldol product)=0.20]. [α]$^{23}_D$+7.2° (c 1.3, CHCl$_3$). $^1$H NMR (300 MHz, CDCl$_3$) δ 1.50–1.60 (m, 7H), 1.90 (m, 1H), 2.20 (m, 1H), 2.31 (d, J=3.6 Hz, 1H), 2.58 (t, J=7.5 Hz), 2.67 (dd, J=13.3, 9.9 Hz), 2.85 (m, 1H), 3.00 (m, 1H), 3.32 (dd, J=13.3, 3.4 Hz), 3.88 (m, 1H), 4.20 (m, 2H), 4.65 (m, 1H), 7.1–7.35 (m, 15H) ppm. Mass spectrum (FAB) m/z 517 (M)$^+$.

Step F (−)-4-Benzyl-3-[3-hydroxy-7-phenyl-2-(2-phenylsulfonylethyl)heptanoyl]-oxazolidin-2-one A solution containing (−)-4-benzyl-3-(4-phenylsulfonylbutanoyl)oxazolidin-2-one (2 g, 5.16 mmol) in anhydrous CH$_2$Cl$_2$ (20 mL) is cooled to 0° C. Di-n-butylboron triflate (1 M in CH$_2$Cl$_2$, 6 mL, 6.03 mmol) is added by syringe over 15 minutes followed by the addition of triethylamine (0.68 g, 6.76 mmol). The clear yellow solution is then cooled to −78° C. Freshly distilled 5-phenylpentanal (0.92 g, 5.72 mmol) in anhydrous CH$_2$Cl$_2$ (2 mL) is added dropwise to the reaction mixture. After 30 min, the reaction mixture is warmed to 0° C. and maintained at this temperature for 1 hour. The reaction mixture is quenched by the slow addition of 3:1 MeOH/pH 7 phosphate buffer (30 mL) followed by 2:1 MeOH/30% H$_2$O$_2$ (30 mL) being careful to keep the temperature below 5° C. After the addition is complete, the reaction is maintained an additional hour at 0° C. then concentrated to half-volume in vacuo. The mixture is then diluted with diethyl ether (100 mL) and water (100 mL) and the layers are separated. The organic phase is washed with 5% NaHCO$_3$ (3×50 mL), aqueous NaHSO$_3$ (3×50 mL), water (50 mL), brine (50 mL), dried over anhydrous Na$_2$SO$_4$, filtered and concentrated. The crude product is combined with the crude material obtained from four additional reactions performed on identical scale and purified by silica gel chromatography (CH$_2$Cl$_2$/diethyl ether, 19:1→9:1) to provide 4 g (35%) of (−)-4-benzyl-3-[3-hydroxy-7-phenyl-2-(2-phenylsulfonylethyl)-heptanoyl]-oxazolidin-2-one as a colorless, viscous oil which is homogeneous by TLC analysis [CH$_2$Cl$_2$/diethyl ether, 19:1, R$_f$ (oxazolidinone)=0.45, R$_f$ (aldol product)=0.40]. [α]$^{23}_D$−20° (c 7.5, CHCl$_3$); $^1$H NMR (300 MHz, CDCl$_3$) δ 1.42–1.58 (m, 6H), 2.06 (m, 1H), 2.20 (m, 1H), 2.24 (d, J=4 Hz, 1H), 2.58 (t, J=7.5 Hz, 2H), 2.69 (dd, J=13.3, 9.9 Hz, 1H), 3.24 (m, 3H), 3.86 (m, 1H), 3.98 (quint. J=4.2 Hz, 1H), 4.16 (m, 2H), 4.65 (m, 1H), 7.18–7.52 (m, 10H), 7.59 (m, 2H), 7.68 (m, 1H), 7.90 (m, 2H) ppm. Mass spectrum (FAB) m/z 550 (M+H)$^+$.

Step G (+)-4-Benzyl-3-[3-hydroxy-7-phenyl-2-(2-phenylsulfonylethyl)]-heptanoyl-oxazolidin-2-one To a solution containing (+)-4-benzyl-3-[3-hydroxy-7-phenyl-2-(2-phenylsulfanylethyl)]-heptanoyl-oxazolidin-2-one (2 g, 3.87 mmol) in CH$_2$Cl$_2$ (100 mL) at 0° C. is added m-CPBA (75%, 0.89 g, 3.87 mmol) and the mixture is stirred at 0° C. for 20 minutes m-CPBA (75%, 0.89 g, 3.87 mmol) is added and the mixture is stirred at 0° C. for a further 20 minutes and then at ambient temperature for 1 hour. The mixture is then diluted with CH$_2$Cl$_2$ (200 mL) and washed successively with water (200 mL), 5% Na$_2$S$_2$O$_3$ (2×100 mL), 5% NaHCO$_3$ (4×100 mL), water (100 mL), brine (100 mL), dried over anhydrous MgSO$_4$, filtered and concentrated to afford a colorless oil. The crude product is combined with the product from a reaction performed on identical scale and chromatographed on silica gel (pet-ether/EtOAc, 2:1) to afford (+)-4-benzyl-3-[3-hydroxy-7-phenyl-2-(2-phenylsulfonylethyl)]-heptanoyl-oxazolidin-2-one (3.8 g, 89%) as a white foam. TLC analysis [pet-ether/EtOAc, 2:1, R$_f$(sulfide)=0.70, R$_f$(sulfone)=0.50]. [α]$^{23}_D$+20.3° (c 0.6, CHCl$_3$). m.p. 40–42° C. $^1$H NMR (300 MHz, CDCl$_3$) δ 1.42–1.58 (m, 6H), 2.06 (m, 1H), 2.20 (m, 1H), 2.24 (d, J=4.0 Hz, 1H), 2.58 (t, J=7.5 Hz, 2H), 2.69 (dd, J=13.3, 9.9 Hz, 1H), 3.24 (m, 3H), 3.86 (m, 1H), 3.98 (quint. J=4.2 Hz, 1H), 4.16 (m, 2H), 4.65 (m, 1H), 7.18–7.52 (m, 10H), 7.59 (m, 2H), 7.68 (m, 1H), 7.90 (m, 2H) ppm. Mass spectrum (FAB) m/z 550 (M+H)$^+$.

Step H (−)-2-(2-Benzenesulfonylethyl)-3-hydroxy-7-phenylheptanoic acid

To a solution containing (+)-4-benzyl-3-[3-hydroxy-7-phenyl-2-(2-phenylsulfonylethyl)]-heptanoyl-oxazolidin-2-one (3.8 g, 6.92 mmol) in THF (40 mL) and water (10 mL) at 0° C. is added 30% H$_2$O$_2$ (2.83 mL, 27.6 mmol) dropwise followed by LiOH monohydrate (0.46 g, 11 mmol) in one portion. The mixture is stirred at 0° C. for 3.5 hours then sodium thiosulfate (3 g) is added and the mixture is stirred for 15 minutes then partitioned between 1N HCl (200 mL) and ethyl acetate (200 mL). The aqueous layer is extracted with ethyl acetate (2×100 mL) and the combined organic extracts are washed successively with 5% NaS$_2$O$_3$ (2×100 mL), water (50 mL), brine (50 mL), dried over anhydrous MgSO$_4$, filtered and concentrated to afford a pale yellow oil. The crude product is combined with the product of an identical reaction performed on 190 mg-scale and chromatographed on silica gel (CH$_2$Cl$_2$→CH$_2$Cl$_2$:Et$_2$O, 2:1) then re-chromatographed on silica (CH$_2$Cl$_2$→CH$_2$Cl$_2$:Et$_2$O, 4:1→2:1→1:1+5% MeOH) to afford (−)-2-(2-benzenesulfonylethyl)-3-hydroxy-7-phenylheptanoic acid (2.55 g, 90%) as a hygroscopic, white foam. TLC analysis [pet-ether/EtOAc, 1:1, R$_f$(oxazolidinone)=0.90, R$_f$(acid)=0.15]. [α]$^{23}_D$−7.1° (c 0.9, CHCl$_3$); $^1$H NMR (300 MHz, CDCl$_3$) δ 1.25–1.62 (m, 7H), 1.91 (broad s, 1H), 2.10 (m, 1H), 2.52 (m, 3H), 3.15 (m, 1H), 3.34 (m, 1H), 3.88 (broad s, 1H), 7.12–7.25 (m, 5H), 7.55 (m, 3H), 7.87 (d, J=7.6 Hz, 2H) ppm. Mass spectrum (EI) m/z 390 (M)$^+$.

Step I (+)-2-(2-Benzenesulfonylethyl)-3-hydroxy-7-phenylheptanoic acid (+)-2-(2-Benzenesulfonylethyl)-3-hydroxy-7-phenylheptanoic acid is prepared from (−)-4-benzyl-3-[3-hydroxy-7-phenyl-2-(2-phenylsulfonylethyl)]-heptanoyloxazolidin-2-one (3.8 g, 6.91 mmol) using the procedure described above. The final product (2.45 g, 91%) is obtained as a hygroscopic, white solid which is identical to its enantiomer by TLC and $^1$H NMR analysis. [α]$^{23}_D$+2.1° (c 4.1, CHCl$_3$). Mass spectrum (FAB) m/z 391 (M+H)$^+$.

Step J (−)-3-(2-Benzenesulfonylethyl)-4-(4-phenylbutyl)oxetan-2-one

To a solution containing (−)-2-(2-benzenesulfonylethyl)-3-hydroxy-7-phenylheptanoic acid (1 g, 2.56 mmol) in anhydrous pyridine (17 mL) under nitrogen atmosphere at 0° C. is added freshly distilled benzenesulfonyl chloride (0.89 g, 5.13 mmol) via syringe. The resulting dark yellow/orange-colored solution is cooled to −20° C. After 16 hours, the mixture is partitioned between ice/water (100 mL) and ethyl acetate (50 mL) and the layers are separated. The aqueous phase is extracted with ethyl acetate (2×50 mL) and the combined organic extracts are washed successively with water (4×50 mL), brine (50 mL), dried over anhydrous $MgSO_4$, filtered and concentrated to afford a yellow oil. The crude product is combined with the product of an identical reaction performed on 1.55 g-scale and chromatographed on silica gel (pet-ether/EtOAc, 4:1) to afford (−)-3-(2-benzenesulfonyl-ethyl)-4-(4-phenylbutyl)-oxetan-2-one (1.07 g, 44%) as a pale yellow oil. TLC analysis [pet-ether/EtOAc, 2:1, $R_f$(acid)=0.05, $R_f$(lactone)=0.65]. $[\alpha]^{23}_D$ −10.1° (c 1.0, $CHCl_3$); $^1H$ NMR (300 MHz, $CDCl_3$) δ 1.36–1.80 (m, 6H), 2.16 (m, 2H), 2.62 (t, J=7.5 Hz, 2H), 3.16 (m, 1H), 3.35 (m, 1H), 3.79 (m, 1H), 4.56 (m, 1H), 7.16 (m, 3H), 7.28 (m, 2H), 7.69 (m, 2H), 7.79 (m, 1H), 7.91 (m, 2H) ppm. Mass spectrum (EI) m/z 373 $(M+H)^+$.

Step K (+)-3-(2-Benzenesulfonylethyl)-4-(4-phenylbutyl)oxetan-2-one (+)-3-(2-Benzenesulfonylethyl)-4-(4-phenylbutyl)oxetan-2-one is prepared from (+)-2-(2-benzenesulfonylethyl)-3-hydroxy-7-phenylheptanoic acid (0.87 g, 2.22 mmol) using the procedure described above. The final product (0.31 g, 37%) is obtained as a viscous, orange-colored oil which is identical to its enantiomer by TLC, MS and $^1H$ NMR analysis. $[\alpha]^{23}_D$+8.9° (c 2.2, $CHCl_3$).

Step L (−)-2-(2-Benzenesulfonyl-ethyl)-3-(3,4-dimethoxyphenylsulfanyl)-7-phenyl-heptanoic acid To a vigorously stirring suspension of cesium carbonate (0.88 g, 2.69 mmol) in anhydrous DMF (10 mL) under a nitrogen atmosphere is added 3,4-dimethoxythiophenol (0.45 g, 2.69 mmol) in a dropwise fashion. The white heterogeneous mixture is stirred for 15 minutes then a solution containing (−)-3-(2-benzenesulfonylethyl)-4-(4-phenylbutyl)-oxetan-2-one (0.50 g, 1.34 mmol) in anhydrous DMF (4 mL) is added. The pale yellow heterogeneous mixture is stirred at room temperature for 2.5 hours then partitioned between water (50 mL) and diethyl ether (50 mL). Aqueous HCl (1 N, 5 mL) is added and the layers are separated. The aqueous phase is extracted with diethyl ether (2×20 mL) and the combined organic extracts are washed with water (10×10 mL), brine (20 mL), dried over anhydrous $MgSO_4$, filtered and concentrated to afford a pale yellow oil. The crude product is chromatographed on silica gel ($CH_2Cl_2 \rightarrow CH_2Cl_2$:MeOH, 19:1) to afford a colorless oil which is dissolved in diethyl ether (100 mL) and washed with water (10×30 mL) to remove residual DMF. The organic phase is washed with brine (30 mL), dried over anhydrous $MgSO_4$, filtered and concentrated to afford (−)-2-(2-benzenesulfonylethyl)-3-(3,4-dimethoxyphenylsulfanyl)-7-phenylheptanoic acid (0.57 g, 78%) as a white foam. TLC analysis [hexane/EtOAc, 2:1, $R_f$(lactone)=0.65, $R_f$(acid)=0.05]. $[\alpha]^{23}_D$−35.3° (c 1.0, $CHCl_3$); $^1H$ NMR (300 MHz, $CDCl_3$) δ 1.31–1.70 (m, 6H), 2.00 (m, 1H), 2.30 (m, 1H), 2.56 (m, 3H), 2.95 (m, 1H), 3.25 (m, 2H), 3.84 (s, 3H), 3.85 (s, 3H), 6.77 (d, J=8.2 Hz, 1H), 6.95 (m, 2H), 7.15 (m, 3H), 7.25 (m, 2H), 7.55 (m, 2H), 7.65 (m, 1H), 7.90 (m, 2H) ppm. Mass spectrum (FAB) m/z 542 $(M)^+$.

Step M (+)-2-(2-Benzenesulfonylethyl)-3-(3,4-dimethoxyphenylsulfanyl)-7-phenylheptanoic acid (+)-2-(2-Benzenesulfonylethyl)-3-(3,4-dimethoxyphenylsulfanyl)-7-phenyl-heptanoic acid is prepared from (+)-3-(2-benzenesulfonylethyl)-4-(4-phenylbutyl)-oxetan-2-one (0.34 g, 0.91 mmol) using the procedure described above. The final product (0.42 g, 85%) is obtained as a white foam which is identical to its enantiomer by TLC, MS and $^1H$ NMR analysis. $[\alpha]^{23}_D$+24.8° (c 2.9, $CHCl_3$).

Step N (−)-N-hydroxy-2-(2-benzenesulfonylethyl)-3-(3,4-dimethoxyphenylsulfanyl)-7-phenylheptanamide To a solution containing (−)-2-(2-benzenesulfonylethyl)-3-(3,4-dimethoxyphenylsulfanyl)-7-phenylheptanoic acid (285 mg, 0.53 mmol) in anhydrous $CH_2Cl_2$ (10 mL) under nitrogen atmosphere is added anhydrous DMF (41 μL, 0.53 mmol) followed by oxalyl chloride (2 M in $CH_2Cl_2$, 0.66 mL, 1.31 mmol). The yellow solution is stirred for 30 minutes then O-(trimethylsilyl)hydroxylamine (0.32 mL, 2.65 mmol) is added dropwise. The resulting white precipitate is stirred for 10 minutes then partitioned between 1 N HCl (50 mL) and ethyl acetate (50 mL). The aqueous layer is extracted with ethyl acetate (2×20 mL) and the combined organic extracts are washed with water (30 mL), brine (30 mL), dried over anhydrous $MgSO_4$, filtered and concentrated to afford a pale yellow oil. The crude product is combined with the product of a reaction performed on identical scale and chromatographed on silica gel ($CH_2Cl_2 \rightarrow CH_2Cl_2$:MeOH, 19:1) to afford (−)-N-hydroxy-2-(2-benzenesulfonylethyl)-3-(3,4-dimethoxyphenylsulfanyl)-7-phenylheptanamide (560 mg, 95%) as a cream-colored foam. TLC analysis [pet-ether/EtOAc, 1:2, $R_f$(carboxylic acid)=0.45, $R_f$(hydroxamate)=0.40]. $[\alpha]^{23}_D$−28° (c 1.1, $CHCl_3$); $^1H$ NMR (300 MHz, $CDCl_3$) δ 1.40–1.80 (m, 6H), 2.10 (m, 1H), 2.22 (m, 1H), 2.60 (m, 2H), 2.68 (m, 1H), 3.05 (broad s, 3H), 3.83 (s, 3H), 3.84 (s, 3H), 6.76 (d, J=8.7 Hz, 1H), 6.98 (m, 2H), 7.12 (m, 3H), 7.28 (m, 2H), 7.52 (m, 2H), 7.64 (t, J=7.3 Hz, 1H), 7.84 (d, J=7.4 Hz, 2H), 8.85 (broad s, 1H) ppm. Mass spectrum (FAB) m/z 557 $(M)^+$.

Step O (+)-N-hydroxy-2-(2-benzenesulfonylethyl)-3-(3,4-dimethoxyphenylsulfanyl)-7-phenylheptanamide (+)-N-hydroxy-2-(2-benzenesulfonylethyl)-3-(3,4-dimethoxyphenylsulfanyl)-7-phenylheptanamide is prepared from (+)-2-(2-benzenesulfonylethyl)-3-(3,4-dimethoxyphenylsulfanyl)-7-phenylheptanoic acid (0.5 g, 0.92 mmol) using the procedure described above. The final product (0.25 g, 48%) is obtained as a white foam which is identical to its enantiomer by TLC, MS and $^1H$ NMR analysis. $[\alpha]^{23}_D$+27.1° (c 1.7, $CHCl_3$).

Step P (−)-(2S, 3R)-N-hydroxy-2-(2-benzenesulfonylethyl)-3-(3,4-dimethoxyphenylsulfonyl)-7-phenylheptanamide To a solution containing (−)-N-hydroxy-2-(2-benzenesulfonylethyl)-3-(3,4-dimethoxyphenylsulfanyl)-7-phenylheptanamide (560 mg, 1.01 mmol) in $CH_2Cl_2$ (25 mL) at 0° C. is added m-CPBA (75%, 0.23 g, 1.01 mmol) in one portion. The mixture is stirred at 0° C. for 15 minutes then m-CPBA (75%, 0.23 g, 1.01 mmol) is added. The mixture is stirred at ambient temperature for 45 minutes then diluted with $CH_2Cl_2$ (100 mL) and washed successively with 5% $NaS_2O_3$ (50 mL), 5% $NaHCO_3$ (50 mL), water (50 mL), brine (50 mL), dried over anhydrous $MgSO_4$, filtered and concentrated to afford a colorless oil. The crude product is chromatographed on silica gel ($CH_2Cl_2 \rightarrow 1\%$ MeOH/$CH_2Cl_2$) to provide a hygroscopic white foam which is re-chromatographed ($CH_2Cl_2 \rightarrow 2\%$ MeOH/$CH_2Cl_2 \rightarrow 5\%$ MeOH/$CH_2Cl_2$) to afford (−)-(2S, 3R)-N-hydroxy-2-(2-benzenesulfonylethyl)-3-(3,4-dimethoxyphenylsulfonyl)-7-phenyl-heptanamide (212 mg, 36%) as a white foam. TLC analysis [pet-ether/EtOAc, 1:2, $R_f$(sulfide)=0.45, $R_f$(sulfone)=0.40]. m.p. 78–81° C. $[\alpha]^{23}_D$ −18.4° (c 3.7, $CHCl_3$). $^1H$ NMR (300 MHz, $d_6$-DMSO) δ 1.06 (m, 2H), 1.22 (m, 2H), 1.69 (m, 2H), 1.90 (m, 2H), 2.30 (m, 2H), 2.82 (m, 1H), 3.08 (m, 2H), 3.34 (m, 1H), 3.79 (s, 3H), 3.83 (s, 3H), 7.01 (d, J=6.9 Hz, 2H), 7.10 (m, 2H), 7.20 (m, 2H), 7.26 (d, J=2.1 Hz, 1H), 7.33 (dd, J=8.5, 2.1 Hz, 1H), 7.66 (m, 2H), 7.85 (m, 1H), 7.90 (m, 2H), 8.88 (s, 1H), 10.68 (s,1H) ppm. Mass spectrum (ISp) m/z 590 (M+H)$^+$. Analysis ($C_{29}H_{35}NO_8S_2$) Calc. for 0.975 mol $H_2O$: C, 57.41; H, 6.14; N, 2.31. Found C, 57.40; H, 5.90; N, 2.16.

Step Q (+)-(2S,3R)-N-hydroxy-2-(2-benzenesulfonylethyl)-3-(3,4-dimethoxyphenylsulfonyl)-7-phenylheptanamide (+)-(2S,3R)-N-hydroxy-2-(2-benzenesulfonylethyl)-3-(3,4-dimethoxyphenyl-sulfonyl)-7-phenylheptanamide is prepared from (+)-N-hydroxy-2-(2-benzenesulfonylethyl)-3-(3,4-dimethoxyphenylsulfanyl)-7-phenylheptanamide (0.10 g, 0.17 mmol) using the procedure described above. The final product (85 mg, 80%) is obtained as a white glass which is identical to its enantiomer by TLC and $^1H$ NMR analysis. m.p. 76–80° C. $[\alpha]^{23}_D$ +16.2° (c 1.7, $CHCl_3$). Mass Spectrum (FAB) m/z 590 (M+H)$^+$. Analysis ($C_{29}H_{35}NO_8S_2$) Calc. for 0.5 mol $H_2O$: C, 58.18; H, 6.06; N, 2.34. Found C, 58.19; H, 6.00; N, 2.26.

EXAMPLE 30

N-hydroxy-3-(3,4-dimethoxybenzenesulfonyl)-4-phenylbutyramide

The titled compound is prepared according to the following steps:

Step A 3-(3,4-Dimethoxyphenylsulfanyl)-4-phenylbutanoic acid

A mixture of 4-phenylbut-2-enoic acid (2 g, 12.33 mmol) prepared as in Example 6, Step B, 3,4-dimethoxybenzenethiol (2.1 mL, 14.79 mmol, 1.2 eq), and piperidine (0.4 mL (3.7 mmol, 0.3 eq) is heated at 110° C. in a bomb for 18 hours. The reaction is partitioned between ethyl ether and 1 N HCl. The organic layer is dried over anhydrous $MgSO_4$ and concentrated in vacuo. The product is purified by flash silica gel chromatography to afford 3-(3,4-dimethoxyphenylsulfanyl)-4-phenylbutanoic acid as a yellow oil. (4.1 g, 100%): $^1$H-NMR (300 MHz, $CDCl_3$) δ (TMS) 2.54(d, 0.5×2H), 2.56(d, 0.5×2H), 2.83(d, 0.5×2H), 2.98(d, 0.5×2H), 3.56(m, 1H), 3.85(s, 3H), 3.88(s, 3H), 6.8(d, 1H), 6.97(d, 1H), 7.05(d, 0.5×1H), 7.09(d, 0.5×1H), 7.15–7.32(m, 5H).

Step B N-hydroxy-3-(3,4-dimethoxyphenylsulfanyl)-4-phenylbutyramide

To a solution of 2 g (6.02 mmol) of 3-(3,4-dimethoxyphenylsulfanyl)-4-phenylbutanoic acid in 50 mL of $CH_2Cl_2$ at 25° C. under argon is added 0.2 mL of DMF followed by 6.02 mL (12.03 mmol, 2 eq) of 2 M solution of oxalyl chloride in $CH_2Cl_2$. After stirring at 25° C. for 3 hours, the mixture is cooled to 0° C. and 3.7 mL (30.08 mmol, 5 eq) of O-trimethylsilylhydroxylamine is added. This mixture is then stirred at 25° C. for 18 hours. The reaction is partitioned between $CH_2Cl_2$ and 1 N HCl. The organic layer is dried over anhydrous $Na_2SO_4$ and concentrated in vacuo. The product is purificatied by flash silica gel chromatography to afford N-hydroxy-3-(3,4-dimethoxyphenylsulfanyl)-4-phenylbutyramide as a yellow crystalline solid. (1.7 g, 81%): $^1$H-NMR (300 MHz, DMSO-$d_6$) δ (TMS) 2.2(m, 2H), 2.81 (m, 2H), 3.6(m, 1H), 3.75(s, 6H), 6.89–7 (m, 3H), 7.17–7.35(m, 5H), 8.85(s, 1H), 10.5(s, 1H).

Step C

N-hydroxy-3-(3,4-dimethoxybenzenesulfonyl)-4-phenylbutyramide

To a solution of 1.7 g (4.9 mmol) of the N-hydroxy-3-(3,4-dimethoxyphenylsulfanyl)-4-phenylbutyramide in 50 mL of methanol at 0° C. is dropped in a solution of 6 g (9.79 mmol, 2 eq) of oxone dissolved in 50 mL of water. After stirring for 18 hours at 25° C. the reaction is concentrated in vacuo, then partitioned between ethyl acetate and water. The organic layer is dried over anhydrous $Na_2SO_4$ then concentrated in vacuo. The product is purificatied by flash silica gel chromatography and crystallized from $Et_2O$/hexanes to afford N-hydroxy-3-(3,4-dimethoxybenzenesulfonyl)-4-phenylbutyramide in the form of a white crystalline solid. (0.898 g, 48%): m.p. 77–79° C. $^1$H NMR (300 MHz, DMSO-$d_6$) δ (TMS) 2.12(d, 0.5×1H), 2.18(d, 0.5×1H), 2.5(d, 0.5×1H), 2.55(d, 0.5×1H), 2.68(d, 0.5×1H), 2.72(d, 0.5×1H), 3.05(d, 0.5×1H), 3.09(d, 0.5×1H), 3.82(s, 3H), 3.89(s, 3H), 3.95(m, 1H), 7.08–7.28(m, 7H), 7.42(d, 0.5×1H), 7.45(d, 0.5×1H), 8.78(s, 1H), 10.5(s, 1H).

EXAMPLE 31

N-hydroxy-3-(3,4-dimethoxybenzenesulfonyl)-3-phenylproprionamide

Step A 3-(3,4-Dimethoxyphenylsulfanyl)-4-phenylpropanoic acid

The titled compound is prepared according to Example 6, Step C except that cinnamic acid is used in place of 4-phenylbut-2-enoic acid and 3,4-dimethoxybenzenethiol is used in place of 4-methoxybenzenethiol to afford a white crystalline solid. (4.025 g, 94%): $^1$H-NMR (300 MHz, $CDCl_3$) δ (TMS) 2.95(m, 2H), 3.68(s, 3H), 3.85(s, 3H), 4.48(t, 1H), 6.6(s, 1H), 6.75(d, 1H), 6.92(d, 1H), 7.15(d, 2H), 7.18–7.28(m, 3H).

Step B

N-hydroxy-3-(3,4-dimethoxyphenylsulfanyl)-3-phenylpropionamide

The titled compound is prepared as in Example 6, Step D to afford a pale orange crystalline solid. (1.36 g, 65%): $^1$H-NMR (300 MHz, DMSO-$d_6$) δ (TMS) 2.58(m, 2H), 3.64(s, 3H), 3.72(s, 3H), 4.6(t, 1H), 6.7(s, 1H), 6.85(s, 2H), 7.15–7.32(m, 5H), 8.78(s, 1H), 10.45(s, 1H).

Step C

N-hydroxy-3-(3,4-dimethoxybenzenesulfonyl)-4-phenylpropionamide

The titled compound is prepared as in Example 6, Step E to afford a pale orange crystalline solid. Triturated with $Et_2O$ and filtered to afford a white powder. (0.43 g, 30%): m.p. 183–184° C. $^1$H-NMR (300 MHz, DMSO-$d_6$) δ (TMS) 2.3–2.4(m, 2H), 3.68(s, 3H), 3.72(s, 3H), 4.72–4.82(m, 1H), 6.9(s, 1H), 7.08(d, 1H), 7.12–7.22(m, 3H), 7.22–7.35(m, 3H), 8.78(s, 1H), 10.45(s, 1H).

EXAMPLE 32

3-(3,4-Dimethoxybenzenesulfonyl)-5-phenylpentanoic acid hydroxamide

Step A

5-Phenylpent-2-enoic acid t-butyl ester

The titled compound is prepared according to Example 6, Step A except that 3-phenylpropanal is used in place of phenylacetaldehyde to afford a yellow oil. (7.03 g, 81%): $^1$H-NMR (300 MHz, CDCl$_3$) δ (TMS) 1.45(s, 9H), 2.45(m, 2H), 2.75(t, 2H), 5.75(d, 0.5×1H), 5.8(d, 0.5×1H), 6.85(t, 0.5×1H), 6.9(t, 0.5×1H), 7.1–7.3(m, 5H).

Step B

5-Phenylpent-2-enoic acid

The titled compound is prepared as in Example 6, Step B to afford a white crystalline solid. (5.27 g, 99%): $^1$H-NMR (300 MHz, CDCl$_3$) δ (TMS) 2.58(m, 2H), 2.8(t, 2H), 5.82(d, 0.5×1H), 5.88(d, 0.5×1H), 7.05–7.35(m, 6H).

Step C 3-(3,4-Dimethoxyphenylsulfanyl)-5-phenylpentanoic acid

The titled compound is prepared as in Example 31, Step A to afford a white crystalline solid. (3.75 g, 95%): $^1$H-NMR (300 MHz, CDCl$_3$) δ (TMS) 1.89(m, 2H), 2.58(d, 0.5×2H), 2.62(d, 0.5×2H), 2.82(m, 1H), 2.95(m, 1H), 3.3(m, 1H), 3.85(s, 3H), 3.9(s, 3H), 6.8(d, 1H), 7 (d, 1H), 7.05(d, 0.5×1H), 7.1 (d, 0.5×1H), 7.15–7.32(m, 5H).

Step D 3-(3,4-Dimethoxyphenylsulfanyl)-5-phenylpentanoic acid hydroxamide

The titled compound is prepared as in Example 31, Step B to afford a Brown oil. (1.77 g, 85%): $^1$H-NMR (300 MHz, CDCl$_3$) δ (TMS) 1.85(m, 2H), 2.32(d, 2H), 2.7–2.95(m, 2H), 3.32(m, 1H), 3.82(s, 3H), 3.88(s, 3H), 6.75(d, 1H), 6.92(s, 1H), 7 (d, 1H), 7.1–7.3(m, 5H), 8.7(bs, 1H)

Step E 3-(3,4-Dimethoxybenzenesulfonyl)-5-phenylpentanoic acid hydroxamide

The titled compound is prepared as in Example 31, Step C and the product triturated with 50% Et$_2$O in hexanes and filtered to afford a white powder. (1.5 g, 78%): m.p. 161–162° C. $^1$H-NMR (300 MHz, DMSO-d$_6$) δ (TMS) 1.7(m, 1H), 1.95(m, 1H), 2.25(d, 0.5×1H), 2.3(d, 0.5×1H), 2.45–2.75(m, 3H), 3.6(m, 1H), 3.82(s, 3H), 3.88(s, 3H), 7.08(d, 2H), 7.15–7.3(m, 5H), 7.42(d, 1H), 8.95(s, 1H), 10.62(s, 1H).

EXAMPLE 33

3-(3,4-Dimethoxybenzenesulfonyl)-6-phenylhexanoic acid hydroxamide

Step A 4-phenylbutrylaldehyde

To a solution of 20 mL (39.94 mmol, 1.2 eq) of oxalyl chloride in 100 mL of CH$_2$Cl$_2$ at −78° C. under argon is added dropwise 5.7 mL (79.88 mmol, 2.4 eq) of DMSO. After stirring for 1 hour at −78° C., 5 g (33.28 mmol) of 4-phenylbutanol dissolved in 20 mL of CH$_2$Cl$_2$ is added dropwise. After stirring for 2 hour at −78° C., 23.2 mL (166.42 mmol, 5 eq) of triethylamine is added dropwise. This then stirred at −78° C. for 0.5 hours, 0° C. for 1 hour, and 25° C. for 1 hour. The reaction is partitioned between CH$_2$Cl$_2$ and 1 N HCl. The organic layer is washed well with water, dried over anhydrous MgSO$_4$ and concentrated in vacuo to afford 4-phenylbutrylaldehyde as a yellow oil. (5 g, 100%): $^1$H-NMR (300 MHz, CDCl$_3$) δ (TMS) 1.88–2.02(m, 2H), 2.45(t, 2H), 2.65(t, 2H), 2.64(t, 2H), 7.1–7.35(m, 5H), 9.72(s, 1H).

Step B

6-Phenylhex-2-enoic acid t-butyl ester

The titled compound is prepared according to Example 6, Step A except that 4-phenylbutrylaldehyde is used in place of phenylacetaldehyde to afford a colorless oil. (2.34 g, 70%): $^1$H-NMR (300 MHz, CDCl$_3$) δ (TMS) 1.45(s, 9H), 1.78(m, 2H), 2.18(m, 2H), 2.64(t, 2H), 5.75(d, 1H), 6.85(t, 0.5×1H), 6.9(t, 0.5×1H), 7.1–7.3(m, 5H).

Step C

6-Phenylhex-2-enoic acid

The titled compound is prepared according to Example 6, Step B to afford a brown oil. (1.8 g, 100%): $^1$H-NMR (300 MHz, CDCl$_3$) δ (TMS) 1.8(m, 2H), 2.25(m, 2H), 2.65(t, 2H), 5.82(d,1H), 7.05–7.3(m, 6H), 11.72(s, 1H).

Step D 3-(3,4-Dimethoxyphenylsulfanyl)-6-phenylhexanoic acid

The titled compound is prepared according to Example 6, Step C to afford a yellow oil. (2.93 g, 78%): $^1$H-NMR (300 MHz, CDCl$_3$) δ (TMS) 1.62(m, 2H), 1.75–2 (m, 2H), 2.5–2.7(m, 4H), 3.32(m, 1H), 3.85(s, 3H), 3.9(s, 3H), 6.75 (d, 1H), 6.95(s, 1H), 7 (d, 1H), 7.15–7.3(m, 5H).

Step E 3-(3,4-Dimethoxyphenylsulfanyl)-6-phenylhexanoic acid hydroxamide

The titled compound is prepared according to Example 6, Step D to afford a yellow oil. (0.41 g, 98%): $^1$H-NMR (300 MHz, DMSO-d$_6$) δ (TMS) 1.32–1.6(m, 2H), 1.6–1.88(m, 2H), 2.1–2.22(m, 2H), 2.74(s, 1H), 2.79(s, 1H), 3.35(m, 1H), 3.78(s, 6H), 6.9(m, 2H), 6.95(s, 1H), 7.12–7.22(m, 3H), 7.22–7.3(m, 2H), 8.8(s, 1H), 10.43(s, 1H).

Step F 3-(3,4-Dimethoxybenzenesulfonyl)-6-phenylhexanoic acid hydroxamide

The titled compound is prepared according to Example 6, Step E to afford a white crystalline solid. (0.285 g, 64%): m.p. 161–162° C. $^1$H-NMR (300 MHz, DMSO-d$_6$) δ (TMS) 1.35–1.85(m, 4H), 2.1–2.22(m, 1H), 2.4–2.6(m, 4H), 3.58 (m, 1H), 3.85(s, 3H), 3.88(s, 3H), 7.04–7.32(m, 7H), 7.39(d, 1H), 8.91(s, 1H), 10.55(s, 1H).

EXAMPLE 34

3-(R*)-(3,4-Dimethoxybenzenesulfonyl)-2-(S*)-isopropyl-7-phenylheptanoic acid hydroxamide Step A 5-phenylpentanal To a solution of 15.9 mL (182.65 mmol, 1.2 eq) of oxalyl chloride in 300 mL of CH$_2$Cl$_2$ at −78° C. under argon is added dropwise 25.9 mL (365.3 mmol, 2.4 eq) of DMSO in 40 mL of CH$_2$Cl$_2$. After stirring for 1 hour at −78° C., 25 g (152.21 mmol) of 5-phenyl-1-pentanol dissolved in 40 mL of CH$_2$Cl$_2$ is added dropwise. After stirring for 2 hour at −78° C., 106 mL (761.03 mmol, 5 eq) of triethylamine is added dropwise. This then stirred at −78° C. for 1 hours then at 25° C. for overnight. The reaction is partitioned between CH$_2$Cl$_2$ and 1 N HCl. The organic layer is washed with water, dried over anhydrous MgSO$_4$ and concentrated in vacuo to afford 23.52 g (95%) of 5-phenylpentanal in the form of a yellow oil.

Step B methyl 3-hydroxy-3-isopropyl-7-phenylheptanoate

To a solution of 2.4 mL (18.49 mmol, 1.5 eq) of isopropylamine in 50 mL of dry THF at −78° C. under argon is added 9.3 mL (14.8 mmol, 1.2 eq) of 1.6 M BuLi in hexanes solution. This is stirred at −78° C. for 1 hour at which time 1.8 mL (13.56 mmol, 1.1 eq) of methyl isovalerate is added dropwise. This mixture is stirred at −78° C. for 1.5 hours at which time 2 g (12.33 mmol) of 5-phenylpentanal in 10 mL of dry THF is added dropwise. This is stirred at −78° C. for 1 hour, then allowed to warm slowly to 0° C. over 3 hours. The reaction is quenched with saturated NH$_4$Cl solution and then partitioned between ether and saturated NH$_4$Cl solution. The organics are dried (Na$_2$SO$_4$) and concentrated in vacuo. The product is purified by flash silica gel chromatography to afford methyl 3-hydroxy-3-isopropyl-7-phenylheptanoate in the form of a yellow oil. (0.88 g, 26%): $^1$H-NMR (300 MHz, CDCl$_3$) δ (TMS) 0.95(t, 6H), 1.45(m, 3H), 1.6(m, 3H), 2.08(bs, 1H), 2.15(m, 1H), 2.35(t, 1H), 2.6(t, 2H), 3.68(s, 3H), 3.85(bm, 1H), 7.15(m, 3H), 7.25(m, 2H).

Step C 3-isopropyl-4-(4-phenylbutyl)oxetan-2-one

To a solution of 0.88 g (3.17 mmol) of the methyl 3-hydroxy-3-isopropyl-7-phenylheptanoate in 30 mL of 1:1:1-THF:MeOH:H$_2$O is added 1.08 g (25.36 mmol, 8 eq) of LiOH monohydrate and this is stirred at 25° C. for 1 month. This mixture is then acidified to pH=6 with 1 N HCl and then partitioned between ethyl acetate and water. The organics are dried (Na$_2$SO$_4$) and concentrated in vacuo to afford methyl 3-hydroxy-3-isopropyl-7-phenylheptanoic acid in the form of a pale yellow crystalline solid. (0.59 g, 70%): $^1$H-NMR (300 MHz, CDCl$_3$) δ (TMS) 0.98(d, 6H), 1.35(m, 1H), 1.55(m, 5H), 2.1(m, 1H), 2.35(t, 1H), 2.6(t, 2H), 3.88(m, 1H), 6.08(bs, 2H), 7.15(m, 3H), 7.25(m, 2H).

Step D 3-isopropyl-4-(4-phenylbutyl)oxetan-2-one

To a solution of 0.53 g (2 mmol) of the methyl 3-hydroxy-3-isopropyl-7-phenylheptanoic acid in 20 mL of pyridine under argon is added 0.51 mL (4 mmol, 2 eq) of benzenesulfonyl chloride. The mixture stirred at 25° C. for 18 hours an is then concentrated in vacuo. The product is purified by flash silica gel chromatography to afford 3-isopropyl-4-(4-phenylbutyl)oxetan-2-one in the form of a yellow oil. (0.38 g, 77%): $^1$H-NMR (300 MHz, CDCl$_3$) δ (TMS) 0.9(d, 3H), 1.15(d, 3H), 1.45(m, 1H), 1.7(m, 5H), 2.15(m, 1H), 2.62(t, 2H), 3.24(d, 0.5×1H), 3.28(d, 0.5×1H), 4.5(m, 1H), 7.15(m, 3H), 7.25(m, 2H).

Step E 3-(3,4-Dimethoxybenzenesulfanyl)-2-isopropyl-7-phenylheptanoic acid

To a solution of 0.35 mL (2.47 mmol, 1.6 eq) of 3,4-dimethoxybenzenethiol in 2 mL of 2-propanol at 0° C. is added 1.85 mL (1.85 mmol, 1.2 eq) of 1 N NaOH solution. The mixture is stirred at 15 minutes at 0° C. and 30 minutes at 25° C. then cooled to 0° C. To this is dropped in a solution of 0.38 g (1.54 mmol) of 3-isopropyl-4-(4-phenylbutyl) oxetan-2-one in 5 mL of 2-propanol. This is stirred at 0° C. for 1 hour then at 25° C. for 3 hours. This is acidified to pH=2 using 1 N HCl and concentrated in vacuo several times from methanol. Purification by flash silica gel chromatography afforded the 3-(3,4-dimethoxybenzenesulfanyl)-2-isopropyl-7-phenylheptanoic acid in the form of a yellow oil. (0.53 g, 82%): $^1$H-NMR (300 MHz, CDCl$_3$) δ (TMS) 1.0(t, 6H), 1.45(m, 1H), 1.6(m, 5H), 2.13(m, 1 H), 2.49(d, 0.5×1H), 2.52(d, 0.5×1H), 2.59 (bt, 2H), 3.1(m, 1H), 3.85(s, 3H), 3.88(s, 3H), 6.78(d,1H), 7.05(m, 2H), 7.15(m, 3H), 7.25(m, 2H).

Step F 3-(3,4-Dimethoxybenzenesulfanyl)-2-isopropyl-7-phenylheptanoic acid hydroxamide To a solution of 0.53 g (1.27 mmol) of 3-(3,4-dimethoxybenzenesulfanyl)-2-isopropyl-7-phenylheptanoic acid in 30 mL of CH$_2$Cl$_2$ at 25° C. under argon is added 3 drops of DMF followed by 1.3 mL (2.54 mmol, 2 eq) of 2 M oxalyl chloride in CH$_2$Cl$_2$ solution. This is stirred at 25° C. for 1.5 hours then 0.78 mL (6.36 mmol. 5 eq) of O-trimethylsilylhydroxylamine is added dropwise. This is stirred at 25° C. for 2 hours then is partitioned between CH$_2$Cl$_2$ and 1N HCl. The organics are dried (Na$_2$SO$_4$) and concentrated in vacuo. The residue is triturated with ether and the solid filtered to afford 3-(3,4-dimethoxybenzenesulfanyl)-2-isopropyl-7-phenylheptanoic acid hydroxamide in the form of a white powder. (0.37 g, 67%): $^1$H-NMR (300 MHz, CDCl$_3$) δ (TMS) 0.9(d, 3H), 0.98(d, 3H), 1.6(m, 6H), 2.1 (m, 2H), 2.49(t, 2H), 3.25(m, 1H), 3.85(s, 3H), 3.88(s, 3H), 6.78(d, 1H), 7.0(m, 2H), 7.14(d, 2H), 7.18(d, 1H), 7.26(m, 2H), 8.35(m, 1H).

Step G 3-(3,4-Dimethoxybenzenesulfonyl)-2-isopropyl-7-phenylheptanoic acid hydroxamide To a solution of 0.37 g (0.86 mmol) of the thiohydroxamic acid (7) in 20 mL of MeOH at 0° C. is dropped in a solution of 2.6 g (4.29 mmol, 5 eq) oxone dissolved in 15 mL of water. This is stirred at 0° C. for 0.5 hours then at 25° C. for 18 hours. The mixture is partitioned between ethyl acetate and water. The organics are dried(Na$_2$SO$_4$) and concentrated in vacuo. Purification by flash silica gel chromatography followed by trituration of the resulting oil with ether and hexanes afforded 3-(R*)-(3,4-Dimethoxybenzenesulfonyl)-2-(S*)-isopropyl-7-phenylheptanoic acid hydroxamide in the form of a white powder. (0.225 g, 57%): m.p. 173–174° C. $^1$H-NMR (300 MHz, DMSO-d$_6$) δ (TMS) 0.8(d, 3H), 0.9(d, 3H), 1.2(m, 1H), 1.4(m, 3H), 1.7(m, 1H), 1.85(m, 1H), 1.95(m, 1H), 2.45(m, 3H), 3.52(m, 1H), 3.8(s, 3H), 3.85(s, 3H), 7.1(m, 4H), 7.25(m, 3H), 7.38(d, 1H), 8.67(s, 1H), 10.5(s, 1H).

EXAMPLE 35

(2R,3R)-3-(3,4-Dimethoxyphenylsulfanyl)-2-methyl-7-phenylheptanoic acid hydroxyamide Step A (1S,2R)-cis-1 -(Toluene-4-sulfonylamino)indan-2-yl-(2S, 3S)-3-hydroxy-2-methyl-7-phenylheptanoate To a solution of (−)-(1S, 2R)-cis-1-toluenesulfonamide-2-proprionyloxy indane (6.4 g, 18 mmol) in CH$_2$Cl$_2$ (80 mL), cooled in an ice bath, is added 1 M titanium tetrachloride (21 mL, 21 mmol) dropwise over 10 minutes. This mixture is allowed to come to room temperature and stirred an additional 15 minutes. Then ethyl diisopropylamine (12 mL, 68 mmol) is added over 2 minutes and this mixture is stirred for 1 hour. In another flask, 5-phenylpentanal (5.8 g, 36 mmol) is dissolved in CH$_2$Cl$_2$ (90 mL) and 1 M titanium tetrachloride (42 mL, 42 mmol) is added over 6 minutes. The solution is then cooled to −78° C. To this is added the ester enolate dropwise over 35 minutes. This mixture is stirred for 1 hour at −78° C. and then quenched with ammonium chloride solution (25 mL). Additional water (100 mL) is added to break up the emulsion that has formed. The layers are separated and the aqueous layer extracted with $CH_2Cl_2$ (50 mL). The combined organic layers are washed with water (3×200 mL) until a pH of 6–7 is obtained and dried over $MgSO_4$. The solvent is removed in vacuo giving 12 g of residue. Two products are isolated by purification with a Prep 500 HPLC (silica, 38% ether in petroleum ether). The slower eluting material (2 g, 21%) is determined to be the syn-diastereoisomer, which gave compound 8 upon saponification. The faster eluting product is determined to be the desired anti-isomer, (1S,2R)-cis-1-(Toluene-4-sulfonylamino)indan-2-yl-(2S,3S)-3-hydroxy-2-methyl-7-phenylheptanoate (2.25 g, 24%): $^1$H NMR (300 MHz, $CDCl_3$) δ 7.81 (d, J=8.2 Hz, 2H), 7.33–7.14 (m, 11H), 5.96 (d, J=9.8 Hz, 1H), 5.37 (t, J=5.1 Hz, 1H), 4.89 (dd, J=9.7, 5.1 Hz, 1H), 3.57 (m, 1H), 3.1 (dd, J=17.2, 5.0 Hz, 1H), 2.88 (d, J=17.1 Hz, 1H), 2.58 (t, J=7.5 Hz, 2H), 2.44 (s, 3H), 2.46–2.42 (m, 1H), 1.54–1.25 (m, 6H), 1.08 (d, J=7.3 Hz, 3H); MS (ion spray) m/e 522 (M+H)$^+$.

Step B (−)-(2S,3S)-3-Hydroxy-2-methyl-7-phenylheptanoic acid

The (1S,2R)-cis-1-(Toluene-4-sulfonylamino)indan-2-yl-(2S,3S)-3-hydroxy-2-methyl-7-phenylheptanoate (2.2 g, 4.3 mmol) is dissolved in THF (20 mL) and to this is added a solution of lithium hydroxide monohydrate (0.45 g, 11 mmol) in water (10 mL). This mixture is stirred at room temperature for 2 hours, then diluted with water (20 mL) and extracted with ethyl acetate (3×30 mL). The aqueous layer is acidified with 2 N HCl to pH 3 and extracted again with ethyl acetate (2×100 mL). The organic layer is washed with brine (15 mL) and dried over $MgSO_4$. The solvent is removed in vacuo to give (−)-(2S,3S)-3-hydroxy-2-methyl-7-phenylheptanoic acid (0.81 g, 80%): $[a]_D^{23}$ −24° (c=1.0, $CHCl_3$); $^1$H NMR (300 MHz, $CDCl_3$) δ 7.30–7.25 (m, 2H), 7.20–7.16 (m, 3H), 3.69 (bs, 1H), 2.63 (t, J=7.5 Hz, 2H), 2.55 (t, J=7.0 Hz, 1H), 1.69–1.38 (m, 6H), 1.24 (d, J=7.3 Hz, 3H); MS (FAB) m/e 237 (M+H)$^+$.

Step C (3S,4S)-3-Methyl-4-(4-phenylbutyl)oxetan-2-one

A solution of (−)-(2S,3S)-3-hydroxy-2-methyl-7-phenylheptanoic acid (0.79 g, 3.3 mmol) in pyridine (30 mL) is cooled to 0° C. and benzenesulfonyl chloride (0.85 mL, 6.7 mmol) is added over 1 minute. The reaction is stirred in ice for 5 minutes, at room temperature for 2 hours and then at 0° C. for 16 hours. The reaction is poured into ice (40 mL) and extracted with ether (100 mL). The organic phase is washed with $NaHCO_3$ (30 mL), 1N HCl (2×20 mL) and water (2×30 mL). The organic phase is dried over $MgSO_4$ and concentrated in vacuo. The crude product is purified by column chromatography (silica, 25% ether in petroleum ether) to give (3S,4S)-3-Methyl-4-(4-phenylbutyl)oxetan-2-one (0.28 g, 39%): $^1$H NMR (300 MHz, $CDCl_3$) δ 7.31–7.21 (m, 2H), 7.19–7.15 (m, 3H), 4.19–4.13 (m, 1H), 3.25–3.16 (m, 1H), 2.64 (t, J=7.6 Hz, 2H), 1.95–1.64 (m, 4H), 1.55–1.40 (m, 2H), 1.36 (d, J=7.8 Hz, 3H); MS (EI) m/e 218 (M$^+$).

Step D (2R,3R)-3-(3,4-Dimethoxyphenylsulfanyl)-2-methyl-7-phenylheptanoic acid

A solution of 3,4-dimethoxybenzenethiol (0.33 g, 1.9 mmol) in isopropanol (3 mL) is cooled in an ice-bath and 1 M sodium hydroxide (1.4 mL, 1.4 mmol) is added over 2 minutes. (3S,4S)-3-Methyl-4-(4-phenylbutyl)oxetan-2-one (0.28 g, 1.3 mmol) is dissolved in isopropanol (3 mL) and cooled to 0° C. Then the thiolate is added to the oxetanone solution over 3 minutes. This mixture is stirred with ice cooling for 5 minutes and then allowed to come to room temperature and stir 3 hours. The reaction is then acidified to pH 5 with HCl/ether. Methanol is added and the reaction mixture azeotroped several times until a semi-solid residue is obtained. The crude product is purified by column chromatography (silica, 1% MeOH in $CH_2Cl_2$) to give (2R,3R)-3-(3,4-dimethoxyphenylsulfanyl)-2-methyl-7-phenylheptanoic acid (0.35 g, 69%): $^1$H NMR (300 MHz, $CDCl_3$) δ 7.28–7.23 (m, 2H), 7.19–7.11 (m, 3H), 7.04–6.97 (m, 2H), 6.76 (d, J=8.3 Hz, 1H), 3.84 (s, 3H), 3.83 (s, 3H), 3.27–3.25 (m, 1H), 2.72–2.68 (m, 1H), 2.56 (t, J=7.1 Hz, 2H), 1.63–1.47 (m, 6H), 1.26 (d, J=7.1 Hz, 3H); MS (EI) m/e 389 (M+H)$^+$.

Step E (+)-(2R,3R)-3-(3,4-Dimethoxyphenylsulfanyl)-2-methyl-7-phenylheptanoic acid hydroxyamide (2R,3R)-3-(3,4-Dimethoxyphenylsulfanyl)-2-methyl-7-phenylheptanoic acid (0.33 g, 0.85 mmol) is dissolved in $CH_2Cl_2$ (4 mL) and cooled to 0° C. and to this is added 2 M oxalyl chloride in $CH_2Cl_2$ (1.3 mL, 2.6 mmol) over 3 minutes. After 10 minutes the ice bath is removed and the reaction is stirred at room temperature for 2 hours. The reaction is concentrated in vacuo and azeotroped with chloroform twice. The residue is dissolved in $CH_2Cl_2$ (4 mL), cooled in ice and O-trimethylsilylhydroxylamine (0.32 mL, 2.6 mmol) is added over 2 minutes. After 10 minutes the reaction is concentrated in vacuo. The residue is dissolved in $CH_2Cl_2$ (50 mL) and washed with 1 N HCl (20 mL). The organic layer is dried over $MgSO_4$ and the solvent removed in vacuo to give (+)-(2R,3R)-3-(3,4-Dimethoxyphenylsulfanyl)-2-methyl-7-phenylheptanoic acid hydroxyamide (0.27 g, 79%): $[a]_D^{23}$ +40° (c=1.0, $CHCl_3$); $^1$H NMR (300 MHz, $CD_3OD$) δ 7.25–7.20 (m, 2H), 7.13–7.11 (m, 3H), 7.00–6.96 (m, 2H), 6.88 (d, J=8.0 Hz, 1H), 3.81 (s, 3H), 3.78 (s, 3H), 3.01–2.95 (m, 1H), 2.57–2.55 (m,1H), 2.23–2.15 (m, 1H), 1.71–1.41 (m, 6H), 1.34 (d, J=6.9 Hz, 3H); MS (FAB) m/e 404 (M+H)$^+$.

Step F (+)-(2R,3R)-3-(3,4-Dimethoxybenzenesulfonyl)-2-methyl-7-phenylheptanoic acid hydroxyamide (2R,3R)-3-(3,4-Dimethoxyphenylsulfanyl)-2-methyl-7-phenylheptanoic acid hydroxyamide (0.17 g, 0.42 mmol) is dissolved in MeOH (2 mL) and THF (2 mL) and cooled in ice. Oxone (0.52 g, 0.84 mmol) is dissolved in water (4 mL) and added to the sulfide solution dropwise over 25 minutes. After 5 minutes, the ice is removed and the reaction allowed to come to room temperature and stir overnight. The solvent is removed in vacuo, $CH_2Cl_2$ (50 mL) added and the solution washed with water (30 mL). The aqueous layer is back-extracted with $CH_2Cl_2$ (15 mL) and the combined organic layers are dried over $MgSO_4$. The solvent is removed in vacuo to give (+)-(2R, 3R)-3-(3,4-dimethoxybenzenesulfonyl)-2-methyl-7-phenylheptanoic acid hydroxyamide (0.16 g, 88%): $[a]_D^{23}$ +5.5° (c=1.0, $CHCl_3$); $^1$H NMR (300 MHz, $CD_3OD$) δ 7.46 (dd, J=8.3 Hz, 1.9 Hz, 1H), 7.35 (d, J=2.0 Hz, 1H), 7.23–7.18 (m, 2H), 7.13–7.10 (m, 2H), 7.03 (d, J=7.0 Hz, 2H), 3.91 (s, 3H), 3.87 (s, 3H), 3.45–3.43 (m, 1H), 2.82–2.77 (m, 1H), 2.43–2.39 (m, 2H), 1.70–1.55 (m, 2H), 1.41–1.28 (m, 3H), 1.36 (d, J=7.0 Hz, 3H), 1.16–1.06 (m, 1H); MS (FAB) m/e 436 (M+H)$^+$.

Following Steps A–F, beginning with the (1R,2S) indane chiral auxiliary provides (−)-(2S,3S)-3-(3,4-Dimethoxybenzenesulfanyl)-2-methyl-7-phenylheptanoic acid hydroxyamide, $[a]_D^{23}$ –44° (c=1.0, CHCl$_3$) and (–)-(2S, 3S)-3-(3,4-Dimethoxybenzenesulfonyl)-2-methyl-7-phenylheptanoic acid hydroxamide, $[a]_D^{23}$ –5.0° (c=1.0, CHCl$_3$).

EXAMPLE 36

(2R,3S)-3-(3,4-Dimethoxybenzenesulfonyl)-2-methyl-7-phenylheptanoic acid hydroxyamide Step A 4-(S)-Benzyl-3-(3-(R)-hydroxy-2-(S)-methyl-7-phenylheptanoyl)oxazolidin-2-one 4-(S)-Benzyl-3-propionyl-2-oxazolidinone (8.4 g, 36 mmol) is dissolved in CH$_2$Cl$_2$ (60 mL), cooled in an ice bath and to this is added 1 M dibutyl boron triflate in CH$_2$Cl$_2$ (40 mL, 40 mmol) over 5 minutes. Then triethylamine (6.3 mL, 45 mmol) is added dropwise at a rate that kept the reaction temperature <3° C. The ice bath is then replaced by dry-ice/acetone and 5-phenylpentanal (7.8 g, 48 mmol) in CH$_2$Cl$_2$ (20 mL) is added over 5 minutes. This mixture is stirred 20 minutes at –78° C. and then for 1 hour at 0° C. The reaction is quenched by the addition of pH 7 phosphate buffer (40 mL), followed by MeOH (120 mL). Then a mixture of MeOH (80 mL) and 30% hydrogen peroxide (40 mL) is added at a rate that kept the reaction temperature <10° C. The reaction is stirred 1 hour and then concentrated in vacuo (bath temperature <30° C.). The residue is extracted into ether (3×200 mL) and the combined ether layers are washed with NaHCO$_3$ (200 mL), brine (200 mL) and dried over MgSO$_4$ and then concentrated in vacuo. The crude product is purified by column chromatography (silica, 10% petroleum ether in CH$_2$Cl$_2$ then a second purification using 45% ether in petroleum ether) to yield 4-(S)-benzyl-3-(3-(R)-hydroxy-2-(S)-methyl-7-phenylheptanoyl)oxazolidin-2-one (9.8 g, 70%): $^1$H NMR (300 MHz, CDCl$_3$) δ 7.37–7.14 (m, 10H), 4.73–4.65 (m,1H), 4.24–4.15 (m, 2H), 3.96–3.91 (m, 1H), 3.79–3.71 (m, 1H), 3.27–3.21 (dd, J=13.4, 3.3 Hz, 1H), 2.88 (d, J=3.0 Hz, 1H), 2.78 (dd, J=13.3, 9.5 Hz, 1H), 2.62 (t, J=7.5 Hz, 2H), 1.70–1.34 (m, 6H), 1.25 (d, J=6.8 Hz, 3H).

Step B (+)-(2S, 3R)-3-Hydroxy-2-methyl-7-phenylheptanoic acid 4-(S)-Benzyl-3-(3-(R)-hydroxy-2-(S)-methyl-7-phenylheptanoyl)oxazolidin-2-one (7.64 g, 19 mmol) is dissolved in 4:1 THF-water (100 mL) and cooled to 0° C. To this is added 30% hydrogen peroxide (8.2 mL, 80 mmol) over 5 minutes, followed by lithium hydroxide monohydrate (1.3 g, 32 mmol) in water (40 mL) added dropwise over 10 minutes, keeping the reaction temperature <10° C. This mixture is stirred for 1 hour. Then sodium sulfite (10 g, 80 mmol), in 60 mL of water, is added carefully to keep the temperature <25° C. The solvent is removed in vacuo and the aqueous residue is washed with CH$_2$Cl$_2$ (3×100 mL). The aqueous layer is then cooled in an ice bath and acidified to pH 1 with 6 N HCl and the product extracted into ethyl acetate (2×100 mL). This solution is dried over MgSO$_4$ and concentrated in vacuo, to yield (+)-(2S, 3R)-3-hydroxy-2-methyl-7-phenylheptanoic acid (3.76 g, 84%): m.p. 75–77° C.; $[a]_D^{23}$ +20° (c=1.0, CHCl$_3$); $^1$H NMR (300 MHz, CDCl$_3$) δ 7.30–7.25 (m, 2H), 7.20–7.16 (m, 3H), 3.95–3.93 (m, 1H), 2.65–2.54 (m, 3H), 1.69–1.34 (m, 6H), 1.20 (d, J=7.2 Hz, 3H); MS (EI) m/e 236 (M$^+$).

Step C (3S, 4R)-3-Methyl-4-(4-phenylbutyl)oxetan-2-one (+)-(2S, 3R)-3-Hydroxy-2-methyl-7-phenylheptanoic acid is added to a solution of triphenylphosphine (0.88 g, 3.4 mmol) and 2,2'-dipyridyl disulfide (0.7 g, 3.2 mmol) in chloroform (20 mL) and is stirred for 20 minutes. Mercury (II) methanesulfonate (1.6 g, 4.2 mmol) is suspended in acetonitrile (52 mL), warmed to 48° C. and the activated ester/chloroform solution is added over 5 minutes. This mixture is heated for 1 minute after completion of the addition and then cooled. The mixture is filtered through Celite, the filtrate concentrated in vacuo and the residue is purified by column chromatography (silica, 25% ether in petroleum ether) to yield (3S,4R)-3-methyl-4-(4-phenylbutyl)oxetan-2-one (0.3 g, 66%). $^1$H NMR (300 MHz, CDCl$_3$) δ 7.31–7.26 (m, 2H), 7.21–7.15 (m, 3H), 4.19–4.13 (m, 1H), 3.25–3.16 (m, 1H), 2.64 (t, J=7.6 Hz, 2H), 1.95–1.64 (m, 4H), 1.55–1.40 (m, 5H), 1.37 (d, J=7.5 Hz, 3H).

Step D (2R,3S)-3-(3,4-Dimethoxyphenylsulfanyl)-2-methyl-7-phenylheptanoic acid

A solution of 3,4-dimethoxybenzenethiol (0.35 g, 2.1 mmol) in isopropanol (2 mL) is cooled in an ice bath and 1 M sodium hydroxide (1.5 mL, 1.5 mmol) is added slowly. This mixture is then added to a 0° C. solution of (3S,4R)-3-methyl-4-(4-phenylbutyl)oxetan-2-one (0.30 g, 1.4 mmol) in isopropanol (2 mL) over 3 minutes. The reaction is stirred for 5 minutes in ice and then allowed to warm to room temperature. After stirring for a total of 1.5 hours, the reaction is neutralized with HCl/ether. Methanol is added and the reaction mixture is azeotroped twice. The crude product is purified by gradient elution column chromatography (silica, 1 to 5% MeOH in CH$_2$Cl$_2$) to yield (2R,3S)-3-(3,4-dimethoxyphenylsulfanyl)-2-methyl-7-phenylheptanoic acid (0.48 g, 90%): $^1$H NMR (300 MHz, CDCl$_3$) δ 7.29–7.25 (m, 2H), 7.19–7.14 (m, 3H), 7.03–6.99 (m, 2H), 6.79 (d, J=8.2 Hz, 1H), 3.86 (s, 3H), 3.85 (s, 3H), 3.35–3.25 (m, 1H), 2.71–2.61 (m, 1H), 2.60 (t, J=7.0 Hz, 2H), 1.75–1.37 (m, 6H), 1.23 (d, J=7.0 Hz, 3H); MS (ion spray) m/e 389 (M$^+$).

Step E (+)-(2R,3S)-3-(3,4-Dimethoxyphenyl-2-methyl-7-phenylheptanoic acid hydroxyamide (2R,3S)-3-(3,4-Dimethoxyphenylsulfanyl)-2-methyl-7-phenylheptanoic acid (0.46 g, 1.2 mmol) is dissolved in CH$_2$Cl$_2$ (4.5 mL) and cooled to 0° C. and to this is added 2 M oxalyl chloride in CH$_2$Cl$_2$ (1.9 mL, 3.8 mmol) over 5 minutes. The ice bath is removed and the reaction allowed to warm to room temperature. After 1.5 hours, the reaction is concentrated in vacuo and azeotroped with chloroform several times. The crude residue is dissolved in CH$_2$Cl$_2$ (4 mL) and O-trimethylsilylhydroxylamine (0.4 g, 3.6 mmol) is added slowly. After 5 minutes, the reaction is diluted with CH$_2$Cl$_2$ (20 mL) and washed with 2 N HCl (15 mL). The aqueous layer is back-extracted with CH$_2$Cl$_2$ (10 mL) and the combined organic layers are washed with water (50 mL), dried over MgSO$_4$ and concentrated in vacuo. The crude residue is azeotroped with ether/petroleum ether and triturated with a large volume of petroleum ether to give (+)-(2R,3S)-3-(3,4-dimethoxyphenylsulfanyl)-2-methyl-7-phenylheptanoic acid hydroxyamide (0.45 g, 94%): $[a]_D^{23}$ +22° (c=1.0, CHCl$_3$); $^1$H NMR (300 MHz, CD$_3$OD) δ 7.25–7.21 (m, 2H), 7.15–7.10 (m, 3H), 7.05–6.98 (m, 2H), 6.87 (d, J=8.2 Hz, 1H), 3.81 (s, 3H), 3.80 (s, 3H), 3.17–3.14 (m,1H), 2.58–2.52 (m, 2H), 2.35–2.30 (m, 1H), 1.75–1.65 (m, 1H), 1.60–1.40 (m, 5H), 1.17 (d, J=7.0 Hz, 3H); MS (ion spray) m/e 404 (M+H)$^+$; Anal. (C$_{22}$H$_{29}$NO$_4$S) C, H, N.

Step F (+)-(2R,3S)-3-(3,4-Dimethoxybenzenesulfonyl)-2-methyl-7-phenylheptanoic acid hydroxyamide (+)-(2R,3S)-3-(3,4-dimethoxyphenylsulfanyl)-2-methyl-7-phenylheptanoic acid hydroxyamide (0.226 g, 0.561 mmol) is dissolved in THF (2.5 mL) and MeOH (2.5 mL) and cooled to 0° C. Oxone (0.69 g, 1.12 mmol) is dissolved in water (2.5 mL) and is added over 2 minutes. The cooling bath is removed and the reaction is stirred 2 hours. The reaction is then partitioned between $CH_2Cl_2$ (25 mL) and water (15 mL). The aqueous layer is back-extracted with $CH_2Cl_2$ (2×10 mL) and the combined organic layers dried over $MgSO_4$. The solvent is removed in vacuo and the residue azeotroped with ether to yield (+)-(2R,3S)-3-(3,4-dimethoxybenzenesulfonyl)-2-methyl-7-phenylheptanoic acid hydroxyamide (0.19 g, 78%): $[a]_D^{23}$+0.5° (c=1.0, $CHCl_3$); $^1H$ NMR (300 MHz, $CD_3OD$) δ 7.47 (dd, J=8.7, 2.3 Hz, 1H), 7.36 (d, J=2.0 Hz, 1H), 7.23–7.14 (m, 2H), 7.12–7.09 (m, 2H), 7.05–7.03 (m, 2H), 3.92 (s, 3H), 3.87 (s, 3H), 3.56–3.51 (m, 1H), 3.03–2.99 (m, 1H), 2.47–2.43 (m, 2H), 1.84–1.77 (m, 2H), 1.47–1.25 (m, 4H), 1.22 (d, J=7.1 Hz, 3H); MS (FAB) m/e 436 $(M+H)^+$; Anal. ($C_{22}H_{29}NO_6S$·0.25 $H_2O$) C, H, N.

Following Steps A–F, beginning with the (4R)-benzyloxazolidinone chiral auxiliary provides (−)-(2S,3R)-3-(3,4-dimethoxyphenylsulfanyl)-2-methyl-7-phenylheptanoic acid hydroxyamide, $[a]_D^{23}$−22° (c=1.0, $CHCl_3$) and (−)-(2S,3R)-3-(3,4-dimethoxybenzenesulfonyl)-2-methyl-7-phenylheptanoic acid hydroxyamide, $[a]_D^{23}$−2.9° (c=1.0, $CHCl_3$).

EXAMPLE 37

1-[1-(3,4-Dimethoxyphenylsulfonyl)-5-phenylpentyl]cyclopentane carboxylic acid hydroxyamide Step A 1-(1-Hydroxy-5-phenylpentyl)cyclopentanecarboxylic acid Diisopropylamine (17.5 mL, 124 mmol) is dissolved in THF (80 mL), cooled to −40° C. and 2.38 M n-butyl lithium in hexanes (52 mL, 124 mmol) is added over 5 minutes. The reaction is allowed to warm to 0° C. and cyclopentanecarboxylic acid (6.7 mL, 62 mmol) in THF (60 mL) is added over 5 minutes. The reaction is heated at 40° C. for 1 hour. The reaction is cooled to −78° C. and 5-phenylpentanal (10 g, 62 mmol) in THF (20 mL) is added dropwise over 15 minutes. The cooling bath is removed and the reaction is allowed to stir at room temperature overnight. The reaction is acidified with 2 N HCl (120 mL) and the organics are removed in vacuo. The resulting aqueous mixture is extracted with $CH_2Cl_2$ (200 mL) and this organic layer is dried over $MgSO_4$. The solution is concentrated in vacuo, and the resulting residue is purified by column chromatography (silica, 50% ether in petroleum ether) to yield 1-(1-hydroxy-5-phenylpentyl)cyclopentanecarboxylic acid (13.1 g, 77%): $^1H$ NMR (300 MHz, $CDCl_3$) δ 7.29–7.24 (m, 2H), 7.19–7.15 (m, 3H), 3.53–3.46 (m, 1H), 2.64–2.58 (m, 2H), 2.20–2.13 (m, 1H), 2.07–1.99 (m, 1H), 1.95–1.73 (m, 1H), 1.67–1.49 (m, 8H), 1.44–1.32 (m, 3H); MS (EI) m/e 276 $(M^+)$.

Step B 3-(4-Phenylbutyl)-2-oxaspiro[3,4]octan-1-one 1-(1-Hydroxy-5-phenylpentyl)cyclopentane carboxylic acid (11.3 g, 40.9 mmol) is dissolved in pyridine (90 mL) and cooled to 0° C. Benzenesulfonyl chloride (10.4 mL, 81 mmol) is added over 1 minute and the reaction is kept at 0° C. overnight. The reaction is poured into ice (100 mL) and the product extracted into ether (2×100 mL). The ether layer is washed with $NaHCO_3$ (100 mL), 1 N HCl (100 mL) and water (2×100 mL). The solution is dried over $MgSO_4$ and the solvent removed in vacuo (without heat). The crude product is purified by column chromatography (silica, 15% ether in petroleum ether) to yield 3-(4-phenylbutyl)-2-oxaspiro[3,4]octan-1-one (5.6 g, 54%): $^1H$ NMR (300 MHz, $CDCl_3$) δ 7.30–7.25 (m, 2H), 7.20–7.15 (m, 3H), 4.31–4.26 (m, 1H), 2.63 (t, J=7.6 Hz, 2H), 2.22–2.13 (m, 1H), 1.99–1.26 (m, 13H).

Step C

1-[1-(3,4-Dimethoxyphenylsulfanyl)-5-phenylpentyl]cyclopentane carboxylic acid 3-(4-Phenylbutyl)-2-oxaspiro[3,4]octan-1-one (2 g, 7.7 mmol) and 3,4-dimethoxybenzenethiol (2 g, 11.7 mmol) are dissolved in isopropanol (30 mL) and cooled to 0° C. A 1 M solution of NaOH (9.7 mL, 9.7 mmol) is added slowly, and after 5 minutes at 0° C., the reaction is allowed to stir at room temperature overnight. The solvent is removed in vacuo and the residue is dissolved in $CH_2Cl_2$ (100 mL). This solution is washed with 1 N HCl (50 mL), brine (30 mL) and dried over $MgSO_4$. The solution is concentrated in vacuo and the crude product is purified by column chromatography (silica, 1% MeOH in $CH_2Cl_2$) to yield 1-[1-(3,4-dimethoxyphenylsulfanyl)-5-phenylpentyl]-cyclopentanecarboxylic acid (2.2 g, 65%). $^1H$ NMR (300 MHz, $CDCl_3$) δ 7.28–7.23 (m, 2H), 7.18–7.09 (m, 3H), 7.01–6.91 (m, 2H), 6.76 (d, J=8.1 Hz, 1H), 3.86 (s, 3H), 3.84 (s, 3H), 3.31 (dd, J=10.0, 3.0 Hz, 1H), 2.58–2.51 (m, 2H), 2.18–2.08 (m, 2H), 1.89–1.40 (m, 12H); MS (EI) m/e 428 $(M^+)$.

Step D

1-[1-(3,4-Dimethoxyphenylsulfonyl)-5-phenylpentyl]cyclopentane carboxylic acid

1-[1-(3,4-Dimethoxyphenylsulfanyl)-5-phenylpentyl]cyclopentane carboxylic acid (1 g, 2.3 mmol) is dissolved in MeOH (6 mL) and THF (6 mL) and cooled to 0° C. Oxone (3.5 g, 5.7 mmol) is dissolved in water (12 mL) and added dropwise over 10 minutes. The reaction is allowed to stir at room temperature overnight. The organics are removed in vacuo and the mixture is extracted with $CH_2Cl_2$ (2×50 mL). The combined organic layers are dried over $MgSO_4$ and concentrated in vacuo to yield 1-[1-(3,4-dimethoxyphenylsulfonyl)-5-phenylpentyl]cyclopentane carboxylic acid (0.93 g, 88%): $^1H$ NMR (300 MHz, $CDCl_3$) δ 7.47 (dd, J=8.5, 1.9 Hz, 1H), 7.36 (d, J=2.1 Hz, 1H), 7.27–7.14 (m, 3H), 7.04 (d, J=6.9 Hz, 2H), 6.89 (d, J=8.7 Hz, 1H), 3.93 (s, 3H), 3.91 (s, 3H), 3.88–3.85 (m, 1H), 2.53 (m, 1H), 2.48–2.43 (m, 2H), 2.08–1.94 (m, 1H), 1.86–1.77 (m, 7H), 1.65–1.50 (m, 1H), 1.46–1.38 (m, 2H), 1.25–1.17 (m, 2H); MS (EI) m/e 460 $(M^+)$.

Step E

1-[1-(3,4-Dimethoxyphenylsulfonyl)-5-phenylpentyl]cyclopentanecarboxylic acid hydroxyamide 1-[1-(3,4-Dimethoxyphenylsulfonyl)-5-phenylpentyl]cyclopentane carboxylic acid (0.69 g, 1.5 mmol) is dissolved in $CH_2Cl_2$ (6 mL), cooled to 0° C. and 2 M oxalyl chloride in $CH_2Cl_2$ (2.2 mL, 4.4 mmol) is added. The reaction is warmed and stirred at room temperature 2 hours. The solvent is removed in vacuo and the residue azeotroped with chloroform (2×10 mL). The residue is dissolved in $CH_2Cl_2$ (2 mL) and cooled to 0° C. Trimethylsilylhydroxylamine (0.52 mL, 4.5 mmol) is added over 1 minute and this mixture is stirred 5 minutes. Then the ice bath is removed and the reaction stirred at room temperature overnight. The solvent is removed in vacuo and $CH_2Cl_2$ (20 mL) added and the solution washed with 1 N HCl (20 mL). The solution is dried over MgSO$_4$ and the solvent removed in vacuo to give 1-[1-(3,4-Dimethoxyphenylsulfonyl)-5-phenylpentyl]cyclopentanecarboxylic acid hydroxyamide (0.48 g, 67%): $^1$H NMR (300 MHz, CD$_3$OD) δ 7.44 (dd, J=8.3, 2.0 Hz, 1H), 7.36 (d, J=2.3 Hz, 1H), 7.22–7.05 (m, 4H), 6.98 (d, J=7.0 Hz, 2H), 3.89 (s, 3H), 3.87 (m, 4H), 2.38 (t, J=7.4 Hz, 2H), 2.35–2.25 (m, 1H), 1.96–1.63 (m, 10H), 1.34–1.27 (m, 2H), 1.21–1.10 (m, 1H), 1.00–0.88 (m, 1H); MS (EI) m/e 476 (M$^+$).

EXAMPLE 38

1-[1-(3,4-Dimethoxyphenylsulfanyl)-5-phenylpentyl]cyclopentane carboxylic acid hydroxyamide The procedure Example 38, Step E is used. From 1-[1-(3,4-Dimethoxyphenylsulfanyl)-5-phenylpentyl]cyclopentane carboxylic acid (0.5 g, 1.2 mmol) the impure product is purified by reverse-phase HPLC (50 to 100% CH$_3$CN in 0.1% TFA/H$_2$O, 30 minutes) to yield 1-[1-(3,4-Dimethoxyphenylsulfanyl)-5-phenylpentyl]cyclopentane carboxylic acid hydroxyamide (0.15 g, 29%): $^1$H NMR (300 MHz, CDCl$_3$) δ 9.03 (bs, 1H), 7.70 (bs, 1H), 7.29–7.24 (m, 2H), 7.20–7.13 (m, 3H), 6.99 (dd, J=8.2, 2.0 Hz, 1H), 6.94 (d, J=2.0 Hz, 1H), 6.78 (d, J=8.5 Hz, 1H), 3.87 (s, 3H), 3.85 (s, 3H), 3.04 (d, J=11.0 Hz, 1H), 2.63–2.57 (m, 2H), 2.38–2.30 (m, 1H), 1.97–1.93 (m, 1H), 1.81–1.38 (m, 12H); MS (EI) m/e 443 (M$^+$).

EXAMPLE 39

3-(3,4-Dimethoxybenzenesulfonyl)-2,2-dimethyl-7-phenylheptanoic acid hydroxyamide Step A Methyl 3-hydroxy-2,2-dimethyl-7-phenylheptanoate Diisopropylamine (7.2 mL, 52 mmol) is dissolved in THF (85 mL), cooled to −78° C. and n-butyl lithium in hexanes (23 mL, 52 mmol) is added slowly. The reaction is allowed to warm to −30° C. over 15 minutes and is then recooled to −78° C. A solution of methyl isobutyrate (6 mL, 52 mmol) in THF (15 mL) is added dropwise over 20 minutes and then stirred an additional 40 minutes. Next solution of 5-phenylpentanal (7 g, 43 mmol) in THF (10 mL) is added dropwise over 10 minutes and the reaction is stirred 1 hour. Acetic acid (3 mL) is added slowly followed by a solution of NH$_4$Cl (20 mL) and the reaction is allowed to warm to room temperature. The reaction is partitioned between ether (200 mL) and water (150 mL). The organic phase is washed with 1 N HCl (2×50 mL), NaHCO$_3$ (50 mL) and brine (50 mL). The solution is dried over MgSO$_4$ and concentrated in vacuo to provide methyl 3-hydroxy-2,2-dimethyl-7-phenylheptanoate (11.2, 99%): $^1$H NMR (300 MHz, CDCl$_3$) δ 7.30–7.24 (m, 2H), 7.18–7.16 (m, 3H), 3.68 (s, 3H), 3.60 (dd, J=9.7, 1.9 Hz, 1H), 2.61 (t, J=7.5 Hz, 2H), 2.37 (s, 1H), 1.73–1.20 (m, 6H), 1.17 (s, 3H), 1.15 (s, 3H); MS (EI) m/e 264 (M$^+$).

Step B

Methyl 3-methanesulfonyloxy-2,2-dimethyl-7-phenylheptanoate

Methyl 3-hydroxy-2,2-dimethyl-7-phenylheptanoate (10 g, 38 mmol) and triethylamine (6.3 mL, 45 mmol) are dissolved in CH$_2$Cl$_2$ (50 mL) and cooled to 0° C. Methanesulfonyl chloride (3.2 mL, 42 mmol) is added and the reaction is allowed to stir at room temperature for 1 hour. The reaction mixture is then washed with NaHCO$_3$ (2×40 mL), 1 N HCl (40 mL) and brine (40 mL). The solution is dried over MgSO$_4$ and the solvent removed in vacuo to yield methyl 3-methanesulfonyloxy-2,2-dimethyl-7-phenylheptanoate (11.2 g, 86%). $^1$H NMR (300 MHz, CDCl$_3$) δ 7.30–7.25 (m, 2H), 7.19–7.15 (m, 3H), 4.99 (dd, J=9.2, 2.0 Hz,1H), 3.69 (s, 3H), 2.93 (s, 3H), 2.62 (t, J=7.4 Hz, 2H), 1.71–1.38 (m, 6H), 1.27 (s, 3H), 1.18 (s, 3H); MS (FAB) m/e 343 (M+H)$^+$.

Step C

Methyl 3-(3,4-dimethoxyphenylsulfanyl)-2,2-dimethyl-7-phenylheptanoate

Sodium (0.5 g, 2.2 mmol) is added to MeOH (10 mL) cooled in ice. When the reaction is complete a solution of 3,4-dimethoxybenzenethiol (6 g, 3.5 mmol) in MeOH (5 mL) is added. After 2 minutes a solution of methyl 3-methanesulfonyloxy-2,2-dimethyl-7-phenylheptanoate (3 g, 8.8 mmol) in MeOH (5 mL) is added. The cooling bath is removed and the reaction is stirred at room temperature overnight. The solvent is removed in vacuo, CH$_2$Cl$_2$ (50 mL) added and the solution washed with NaHCO$_3$ (50 mL), 1 N HCl (50 mL) and brine (50 mL). The solution is dried over MgSO$_4$ and the solvent removed in vacuo. The product is purified by column chromatography (silica, 20% ether in petroleum ether) to yield methyl 3-(3,4-dimethoxyphenylsulfanyl)-2,2-dimethyl-7-phenylheptanoate (0.65 g, 18%): $^1$H NMR (300 MHz, CDCl$_3$) δ 7.29–7.24 (m, 2H), 7.19–7.11 (m, 3H), 7.02–6.91 (m, 2H), 6.77 (d, J=8.2 Hz, 1H), 3.87 (s, 3H), 3.85 (s, 3H), 3.57 (s, 3H), 3.22 (dd, J=10.0, 3.2 Hz, 1H), 2.64–2.51 (m, 3H), 1.81–1.74 (m, 1H), 1.66–1.42 (m, 4H), 1.27 (s, 3H), 1.22 (s, 3H); MS (FAB) m/e 416 (M$^+$).

Step D

Methyl 3-(3,4-dimethoxybenzenesulfonyl)-2,2-dimethyl-7-phenylheptanoate

Methyl 3-(3,4-dimethoxyphenylsulfanyl)-2,2-dimethyl-7-phenylheptanoate (0.81 g, 1.9 mmol) is dissolved in MeOH (5 mL) and THF (5 mL) and cooled to 0° C. Oxone (2.39 g, 3.9 mmol) is dissolved in water (10 mL) and added dropwise over 45 minutes. The reaction is warmed to room temperature and stirred overnight. The solvent is removed in vacuo, CH$_2$Cl$_2$ (50 mL) is added and the solution washed with water (50 mL). The aqueous layer is back extracted with CH$_2$Cl$_2$ (20 mL) and the combined organic layers dried over MgSO$_4$. The solvent is removed in vacuo to yield methyl 3-(3,4-dimethoxybenzenesulfonyl)-2,2-dimethyl-7-phenylheptanoate (0.80 g, 95%): $^1$H NMR (300 MHz, CDCl$_3$) δ 7.46 (dd, J=8.3, 2.0 Hz, 1H), 7.33 (d, J=2.0 Hz, 1H), 7.26–7.16 (m, 3H), 7.02 (d, J=6.9 Hz, 2H), 6.91 (d, J=8.3 Hz, 1H), 3.94 (s, 3H), 3.93 (s, 3H), 3.77 (s, 3H), 3.75–3.72 (m, 1H), 2.46–2.39 (m, 2H), 2.04–1.94 (m, 1H), 1.67–1.61 (m, 2H), 1.46 (s, 3H), 1.42–1.32 (m, 3H), 1.23 (s, 3H); MS (FAB) m/e 449 (M+H)$^+$.

Step E 3-(3,4-Dimethoxyphenylsulfonyl)-2,2-dimethyl-7-phenylheptanoic acid

A solution of sodium hydroxide (0.31 g, 7.7 mmol) in water (4 mL) is added to a solution of methyl 3-(3,4-dimethoxybenzenesulfonyl)-2,2-dimethyl-7-phenylheptanoate (0.78 g, 1.7 mmol) in MeOH (6 mL). The reaction is heated at reflux 24 hours. The solvent is then removed in vacuo, CH$_2$Cl$_2$ (20 mL) added and the solution washed with 1 N HCl (2×40 mL). The organic layer is dried over MgSO$_4$ and the solvent removed in vacuo to afford 3-(3,4-dimethoxyphenylsulfonyl)-2,2-dimethyl-7-phenylheptanoic acid (0.54 g, 73%) $^1$H NMR (300 MHz, CDCl$_3$) δ 7.47 (dd, J=8.5, 2.1 Hz, 1H), 7.36 (d, J=2.1 Hz, 1H), 7.26–7.16 (m, 3H), 7.02 (d, J=7.0 Hz, 2H), 6.90 ( d, J=8.4 Hz, 1H), 3.93 (s, 3H), 3.92 (s, 3H), 3.76–3.73 (m, 1H), 2.46–2.41 (m, 2H), 2.06–2.00 (m, 1H), 1.65–1.60 (m, 2H), 1.48 (s, 3H), 1.45–1.35 (m, 3H), 1.29 (s, 3H); MS (FAB) m/e 434 (M⁺).

Step F 3-(3,4-Dimethoxybenzenesulfonyl)-2,2-dimethyl-7-phenylheptanoic acid hydroxyamide.

3-(3,4-Dimethoxyphenylsulfonyl)-2,2-dimethyl-7-phenylheptanoic acid (0.5 g, 1.2 mmol) is dissolved in $CH_2Cl_2$ (6 mL), cooled in ice and 2 M oxalyl chloride in $CH_2Cl_2$ (1.7 mL, 3.5 mmol) is added. The reaction is warmed to room temperature and after 4 hours the solvent is removed in vacuo and the residue azeotroped twice with chloroform. The residue is dissolved in $CH_2Cl_2$ (4 mL) and trimethylsilylhydroxylamine (0.42 mL, 3.6 mmol) is added. The reaction is stirred 15 minutes and then the solvent is removed in vacuo, $CH_2Cl_2$ (10 mL) added and the solution washed with 1 N HCl. The organic layer is dried over $MgSO_4$ and the solvent removed in vacuo to yield 3-(3,4-dimethoxybenzenesulfonyl)-2,2-dimethyl-7-phenylheptanoic acid hydroxyamide (0.34 g, 83%): ¹H NMR (300 MHz, CD₃OD) δ 7.45 (dd, J=8.3, 2.0 Hz, 1H), 7.38 (d, J=2.2 Hz, 1H), 7.21–7.05 (m, 4H), 6.98–6.95 (m, 2H), 3.89 (s, 3H), 3.88 (s, 3H), 3.86–3.84 (m, 1H), 2.38–2.33 (m, 2H), 1.93–1.84 (m, 1H), 1.69–1.64 (m, 1H), 1.43 (s, 3H), 1.34–1.23 (m, 3H), 1.23 (s, 3H), 0.98–0.85 (m, 1H); MS (FAB) m/e 450 (M+H)⁺.

EXAMPLE 40

3-(4-Methoxybenzenesulfonyl)-2,2-dimethyl-7-phenylheptanoic acid hydroxyamide

Step A

Methyl 3-(4-methoxyphenylsulfanyl)-2,2-dimethyl-7-phenylheptanoate

Methyl 3-methanesulfonyloxy-2,2-dimethyl-7-phenylheptanoate (7.7 g, 23 mmol) and 4-methoxybenzenethiol (5.5 mL, 45 mmol) are dissolved in MeOH (40 mL) and potassium carbonate (4.8 g, 35 mmol) is added and the reaction is heated at 60° C. for 24 hours. The solvent is removed in vacuo and $CH_2Cl_2$ (100 mL) added and then washed with $NaHCO_3$ (60 mL), 1 N HCl (60 mL) and brine (100 mL). The solvent is removed in vacuo and the residue purified by column chromatography (silica, 40% petroleum ether in $CH_2Cl_2$) to yield methyl 3-(4-methoxyphenylsulfanyl)-2,2-dimethyl-7-phenylheptanoate (2.1 g, 24%). ¹H NMR (300 MHz, CDCl₃) δ 7.36–7.33 (m, 2H), 7.29–7.12 (m, 5H), 6.82–6.79 (m, 2H), 3.79 (s, 3H), 3.55 (s, 3H), 3.18–3.15 (m, 1H), 2.60–2.53 (m, 2H), 1.85–1.73 (m, 1H), 1.57–1.40 (m, 5H), 1.26 (s, 3H), 1.20 (s, 3H); MS (FAB) m/e 386 (M⁺).

Step B

Methyl 3-(4-methoxybenzenesulfonyl)-2,2-dimethyl-7-phenylheptanoate

Methyl 3-(4-methoxyphenylsulfanyl)-2,2-dimethyl-7-phenylheptanoate (1 g, 2.6 mmol) is dissolved in MeOH (6 mL) and THF (6 mL) and cooled in ice. Oxone (3.2 g, 5.2 mmol) is dissolved in water (12 mL) and added dropwise over 30 minutes. The reaction stirred at room temperature overnight. The solvent is removed in vacuo and $CH_2Cl_2$ (60 mL) added and then washed with water (40 mL). The aqueous layer is back extracted with $CH_2Cl_2$ (15 mL), the combined organic layers dried over $MgSO_4$ and the solvent removed in vacuo to yield methyl 3-(4-methoxybenzenesulfonyl)-2,2-dimethyl-7-phenylheptanoate (1.1 g, 99%): ¹H NMR (300 MHz, CDCl₃) δ 7.79–7.75 (m, 2H), 7.26–7.14 (m, 3H), 7.03–6.93 (m, 4H), 3.86 (s, 3H), 3.77 (s, 3H), 3.73–3.69 (m, 1H), 2.45–2.39 (m, 2H), 2.05–1.92 (m, 1H), 1.68–1.57 (m, 1H), 1.45 (s, 3H), 1.42–1.28 (m, 2H), 1.22 (s, 3H), 1.18–1.05 (m, 2H); MS (FAB) m/e 419 (M+H)⁺.

Step C 3-(4-Methoxybenzenesulfonyl)-2,2-dimethyl-7-phenylheptanoic acid

A solution of sodium hydroxide (0.40 g, 10 mmol) in water (6 mL) is added to a solution of methyl 3-(4-methoxybenzenesulfonyl)-2,2-dimethyl-7-phenylheptanoate (1.00 g, 2.4 mmol) in MeOH (8 mL). The reaction is heated at reflux 24 hours. The solvent is then removed in vacuo, $CH_2Cl_2$ (50 mL) added and the solution washed with 1 N HCl (2×40 mL). The organic layer is dried over $MgSO_4$ and the solvent removed in vacuo to yield 3-(4-methoxybenzenesulfonyl)-2,2-dimethyl-7-phenylheptanoic acid (0.64 g, 66%): ¹H NMR (300 MHz, CDCl₃) δ 7.90–7.80 (m, 2H), 7.26–7.16 (m, 3H), 7.00–6.92 (m, 4H), 4.05–3.92 (m, 1H), 3.78 (s, 3H), 2.40–2.30 (m, 2H), 2.00–1.85 (m, 1H), 1.70–1.55 (m, 1H), 1.44 (s, 3H), 1.40–1.25 (m, 3H), 1.21 (s, 3H), 1.12–0.95 (m, 1H).

Step D 3-(4-Methoxybenzenesulfonyl)-2,2-dimethyl-7-phenylheptanoic acid hydroxyamide 3-(4-Methoxybenzenesulfonyl)-2,2-dimethyl-7-phenylheptanoic acid (0.60 g, 1.5 mmol) is dissolved in $CH_2Cl_2$ (4 mL), cooled in ice and 2 M oxalyl chloride in $CH_2Cl_2$ (2 mL, 4 mmol) is added. The reaction is warmed to room temperature and after 3 hours the solvent is removed in vacuo and the residue azeotroped twice with chloroform. The residue is dissolved in $CH_2Cl_2$ (4 mL) and trimethylsilylhydroxylamine (0.2 mL, 4.5 mmol) is added. The reaction is stirred 15 minutes and then the solvent is removed in vacuo, $CH_2Cl_2$ (40 mL) added and the solution washed with 1 N HCl (20 mL) and brine (20 mL). The organic layer is dried over $MgSO_4$ and the solvent removed in vacuo to yield 3-(4-methoxybenzenesulfonyl)-2,2-dimethyl-7-phenylheptanoic acid hydroxamide (0.49 g, 78%): ¹H NMR (300 MHz, CD₃OD) δ 7.80–7.76 (m, 2H), 7.22–7.05 (m, 5H), 6.99 (d, J=7.0 Hz, 2H), 3.87 (s, 3H), 3.83–3.78 (m, 1H), 2.37 (t, J=7.5 Hz,2H), 1.89–1.84 (m, 1H), 1.68–1.65 (m, 1H), 1.42 (s, 3H), 1.35–1.25 (m, 2H), 1.23 (s, 3H), 1.20–1.09 (m,1 H), 0.99–0.85 (m, 1H); MS (FAB) m/e 420 (M+H)⁺.

EXAMPLE 41

3-(4-Methoxybenzenesulfinyl)-7-phenylheptanoic acid hydroxamide

A solution of oxone (2.34 g, 3.8 mmol) in 10 mL of water is added dropwise over 25 minutes to a solution of 3-(4-methoxybenzenesulfanyl)-7-phenylheptanoic acid hydroxamide (2.84 g, 7.9 mmol) in 10 mL of methanol at 0° C. After one hour, the solvent is removed in vacuo and dichloromethane is added and washed with water. The aqueous layer is extracted with dichloromethane and the combined organic layers dried over $MgSO_4$ and the solvent removed in vacuo. ¹H NMR indicated the ratio of diastereoisomers to be 9:1. The crude product is recrystallized from dichloromethane-methanol-petroleum ether to give a single diastereomer, 29 (0.21 g, 7%): m.p. 150–1° C.; ¹H NMR (300 MHz, CD₃OD) δ 7.57–7.52 (m, 2H), 7.26–7.20 (m, 2H), 7.16–7.10 (m, 5H), 3.86 (s, 3H), 3.14–3.09 (m, 1H), 2.62–2.54 (m, 2H), 2.26–2.22 (m, 2H), 1.85–1.47 (m, 6H); MS (FAB) m/e 376 (M+H)⁺.

EXAMPLE 42

(±)-N-hydroxy-3-(3,4-Dimethoxyphenyl)sulfonyl-7-phenylheptanamide and (±)-N-hydroxy-3-(3,4-methylenedioxyphenyl)sulfonyl-7-phenylheptanamide Step A (3,4-Methylenedioxy)benzenethiol To a suspension of magnesium powder (1.35 g, 55.3 mmol) in anhydrous THF (150 mL) at reflux is added 1,2-dibromoethane (0.32 mL, 3.69 mmol) via syringe. The mixture is stirred at reflux for 10 minutes then a solution of 4-bromo-1,2-(methylenedioxy)benzene (36.9 mmol) in THF (50 mL) is added via syringe. The dark brown mixture is stirred at reflux for 1 hour then cooled to 0° C. and added via cannula to a stirring suspension of sulfur (1.3 g, 40.6 mmol) in THF (50 mL). The resulting green solution is allowed to warm to room temperature and stir overnight.

The mixture is partitioned between ice water (400 mL) containing conc. HCl (40 mL) and ether (200 mL). Aqueous layer is extracted with ether (3×200 mL) and combined organic phases are washed successively with 1 N HCl (200 mL), water (200 mL), 0.1 N NaOH (200 mL), water (200 mL) and brine (200 mL) then dried over $MgSO_4$ and concentrated. The residue is combined with the product from an identical reaction on identical scale and the mixture is chromatographed on silica gel (3% pet-ether/EtOAc) to afford a 2:1 mixture of disulfide and thiol. 1.75 g of (3,4-methylenedioxy)benzenethiol is obtained as a colorless oil. The thiol is isolated by chromatography on silica gel TLC analysis [pet-ether/EtOAc, 19:1, $R_f$(bromide)=0.40, $R_f$(thiol)=0.35, $R_f$(disulfide)=0.30]. $^1H$ NMR (300 MHz, $CDCl_3$) δ 3.40 (s, 1H), 5.95 (s, 2H), 6.70 (d, 1H), 6.82 (m, 2H) ppm. Mass spectrum (EI) m/z 154 $(M)^+$.

Step B (E)-t-butyl 7-phenyl-2-heptenoate

To a solution of 5-phenylpentanal (60 mmol) in anhydrous THF (100 mL) at room temperature is added (t-butoxycarbonylmethylene)triphenyl-phosphorane (27.5 g, 72 mmol). The resulting orange solution is stirred for 2.5 hours, after which TLC analysis indicated complete reaction. The reaction mixture is concentrated in vacuo to afford a crude product which is chromatographed on silica gel (hexane/EtOAc, 19:1) to afford 12.4 g of t-butyl 7-phenyl-2-heptenoate (80%) as a colorless oil. TLC [pet-ether/EtOAc, 9:1, $R_f$ (aldehyde)=0.60, $R_f$ (ester)=0.80]. $^1H$ NMR (300 MHz, $CDCl_3$) δ 1.45 (s, 9H), 1.65 (m, 4H), 2.18 (q, 2H), 2.61 (t, 2H), 5.70 (d, 1H), 6.82 (dt, 1H), 7.10–7.30 (m, 5H) ppm.

Step C (±)-t-butyl-3-(3,4-dimethoxyphenyl)sulfanyl-7-phenylheptanoate

To a solution of 3,4-dimethoxythiophenol (8.25 mL, 57.6 mmol) in anhydrous THF (100 mL) at 0° C., is added n-BuLi (2.5 M in hexane, 0.77 mL, 1.92 mmol) and the solution is stirred for 15 minutes under a nitrogen atmosphere. t-butyl 7-phenyl-2-heptenoate (10 g, 38.4 mmol) in THF (100 mL) is added dropwise and the mixture is allowed to warm to room temperature and stir overnight. TLC analysis indicated complete reaction. The reaction mixture is diluted with water (300 mL) and extracted with ether (3×250 mL). Combined organic extracts are washed successively with sat. $Na_2CO_3$ solution (4×200 mL), water (200 mL) and brine (200 mL) then dried over $MgSO_4$ and concentrated to afford a pale yellow oil which is chromatographed on silica gel (pet-ether/EtOAc, 9:1) to afford 14.9 g of (±)-t-butyl-3-(3,4-dimethoxyphenyl)sulfanyl-7-phenylheptanoate (90%) as a colorless oil. TLC analysis [pet-ether/EtOAc, 9:1, $R_f$ (heptenoate)=0.80, $R_f$ (heptanoate)=0.50]. $^1H$ NMR (300 MHz, $CDCl_3$) δ 1.44 (s, 9H), 1.48–1.68 (m, 6H), 2.42 (dABq, 2H), 2.60 (t, 2H), 3.28 (t, 1H), 3.85 (d, 6H), 6.75 (d, 1H), 7.0 (dd, 2H), 7.15 (d, 3H), 7.25 (t, 2H) ppm. Mass spectrum (FAB) m/z 447 $(M+H)^+$.

Step D (±)-t-butyl-3-(3,4-methylenedioxyphenyl)sulfanyl-7-phenylheptanoate

The above procedure is applied using (3,4-methylenedioxy)benzenethiol to afford 3.6 g of (±)-t-butyl-3-(3,4-methylenedioxyphenyl)sulfanyl-7-phenylheptanoate (77%) as a pale yellow oil. TLC analysis [pet-ether/EtOAc, 19:1, $R_f$(heptenoate)=0.75, $R_f$ (heptanoate)=0.35]. $^1H$ NMR (300 MHz, $CDCl_3$) δ 1.45 (s, 9H), 1.58 (m, 6H), 2.40, (m, 2H), 2.60 (app. t, 2H), 3.25 (m, 1H), 5.96 (s, 2H), 6.74 (d, 1H), 6.95 (m, 2H), 7.10–7.30 (m, 5H) ppm.

Step E (±)-3-(3,4-Dimethoxyphenyl)sulfanyl-7-phenylheptanoic acid

To a solution of t-butyl-3-(3,4-dimethoxyphenyl)sulfanyl-7-phenylheptanoate (14.9 g, 0.03 mol) in $CH_2Cl_2$ (150 mL) cooled to 0° C., is added trifluoroacetic acid (30 mL). The solution is allowed to warm to room temperature and stir overnight after which TLC analysis indicated complete reaction. The reaction mixture is concentrated in vacuo and the brown residue is chromatographed on silica gel (pet-ether/EtOAc, 1:1) to afford 11.9 g of (±) 3-(3,4-dimethoxyphenyl)sulfanyl-7-phenylheptanoic acid (91%) as a pale yellow oil. TLC analysis [pet-ether/EtOAc, 1:1, $R_f$(heptanoate)=0.95, $R_f$(acid)=0.15]. $^1H$ NMR (300 MHz, $CDCl_3$) δ 1.5–1.65 (m, 6H), 2.55 (m, 4H), 3.30 (t, 1H), 3.85, (d, 6H), 6.80 (d, 1H), 6.98–7.31 (m, 7H) ppm. Mass spectrum (FAB) m/z 374 $M^+$.

Step F (±)-3-(3,4-Methylenedioxyphenyl)sulfanyl-7-phenylheptanoic acid

The above procedure is applied to (±)-t-butyl-3-(3,4-methylenedioxyphenyl)sulfanyl-7-phenylheptanoate to afford 2.33 g of (±)-3-(3,4-methylene dioxyphenyl)sulfanyl-7-phenylheptanoic acid (75%) as a pale yellow oil. TLC analysis [pet-ether/EtOAc, 4:1, $R_f$(heptanoate)=0.50, $R_f$(acid)=0.15]. $^1H$ NMR (300 MHz, $CDCl_3$) δ 1.55 (m, 6H), 2.55 (m, 4H), 4.45 (br s, 1H), 5.95 (s, 2H), 6.72 (d, 1H), 6.92 (d, 2H), 7.10–7.30 (m, 5H) ppm. Mass spectrum (APCI) 359 $(M+H)^+$.

Step G (±)-N-hydroxy-3-(3,4-Dimethoxyphenyl)sulfanyl-7-phenylheptanamide

To a solution containing (±)-3-(3,4-dimethoxyphenyl)sulfanyl-7-phenylheptanoic acid (0.5 g, 1.34 mmol) and DMF (0.1 mL, 1.34 mmol) in anhydrous $CH_2Cl_2$ (25 mL) is added oxalyl chloride (0.29 mL, 3.34 mmol) dropwise. After 30 minutes, $TMSONH_2$ (0.82 mL, 6.7 mmol) is added dropwise and the resulting white suspension is stirred for 10 minutes after which TLC analysis indicated complete reaction. The reaction mixture is partitioned between 1N HCl (100 mL) and $CH_2Cl_2$ (50 mL). Aqueous layer is extracted with EtOAc (2×50 mL) and combined organic phases are washed with water (50 mL) and brine (50 mL) then dried over $MgSO_4$ and concentrated to afford a light brown oil.

The crude hydroxamic acid is combined with the products of two identical reactions performed on 14 mmol scale and the residue is chromatographed on silica gel (CH$_2$Cl$_2$→2% MeOH/CH$_2$Cl$_2$→3% MeOH/CH$_2$Cl$_2$) to afford 9.83 g of (±)-N-hydroxy-3-(3,4-dimethoxyphenyl)sulfanyl-7-phenylheptanamide (91%) as a light brown gum. TLC analysis [hexane/EtOAc, 1:2, R$_f$(acid)=0.20, R$_f$(hydroxamic acid)=0.20]. $^1$H NMR (300 MHz, d$_6$-DMSO) δ 1.30–1.60 (m, 6H), 2.22 (m, 2H), 2.50, (m, 2H), 3.25 (br s, 1H), 3.72 (br s, 6H), 6.92 (d, 3H), 7.14 (d, 3H), 7.25 (t, 2H), 8.80 (s, 1H), 10.40 (s, 1H) ppm. Mass spectrum (FAB) m/z 389 (M)$^+$.

Step H (±)-N-hydroxy-3-(3,4-methylenedioxyphenyl)sulfanyl-7-phenylheptanamide

The above procedure is applied to (±)-3-(3,4-methylenedioxyphenyl)sulfanyl-7-phenylheptanoic acid to afford 0.36 g of (±)-N-hydroxy-3-(3,4-methylenedioxyphenyl)sulfanyl-7-phenylheptanamide (35%) as a pale yellow oil. TLC analysis [pet-ether, EtOAc, 1:1, R$_f$(acid)=0.20, R$_f$(hydroxamic acid)=0.10]. $^1$H NMR (300 MHz, CDCl$_3$) δ 1.58 (m, 6H), 2.31 (br d, 2H), 2.58 (br t, 2H), 3.28 (m, 1H), 5.95 (s, 2H), 6.70 (d, 1H), 6.90 (d, 2H), 7.10–7.30 (m, 5H) ppm. Mass spectrum (FAB) m/z 374 (M+H)$^+$.

Step I (±)-N-hydroxy-3-(3,4-Dimethoxyphenyl)sulfonyl-7-phenylheptanamide

To a solution of (±)-N-hydroxy-3-(3,4-dimethoxyphenyl)sulfanyl-7-phenylheptanamide (5.3 g, 13.6 mmol) in methanol (200 mL) at 0° C. is added a solution of oxone (12.56 g, 20.4 mmol) in water (200 mL) via addition funnel. The resulting white suspension is allowed to warm to room temperature and stir overnight after which TLC analysis indicated complete reaction. The mixture is concentrated to half volume then partitioned between water (200 mL) and EtOAc (200 mL). The aqueous layer is extracted with EtOAc (2×200 mL) and combined organic phases are washed with brine (100 mL) then dried over MgSO$_4$ and evaporated. The crude sulfone is chromatographed on silica gel (CH$_2$Cl$_2$→2% MeOH/CH$_2$Cl$_2$) then triturated with CHCl$_3$ to afford 3.1 g of (±)-N-hydroxy-3-(3,4-dimethoxyphenyl)sulfonyl-7-phenylheptanamide (54%) as a white solid. TLC analysis [CH$_2$Cl$_2$/MeOH, 19:1, R$_f$(sulfide)=0.2, R$_f$(sulfone)=0.18]. m.p. 157–159° C. $^1$H NMR (300 MHz, d$_6$-DMSO) δ 1.2–1.54 (m, 6H), 1.72 (m, 1H), 2.10 (dd, 1H), 3.82 (d, 6H), 7.06–7.30 (m, 7H), 7.40 (d, 1H) 8.88 (s, 1H), 10.50 (s, 1H) ppm. Mass spectrum (FAB) m/z 422 (M+H)$^+$.

Step J (±)-N-hydroxy-3-(3,4-methylenedioxyphenyl)sulfonyl-7-phenylheptanamide

The above procedure is applied to (±)-N-hydroxy-3-(3,4-methylenedioxyphenyl)sulfanyl-7-phenylheptanamide to afford 0.14 g of (±)-N-hydroxy-3-(3,4-methylenedioxyphenyl)sulfonyl-7-phenylheptanamide (36%) as a white foam. TLC analysis [pet-ether/EtOAc, 1:1, R$_f$(sulfide)=0.10, R$_f$(sulfone)=0.05]. $^1$H NMR (300 MHz, d$_6$-DMSO) δ 1.18–1.52 (m, 6H), 1.70 (m, 1H), 2.08 (dd, 1H), 2.40 (m, 2H), 3.49 (m, 1H), 6.15 (s, 2H), 7.10 (dd, 4H), 7.20 (m, 2H), 7.30 (m, 2H), 8.88 (s, 1H), 10.52 (s, 1H) ppm. Mass spectrum (FAB) m/z 406 (M+H)$^+$.

EXAMPLE 43

(−)-N-hydroxy-3-(3,4-dimethoxyphenyl)sulfonyl-7-phenylheptanamide and (+)-N-hydroxy-3-(3,4-dimethoxyphenyl)sulfonyl-7-phenylheptanamide The two enantiomers of (±)-N-Hydroxy-3-(3,4-Dimethoxyphenyl)sulfonyl-7-phenylheptanamide are separated by HPLC (Chiralpak AD, heptane/isopropanol, 3:1; Flow rate: 1 mL/minutes; UV Detection at 230 nm) to afford the two enantiomers, (+)- and (−)-N-hydroxy-3-(3,4-dimethoxyphenyl)sulfonyl-7-phenylheptanamide, as white foams after trituration with diethyl ether.

(−)-N-hydroxy-3-(3,4-dimethoxyphenyl)sulfonyl-7-phenylheptanamide: HPLC analysis: t$_R$=7.12 minutes, ee=99.5%. [α]$_D$-7.8°. m.p. 64–66° C.

(+)-N-hydroxy-3-(3,4-dimethoxyphenyl)sulfonyl-7-phenylheptanamide: HPLC analysis: t$_R$=9.08 minutes, ee=99.3%. [α]$_D$+8.0°. m.p. 62–66° C.

Following the aforesaid method but using racemic 3-(4-methoxyphenylsulfonyl)-7-phenylheptanoic acid hydroxamide instead of (±)-N-hydroxy-3-(3,4-dimethoxyphenyl) sulfonyl-7-phenylheptanamide, affords (+)-3-(4-methoxyphenylsulfonyl)-7-phenylheptanoic acid hydroxamide and (−)-3-(4-methoxyphenylsulfonyl)-7-phenylheptanoic acid hydroxamide.

EXAMPLE 44

(±)-N-hydroxy-3-(3,4-dimethoxyphenyl)sulfinyl-7-phenylheptanamide

To a solution of (±)-N-hydroxy-3-(3,4-dimethoxyphenyl) sulfanyl-7-phenylheptanamide (1.26 g, 3.24 mmol) in anhydrous CH$_2$Cl$_2$ (20 mL) at 0° C. is added m-CPBA (0.56 g, 3.24 mmol) in one portion. The mixture is stirred for 10 minutes after which TLC analysis indicated complete reaction. Ethanol (2 mL) is added and the mixture is partitioned between water (100 mL) and EtOAc (100 mL). Aqueous layer is extracted with EtOAc (2×50 mL) and combined organic phases are washed successively with 5% aqueous Na$_2$S$_2$O$_3$ (50 mL), water (50 mL), 5% aqueous NaHCO$_3$ (50 mL), water (50 mL) and brine (50 mL) then dried over MgSO$_4$ and concentrated. The resulting yellow oil is chromatographed on silica gel (CH$_2$Cl$_2$→2% MeOH/CH$_2$Cl$_2$→5% MeOH/CH$_2$Cl$_2$) to afford 0.5 g of (±)-N-hydroxy-3-(3,4-dimethoxyphenyl)sulfinyl-7-phenylheptanamide (38%) as a mixture (2:1) of diastereomers in the form of a white foam. TLC analysis [CH$_2$Cl$_2$/MeOH, 19:1, R$_f$(sulfide)=0.20, R$_f$(sulfoxide)=0.10]. $^1$H NMR (300 MHz, d$_6$-DMSO) δ 1.35–1.72 (m, 6H), 1.88–2.20 (m, 2H), 2.49 (m, 2H), 3.05 (m, 1H), 3.78 (br s, 6H), 7.0–7.18 (m, 6H), 7.22 (m, 2H), 8.80 (m, 1H), 10.49 (m,1H) ppm. Mass spectrum (FAB) m/z 406 (M+H)$^+$.

EXAMPLE 45

(±)-(2R*, 3R*)-3-(4-Methoxybenzenesulfonyl)-7-phenyl-2-(2-phenoxyethyl)heptanoic acid hydroxyamide Step A 4-Benzyl, 1-t-butyl 2-(diethoxyphosphoryl)succinate A solution of sodium hexamethyidisilylazide in THF (111 mL, 111 mmol) is added over 15 minutes to a solution of t-butyl diethylphosphonoacetate (23.4 g, 92.8 mmol) in THF (45 mL) at 0° C. After 10 minutes a solution of benzyl 2-bromoacetate (24.4 g, 107 mmol) in THF (15 mL) is added dropwise over 30 minutes. The reaction is then stirred at 23° C. for 12 hours. The THF is then removed in vacuo, the residue taken up in ether (200 mL) and washed with 1N HCl (3×60 mL) and brine (100 mL). The solution is dried (MgSO$_4$) and concentrated in vacuo to yield 4-benzyl, 1-t-butyl 2-(diethoxyphosphoryl)succinate as an oil (37 g) which is used without further purification.

Step B

4-Benzyl, 1-t-butyl 2-(5-phenylpentylidene)succinate

A mixture of 5-phenylpentanal (11 g, 68 mmol) and 4-benzyl, 1-t-butyl 2-(diethoxyphosphoryl)succinate (33 g, 81 mmol) are dissolved in THF (140 mL) and cooled to 0° C. A solution of sodium hexamethyldisilylazide in THF (75 mL, 75 mmol) is added over 20 minutes and the reaction is allowed to warm to 23° C. After 30 minutes the reaction is partitioned between petroleum ether (300 mL) and 1 N HCl (150 mL). The organic layer is washed with $NaHCO_3$ (100 mL), brine (75 mL), dried ($MgSO_4$) and concentrated in vacuo. The residue is purified by column chromatography (silica, 20% ether in petroleum ether) to provide 4-benzyl, 1-t-butyl 2-(5-phenylpentylidene)succinate (18.5 g, 67% over 2 steps) as a mixture (3.3:1; E/Z) as measured by $^1$H NMR: $^1$H NMR (300 MHz, $CDCl_3$) δ 7.35–7.13 (m, 10H), 6.86 (t, 0.77H, (E)—C$\underline{H}$=), 5.94 (t, 0.23H, (Z)—C$\underline{H}$=), 5.12 (s, 0.23H), 5.10 (s, 0.77H), 3.33 (s, 0.77H), 3.24 (s, 0.23H), 2.63–2.53 (m, 2.23H), 2.17 (q, 2H), 1.68–1.56 (m, 2.77H), 1.52–1.44 (m, 1H), 1.41 (s, 9H); MS (FAB) m/e 409 $(M+H)^+$.

Step C

4-Benzyl, 1-t-butyl 2-(R*)-[1-(R*)-(4-methoxyphenylsulfonyl)-5-phenylpentyl]succinate 4-Methoxybenzenethiol (9.2 g, 66 mmol) is dissolved in THF (10 mL) and cooled to 0° C. A catalytic amount of n-BuLi (2.3 M in hexanes; 1.6 mL, 3.7 mmol) is added slowly. A solution of 4-benzyl, 1-t-butyl 2-(5-phenylpentylidene)succinate in THF (20 mL) is added and the reaction is allowed to warm to 23° C. and stir for 12 hours. The solvent is removed and the inseparable mixture of diastereomers is oxidized without purification.

The crude thiol addition product is dissolved in THF (170 mL) and MeOH (100 mL) and cooled to 0° C. A solution of oxone (81 g, 132 mmol) in water (270 mL) is added slowly over 15 minutes. The reaction is stirred 24 hours and the organic phase is removed in vacuo. The remaining aqueous suspension is partitioned between $CH_2Cl_2$ (500 mL) and additional water (300 mL). The layers are separated and the aqueous phase is back extracted with additional $CH_2Cl_2$ (2×100 mL). The combined organic solution is dried ($MgSO_4$) and concentrated in vacuo to yield a mixture of diastereomers which are separated by gradient elution column chromatography (silica, 0.5% to 3% MeOH in $CH_2Cl_2$). Faster eluting isomer (2.2 g, 10%): $^1$H NMR (300 MHz, $CDCl_3$) δ 7.78 (d, J=8.7 Hz, 2H), 7.37–7.30 (m, 5H), 7.28–7.20 (m, 2H), 7.18–7.08 (m, 3H), 6.98–6.95 (m, 2H), 5.12 (m, 2H), 3.85 (s, 3H), 3.58–3.54 (m, 1H), 3.47–3.42 (m, 1H), 2.90 (dd, J=16.7, 2.6 Hz, 1H), 2.67 (dd, J=16.7, 11.5 Hz, 1H), 2.53 (t, J=7.5 Hz, 2H), 2.09–1.95 (m, 1H) 1.68–1.52 (m, 4H), 1.32–1.27 (m, 1H), 1.29 (s, 9H); Slower eluting isomer, 4-benzyl, 1-t-butyl 2-(R*)-[1-(R*)-(4-methoxyphenylsulfonyl)-5-phenylpentyl]succinate, (16.3 g, 76%): $^1$H NMR (300 MHz, $CDCl_3$) δ 7.78 (d, J=8.6 Hz, 2H), 7.37–7.30 (m, 5H), 7.25–7.15 (m, 3H), 7.05–6.97 (m, 4H), 5.16 (m, 2H), 3.85 (s, 3H), 3.82–3.76 (m, 1H), 3.33–3.16 (m, 2H), 2.64 (dd, J=16.5, 2.0 Hz, 1H), 2.44 (t, J=7.5 Hz, 2H), 1.73–1.65 (m, 2H), 1.57–1.18 (m, 4H), 1.43 (s, 9H); MS (FAB) m/e 581 $(M+H)^+$.

Step D (±)-1-t-butyl 2-(R*)-[1-(R*)-(4-methoxyphenylsulfonyl)-5-phenylpentyl]succinic acid 4-Benzyl, 1-t-butyl 2-(R*)-[1-(R*)-(4-methoxyphenylsulfonyl)-5-phenylpentyl]succinate (4.6 g, 7.9 mmol) is dissolved in MeOH (60 mL) and THF (6 mL) and the solution is purged with $N_2$. Palladium (10%) on carbon (0.55 g) is added and the reaction is again purged with $N_2$. The reaction is then purged with $H_2$ and is vigorously stirred for 2 hours. The reaction is purged with $N_2$, filtered through Celite and washed with MeOH. The filtrate is concentrated in vacuo to yield (±)-1-t-butyl 2-(R*)-[1-(R*)-(4-methoxyphenylsulfonyl)-5-phenylpentyl] succinic acid (3.8 g, 98%): $^1$H NMR (300 MHz, $CDCl_3$) δ 9.2 (bs, 1H), 7.79 (d, J=8.8 Hz, 2H), 7.27–7.13 (m, 3H), 7.05 (d, J=7.0 Hz, 2H), 7.00 (d, J=8.8 Hz, 2H), 3.87 (s, 3H), 3.73 (m, 1H), 3.28–3.10 (m, 2H), 2.65 (d, J=16 Hz, 1H), 2.52–2.47 (m, 2H), 1.73–1.66 (m, 2H), 1.62–1.18 (m, 4H), 1.49 (s, 9H).

Step E (±)-t-butyl (2R*,3R*)-2-(2-hydroxyethyl)-3-(4-methoxybenzenesulfonyl)-7-phenylheptanoate (±)-1-t-Butyl 2-(R*)-[1-(R*)-(4-methoxyphenylsulfonyl)-5-phenylpentyl]succinic acid (1.8 g, 3.7 mmol) is dissolved in THF (15 mL) and cooled to 0° C. A 1 M solution of borane-THF (6.5 mL, 6.5 mmol) is added dropwise over 5 minutes. After 5 minutes at 0° C. the reaction is warmed to 23° C. and stirred for 6 hours. The reaction is carefully quenched with 1 N HCl (5 mL) and extracted with $CH_2Cl_2$ (100 mL). The organic phase is washed with brine (40 mL), dried ($MgSO_4$) and concentrated to yield the crude alcohol. The impure product is purified by gradient elution chromatography (silica, 1% to 3% MeOH in $CH_2Cl_2$) to yield (±)-t-butyl (2R*,3R*)-2-(2-hydroxyethyl)-3-(4-methoxybenzenesulfonyl)-7-phenylheptanoate (1.66 g, 94%): $^1$H NMR (300 MHz, $CDCl_3$) δ 7.79 (d, J=8.8 Hz, 2H), 7.27–7.12 (m, 3H), 7.08 (d, J=6.8 Hz, 2H), 6.98 (d, J=8.8 Hz, 2H), 3.87 (s, 3H), 3.73–3.61 (m, 2H), 3.55–3.49 (m, 1H), 2.92–2.87 (m, 1H), 2.50 (t, J=7.5 Hz, 2H), 2.28–2.17 (m, 1H), 1.92–1.75 (m, 3H), 1.60–1.24 (m, 4H), 1.49 (s, 9H); MS (FAB) m/e 477 $(M+H)^+$.

Step F (±)-t-butyl (2R*,3R*)-3-(4-methoxybenzenesulfonyl)-7-phenyl-2-(2-phenoxyethyl)heptanoate (±)-t-Butyl (2R*,3R*)-2-(2-hydroxyethyl)-3-(4-methoxybenzenesulfonyl)-7-phenylheptanoate (0.36 g, 0.75 mmol), phenol (92 mg, 0.97 mmol) and triphenylphosphine (0.23 g, 0.9 mmol) are dissolved in THF (4 mL) and cooled to 0° C. Diisopropyl azodicarboxylate (0.18 mL, 0.9 mmol) is added dropwise and the reaction is heated at 50° C. for 7 hours. The reaction is cooled, diluted with ether (100 mL) and washed with 1 N HCl (40 mL), water (40 mL), $NaHCO_3$ (50 mL) and brine (40 mL). After drying over $MgSO_4$, the solution is concentrated in vacuo and the residue purified by column chromatography (silica, 30% ether in petroleum ether) to yield (±)-t-butyl (2R*, 3R*)-3-(4-methoxybenzenesulfonyl)-7-phenyl-2-(2-phenoxyethyl) heptanoate (0.14 g, 34%): $^1$H NMR (300 MHz, $CDCl_3$) δ 7.80 (d, J=8.8 Hz, 2H), 7.30–6.91 (m, 10H), 6.81 (d, J=8.0 Hz, 2H), 4.15–4.09 (m, 1H), 4.04 (m, 1H), 3.87 (s, 3H), 3.65 (m, 1H), 3.02–2.96 (m, 1H), 2.61 (t, J=7.7 Hz, 2H), 2.50 (m, 2H), 2.49–2.37 (m, 1H), 2.23–2.17 (m, 1H), 1.84–1.76 (m, 1H), 1.70–1.51 (m, 2H), 1.50 (s, 9H), 1.35–1.23 (m, 1H).

Step G (±)-(2R*,3R*)-3-(4-Methoxybenzenesulfonyl)-7-phenyl-2-(2-phenoxyethyl)heptanoic acid (±)-t-Butyl (2R*,3R*)-3-(4-methoxybenzenesulfonyl)-7-phenyl-2-(2-phenoxyethyl)heptanoate (0.3 g, 0.54 mmol) is dissolved in $CH_2Cl_2$ (7 mL), cooled to 0° C. and TFA (1 mL) is added slowly. The bath is removed and the reaction is stirred for 4 hours. The reaction is concentrated in vacuo and the residue purified by reverse phase HPLC (50–100% $CH_3CN$ in 0.1% TFA/$H_2O$) to yield (±)-(2R*,3R*)-3-(4- methoxybenzenesulfonyl)-7-phenyl-2-(2-phenoxyethyl) heptanoic acid (0.19 g, 70%). $^1$H NMR (300 MHz, CDCl$_3$) δ 7.81 (d, J=8.8 Hz, 2H), 7.29–7.15 (m, 5H), 7.08 (d, J=7.3 Hz, 2H), 6.98–6.91 (m, 3H), 6.81 (d, J=8.3 Hz, 2H), 4.17–4.03 (m, 2H), 3.83 (s, 3H), 3.80–3.75 (m, 1H), 3.17–3.14 (m, 1H), 2.58–2.50 (m, 3H), 2.30–2.18 (m, 1H), 1.90–1.77 (m, 2H), 1.60–1.45 (m, 3H), 1.41–1.30 (m, 1H); MS (FAB) m/e 497 (M+H)$^+$.

Step H (±)-(2R*, R*)-3-(4-Methoxybenzenesulfonyl)-7-phenyl-2-(2-phenoxyethyl)heptanoic acid hydroxyamide (±)-(2R*,3R*)-3-(4-Methoxybenzenesulfonyl)-7-phenyl-2-(2-phenoxyethyl)heptanoic acid (0.17 g, 0.34 mmol) is dissolved in CH$_2$Cl$_2$ (1 mL) and cooled to 0° C. A solution of oxalyl chloride in CH$_2$Cl$_2$ (0.5 mL, 1 mmol) is added dropwise, the bath removed and the reaction allowed to warm and stir at 23° C. for 3 hours. The reaction is then concentrated in vacuo and azeotroped with CHCl$_3$. The resulting oil is dissolved in CH$_2$Cl$_2$ (3 mL), cooled to 0° C. and O-(trimethylsilyl)hydroxylamine (0.16 g, 1.7 mmol) is added dropwise. The bath is removed and the reaction is allowed to warm to 20° C. The reaction is then partitioned between CH$_2$Cl$_2$ (20 mL) and 1 N HCl (10 mL). The organic layer is then separated and washed with water (10 mL), dried (MgSO$_4$) and concentrated in vacuo. The product is purified by reverse phase HPLC (65% CH$_3$CN in 0.1% TFA/H$_2$O) to yield (±)-(2R*, R*)-3-(4-methoxybenzenesulfonyl)-7-phenyl-2-(2-phenoxyethyl)heptanoic acid hydroxyamide (0.12 g, 69%): $^1$H NMR (300 MHz, CDCl$_3$) δ 7.73 (d, J=8.8 Hz, 2H), 7.28–7.14 (m, 5H), 7.08 (d, J=7.0 Hz, 2H), 6.97–6.89 (m, 3H), 6.73 (d, J=8.1 Hz, 2H), 3.89–3.71 (m, 5H), 3.27–3.20 (m, 2H), 2.51 (t, J=7.2 Hz, 2H), 2.45–2.32 (m, 1H), 1.98–1.75 (m, 3H), 1.55–1.38 (m, 3H), 1.35–1.22 (m, 1H); $^{13}$C NMR (75.5 MHz, CDCl$_3$) δ 168.74, 164.06, 158.25, 141.93, 130.70, 129.46, 128.88, 128.34, 128.30, 125.78, 121.06, 114.63, 114.36, 66.37, 65.16, 55.67, 38.36, 35.30, 31.00, 30.35, 27.75, 25.34; MS (FAB) m/e 512 (M+H)$^+$; Anal. (C$_{28}$H$_{33}$NO$_6$S.0.2 H$_2$O) C, H, N.

EXAMPLE 46

(±)-(2R*,3R*)-3-(4-Methoxybenzenesulfonyl)-7-phenyl-2-(2-phenylsulfanylethyl)heptanoic acid hydroxyamide Step A (±)-t-butyl (2R*,3R*)-3-(4-methoxyphenylsulfonyl)-7-phenyl-2-(2-phenylsulfanylethyl)heptanoate (±)-t-Butyl (2R*,3R*)-2-(2-hydroxyethyl)-3-(4-methoxybenzenesulfonyl)-7-phenylheptanoate (1.1 g, 2.3 mmol) and phenyldisulfide (1 g, 4.6 mmol) are dissolved in CH$_2$Cl$_2$ (10 mL), cooled to 0° C. and n-tributyl phosphine (1.2 mL, 4.6 mmol) is added dropwise. After 2 hours the reaction is partitioned between NaHCO$_3$ (150 mL) and CH$_2$Cl$_2$ (100 mL). The organic phase is back-extracted with CH$_2$Cl$_2$ (50 mL) and the combined organic phase is washed with H$_2$O (50 mL), dried (MgSO$_4$) and concentrated in vacuo. The residue is purified by column chromatography (silica, 25% ether in petroleum ether) to yield (±)-t-butyl (2R*, 3R*)-3-(4-methoxyphenylsulfonyl)-7-phenyl-2-(2-phenylsulfanylethyl)heptanoate (0.74 g, 57%): $^1$H NMR (300 MHz, CDCl$_3$) δ 7.76 (d, J=8.9 Hz, 2H), 7.27–7.13 (m, 8H), 7.06 (d, J=8.3 Hz, 2H), 6.97 (d, J=8.9 Hz, 2H), 3.86 (s, 3H), 3.52–3.48 (m, 1H), 3.27–3.18 (m, 1H), 2.99–2.87 (m, 2H), 2.45 (t, J=7.3 Hz, 2H), 2.43–2.32 (m, 1H), 1.98–1.82 (m, 1H), 1.72–1.58 (m, 3H), 1.50 (s, 9H), 1.45–1.15 (m, 3H); $^{13}$C NMR (75.5 MHz, CDCl$_3$) δ 171.23, 163.63, 141.98, 135.74, 130.64, 128.96, 128.88, 128.26, 125.96, 125.76, 114.29, 81.70, 66.31, 55.63, 42.91, 35.32, 32.10, 30.79, 28.01, 26.86, 26.65, 26.20; MS (FAB) m/e 568 (M$^+$).

Step B (±)-(2R*, 3R*)-3-(4-Methoxybenzenesulfonyl)-7-phenyl-2-(2-phenylsulfanylethyl)heptanoic acid The titled compound is prepared according to the method used in the preparation of (±)-(2R*,3R*)-3-(4-Methoxybenzenesulfonyl)-7-phenyl-2-(2-phenoxyethyl) heptanoic acid, except using (±)-t-butyl (2R*, 3R*)-3-(4-methoxyphenylsulfonyl)-7-phenyl-2-(2-phenylsulfanylethyl)heptanoate as the starting material. (±)-t-butyl (2R*, 3R*)-3-(4-methoxyphenylsulfonyl)-7-phenyl-2-(2-phenyl-sulfanylethyl)heptanoate (0.8 g, 1.4 mmol) provides (±)-(2R*, 3R*)-3-(4-Methoxybenzenesulfonyl)-7-phenyl-2-(2-phenylsulfanylethyl)heptanoic acid (0.7 g, 97%). Analytically pure sample is prepared by recrystallization (EtOAc/hexanes); m.p. 99–101° C.; $^1$H NMR (300 MHz, CDCl$_3$) δ 9.3–8.7 (bs, 1H), 7.78 (d, J=8.9 Hz, 2H), 7.28–7.13 (m, 8H), 7.06 (d, J=8.3 Hz, 2H), 6.97 (d, J=8.9 Hz, 2H), 3.85 (s, 3H), 3.70–3.64 (m, 1H), 3.39–3.31 (m, 1H), 3.19–3.15 (m, 1H), 3.03–2.93 (m, 1H), 2.57–2.50 (m, 1H) 2.47 (t, J=7.1 Hz, 2H), 1.97–1.88 (m, 1H), 1.72–1.32 (m, 5H), 1.25–1.12 (m, 1H); MS (FAB) m/e 512 (M$^+$); Anal. (C$_{28}$H$_{32}$O$_5$S) C, H, N.

Step C (±)-(2R*, 3R*)-3-(4-Methoxybenzenesulfonyl)-7-phenyl-2-(2-phenylsulfanylethyl)heptanoic acid hydroxyamide The titled compound is prepared according to the method used in the preparation of (±)-(2R*, R*)-3-(4-methoxybenzenesulfonyl)-7-phenyl-2-(2-phenoxyethyl) heptanoic acid hydroxyamide, except using (±)-(2R*, 3R*)-3-(4-methoxybenzenesulfonyl)-7-phenyl-2-(2-phenylsulfanyl-ethyl)heptanoic acid as the starting material. From (±)-(2R*, 3R*)-3-(4-methoxybenzenesulfonyl)-7-phenyl-2-(2-phenylsulfanylethyl)heptanoic acid (0.64 g, 1.2 mmol) provides (±)-(2R*, 3R*)-3-(4-methoxybenzenesulfonyl)-7-phenyl-2-(2-phenylsulfanylethyl)heptanoic acid hydroxyamide (0.5 g, 79%): $^1$H NMR (300 MHz, CDCl$_3$) δ 9.44 (bs, 1H), 7.75 (d, J=8.9 Hz, 2H), 7.28–7.14 (m, 8H), 7.05 (d, J=7.2 Hz, 2H), 6.99 (d, J=9.0 Hz, 2H), 3.88 (s, 3H), 3.28–3.25 (m, 1H), 3.00–2.93 (m, 2H), 2.75–2.66 (m, 1H), 2.46 (t, J=7.3 Hz, 2H), 2.43–2.30 (m, 1H) 1.83–1.17 (m, 8H); MS (FAB) m/e 528 (M+H)$^+$; Anal. (C$_{28}$H$_{33}$O$_5$NS$_2$.0.3 H$_2$O) C, H, N.

Enantiomers separated by chiral HPLC using a Chiral pack AD column eluting with a 40/60 mixture of 0.1% TFA in EtOH/heptane to provide a faster eluting isomer, (2R*, 3R*)-3-(4-methoxybenzenesulfonyl)-7-phenyl-2-(2-phenylsulfanylethyl)heptanoic acid hydroxyamide; [a]$_D$=−50°, and a slower eluting isomer, (2R*, 3R*)-3-(4-methoxybenzenesulfonyl)-7-phenyl-2-(2-phenylsulfanylethyl)heptanoic acid hydroxyamide; [a]$_D$=+40°.

EXAMPLE 47

(2R*, 3R*)-3-(4-methoxybenzenesulfonyl)-7-phenyl-2-(2-phenylsulfanylethyl)heptanoic Acid Hydroxyamide and (±)-(2R*,3S*)-3-(4-Methoxybenzenesulfonyl)-7-phenyl-2-(benzenesulfonylmethyl)heptanoic Acid Hydroxyamide Step A t-butyl 2-(1-hydroxy-5-phenylpentyl)acrylate t-Butyl acrylate (6.7 g, 46 mmol), 5-phenyl pentanal (3.7 g, 23 mmol) and 3-quinuclidinol (0.38 g, 3 mmol) are combined and stirred under $N_2$. After 24 hours stirring is halted and the resulting solution is allowed to sit at ambient temperature for 16 days. TLC analysis (30% ether in petroleum ether) showed that the reaction is nearly complete. The product is purified by column chromatography (silica, 20% ether in petroleum ether) to yield t-butyl 2-(1-hydroxy-5-phenylpentyl)acrylate (6 g, 45%): $^1$H NMR (300 MHz, $CDCl_3$) δ 7.29–7.24 (m, 2H), 7.18–7.14 (m, 3H), 6.10 (d, J=1.1 Hz, 1H), 5.67 (s, 1H), 4.33 (q, J=6.7 Hz, 1H), 2.74 (d, J=6.7 Hz, 1H), 2.61 (t, J=7.6 Hz, 2H), 1.70–1.53 (m, 4H), 1.50 (s, 9H), 1.50–1.32 (m, 2H); $^{13}$C NMR (75.5 MHz, $CDCl_3$) δ 165.93, 143.91, 142.51, 128.32, 128.20, 125.57, 123.82, 81.35, 71.79, 36.17, 35.82, 31.26, 28.04, 25.54; MS (EI) m/e 291 $(M+H)^+$.

Step B (E)-2-t-Butoxycarbonyl-7-phenylhept-2-enyl benzoate

Diisopropyl azodicarboxylate (5 mL, 25 mmol) is added dropwise over 5 minutes to a solution of t-butyl 2-(1-hydroxy-5-phenylpentyl)acrylate (5.59 g, 19.3 mmol), benzoic acid (3 g, 25 mmol) and triphenyl phosphine (6.5 g, 25 mmol) in THF (100 mL) at −55° C. The reaction is maintained between −55 and −50° C. for 45 minutes and then the reaction is allowed to warm to 0° C. The solution is diluted with ether (300 mL) and washed with 1 N NaOH (2×40 mL) and brine (70 mL). The resulting solution is dried ($MgSO_4$) and concentrated in vacuo. The crude reaction product is partially dissolved in 20% ether/petroleum ether and applied to a silica gel column as a slurry. The column is eluted using gradient elution (silica, 10 to 20% ether in petroleum ether) to obtain (E)-2-t-Butoxycarbonyl-7-phenylhept-2-enyl benzoate (6.2 g, 82%): $^1$H NMR (300 MHz, $CDCl_3$) δ 8.01 (d, J=7.0 Hz, 2H), 7.53–7.49 (m, 1 H), 7.41 (t, J=7.5 Hz, 2H), 7.28–7.23 (m, 2H), 7.20–7.10 (m, 3H), 6.99 (t, J=7.8 Hz, 1H), 5.05 (s, 2H), 2.61 (t, J=7.5 Hz, 2H), 2.36 (q, J=7.5 Hz, 2H), 1.72–1.46 (m, 4H), 1.47 (s, 9H); MS (FAB) m/e 395 $(M+H)^+$.

Step C t-butyl (E)-2-hydroxymethyl-7-phenylhept-2-enoate (E)-2-t-Butoxycarbonyl-7-phenylhept-2-enyl benzoate (5.9 g, 15 mmol) is dissolved in MeOH (75 mL) and cooled to 0° C. $K_2CO_3$ (2 g, 15 mmol) is added with stirring and the reaction is allowed to warm to 23° C. After 2 hours the reaction is neutralized with HOAc and the reaction is concentrated to approximately half of its volume. After diluting with ether (500 mL), the solution is washed with water (50 mL) and brine (50 mL). The resulting solution is dried ($MgSO_4$) and concentrated in vacuo. The crude reaction mixture is purified by column chromatography (silica, 25% ether in petroleum ether) to give t-butyl (E)-2-hydroxymethyl-7-phenylhept-2-enoate (2.2 g, 51%): $^1$H NMR (300 MHz, $CDCl_3$) δ 7.30–7.25 (m, 2H), 7.20–7.15 (m, 3H), 6.75 (t, J=7.7 Hz, 1H), 4.28 (d, J=6.8 Hz, 2H), 2.65–2.60 (m, 3H), 2.26 (q, J=7.5 Hz, 2H), 1.71–1.61 (m, 2H), 1.53–1.43 (m, 11H).

Step D (±)-t-butyl (2R*,3R*)-2-hydroxymethyl-3-(4-methoxyphenylsulfanyl)-7-phenylheptanoate A solution of n-butyl lithium in hexanes (0.6 mL, 1.4 mmol) is added slowly to a mixture of 4-methoxybenzenethiol (2 g, 14 mmol) in THF (10 mL) at 0° C. After 2 minutes a solution of t-butyl (E)-2-hydroxymethyl-7-phenylhept-2-enoate (2.2 g, 7.59 mmol) in THF (7 mL) is added and the reaction is allowed to warm to room temperature. After 1 hours the reaction is concentrated in vacuo and the crude product is purified by column chromatography using gradient elution (silica, 15 to 30% ether in petroleum ether) to give (±)-t-butyl (2R*,3R*)-2-hydroxymethyl-3-(4-methoxyphenylsulfanyl)-7-phenylheptanoate (3 g, 92%): $^1$H NMR (300 MHz, $CDCl_3$) δ 7.39–7.34 (m, 2H), 7.30–7.25 (m, 2H), 7.20–7.13 (m, 3H), 6.86–6.81 (m, 2H), 4.07–3.98 (m,1H), 3.93–3.86 (m, 1H), 3.80 (s, 3H), 3.26–3.19 (m, 1H), 2.67–2.60 (m, 1H), 2.58 (t, J=7.2 Hz, 2H), 2.38 (t, J=6.6 Hz, 1H), 1.65–1.47 (m, 6H), 1.46 (s, 9H); MS (FAB) m/e 430 $(M^+)$.

Step E (±)-t-butyl (2R*,3R*)-2-hydroxymethyl-3-(4-methoxybenzenesulfonyl)-7-phenylheptanoate A solution of oxone (6.4 g, 10 mmol) in water (30 mL) is added dropwise to a solution of (±)-t-butyl (2R*,3R*)-2-hydroxymethyl-3-(4-methoxyphenylsulfanyl)-7-phenylheptanoate (3 g, 7 mmol) in THF (10 mL) and methanol (15 mL) at 0° C. The reaction is warmed to 23° C. and stirred 6 hours. The mixture is then partitioned between $CH_2Cl_2$ (150 mL) and water (75 mL). The layers are separated and the aqueous phase is back-extracted with $CH_2Cl_2$ (2×30 mL). The organic layers are combined, washed with $NaHCO_3$ (50 mL), dried ($MgSO_4$) and concentrated in vacuo to yield (±)-t-butyl (2R*,3R*)-2-hydroxymethyl-3-(4-methoxybenzenesulfonyl)-7-phenylheptanoate (3.1 g, 96%) which is used without further purification. $^1$H NMR (300 MHz, $CDCl_3$) δ 7.81–7.76 (m, 2H), 7.27–7.22 (m, 2H), 7.19–7.14 (m, 1H), 7.09–6.98 (m, 4H), 4.30–4.21 (m, 1H), 3.91–3.82 (m, 1H), 3.88 (s, 3H), 3.67–3.61 (m, 1H), 2.94–2.89 (m, 1H), 2.82 (dd, J=9.0, 5.5 Hz, 1H), 2.48 (t, J=7.4 Hz, 2H), 1.76–1.69 (m, 2H), 1.51 (s, 9H), 1.51–1.35 (m, 3H), 1.25–1.13 (m, 1H); MS (FAB) m/e 463 $(M+H)^+$.

Step F (±)-(2R*,3R*)-2-Hydroxymethyl-3-(4-methoxybenzenesulfonyl)-7-phenylheptanoic acid Trifluoroacetic acid (5 mL) is added to a solution of (±)-t-butyl (2R*,3R*)-2-hydroxymethyl-3-(4-methoxybenzenesulfonyl)-7-phenylheptanoate (3.1 g, 6.7 mmol) in $CH_2Cl_2$ (20 mL). The reaction is monitored by TLC analysis (5% MeOH in $CH_2Cl_2$) and before all of the ester is consumed the reaction is concentrated and azeotroped with $CHCl_3$ (3×15 mL). The crude product is purified by column chromatography (silica, 5% MeOH in $CH_2Cl_2$) to yield pure (±)-(2R*, 3R*)-2-Hydroxymethyl-3-(4-methoxybenzenesulfonyl)-7-phenylheptanoic acid (1.4 g, 51%): $^1$H NMR (300 MHz, $CDCl_3$) δ 7.78 (d, J=7.0 Hz, 2H), 7.25–7.11 (m, 3H), 7.07–6.93 (m, 4H), 6.5–5.7 (bs, 1H), 4.34–4.26 (bm, 1H), 3.95–3.89 (bm, 1H), 3.82 (s, 3H), 3.81–3.69 (bm, 1H), 3.13–3.06 (bm, 1H), 2.46–2.37 (bm, 2H), 1.75–1.67 (bm, 2H), 1.48–1.30 (bm, 3H), 1.22–1.09 (bm, 1H); MS (FAB) m/e 406 $(M+H)^+$.

Step G (±)-3-(R*)-[1-(R*)-(4-Methoxybenzenesulfonyl)-5-phenylpentyl]oxetan-2-one Diethyl azodicarboxylate (0.45 mL, 2.7 mmol) is added dropwise to a solution of triphenyl phosphine (0.71 g, 2.7 mmol) in THF (18 mL) at −78° C. After 15 minutes a solution of (±)-(2R*, 3R*)-2-Hydroxymethyl-3-(4-methoxybenzenesulfonyl)-7-phenylheptanoic acid (1 g, 2.5 mmol) in THF (8 mL) is added dropwise over 5 minutes. After 30 minutes the bath is removed and the reaction is allowed to warm to 23° C. and stir for 45 minutes. The reaction is concentrated in vacuo and the crude reaction mixture is purified by column chromatography (silica, $CH_2Cl_2$) to yield pure (±)-3-(R*)-[1-(R*)-(4-methoxybenzenesulfonyl)-5-phenypentyl]oxetan-2-one (0.63 g, 63%): $^1$H NMR (300 MHz, CDCl$_3$) δ 7.75–7.70 (m, 2H), 7.28–7.23 (m, 2H), 7.19–7.14 (m, 1H), 7.12–7.09 (m, 2H), 7.03–6.95 (m, 2H), 4.41 (t, J=6.2 Hz, 1H), 4.31 (t, J=5.4 Hz, 1H), 4.03–3.95 (m, 1H), 3.87 (s, 3H), 3.44–3.37 (m, 1H), 2.53 (t, J=7.2 Hz, 2H), 1.89–1.81 (m, 2H), 1.58–1.38 (m, 4H); $^{13}$C NMR (75.5 MHz, CDCl$_3$) δ 167.83, 164.25, 141.89, 130.91, 128.21, 128.17, 125.65, 114.65, 113.91, 65.04, 63.83, 55.68, 50.47, 35.16, 30.91, 27.04, 25.73; MS (FAB) m/e 389 (M+H)$^+$.

Step H (±)-(2R*,3S*)-3-(4-Methoxybenzenesulfonyl)-7-phenyl-2-(phenylsulfanylmethyl)heptanoic acid A 60% suspension of NaH in mineral oil (84 mg, 2.2 mmol) is carefully added to a solution of thiophenol (0.30 g, 2.7 mmol) in THF (10 mL) at 0° C. The mixture is allowed to warm to ambient temperature and is transferred to a solution of (±)-3-(R*)-[1-(R*)-(4-methoxybenzenesulfonyl)-5-phenylpentyl]-oxetan-2-one (0.63 g, 1.6 mmol) in THF (10 mL). The reaction is stirred 14 hours and then acidified with acetic acid. The crude mixture is azeotroped with methanol (2×50 mL) and purified by column chromatography using gradient elution (silica, 1 to 3% MeOH in CH$_2$Cl$_2$) to yield pure (±)-(2R*,3S*)-3-(4-methoxybenzenesulfonyl)-7-phenyl-2-(phenylsulfanylmethyl)heptanoic acid (0.64 g, 82%): m.p. 133–135; $^1$H NMR (300 MHz, CDCl$_3$) δ 7.75 (d, J=8.6 Hz, 2H), 7.30–7.17 (m, 8H), 7.06 (d, J=7.3 Hz, 2H), 6.93 (d, J=8.6 Hz, 2H), 3.84 (s, 3H), 3.63 (bs, 1H), 3.52 (dd, J=14.2, 7.7 Hz, 1H), 3.14 (dd, J=14.2, 5.2 Hz, 1H), 2.98 (bs, 1H), 2.43 (t, J=7.4 Hz, 2H), 1.95–1.83 (m, 1H), 1.78–1.62 (m, 1H), 1.50–1.34 (m, 2H), 1.28–1.07 (m, 2H); MS (FAB) m/e 489 (M$^+$); Anal. (C$_{27}$H$_{30}$O$_5$S$_2$) C, H, N.

Step I (±)-(2R*,3S*)-3-(4-Methoxybenzenesulfonyl)-7-phenyl-2-(phenylsulfanylmethyl)heptanoic acid hydroxyamide (±)-(2R*,3S*)-3-(4-Methoxybenzenesulfonyl)-7-phenyl-2-(phenylsulfanylmethyl)heptanoic acid (0.42 g, 0.84 mmol) is dissolved in CH$_2$Cl$_2$ (3 mL) and cooled to 0° C. A solution of oxalyl chloride in CH$_2$Cl$_2$ (1.5 mL, 3 mmol) is added dropwise, the bath removed and the reaction allowed to warm and stir at 23° C. for 1 hour. The reaction is then concentrated in vacuo and azeotroped with CHCl$_3$. The resulting oil is dissolved in CH$_2$Cl$_2$ (2 mL), cooled to 0° C. and O-(trimethylsilyl)hydroxylamine (0.3 mL, 2.6 mmol) is added dropwise. The bath is removed and the reaction is allowed to warm to 20° C. The reaction is then partitioned between CH$_2$Cl$_2$ (20 mL) and 1 N HCl (10 mL). The organic layer is then separated and washed with water (10 mL), dried (MgSO$_4$) and concentrated in vacuo to yield (±)-(2R*,3S*)-3-(4-methoxybenzenesulfonyl)-7-phenyl-2-(phenylsulfanylmethyl)heptanoic acid hydroxyamide (0.37 g, 87%) The material obtained from the reaction is analytically pure: $^1$H NMR (300 MHz, CD$_3$OD) δ 7.74–7.69 (m, 2H), 7.32–7.17 (m, 1H), 7.15–7.08 (m, 1H), 7.06–7.01 (m, 4H), 3.87 (s, 3H), 3.49 (dd, J=13.8, 5.3 Hz, 1H), 3.39 (q, J=5.3 Hz, 1H), 3.21 (dd, J=13.8, 9.8 Hz, 1H), 2.98–2.85 (m, 1H), 2.43 (t, J=7.3 Hz, 2H), 1.78–1.71 (m, 2H), 1.41–1.10 (m, 4H); MS (FAB) m/e 514 (M+H)$^+$; Anal. (C$_{27}$H$_{31}$NO$_5$S$_2$) C, H, N.

Step J (±)-(2R*,3S*)-3-(4-Methoxybenzenesulfonyl)-7-phenyl-2-(benzenesulfonylmethyl)heptanoic acid hydroxyamide The procedure for the oxidation of (±)-t-butyl (2R*,3R*)-2-hydroxymethyl-3-(4-methoxyphenylsulfanyl)-7-phenylheptanoate to (±)-t-butyl (2R*,3R*)-2-hydroxymethyl-3-(4-methoxybenzenesulfonyl)-7-phenylheptanoate is used to convert (±)-(2R*,3S*)-3-(4-methoxy-benzenesulfonyl)-7-phenyl-2-(phenylsulfanylmethyl)heptanoic acid hydroxyamide (80 mg) to (±)-(2R*,3S*)-3-(4-Methoxybenzenesulfonyl)-7-phenyl-2-(benzenesulfonylmethyl)heptanoic acid hydroxyamide (78 mg, 87%). The material obtained from the reaction is analytically pure: $^1$H NMR (300 MHz, CD$_3$OD) δ 7.92 (d, J=7.5 Hz, 2H), 7.78–7.61 (m, 5H), 7.23–7.02 (m, 7H), 3.92–3.78 (m, 5H), 3.35–3.23 (m, 2H), 2.41 (t, J=7.4 Hz, 2H), 1.68–1.62 (m, 2H), 1.40–1.05 (m, 4H); MS (FAB) m/e 545 (M+H)$^+$; Anal. (C$_{27}$H$_{31}$NO$_7$S$_2$) C, H, N.

EXAMPLE 48

(±) 2-Hydroxy-3-(4-methoxybenzenesulfonyl)-2-methyl-7-phenylheptanoic Acid Hydroxyamide Step A 1-(5-Phenylpentane-1-sulfonyl)-4-methoxybenzene Phosphorous tribromide (7.1 mL, 75 mmol) is added slowly with stirring to 5-phenylpentanol (25 g, 150 mmol) at 0° C. The bath is removed and the reaction is stirred at 23° C. for 2 h and then warmed to 70° C. After 3 hours the reaction is cooled and poured onto ice (250 g). The mixture is extracted with ether (500 mL). The organic phase is washed with water (100 mL), NaHCO$_3$ (2×200 mL) and dried (MgSO$_4$). The resulting solution is concentrated in vacuo to yield the bromide (28 g) which is used without further purification. The crude bromide is dissolved in EtOH (70 mL) and 4-methoxybenzenethiol (18 g, 130 mmol) and cooled to 0° C. A 21% (w/w) solution of NaOEt in EtOH (46 mL, 120 mmol) is slowly added, and the reaction is warmed to 50° C. After 26 hours the reaction is cooled and concentrated in vacuo to yield crude sulfide (36 g) which is used without further purification. The crude sulfide is dissolved in MeOH (500 mL) and THF (75 mL) and cooled to 10° C. A solution of oxone (115 g, 187 mmol) in water (500 mL) is added slowly over 1 hours. The reaction is allowed to warm to ambient temperature and is stirred 18 hours. The organic phase is removed in vacuo and the resulting mixture is partitioned between CH$_2$Cl$_2$ (800 mL) and water (500 mL). The aqueous phase is back-extracted with CH$_2$Cl$_2$ (2×100 mL) and the organic layers are combined. After drying (MgSO$_4$), the organic phase is concentrated in vacuo, and the solid is recrystallized from MeOH twice to yield pure 1-(5-Phenylpentane-1-sulfonyl)-4-methoxybenzene (28.3 g, 58% for 3 steps): m.p. 64–65° C.; $^1$H NMR (300 MHz, CDCl$_3$) δ 7.81 (d, J=8.7 Hz, 2H), 7.28–7.23 (m, 2H), 7.17 (d, J=6.7 Hz, 1H), 7.11 (d, J=7.5 Hz, 2H), 7.01 (d, J=8.7 Hz, 2H), 3.88 (s, 3H), 3.06–3.01 (m, 2H), 2.57 (t, J=7.6 Hz, 2H), 1.77–1.66 (m, 2H), 1.62–1.54 (m, 2H), 1.43–1.35 (m, 2H); MS (FAB) m/e 319 (M+H)$^+$.

Step B (±)-Methyl 2-hydroxy-3-(4-methoxybenzenesulfonyl)-2-methyl-7-phenylheptanoate A solution of n-butyl lithium in hexanes (1.9 mL, 4.4 mmol) is added dropwise to a solution of 1-(5-phenylpentane-1-sulfonyl)-4-methoxybenzene (1.35 g, 4.24 mmol) in THF (15 mL) at −78° C. The reaction is stirred at −78° C. for 15 minutes, raised to −30° C. for 15 minutes and then returned to −78° C. This solution is then cannulated into a solution of methyl pyruvate (0.82 g, 7.2 mmol) in THF (5 mL) precooled to −78° C. After 15 minutes the reaction is slowly warmed to −30° C. and stirred 15 minutes before quenching with a solution of NH$_4$Cl (15 mL). The reaction is partitioned between ether (150 mL) and water (50 mL), and the layers are separated. The ether layer is washed with brine (50 mL), dried (MgSO$_4$) and concentrated in vacuo. The crude product is purified by gradient elution chromatography (silica, CH$_2$Cl$_2$ to 1% MeOH in CH$_2$Cl$_2$) to yield a diastereomeric mixture (2:3 ratio) of methyl 2-hydroxy-3-(4-methoxybenzenesulfonyl)-2-methyl-7-phenylheptanoate products (0.60 g, 35%). An analytical sample of each isomer is obtained by additional chromatography using identical conditions; upper isomer, methyl 2-hydroxy-3-(4-methoxybenzenesulfonyl)-2-methyl-7-phenylheptanoate: $^1$H NMR (300 MHz, CDCl$_3$) δ 7.78 (d, J=8.7 Hz, 2H), 7.28–7.23 (m, 2H), 7.19–7.14 (m, 1H), 7.06 (d, J=7.6 Hz, 2H), 6.99–6.94 (m, 2H), 4.0–3.7 (br,1H), 3.87 (s, 3H), 3.78 (s, 3H), 3.34–3.30 (m, 1H), 2.45 (t, J=7.5 Hz, 2H), 1.98–1.75 (m, 2H), 1.61 (s, 3H), 1.48–1.38 (m, 2H), 1.29–1.10 (m, 2H); MS (FAB) m/e 421 (M+H)$^+$; lower isomer methyl 2-hydroxy-3-(4-methoxybenzenesulfonyl)-2-methyl-7-phenylheptanoate: $^1$H NMR (300 MHz, CDCl$_3$) δ 7.77–7.74 (m, 2H), 7.28–7.23 (m, 2H), 7.20–7.15 (m, 1H), 7.09 (d, J=7.6 Hz, 2H), 6.99–6.94 (m, 2H), 3.87 (s, 3H), 3.84 (s, 3H), 3.64 (bs, 1H), 3.52 (t, J=6.5 Hz, 1H), 2.51 (t, J=7.5 Hz, 2H), 1.92–1.86 (m, 2H), 1.52–1.33 (m, 4H), 1.41 (s, 3H); MS (FAB) m/e 421 (M+H)$^+$.

Step C (±) 2-Hydroxy-3-(4-methoxybenzenesulfonyl)-2-methyl-7-phenylheptanoic acid hydroxyamide Sodium spheres (0.13 g, 5.7 mmol) are added to a solution of hydroxylamine hydrochloride (0.29 g, 4.2 mmol) in MeOH (4 mL) at 0° C. The reaction is allowed to warm until all of the sodium is reacted. The mixture is added to (±)-methyl 2-hydroxy-3-(4-methoxybenzenesulfonyl)-2-methyl-7-phenylheptanoate (0.6 g, 1.4 mmol) and stirred at 23° C. After 12 hours additional hydroxylamine hydrochloride (0.15 g, 2.2 mmol) and sodium (60 mg, 2.6 mmol) are added sequentially with cooling. After 1 hour the reaction is partitioned between CH$_2$Cl$_2$ (100 mL) and saturated NH$_4$Cl solution (50 mL). The aqueous phase is back-extracted with CH$_2$Cl$_2$ (2×20 mL). The combined organic layer is washed with 0.5 N HCl (30 mL), brine (30 mL), dried (MgSO$_4$) and concentrated in vacuo. The crude product is purified by reverse phase HPLC (40% to 100% CH$_3$CN in 0.1% TFA/H$_2$O, 30 minutes) to provide hydroxamic acid (±) 2-Hydroxy-3-(4-methoxybenzenesulfonyl)-2-methyl-7-phenylheptanoic acid hydroxyamide as a mixture of diastereomers. The diastereomers are separated by preparative TLC (silica, 4% MeOH in CH$_2$Cl$_2$) with multiple elutions; upper isomer, 2-Hydroxy-3-(4-methoxybenzenesulfonyl)-2-methyl-7-phenylheptanoic acid hydroxyamide: $^1$H NMR (300 MHz, CDCl$_3$) δ 9.25 (bs, 1H), 7.77 (d, J=8.7 Hz, 2H), 7.27–7.12 (m, 3H), 7.06–6.96 (m, 4H), 4.34 (bs, 1H), 3.87 (s, 3H), 3.47–3.42 (m, 1H), 2.37 (t, J=7.6 Hz, 2H), 1.78–1.52 (m, 4H), 1.70 (s, 3H), 1.45–1.10 (m, 2H); MS (ion spray) m/e 422 (M+H)$^+$; lower isomer, 2-Hydroxy-3-(4-methoxybenzenesulfonyl)-2-methyl-7-phenylheptanoic acid hydroxyamide: $^1$H NMR (300 MHz, CDCl$_3$) δ 9.50 (bs, 1H), 7.74 (bm, 2H), 7.28–7.12 (m, 3H), 7.07–7.03 (m, 4H), 5.0–4.4 (br, 1H), 3.87 (s, 3H), 3.65–3.55 (bm, 1H), 2.48 (bt, 2H), 1.98–1.90 (bm, 2H), 1.55–1.18 (bm, 7H); MS (ion spray) m/e 422 (M+H)$^+$.

EXAMPLE 49

(±)-3-(4-Methoxyphenylsulfanyl)-2-methyl-7-phenylheptanoic Acid Hydroxyamide (E)-Ethyl 2-methyl-7-phenyl-hept-2-enoate Triethyl-2-phosphonopropionate (12 g, 50 mmol) and 5-phenylpentanal (7 g, 43 mmol) are dissolved in dry THF (100 mL) and cooled to 10° C. A solution of sodium ethoxide in ethanol (23 mL, 21%, 43 mmol) is added slowly over 20 minutes and the reaction is warmed to 23° C. After stirring 1 hour, the reaction is quenched by the addition of a saturated NH$_4$Cl solution (30 mL). The reaction is concentrated to remove the THF in vacuo, diluted with petroleum ether (400 mL) and washed with 1 N HCl (100 mL), H$_2$O (100 mL), NaHCO$_3$ (100 mL), brine (100 mL) and dried (MgSO$_4$). The solution is concentrated in vacuo and purified by filtration through a plug of silica gel using 2% ether/pet ether as the eluant to yield (E)-ethyl 2-methyl-7-phenylhept-2-enoate, (8.9 g, 84%) which contains a small amount (10%) of the Z-isomer: $^1$H NMR (CDCl$_3$) δ 7.29–7.23 (m, 2H), 7.19–7.14 (m, 3H), 6.75 (dt, J=15.5, 1.5 Hz, 1H), 4.18 (q, J=7.1 Hz, 2H), 2.62 (t, J=7.5 Hz, 2H), 2.18 (q, J=7.0 Hz, 2H), 1.81 (s, 3H), 1.70–1.59 (m, 2H), 1.54–1.42 (m. 2H), 1.28 (t, J=7.1 Hz, 3H); MS (FAB) m/e 247 (M+H)$^+$.

Step B (E)-2-Methyl-7-phenyl-hept-2-enoic acid

Sodium hydroxide (1.4 g, 35 mmol) is added to a solution of (E)-ethyl 2-methyl-7-phenyl-hept-2-enoate (8.6 g, 35 mmol) in MeOH (40 mL) and water (2 mL) at 0° C. The reaction is stirred at 23° C. for 2 hours and then heated at 50° C. for 24 hours. After cooling, the reaction is concentrated in vacuo and partitioned between 2N HCl (15 mL) and CH$_2$Cl$_2$ (60 mL). The aqueous layer is back-extracted with CH$_2$Cl$_2$ (2×30 mL) and the organic layers are combined and dried (MgSO$_4$). The solution is concentrated in vacuo and purified by gradient elution chromatography (silica, 20 to 40% ether in petroleum ether) to yield (E)-2-Methyl-7-phenyl-hept-2-enoic acid (4.9 g, 65%): $^1$H NMR (CDCl$_3$) δ 7.30–7.23 (m, 2H), 7.20–7.14 (m, 3H), 6.90 (dt, J=15.4, 1.3 Hz, 1 H), 2.62 (t, J=7.5 Hz, 2H), 2.22 (q, J=7.0 Hz, 2H), 1.81 (s, 3H), 1.69–1.58 (m, 2H), 1.55–1.43 (m, 2H); MS (FAB) m/e 219 (M+H)$^+$.

Step C (±)-3-(4-Methoxyphenylsulfanyl)-2-methyl-7-phenylheptanoic acid (E)-2-Methyl-7-phenyl-hept-2-enoic acid (2.2 g, 10 mmol), 4-methoxybenzenethiol (2.8 g, 20 mmol) and piperidine (0.1 mL, 1 mmol) are combined and heated at 85° C. for 12 hours. The reaction is cooled and purified by gradient elution chromatography (silica, 35 to 100% ether in petroleum ether) to yield (±)-3-(4-Methoxyphenylsulfanyl)-2-methyl-7-phenylheptanoic acid (0.9 g, 25%) as a 50/50 mixture of diastereomers: $^1$H NMR (300 MHz, CDCl$_3$) δ 7.39–7.34 (m, 2H), 7.29–7.25 (m, 2H), 7.20–7.11 (m, 3H), 6.81 (m, 2H), 3.79 (s, 1.5H), 3.78 (s, 1.5H), 3.30–3.16 (m, 1H), 2.70–2.54 (m, 3H), 1.72–1.40 (m, 6H), 1.28 (d, J=7.0 Hz, 1.5H), 1.22 (d, J=7.0 Hz, 1.5H); MS (FAB) m/e 359 (M+H)$^+$.

Step D (±)-3-(4-Methoxyphenylsulfanyl)-2-methyl-7-phenylheptanoic acid hydroxyamide (±)-3-(4-Methoxyphenylsulfanyl)-2-methyl-7-phenylheptanoic acid (0.38 g, 1.1 mmol) is dissolved in CH$_2$Cl$_2$ (1 mL) and cooled to 0° C. A solution of oxalyl chloride in CH$_2$Cl$_2$ (0.7 mL, 1.4 mmol) is added dropwise, the bath removed and the reaction allowed to warm and stir at 23° C. for 3 hours. The reaction is then concentrated in vacuo and azeotroped with CHCl$_3$. The resulting oil is dissolved in CH$_2$Cl$_2$ (3 mL), cooled to 0° C. and O-(trimethylsilyl)hydroxylamine (0.4 mL, 3.4 mmol) is added dropwise. The bath is removed and the reaction is allowed to warm to 20° C. The reaction is then partitioned between CH$_2$Cl$_2$ (20 mL) and 1 N HCl (10 mL). The organic layer is then separated and washed with water (10 mL), dried (MgSO$_4$) and concentrated in vacuo to yield (±)-3-(4-methoxyphenylsulfanyl)-2-methyl-7-phenylheptanoic acid hydroxyamide (0.37 g, 90%) which is used without further purification: $^1$H NMR (300 MHz, CDCl$_3$) δ 7.30–7.18 (m, 4H), 7.14–7.07 (m, 3H), 7.80–7.73 (m, 2H), 3.73 (s, 1.5H), 3.72 (s, 1.5H), 3.12–3.06 (m, 0.5H), 2.97–2.90 (m, 0.5H), 2.53 (m, 2H), 2.32–2.19 (m, 1H), 1.68–1.25 (m, 6H) 1.16 (d, J=7.0 Hz, 1.5H), 1.11 (d, J=7.0 Hz, 1.5H); MS (FAB) m/e 374 (M+H)$^+$.

Step E (±)-3-(4-Methoxybenzenesulfonyl)-2-methyl-7-phenylheptanoic acid hydroxyamide A solution of (±)-3-(4-methoxyphenylsulfanyl)-2-methyl-7-phenylheptanoic acid hydroxyamide (0.37 g, 1.1 mmol) in MeOH (10 mL) is cooled to 0° C. and a solution of oxone (1.2 g, 1.9 mmol) in water (8 mL) is added dropwise over 10 minutes. The bath is removed and the reaction is allowed to warm to 20° C. and stir for 16 hours. The mixture is then partitioned between CH$_2$Cl$_2$ (70 mL) and water (50 mL). The aqueous layer is back-extracted (2×20 mL), the organic fractions are combined, washed with brine and dried (MgSO$_4$). The solution is concentrated in vacuo and purified by reverse-phase HPLC using CH$_3$CN/0.1% TFA to yield (±)-3-(4-methoxybenzenesulfonyl)-2-methyl-7-phenylheptanoic acid hydroxyamide (0.35 g, 79%); MS (FAB) m/e 406 (M+H)$^+$. The diastereomers are separated by reverse-phase HPLC using MeOH/0.2% TFA to yield the faster eluting isomer 3-(4-Methoxybenzenesulfonyl)-2-methyl-7-phenylheptanoic acid hydroxyamide (15 mg): $^1$H NMR (300 MHz, DMSO) δ 10.60 (s, 1H), 8.88 (bs, 1H), 7.76 (d, J=8.7 Hz, 2H), 7.24 (t, J=7.7 Hz, 2H), 7.16–7.12 (m, 3H), 7.06 (d, J=7.0 Hz, 2H), 3.85 (s, 3H), 3.34–3.27 (m, 1H), 2.65–2.58 (m, 1H), 2.40–2.31 (m, 2H), 1.62–1.05 (m, 6H), 1.19 (d, J=6.9 Hz, 3H); and the slower eluting isomer 3-(4-methoxybenzenesulfonyl)-2-methyl-7-phenylheptanoic acid hydroxyamide (60 mg): $^1$H NMR (300 MHz, DMSO) δ 10.57 (s, 1H), 8.75 (bs, 1H), 7.76 (d, J=8.6 Hz, 2H), 7.24 (t, J=7.7 Hz, 2H), 7.16–7.13 (m, 3H), 7.06 (d, J=7.0 Hz, 2H), 3.85 (s, 3H), 3.43–3.38 (m, 1H), 2.88–2.83 (m, 1H), 2.42–2.35 (m, 2H), 1.75–1.67 (m, 2H), 1.41–1.30 (m, 2H), 1.23–1.10 (m, 2H), 1.06 (d, J=7.1 Hz, 3H).

EXAMPLE 50

4-(2',4'-Dimethoxyphenyl-O-methylhydroxylamine) phenoxymethyl-copoly(styrene-1%-divinylbenzene)-resin (100–200 mesh).

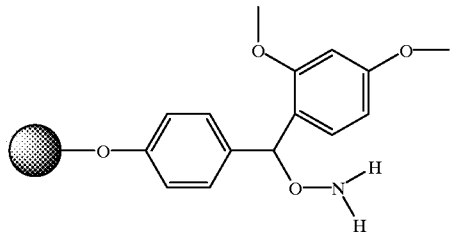

Rink acid resin (1 g; 0.63 mmol) is swelled in DMF (10 mL) for 15 minutes at ambient temperature. N-hydroxyphthalimide (514 mg; 3.15 mmol) is added to the resin suspension followed by benzene sulfonic acid (19 mg; 0.13 mmol). The mixture is stirred by means of a mechanical stirrer and heated to 50° C. for five hours. The mixture is then cooled to ambient temperature and stirred for an additional 12 hours, after which the resin is filtered and washed extensively with DMF (5×25 mL); DMF:H$_2$O (70:30; 5×25 mL); THF (10×25 mL); and diethyl ether (10×25 mL). The resin is then dried overnight under high vacuum at 40° C. The IR spectrum of resin II shows a carbonyl absorbance at 1733 cm$^{-1}$ corresponding to the phthalimido carbonyl stretch. Elemental analysis on %N found 0.26; 0.28 calc. loading=0.18 mmol/g). Alternate procedure using camphor sulfonic acid instead of benzene sulfonic acid (carbonyl stretch at 1734 cm$^{-1}$).

The resin is swelled in 20 mL of t-butanol for ten minutes. Hydrazine hydrate (10 mL) is added to the mixture and the reaction is warmed to 60° C. with mechanical stirring for 12 hours. After which the reaction is cooled to ambient temperature. The resin is filtered and washed extensively with DMF (10×25 mL), THF (10×25 mL), and diethyl ether (10×25 mL), then dried under high vacuum at 40° C. overnight. The IR spectrum of resin III showed the loss of the carbonyl stretch at 1733 cm$^{-1}$ which is present in the starting material. Elemental Analysis %N found=0.43; 0.42 (coresponding to a loading level of 0.3 mmol/g) (camphor sulphonic acid used in the synthesis) %N found=0.57; 0.54 (corresponding to a loading of 0.38 mmol/g).

EXAMPLE 51

Coupling of 3-(4-methoxyphenylsulfonyl)propionic Acid to Resin III.

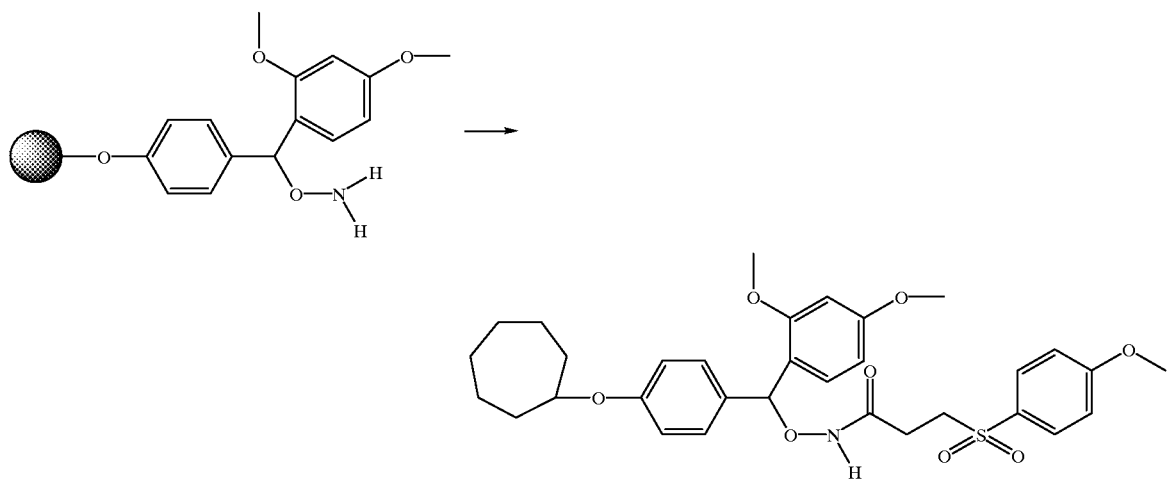

Resin III 200 mg is swelled in DMF (3 mL). To this suspension is added 3-(4-methoxyphenylsulfonyl)propionic acid (610 mg; 2.5 mmol) and 1-(3-dimethylaminopropyl)-3-ethyl carbodiimide hydrochloride (EDCl; 477 mg; 2.5 mmol) at ambient temperature. The reaction mixture is shaken at ambient temperature using a vortex shaker for 12 h, after which the resin is filtered and washed extensively with DMF:H$_2$O (80:20; 5×5 mL), DMF (5×5 mL), THF (5×5 mL), and diethyl ether (5×5 mL). The resin IV is dried under high vacuum at 40° C. for 12 hours. The IR spectrum shows a carbonyl absorbance at 1675 cm$^{-1}$ corresponding to the bound hydroxamate.

EXAMPLE 52

Cleavage of the Hydroxamic Acid from Resin IV

Resin IV (200 mg) is swelled in 3 mL of methylene chloride for 10 minutes. Trifluoroacetic acid (TFA; 0.3 mL) is added to the mixture dropwise at ambient temperature and the resulting mixture is vortexed for 30 minutes. The resin turned a dark blue upon addition of the TFA. The mixture is then filtered and washed with two 5 mL portions of methylene chloride. The filtrate is evaporated by rotary evaporation to yield 20 mg of crude product. An LC/MS trace of the crude reaction mixture showed it to contain better than 75 area % of the desired product, (3-(4-methoxyphenylsulfonyl)propionic acid is present in 6 area %). $^1$HMR (MeOH-d$_4$) 2.45 (t,2H); 3.45 (t,2H); 3.90 (s,3H); 7.15 (d, 2H); 7.85 (d, 2H).

EXAMPLE 53

Synthesis of 4-O-Methylhydroxylamine) phenoxymethylcopoly(styrene-1%-divinylbenzene)-resin (100–200 mesh)

To a 1-L jacketed reactor with a bottom valve and overhead stirrer (Ace catalog #8090) is charged Wang resin (18.35 g, 20 meq) and anhydrous tetrahydrofuran (THF, 450 mL). This mixture is stirred gently for about 15 minutes, then as much solvent as possible is removed through a tube fitted with a porous glass frit via vacuum aspiration. Fresh THF is added, followed by triphenylphosphine (15.74 g, 60 mmol) and N-hydroxyphthalimide (16.31 g, 100 mmol). The resulting mixture is stirred and cooled to −5-0° C. Diisopropyl azodicarboxylate (11.8 mL, 60 mmol) is added slowly so as to maintain the temperature at <5° C. When the addition is complete, the stirred mixture is allowed to warm slowly to room temperature and stirred overnight. As much of the reaction liquors as possible is removed by aspiration through the dip tube as above. The resin is washed by charging N,N-dimethylformamide (DMF, 200 mL), stirring the mixture for 3–5 minutes, and then removing by aspiration as much of the wash solution as possible. Similarly, the resin is washed sequentially with an additional portion of DMF and portions of methanol (twice), THF (twice), and methanol (once). A portion of the resin may be removed for analysis: IR 1734 cm$^{-1}$ (C=O).

To the resin remaining in the reactor is added THF (400 mL) and 200 mL of a 40% aqueous solution of methylamine (2.31 mol). This reaction mixture is stirred gently at 40° C. for 2 hours, then cooled to room temperature (the mixture may be held overnight at this temperature). As much of the reaction liquors as possible is removed by aspiration, and the resin is washed with the solvent array as above. Following the final methanol wash, additional methanol is used to flush the resin out of the bottom of the reactor and isolate it by filtration. The filtered resin is dried at NMT 40° C. under vacuum. Yield 18–18.5 g resin: amine load 1.02 meq/g (based on potentiometric titration of a THF suspension with p-toluenesulfonic acid); IR (microscopy) 3316 cm$^{-1}$ (w, —NH$_2$). Analysis found C, 87.07%; H, 7.77%; N, 1.58%, which corresponds to 1.13 nitrogen atoms/g resin.

Assay of resin:

Preparation of 4-nitrophenylethanehydroxamic acid. A 200 mg sample of the dried resin (ca. 0.2 mmol) is charged to a 5- or 10-mL resin reactor (a polypropylene syringe barrel fitted with a polypropylene frit). The resin is swelled for about 15 minutes in dry DMF, and then 115 mg 1-(3-dimethylaminopropyl)-3-ethylcarbodiimide hydrochloride (EDCl, 0.6 mmol) is added. To this mixture is then added 4-nitrophenylacetic acid (115 mg, 0.6 mmol). The reactor is capped and the mixture is agitated slowly overnight (a rocker bed apparatus is used). The reaction liquors are removed by vacuum filtration (the resin reactor is inserted through a small rubber vacuum flask adapter), and the resin is washed by several small (2–3 mL) portions of the following solvents: DMF (4–5 portions), MeOH or 50% aq. DMF (3–4 portions), THF (3–4 portions), and MeOH (2–3 portions). The resin (still in the syringe reactor) is dried for at least 4 hours under vacuum at NMT 40° C.

To this dried resin is added 2 mL dichloromethane (DCM) followed by 2 mL trifluoroacetic acid (TFA). Additionally, 20 mL water is added (believed to reduce "anhydride" formation from hydroxamic acid product). The mixture is allowed to react for about 1 hr, and the reaction liquors are drained into a tared collector. The resin is washed with 1–2 1-mL portions of DCM followed by 1–2 1-mL portions of toluene. The combined filtrates are concentrated to about 2 mL at NMT 30° C., 2 mL additional toluene is added, and the resulting solution is concentrated to dryness under vacuum (rotary evaporator followed by vacuum oven at NMT 30° C.; note that heating in the presence of TFA promotes formation of the "anhydride" impurity). The residue is weighed and analyzed for weight % purity (HPLC, using the carboxylic acid as a response factor standard). Typical results for 4-nitrophenylethanehydroxamic acid: 29–30 mg solids at 60–70 wt % purity, 90–97 A% purity (261 nm); $^1$H NMR (CD$_3$OD) δ 8.13 (d, 2H), 7.25 (d, 2H), 4.85 (bs, OH, NH), 3.55 (s, 2H); $^{13}$C NMR δ 169.4, 144.3, 131.3, 124.6, 40.2. This reflects a load/clip chemical yield of 50–55% from resin at 1 meq/g.

EXAMPLE 54

Wang Resin Syntheses

Step A

Wang resin (20 g, 15 mmol) is swelled in 300 mL of anhydrous DMF for 15 minutes. Then a solution of diethyl phosphonoacetic acid (8.83 g, 45 mmol) in 50 mL of DMF is added followed by pyridine (7.12 g, 90 mmol) and 2,6-dichlorobenzoyl chloride (9.4 g, 45 mmol). The mixture is agitated for 20 hours at room temperature. The resin is filtered and washed successively with DMF (3×), H$_2$O (3×), DMF (3×), THF (10×) and Et$_2$O (10×) followed by drying in vacuo at 40° C. for 20 hours.

IR (micro) u c=o 1738 cm$^{-1}$

Step B

The loaded resin from Step A (1 g, 0.75 mmol) is swelled in anhydrous THF (10 mL) for 15 minute followed by the addition of a 0.5 M solution of potassium bis(trimethylsilyl) amide in toluene (4 mL) at 0° C. The mixture is allowed to warm up to room temperature and is shaken for 30 minutes. The solvent is then drained to the top of the resin followed by the addition of anhydrous cyclohexane (10 mL) and isovaleraldehyde (0.17 g, 2 mmol). The mixture is shaken for approximately 72 hours and worked up as described in Step A.

IR (micro) u c=o 1718 cm$^{-1}$

Step C

To a solution of 3,4-dimethoxybenzenethiol (11.9 g, 70 mmol) in anhydrous THF (54.4 mL) at 0° C. is added a 2.5 M solution of n-butyllithium (5.6 mL, 14 mmol) and the solution is stirred at room temperature for 15 minutes.

The resin from Step B (0.25 g, 0.19 mmol) is swelled in anhydrous THF (2.5 mL) for 15 minutes and 4 mL of the above prepared 1 N thiol/thiolate stock solution is added. The mixture is shaken for approximately 100 hours and worked up as described in Step A.

IR (micro) u c=o 1732 cm$^{-1}$

Step D

The resin from step 3 (0.25 g, 0.19 mmol) is swelled in 1,4-dioxane (5 mL) for 15 minutes and a solution of m-chloroperoxybenzoic acid (0.44 g, 2.5 mmol) in 2 mL of 1,4-dioxane is added. The mixture is shaken for 16 hours and worked up as described in Step A.

Step E

The resin from Step D (0.25 g, 0.19 mmol) is treated with 1:1 dichloromethane/trifluoroacetic acid (3 mL) for 1–2 hours. The resin is filtered and washed with dichloromethane (2×1 mL). The combined filtrates are concentrated in vacuo to provide 3-(3,4-dimethoxybenzenesulfonyl)-5-methylhexanoic acid (9.8 mg).

$^1$H NMR (300 MHz, CDCl$_3$) δ 0.85 (d, 3H), 0.92 (d, 3H), 1.4 (m, 1H), 1.6–1.8 (m, 2H), 2.55 (dd, 1H), 2.9 (dd, 1H), 3.65 (m, 1H), 3.92 (s, 3H), 3.95 (s, 3H), 7.0 (d, 1H), 7.32 (s, 1H), 7.5 (d, 1H).

MS (APCl; Loop) m/z 348 (M+NH$_4$)$^+$, 331 (M+H)$^+$.

Step F

The hydroxylamine bound Wang resin (50 mg, 0.037 mmol) is swelled in anhydrous DMF (1 mL) for 15 minutes followed by the addition of 1-(3-dimethyl-aminopropyl)-3-ethylcarbodiimide hydrochloride (30 mg, 0.16 mmol) and a solution of the carboxylic acid from Step E in 1 mL of anhydrous DMF. The mixture is shaken for 20 hours and worked up as described in Step A.

Step G

The resin from Step F is treated with 1:1 dichloromethane/trifluoroacetic acid (2 mL) for 1.5 hours. The resin is filtered and washed with dichloromethane (2×1 mL). The combined filtrates are concentrated in vacuo to provide 3-(3,4-dimethoxybenzenesulfonyl)-5-methylhexanoic acid hydroxyamide (9.8 mg).

MS (H-isp; LCMS) m/z 363 (M+NH$_4$)$^+$, 346 (M+H)$^+$.

The following hydroxamic compounds are synthesized using appropriate starting materials and following the steps of this example:

5-(4-Butoxyphenyl)-3-(3,4-dimethoxybenzenesulfonyl)-pentanoic acid hydroxyamide. MS (APCl; LCMS) m/z 466 (M+H)$^+$ 3-(3,4-Dimethoxybenzenesulfonyl)hexanoic acid hydroxyamide. MS (H-isp; LCMS) m/z 332 (M+H)$^+$ 3-(3,4-Dimethoxybenzenesulfonyl)-4-methylpentanoic acid hydroxyamide. MS (H-isp; LCMS) m/z 332 (M+H)$^+$ 3-(3,4-Dimethoxybenzenesulfonyl)-5-methylhexanoic acid hydroxyamide. MS (H-isp; LCMS) m/z 346 (M+H)$^+$ 3-(3-Benzyloxyphenyl)-3-(3,4-dimethoxybenzenesulfonyl)-N-hydroxypropionamide. MS (H-isp; LCMS) m/z 472 (M+H)$^+$ 3-(2-Benzyloxyphenyl)-3-(3,4-dimethoxybenzenesulfonyl)-N-hydroxypropionamide. MS (APCl; LCMS) m/z 472 (M+H)$^+$ 3-(3-Benzyloxy-4-methoxyphenyl)-3-(3,4-dimethoxybenzenesulfonyl)-N-hydroxypropionamide. MS (APCl; LCMS) m/z 502 (M+H)$^+$ 3-(3,4-Dimethoxybenzenesulfonyl)-N-hydroxy-3-(3-phenoxyphenyl)propionamide. MS (APCl; LCMS) m/z 458 (M+H)$^+$ 3-(3-(4-Chlorophenoxy)phenyl)-3-(3,4-dimethoxybenzenesulfonyl)-N-hydroxypropionamide. MS (H-isp; LCMS) m/z 492 (M+H)$^+$ 3-(3,4-Dimethoxybenzenesulfonyl)-N-hydroxy-3-(3-(4-methoxyphenoxy)phenyl)propionamide. MS (H-isp; LCMS) m/z 488 (M+H)$^+$ 2-[Biphenyl-4-yl-(3,4-dimethoxybenzenesulfonyl)methyl]-4-methylpentanoic acid hydroxyamide via 2-[Biphenyl-4-yl-(3,4-dimethoxybenzenesulfonyl)methyl]-4-methylpentanoic acid (16 mg). $^1$H NMR (300 MHz, CDCl$_3$) δ 0.9–1.1 (2xd, 6H), 1.6 (m, 1H), 1.9 (m, 1H), 2.35 (m, 1H), 3.55 (s, 3H), 3.7 (m, 1H), 3.9 (s, 3H), 4.3 (d, 1H), 6.6–7.5 (series m, 12H). MS (APCl; LCMS) m/z 500 (M+NH$_4$)$^+$, 483 (M+H)$^+$ yields 2-[Biphenyl-4-yl-(3,4-dimethoxybenzenesulfonyl)methyl]-4-methylpentanoic acid hydroxyamide (4.9 mg). MS (APCl; LCMS) m/z 515 (M+NH$_4$)$^+$, 498 (M+H)$^+$.

2-[(3,4-Dimethoxybenzenesulfonyl)-(4-phenoxyphenyl) methyl]-N-hydroxy-4-(2-methoxyethoxy)butyramide. MS (APCl; LCMS) m/z 560 (M+H)$^+$.

2-[(3,4-Dimethoxybenzenesulfonyl)-(4-phenoxyphenyl) methyl]-N-hydroxybutyramide. MS (APCl; LCMS) m/z 486(M+H)$^+$.

4-Benzenesulfonyl-2-[biphenyl-4-yl-(3,4-dimethoxybenzenesulfonyl)methyl]-N-hydroxybutyramide. MS (isp; Loop) m/z 610 (M+H)$^+$.

2-[Biphenyl-4-yl-(3,4-dimethoxybenzenesulfonyl)methyl]-N-hydroxy-4-phenylbutyramide. MS (APCl; LCMS) m/z 546 (M+H)$^+$.

2-[Biphenyl-4-yl-(3,4-dimethoxybenzenesulfonyl)methyl]-N-hydroxy-4-(2-methoxy-ethoxy)-butyramide. MS (isp; Loop) m/z 544 (M+H)$^+$.

2-[Biphenyl-4-yl-(3,4-dimethoxybenzenesulfonyl)methyl]-N-hydroxybutyramide. MS (APCl; LCMS) m/z 470 (M+H)$^+$.

2-[Biphenyl-4-yl-(3,4-dimethoxybenzenesulfonyl)methyl]-4-methylpentanoic acid hydroxyamide. MS (APCl; LCMS) m/z 498 (M+H)$^+$.

2-[Biphenyl-4-yl-(3,4-dimethoxybenzenesulfonyl)methyl]-N-hydroxy-3-methylbutyramide. MS (APCl; LCMS) m/z 484 (M+H)$^+$.

2-[Biphenyl-4-yl-(3,4-dimethoxybenzenesulfonyl)methyl]-7-phenylheptanoic acid hydroxyamide. MS (APCl; LCMS) m/z 588 (M+H)$^+$.

2-[Biphenyl-4-yl-(3,4-dimethoxybenzenesulfonyl)methyl]-5-phenylpentanoic acid hydroxyamide. MS (APCl; LCMS) m/z 560 (M+H)$^+$.

2-[(3,4-Dimethoxybenzenesulfonyl)-(4-phenoxyphenyl) methyl]-N-hydroxy-3-methyl-butyramide. MS (APCl; LCMS) m/z 500 (M+H)$^+$.

2-[(3,4-Dimethoxybenzenesulfonyl)-(4-phenoxyphenyl) methyl]-7-phenylheptanoic acid hydroxyamide. MS (APCl; LCMS) m/z 604 (M+H)$^+$.

3-(3,4-Dimethoxybenzenesulfonyl)-2-ethylhexanoic acid hydroxyamide. MS (APCl; LCMS) m/z 360 (M+H)$^+$. Modified procedure for Step C. Reaction temperature=60° C., Reaction time=2×20 hours.

3-(3,4-Dimethoxybenzenesulfonyl)-2-(3-phenyl-propyl) hexanoic acid hydroxyamide. MS (APCl; LCMS) m/z 450 (M+H)$^+$. Modified procedure for Step C. Reaction temperature=60° C., Reaction time=2×20 hours.

2-[(3-Benzyloxyphenyl)-(3,4-dimethoxybenzenesulfonyl) methyl]-5-phenylpentanoic acid hydroxyamide. MS (APCl; Loop) m/z 590 (M+H)$^+$. Modified procedure for Step C. Reaction temperature=60° C., Reaction time=2×20 hours.

EXAMPLE 55

Rink Resin Syntheses

Step A

The hydroxylamine bound Rink resin (0.1 g, 0.031 mmol) is swelled in anhydrous DMF (1 mL) for 15 minutes followed by the addition of 1-(3-dimethyl-aminopropyl)-3-ethylcarbodiimide hydrochloride (30 mg, 0.16 mmol) and a solution of the appropriate carboxylic acid prepared as in Example 54, Steps A–E in 1 mL of anhydrous DMF. The mixture is shaken for 20 hours and worked up as described in Example 54, Step A.

Step B

The resin from Step A (0.1 g, 0.031 mmol) is treated with 9:1 dichloro-methane/trifluoroacetic acid (2 mL) for 1 hour. The resin is filtered and washed with dichloromethane (2×1 mL). The combined filtrates are concentrated in vacuo to provide the following hydroxamic acids:

N-[2-(3,4-Dimethoxybenzenesulfonyl)-3-hydroxycarbamoyl-propyl]-N methylbenzamide. MS (APCl; Loop) m/z 437 (M+H)$^+$ N-[2-(3,4-Dimethoxybenzenesulfonyl)-3-hydroxycarbamoyl-butyl]-N methylbenzamide. MS (APCl; Loop) m/z 451 (M+H)$^+$ Methyl-phenyl-carbamic acid 3-(3,4-dimethoxybenzenesulfonyl)-4-hydroxycarbamoyl-butyl ester. MS (APCl; Loop) m/z 452 (M+H)$^+$-15

[3-(3,4-Dimethoxybenzenesulfonyl)-4-hydroxycarbamoyl-butyl]methylcarbamic acid benzyl ester. MS (APCl; Loop) m/z 481 (M+H)$^+$ 3-(3,4-Dimethoxybenzenesulfonyl)hexanedioic acid-1-hydroxyamide-6-(methyl-phenyl-amide). MS (APCl; Loop) m/z 451 (M+H)$^+$ 3-(3,4-Dimethoxybenzenesulfonyl)heptanedioic acid-1-hydroxyamide-7-(methyl-phenyl-amide). MS (APCl; Loop) m/z 465 (M+H)$^+$ 3-(3,4-Dimethoxybenzenesulfonyl)-6-(1,3-dioxo-1,3-dihydro-isoindol-2-yl)hexanoic acid hydroxyamide. MS (APCl; Loop) m/z 477 (M+H)$^+$ 7-(3,4-Dihydro-2H-quinolin-1-yl)-3-(3,4-dimethoxybenzenesulfonyl)-7-oxo-heptanoic acid hydroxyamide. MS (APCl; Loop) m/z 491 (M+H)$^+$ 7-(3,4-Dihydro-2H-quinolin-1-yl)-3-(3,4-dimethoxybenzenesulfonyl)-6-oxo-hexanoic acid hydroxyamide. MS (APCl; Loop) m/z 477 (M+H)$^+$ 7-Benzo(1,3)dioxol-5-yl-3-(3,4-dimethoxybenzenesulfonyl)heptanoic acid hydroxyamide. MS (APCl; Loop) m/z 466 (M+H)$^+$ 3-(3,4-Dimethoxybenzenesulfonyl)-3-(thien-3-yl)-N-hydroxypropionamide. MS (APCl; Loop) m/z 372 (M+H)$^+$ 3-(3,4-Dimethoxybenzenesulfonyl)-5-phenylpentanoic acid hydroxyamide. MS (APCl; Loop) m/z 394 (M+H)$^+$ 3-(3,4-Dimethoxybenzenesulfonyl)-5-(3-phenoxyphenyl) pentanoic acid hydroxyamide. MS (APCl; Loop) m/z 486 (M+H)$^+$ 5-(4-Benzyloxyphenyl)-3-(3,4-dimethoxybenzenesulfonyl) pentanoic acid hydroxyamide. MS (APCl; Loop) m/z 500 (M+H)$^+$

EXAMPLE 56

Additional Resin Based Syntheses

Step A

Wang resin (2 g, 1.5 mmol) is swelled in 20 mL of anhydrous DMF for 15 minutes. Then a solution of the phosphonoacetic acid in DMF (1.13 g, 4.5 mmol) is added followed by pyridine (0.71 g, 9 mmol) and 2,6-dichlorobenzoyl chloride (0.94 g, 4.5 mmol). The mixture is agitated for 20 hours at room temperature. The resin is filtered and washed successively with DMF (3×), H$_2$O (3×), DMF (3×), THF (10×) and Et$_2$O (10×) followed by drying in vacuo at 40° C. for 20 hours.

IR (micro) u c=o 1730 cm$^{-1}$

Step B

The loaded resin from Step A (0.5 g, 0.375 mmol) is swelled in anhydrous THF (5 mL) for 15 minute followed by the addition of a 0.5 M solution of potassium bis (trimethylsilyl)amide in toluene (2 mL) at 0° C. The mixture is allowed to warm up to room temperature and is shaken for 30 minutes. The solvent is drained to the top of the resin followed by the addition of anhydrous cyclohexane(10 mL) and the aldehyde (0.25 g, 1 mmol). The mixture is shaken for approximately 72 hours and worked up as described in Step A.

IR (micro) u c=o 1704 cm$^{-1}$

Step C

To a solution of 3,4 dimethoxybenzenethiol(11.9 g, 70 mmol) in anhydrous THF (54.4 mL) at 0° C. is added a 2.5 M solution of n-butyllithium (5.6 mL, 14 mmol) and the solution is stirred at room temperature for 15 minutes.

The resin from step 2 (0.2 g, 0.15 mmol) is swelled in anhydrous THF (2.5 mL) for 15 minutes and 4 mL of the above prepared 1 N thiol/thiolate stock solution is added. The mixture is shaken for approximately 100 hours and worked up as described in step 1. The thiol addition did not go to completion as evidenced by IR spectra (u c=o 1703 cm$^{-1}$). The reaction is driven to completion by repeating the above procedure twice.

IR (micro) u c=o 1731 cm$^{-1}$

Step D

The resin from Step C (0.2 g, 0.15 mmol) is swelled in dioxane (5 mL) for 15 minutes and a solution of m-chloroperoxybenzoic acid (0.44 g, 2.5 mmol) in 2 mL of dioxane is added. The mixture is shaken for 16 hours and worked up as described in step 1.

Step E

The resin from Step D (0.2 g, 0.15 mmol) is treated with 1:1 dichloromethane/trifluoroacetic acid (3 mL) for 1–2 hours. The resin is filtered and washed with dichloromethane (2×1 mL). The combined filtrates are concentrated in vacuo to provide 2-{(3,4-dimethoxybenzenesulfonyl)-[4-(4-fluorobenzyloxyphenyl]methyl}-4-methylpentanoic acid (40 mg).

$^1$H NMR (300 MHz, CDCl$_3$) δ 0.7–1.1 (2xd, 6H), 1.55 (m, 1H), 1.85 (m, 1H), 2.35 (m, 1H), 3.65 (s, 3H), 3.85 (s, 3H), 4.18 (d, 1H), 4.9 (s, 2H), 6.6–7.4 (series of m, 11H).

MS (H-isp; Loop) m/z 548 (M+NH$_4$)$^+$, 531 (M+H)$^+$.

Step F

The hydroxylamine bound Rink resin (0.1 g, 0.031 mmol) is swelled in anhydrous DMF (1 mL) for 15 minutes followed by the addition of 1-(3-dimethylaminopropyl)-3-ethylcarbodiimide hydrochloride (20 mg, 0.1 mmol) and a solution of the carboxylic acid from step 5 in 1 mL of anhydrous DMF. The mixture is shaken for 20 hours and worked up as described in step A.

Step G

The resin from Step F (0.1 g, 0.031 mmol) is treated with 9:1 dichloromethane/trifluoroacetic acid (2 mL) for 1 hour. The resin is filtered and washed with dichloromethane (2×1 mL). The combined filtrates are concentrated in vacuo to provide 2-{(3,4-dimethoxybenzenesulfonyl)-[4-(4-fluorobenzyloxyphenyl]methyl}-4-methylpentanoic acid hydroxyamide (2.3 mg). MS (H-isp; LCMS) m/z 546 (M+H)$^+$.

The following hydroxamic compounds are synthesized using appropriate starting materials and following the steps of this example:

3-(3,4-dimethoxybenzenesulfonyl)-7-phenyl-2-(4-phenylbutyl)heptanoic acid hydroxyamide. MS (APCl; LCMS) m/z 554 (M+H)$^+$.

2-[1-(3-(3,4-dimethoxybenzenesulfonyl)-5-phenylpentyl]-N 1-hydroxy-N 4-methyl-N 4-phenylsuccinamide. MS (APCl; LCMS) m/z 568 (M)$^+$.

3-(3,4-dimethoxybenzenesulfonyl)-7-phenyl-2-(3-phenylpropyl)heptanoic acid hydroxyamide. MS (APCl; LCMS) m/z 540 (M+H)$^+$.

3-(3,4-dimethoxybenzenesulfonyl)-2-isopropyl-7-phenylheptanoic acid hydroxyamide. MS (APCl; LCMS) m/z 464 (M+H)$^+$.

3-(3,4-dimethoxybenzenesulfonyl)-2-isobutyl-7-phenylheptanoic acid hydroxyamide. MS (APCl; LCMS) m/z 478 (M+H)$^+$.

3-(3,4-dimethoxybenzenesulfonyl)-7-phenyl-2-propylheptanoic acid hydroxyamide. MS (APCl; LCMS) m/z 464 (M+H)$^+$.

3-(3,4-dimethoxybenzenesulfonyl)-7-phenyl-2-(4-phenylbutyl)heptanoic acid hydroxyamide. MS (APCl; LCMS) m/z 450 (M+H)$^+$.

3-(3,4-dimethoxybenzenesulfonyl)-2-[2-(2-methoxyethoxy)ethyl]-7-phenylheptanoic acid hydroxyamide. MS (APCl; LCMS) m/z 524 (M+H)$^+$.

3-(3,4-dimethoxybenzenesulfonyl)-2-benzenesulfonylethyl-7-phenylheptanoic acid hydroxyamide. MS (APCl; LCMS) m/z 590 (M+H)$^+$.

3-(3,4-dimethoxybenzenesulfonyl)-7-phenyl-2-(5-phenylpentyl)heptanoic acid hydroxyamide. MS (APCl; LCMS) m/z 568 (M+H)$^+$.

4-Benzenesulfonyl-2-{(3,4-dimethoxybenzenesulfonyl)-[4-(4-fluorobenzyloxy)phenyl]methyl}-N-hydroxy-butyramide. MS (APCl; LCMS) m/z 658 (M+H)$^+$.

2-{(3,4-dimethoxybenzenesulfonyl)-[4-(4-fluorobenzyloxy)phenyl]methyl}-N-hydroxy-4-phenyl-butyramide. MS (APCl; LCMS) m/z 594 (M+H)$^+$.

2-{(3,4-dimethoxybenzenesulfonyl)-[4-(4-fluorobenzyloxy)phenyl]methyl}-N-hydroxy-4-(2-methoxyethoxy)butyramide. MS (APCl; LCMS) m/z 592 (M+H)$^+$.

2-{(3,4-dimethoxybenzenesulfonyl)-[4-(4-fluorobenzyloxy)phenyl]methyl}-N-hydroxy-butyramide. MS (APCl; LCMS) m/z 518 (M+H)$^+$.

2-{(3,4-dimethoxybenzenesulfonyl)-[4-(4-fluorobenzyloxy)phenyl]methyl}-pentanoic acid hydroxyamide. MS (APCl; LCMS) m/z 532 (M+H)$^+$.

2-{(3,4-dimethoxybenzenesulfonyl)-[4-(4-fluorobenzyloxy)phenyl]methyl}-4-methylpentanoic acid hydroxyamide. MS (APCl; LCMS) m/z 546 (M+H)$^+$.

2-{(3,4-dimethoxybenzenesulfonyl)-[4-(4-fluorobenzyloxy)phenyl]methyl}-N-hydroxy-3-methylbutyramide. MS (APCl; LCMS) m/z 532 (M+H)$^+$.

2-{(3,4-dimethoxybenzenesulfonyl)-[4-(4-fluorobenzyloxy)phenyl]methyl}-7-phenylheptanoic acid hydroxyamide. MS (APCl; LCMS) m/z 636 (M+H)$^+$.

2-{(3,4-dimethoxybenzenesulfonyl)-[4-(4-fluorobenzyloxy)phenyl]methyl}-5-phenylpentanoic acid hydroxyamide. MS (APCl; LCMS) m/z 608 (M+H)$^+$.

2-{(3,4-dimethoxybenzenesulfonyl)-[4-(4-fluorobenzyloxy)phenyl]methyl}-N 1-hydroxy-N 4-methyl-N 4-phenyl-succinimide. MS (APCl; LCMS) m/z 637 (M+H)$^+$.

2-{(3,4-dimethoxybenzenesulfonyl)-[4-(4-fluorobenzyloxy)phenyl]methyl}-6-phenylhexanoic acid hydroxyamide. MS (APCl; LCMS) m/z 622 (M+H)$^+$.

EXAMPLE 57

Additional Resin Based Syntheses

Step A

Wang resin (20 g, 15 mmol) is swelled in 300 mL of anhydrous DMF for 15 minutes. Then a solution of diethyl phosphonoacetic acid (8.83 g, 45 mmol) in 50 mL of DMF is added followed by pyridine (7.12 g, 90 mmol) and 2,6-dichlorobenzoyl chloride (9.4 g, 45 mmol). The mixture is agitated for 20 hours at room temperature. The resin is filtered and washed successively with DMF (3×), H$_2$O (3×), DMF (3×), THF (10×) and Et$_2$O (10×) followed by drying in vacuo at 40° C. for 20 hours.

IR (micro) u c=o 1738 cm$^{-1}$

Step B

The loaded resin from Step A (1 g; 0.63 mmol) is swelled in anhydrous THF (10 mL) for 15 minute followed by the addition of a 1 M solution of lithium bis(trimethylsilyl)

amide in THF (1.6 mL; 1.57 equiv.) at 0° C. The mixture is allowed to warm up to room temperature and is shaken for 30 minutes. The solvent is then drained to the top of the resin followed by the addition of anhydrous cyclohexane (10 mL) and 4-ethoxy-benzaldehyde (0.5 g; 3.3 mmol). The mixture is shaken for approximately 72 hours. The resin is then filtered and washed successively with DMF (3×), $H_2O$ (3×), DMF (3×), THF (10×) and $Et_2O$ (10×) followed by drying in vacuo at 40° C. for 20 hours.

IR (micro) u c=o 1709 cm$^{-1}$

Step C

To a solution of 4-methoxybenzene thiol (0.6 mL; 5 mmol) in anhydrous THF (1 mL) at 0° C. is added n-butyllithium (2.5 M in hexanes; 0.02 mL; 0.05 mmol) and the solution is stirred at room temperature for 15 minutes. The resin from step 2 (1 g; 0.63 mmol) contained in a polypropylene peptide synthesis cartridge is swelled in anhydrous THF (10 mL) for 15 minutes. The above prepared 1 N thiol/thiolate stock solution is added. The mixture is shaken for approximately 100 hours. The resin is then filtered and washed successively with DMF (3×), $H_2O$ (3×), DMF (3×), THF (10×) and $Et_2O$ (10×) followed by drying in vacuo at 40° C. for 20 hours.

IR (micro) u c=o 1734 cm$^{-1}$

Step D

The resin from Step C (1 g, 0.63 mmol) is swelled in 1,4-dioxane (5 mL) for 15 minutes and a solution of m-chloroperoxybenzoic acid (0.863 g; 5 mmol) in 2 mL of 1,4-dioxane is added. The mixture is shaken for 16 hours, the resin is then filtered and washed successively with DMF (3×), $H_2O$ (3×), DMF (3×), THF (10×) and $Et_2O$ (10×) followed by drying in vacuo at 40° C. for 20 hours.

Step E

The resin from Step D (1 g, 0.63 mmol) is treated with 1:1 dichloromethane/trifluoroacetic acid (8 mL) for 1–2 hours. The resin is filtered and washed with dichloromethane (2×1 mL). The combined filtrates are concentrated in vacuo to provide 3-(4-methoxybenzenesulfonyl)-3-(ethoxyphenyl) propionic acid (84 mg; 34%).

$^1$H NMR (300 MHz, CDCl$_3$-d3) δ 1.42 (t, J=9.0 Hz, 3H); 3.08 (dd, J=10.8 Hz, $^1$H); 3.44 (dd, J=7.2 Hz, 1H); 3.86 (s, 3H ); 4.02 (q, J=9.0 Hz, 2H); 4.54 (dd, J=7.1 Hz, 1H); 6.72 (d, J=12.6 Hz, 2H); 6.82 (d, J=12.3 Hz, 2H); 6.98 (d, J=12.4 Hz, 2H); 7.42 (d, J=12.3 Hz, 2H); 7.52 (bs, 1H).

MS (H-isp; LCMS); m/z=387 [M+Na]$^+$, 382 [M+NH$_4$]$^+$, 365 [M+H]$^+$.

Step F

The hydroxylamine bound Rink resin (200 mg, 0.04 mmol) is swelled in anhydrous DMF (1 mL) for 15 minutes followed by the addition of 1-(3-dimethyl-aminopropyl)-3-ethylcarbodiimide hydrochloride (38 mg, 0.2 mmol) and a solution of the carboxylic acid from step 5 (84 mg; 0.2 mmol) in 1 mL of anhydrous DMF. The mixture is shaken for 20 hours. The resin is then filtered and washed successively with DMF (3×), $H_2O$ (3×), DMF (3×), THF (10×) and $Et_2O$ (10×) followed by drying in vacuo at 40° C. for 20 hours.

Step G

The resin from Step F (200 mg; 0.04 mmol) is treated with 1:1 dichloromethane/trifluoroacetic acid (3 mL) for 30 minutes. The resin is filtered and washed with dichloromethane (2×1 mL). The combined filtrates are concentrated in vacuo to provide 3-(4-methoxybenzenesulfonyl)-3-(4-ethoxyphenyl)propionic acid hydroxyamide (9.6 mg). MS (H-isp; LCMS); m/z=402 [M+Na]$^+$, 380 [M+H]$^+$.

The following hydroxamic compounds are synthesized using appropriate starting materials and following the steps of this example:

3-(4-methoxybenzenesulfonyl)-3-(4-biphenyl)propionic acid hydroxy amide) MS (H-isp; LCMS); m/z=412 [M+H]$^+$. A%=89% @ 220 nm

EXAMPLE 3

3-(4-methoxybenzenesulfonyl)-3-(4-phenoxyphenyl) propionic acid hydroxy amide MS (H-isp; LCMS); m/z=428 [M+H]$^+$. A%=75% @ 220 nm

EXAMPLE 4

3-(4-methoxybenzenesulfonyl)-3-(4-benzyloxyphenyl)-propionic acid hydroxy amide MS (H-isp; LCMS); m/z=442 [M+H]$^+$. A%=60% @ 220 nm

EXAMPLE 6

3-(4-methoxybenzenesulfonyl)-3-(4-fluorobenzyloxyphenyl)-propionic acid hydroxy amide MS (H-isp; LCMS); m/z=460 [M+H]$^+$. A%=68% @ 220 nm

EXAMPLE 7

3-(4-methoxybenzenesulfonyl)-3-(4-(3-trifluoromethylphenoxy)-phenyl-propionic acid hydroxy amide MS (H-isp; LCMS); m/z=496 [M+H]$^+$. A%=74% @ 220 nm The compounds of formula I exhibit useful pharmacological activity and accordingly are incorporated into pharmaceutical compositions and used in the treatment of patients suffering from certain medical disorders.

More especially, compounds within the scope of the invention are cyclic AMP phosphodiesterase inhibitors, in particular type IV cyclic AMP phosphodiesterase inhibitors. The present invention provides compounds of formula I, and compositions containing compounds of formula I, which are of use in a method for the treatment of a patient suffering from, or subject to, conditions which can be ameliorated or prevented by the administration of an inhibitor of cyclic AMP phosphodiesterase, especially type IV cyclic AMP phosphodiesterase. For example, compounds within the present invention are useful as bronchodilators and asthma-prophylactic agents and agents for the inhibition of eosinophil accumulation and of the function of eosinophils, e.g., for the treatment of inflammatory airways disease, especially reversible airway obstruction or asthma, and for the treatment of other diseases and conditions characterized by, or having an etiology involving, morbid eosinophil accumulation. As further examples of conditions which may be ameliorated or prevented by the administration of inhibitors of cyclic AMP phosphodiesterase, such as compounds of formula I, there may be mentioned inflammatory diseases, such as atopic dermatitis, urticaria, allergic rhinitis, psoriasis, rheumatic arthritis, ulcerative colitis, Crohn's disease, adult respiratory distress syndrome and diabetes insipidus, other proliferative skin diseases such as keratosis and various types of dermatitis, conditions associated with cerebral metabolic inhibition, such as cerebral senility, multi-infarct dementia, senile dementia (Alzheimer's disease), and memory impairment associated with Parkinson's disease, and conditions ameliorated by neuroprotectant activity, such as cardiac arrest, stroke, and intermittent claudication.

Additionally, compounds within the scope of the invention are also inhibitors of tumor necrosis factor, especially TNF-α. Thus, the present invention provides compounds of formula I, and compositions containing compounds of formula I, which are of use in a method for treating a patient suffering from, or subject to, conditions which can be ameliorated or prevented by the administration of an inhibitor of TNF-α. For example compounds of the present invention are useful in inflammatory, infectious, immunological or malignant diseases. For example, compounds according to the invention are useful in treating joint inflammation, including arthritis, rheumatoid arthritis and other arthritic conditions such as rheumatoid spondylitis and osteoarthritis. Additionally, the compounds are useful in treatment of Crohn's disease, haemodynamic shock, psoriasis, congestive heart failure, fibrotic disease, multiple sclerosis, radiation damage, toxicity following administration of immunosuppressive monoclonal antibodies such as OKT3 or CAMPATH-1 and hypertoxic alveolar injury, sepsis syndrome, septic shock, gram negative sepsis, toxic shock syndrome, acute respiratory distress syndrome, asthma and other chronic pulmonary diseases, bone resorption diseases, reperfusion injury, graft vs. host reaction, allograft rejection and leprosy. Furthermore, the compounds are useful in the treatment of infections such as viral infections and parasitic infections, for example malaria such as cerebral malaria, mycobacterial infection, meningitis, fever and myalgias due to infection, HIV, AIDS, cachexia such as cachexia secondary to AIDS or to cancer.

Another group of conditions which may be treated with the compounds of formula I includes diseases and disorders of the central nervous system such as brain trauma, ischaemia, Huntington's disease and tardive dyskinaesia.

Other disease states that may be treated with the compounds of formula I include Crohn's disease, ulcerative colitis, pyresis, systemic lupus erythematosus, multiple sclerosis, type I diabetes mellitus, psoriasis, Beçhet's disease, anaphylactoid purpura nephritis, chronic glomerulonephritis, inflammatory bowel disease and leukemia.

A special embodiment of the therapeutic methods of the present invention is the treating of asthma. Another special embodiment of the therapeutic methods of the present invention is the treating of joint inflammation.

In addition, compounds within the scope of the invention are inhibitors of matrix metalloproteinases (MMPs), especially collagenase, stromelysin and gelatinase, or as described by Schwartz M A, Van Wart H E, *Prog. Med. Chem.*, 29, 271–334 (1992). Thus, the present invention provides compounds of formula I, and compositions containing compounds of formula I, which are of use in a method for treating a patient suffering from, or subject to, conditions which can be ameliorated or prevented by the administration of an inhibitor of an MMP. The treatment or prophylaxis of pathological conditions such as tissue breakdown, for example rheumatoid arthritis, osteoarthritis, osteopenias such as osteoporosis, periodontitis, gingivitis, corneal epidermal or gastric ulceration, and tumor metastasis, invasion and growth may be mediated by an inhibitor of an MMP. MMP inhibitors also inhibit the production of TNF, and, thus are useful in the treatment or prophylaxis of conditions which inhibit the production or action of TNF such as in the treatment or prophylaxis of disease states associated with detrimental amounts of TNF, as described above.

Since excessive TNF production has been noted in several diseases or conditions also characterized by MMP-mediated tissue degradation, compounds which inhibit both MMPs and TNF production may have particular advantages in the treatment or prophylaxis of diseases or conditions in which both mechanisms are involved.

According to a further feature of the invention there is provided a method for the treatment of a human or animal patient suffering from, or subject to, conditions which may be ameliorated or prevented by the administration of an inhibitor of cyclic AMP phosphodiesterase, especially type IV cyclic AMP phosphodiesterase, or of TNF, especially TNF-α, or of an MMP, for example conditions as hereinbefore described, which comprises the administration to the patient of an effective amount of compound of formula I or a composition containing a compound of formula I. "Effective amount" is meant to describe an amount of compound of the present invention effective in inhibiting cyclic AMP phosphodiesterase and/or TNF and thus producing the desired therapeutic effect.

Reference herein to treatment should be understood to include prophylactic therapy as well as treatment of established conditions.

The present invention also includes within its scope pharmaceutical compositions which comprise pharmaceutically acceptable amount of at least one of the compounds of formula I in association with a pharmaceutically acceptable carrier or excipient.

In practice compounds or compositions for treating according to the present invention may administered by any suitable means, for example, by inhalation, topically, parenterally, rectally or orally, but they are preferably administered orally.

The compounds of formula I may be presented in forms permitting administration by the most suitable route and the invention also relates to pharmaceutical compositions containing at least one compound according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and may contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silica gels combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they may contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation and/or microfiltration.

Topical administration, gels (water or alcohol based), creams or ointments containing compounds of the invention may be used. Compounds of the invention may be also incorporated in a gel or matrix base for application in a patch, which would allow a controlled release of compound through transdermal barrier.

For administration by inhalation, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses are determined in accordance with the factors distinctive to the patient to be treated, such as age, weight, general state of health and other characteristics which can influence the efficacy of the compound according to the invention.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for other patients, it will be necessary to prescribe not more than one or two doses per day.

The compounds of the present invention may also be formulated for use in conjunction with other therapeutic agents such as agents which increase cyclic AMP production including b-agonists and $PGE_2$. It is understood that the present invention includes combinations of compounds of the present invention with one or more of the aforementioned therapeutic agents.

Compounds within the scope of the present invention exhibit marked pharmacological activities according to tests described in the literature which tests results are believed to correlate to pharmacological activity in humans and other mammals. The following pharmacological in vitro and in vivo test results are typical for characterizing compounds of the present invention.

IN VITRO AND IN VIVO TEST PROCEDURES 1. (a) Inhibitory effects of compounds on PDE IV activity.
1.1 Preparation of PDE from guinea pig macrophages.

The method is described in Turner et al. Br. J. Pharmacol., 108, 876 (1993). Briefly, cells are harvested from the peritoneal cavity of horse-serum treated (0.5 mL i.p.) Dunkin Hartley guinea pigs (250–400 g) and the macrophages purified by discontinuous (55%, 65%, 70% v/v) gradient (Percoll) centrifugation. Washed macrophages are plated out in cell culture flasks and allowed to adhere. The cells are washed with Hank's balanced salt solution, scraped from the flasks and centrifuged (1000 g). The supernatant is removed and the pellets stored at −80° C. until use. The pellet is homogenized in 20 mM tris(hydroxymethyl)aminomethane HCl, pH 7.5, 2 mM magnesium chloride, 1 mM dithiothreitol, 5 mM ethylenediaminetetraacetic acid, 0.25 mM sucrose, 20 mM p-tosyl-L-lysine chloromethyl ketone, 10 mg/mL leupeptin and 2000 U/mL aprotinin.

1.2 Measurement of PDE activity.

PDE activity is determined in macrophage homogenates by the two-step radioisotopic method of Thompson et al., (Adv. Cyclic Nucl. Res., 10, 69 (1979). The reaction mixture contains 20 mM tris(hydroxymethyl)aminomethane HCl (pH 8), 10 mM magnesium chloride, 4 mM 2-mercaptoethanol, 0.2 mM ethylenebis(oxyethylenenitrilo) tetraacetic acid and 0.05 mg of bovine serum albumin/mL. The concentration of substrate is 1 $\mu$M. The $IC_{50}$ values (i.e. concentrations which produce 50% inhibition of substrate hydrolysis) for the compounds examined are determined from concentration-response curves in which concentrations range from 0.01 nM to 40 $\mu$M.

1.3 Preparation of PDE from human platelets.

The method is described in R. E. Weishaar et al. (Biochem. Pharmacol., 35, 787 (1986).

1.4 Measurement of PDE activity.

PDE activity is determined by the radioisotopic method of Thompson et al., (Adv. Cyclic Nucl. Res., 10, 69 (1979). Following incubation for 30 minutes at 30° C. [$^3$H]-Guanosine 5'-monophosphate is separated from the substrate, guanosine [$^3$H]-guanosine 3':5'-cyclic monophosphate, by elution on cation-exchange columns, and radioactivity is determined using a liquid scintillation counter (LS 1701, Beckman) using a liquid scintillation cocktail (Flow Scint III, Packard). The concentration of substrate is 1 $\mu$M. The $IC_{50}$ values (i.e. concentrations which produce 50% inhibition of substrate hydrolysis) for the compounds examined are determined from concentration-response curves in which concentrations range from $10^{-11}$M to $10^{-5}$M.

2. In vivo bronchodilator actions of compounds.
2.1 Measurement of bronchodialation.

Bronchorelaxant activity is measured in in vivo tests in the anaesthetized guinea-pig or rat according to the method described in Underwood et al., Pulm. Pharmacol. 5, 203 (1992) in which the effects on bronchospasm induced by histamine (or other spasmogens such as methacholine or leukotriene $D_4$) is determined. Compounds are administered orally 1 hour prior to administration of spasmogen.

3. In vivo actions of compounds on antigen (ovalbamin)-induced eosinophilia in guinea-pigs.
3.1 Treatment of animals and measurement of eosinophil numbers.

Male Dunkin-Hartley guinea-pigs weighing 200–250 g are sensitized using 10 μg ovalbumin in 1 mL of a 100 mg/mL suspension of aluminum hydroxide, i.p. 28 days after sensitization guinea-pigs are dosed orally. 23 Hours later this procedure is repeated and 60 minutes later the guinea-pigs are challenged with nebulized saline or ovalbumin (1% in saline) for 15 seconds. 24 Hours after challenge the guinea-pigs are killed and the lungs are lavaged with warm saline. Total and differential cell counts are made.

4. Inhibitory effects of compounds against antigen-induced eosinophilia in the rat in vivo.

4.1. Treatment of rats and measurement of eosinophil numbers.

Male Brown Norway rats weighing 150–250 g are sensitized on days 0, 12 and 21 with ovalbumin (100 pg, i.p.). Rats are challenged on any one day between days 27–32. 24 hours and 1 hour before antigen challenge rats are dosed orally. Rats are challenged by exposure for 30 minutes to Nebulized saline or ovalbumin (1% in saline). 24 hours after challenge, rats are killed and the airways are lavaged with physiological salt solution. Total and differential cell counts are made.

5. In Vitro Inhibitory Effects on TNF-α Release by Human Monocytes

The effects of compounds on TNF-α production by human peripheral blood monocytes (PBMs) are examined as follows.

5.1. Preparation of blood leukocytes.

Blood is drawn from normal donors, mixed with dextran, and the erythrocytes allowed to sediment for 35 minutes at 37° C. Leukocytes are fractionated by centrifugation through a discontinuous (18, 20 and 22%) metrizamide gradient. The mononuclear cell fraction comprising 30–40% PBMs is suspended in Hank's balanced salt solution and stored at 4° C. until use.

5.2. Measurement of TNF-α.

Cells from the PBM-rich metrizamide fraction are spun down (200 g for 10 minutes at 20° C.), resuspended at $10^6$ PBMs/mL of medium; RPMI 1640 containing 1%v/v FCS, 50 U/mL penicillin and 50 mg/mL streptomycin (Gibco, U.K.), then plated out in 96 well plates at $2 \times 10^5$ cells/well. The medium (200 μL) is changed to remove any non-adherent cells and the remaining, adherent PBMs left in the incubator overnight (18 hours). One hour prior to challenge, the medium is changed to that containing compound for test or drug vehicle. Control treatments and compounds for test are assayed in quadruplicate wells. Compounds are tested within the concentration range of $3 \times 10^{-10}$M to $3 \times 10^{-6}$M. Medium (50 μL) with or without 10 ng/mL LPS (E. Coli, 055 B5 from Sigma, U.K.) is then added. The incubation is then continued for a further 4 hours. Cell supernatants are removed for storage at −20° C.

TNF-α levels in cell supernatants are quantified using a standard sandwich ELISA technique. ELISA plates (Costar, U.K.) are coated overnight at 4° C. with 3 mg/mL polyclonal goat anti-human TNF-α antibody (British Biotechnology, U.K.) in pH 9.9 bicarbonate buffer. Rabbit polyclonal anti-human TNF-α antiserum (Janssen Biochimicha, Belgium) at 1/500 dilution is used as the second antibody and polyclonal goat anti-rabbit IgG horseradish peroxidase (Calbiochem, U.S.A.) at 1/8000 dilution is used as the detection antibody. Color development is measured by absorbance at 450 nm using a Titek plate reader.

TNF-α levels are calculated by interpolation from a standard curve using recombinant human TNF-α (British Biotechnology U.K.) (0.125–8 ng/mL). Data (log-conc. vs. log-resp) are fitted by linear regression (p>0.99) using a Multicalc (Wallac Pharmacia, U.K.) software program. Basal TNF-α levels are less than 100 pg/mL whilst LPS (lipopolysaccharide) stimulation of the PBMs increases TNF-α levels to 3–10 ng/mL.

5.3 Results.

Compounds within the scope of the invention produce inhibition of induced TNF-α release from human PBMs at concentrations from about 0.01 nM to about 10 μM.

6. Inhibitory effects of compounds on antigen-induced bronchoconstriction in the conscious guinea-pig.

6.1. Sensitization of guinea-pigs and measurement of antigen-induced bronchoconstriction.

Male Dunkin-Hartley guinea-pigs (550–700 g) are sensitized as above. Specific airways resistance (SRaw) is measured in conscious animals by whole body plethysmography using a variation of the method of Pennock et al., J. Appl. Physiol., 46,399 (1979). Test compounds or vehicle are administered orally 24 hours and 1 hour before antigen challenge. 30 Minutes before challenge the animals are injected with mepyramine (30 mg/kg i.p.) to prevent anaphylactic collapse and placed into the plethysmography chambers where SRaw is determined at 1 minute intervals. Resting SRaw is then determined. Animals are challenged with an aerosol of ovalbumin and SRaw is determined every 5 minutes for 15 minutes.

7. Inhibitory effects of compounds against antigen-induced bronchoconstriction in the anaesthetized rat in vivo.

7.1. Treatment of rats and measurement of antigen-induced bronchoconstriction.

Male Brown Norway rats weighing 150–250 g are sensitized on days 0, 12 and 21 with ovalbumin (100 pg, i.p.). Rats are challenged on any one day between days 27–32. 24 hours and 1 hour before antigen challenge rats are dosed orally. Rats are anaesthetized to allow recording of lung function (airway resistance and lung compliance) using respiratory mechanics software. Rats are challenged with ovalbumin i.v. and the peak changes in airway resistance and lung compliance are determined.

8. Inhibitory effects of compounds on serum TNF-α levels in LPS-challenged mice.

8.1. Treatment of animals and measurement of murine TNF-α.

Female Balb/c mice (age 6–8 weeks, weight 20–22 g from Charles River, U.K.) in groups of five or more animals are dosed p.o. with compounds suspended in 1.5% (w/v) carboxymethyl cellulose then challenged after a minimum period of 30 minutes with 30 mg of LPS i.p. After 90 minutes the animals are killed by carbon dioxide asphyxiation and bled by cardiac puncture. Blood is allowed to clot at 4° C., centrifuged (12,000 g for 5 minutes) and serum taken for TNF-α analysis. TNF-α levels are measured using a commercially available murine TNF-α ELISA kit, purchased from Genzyme (Cat. no. 1509.00), as recommended by the manufacturer. Values for TNF-α are calculated from a recombinant murine TNF-α standard curve.

9. Systemic bioavailability in female Balb/c mouse. Intravenous administration:

Following surgery to expose the jugular vein for dosing, a solution of test compound in dimethylsulphoxide is added at a dose of 1 mg/kg body weight. Oral administration:

A suspension of test compound in 1.5% aqueous carboxymethylcellulose is introduced into the stomach by gavage at a dose of 1 mg/kg body weight. Following either i.v.

or oral dosing, blood is obtained by cardiac puncture following carbon dioxide asphyxiation and is obtained at a single time post-dose for each animal. Three animals are sacrificed at each time point. Blood samples are obtained at the following times after dosing by both the i.v. and oral routes; 5 minutes (i.v. only), 0.25, 0.5, 1, 2, 3, 4, 5.5, 7 and 24 hours. Corresponding plasma is obtained by centrifugation of each blood sample. The drug content in the plasma samples is then determined using conventional methods.

9.1 Metabolism.

(i) Preparation of mouse liver homogenate

Fresh mouse liver is homogenized in sucrose-phosphate buffer. Following centrifugation the resulting supernatant (liver homogenate) is used fresh or frozen in liquid nitrogen for one minute and stored at −30° C. to −40° C. prior to use.

(ii) Incubation of compounds with mouse liver homogenate

To 0.5 mL of mouse liver homogenate is added 0.5 mL taken from a vortexed mixture of 8 mg NADPH added to a mixture of aqueous magnesium chloride (1 mL, 0.15 M) nicotinamide (1 mL, 0.5M) and pH 7.4 tris buffer (8.5 mL, 0.1 M). The compound is added at a concentration of 1 mg/mL in 10 mL of solvent. Incubates are maintained at 37° C. Samples are taken at 0 minutes, 5 minutes, 10 minutes, 20 minutes and 30 minutes and the incubation stopped by the addition of 100 mL acetonitrile. The drug content in the incubation samples is determined using conventional methods.

10. Streptococcal Cell Wall-Induced Arthritis in Rats.

10.1 Preparation of S. pyogenes purified cell wall.

Purified S. pyogenes cell wall is prepared from the cell pellet of a log-phase culture of S. pyogenes, group A, strain D-58. The whole bacteria are homogenized by grinding with glass beads and the crude cell wall collected by centrifugation and subsequently washed with 2% sodium dodecyl sulphate in phosphate buffered saline followed by phosphate buffered saline to remove contaminating proteins and nucleic acids. The cell wall is further purified by sonication and differential centrifugation to obtain a purified preparation which pelleted at 100,000 g. This material is suspended in sterile phosphate buffered saline and the quantity of cell wall determined by measuring the rhamnose content of the preparation (purified cell wall contains 28% rhamnose by weight). The material is filtered through a 0.22 mM filter and stored at 4° C. until used for arthritis induction.

10.2 Arthritis Induction and measurement of joint diameters.

Female Lewis rats weighing 140–160 g are injected intra-articularly into the left or right tibio-tarsal joint on day 0 with purified S. pyogenes cell wall extract (10 mg in 10 mL sterile saline). On day 20, rats received an intravenous injection of purified cell wall (100 mg in 100 mL sterile saline) via the lateral vein of the tail. Joint diameters are measured with calipers across the lateral and medial malleoli of the previously intra-articularly injected joint immediately prior to the i.v. injection and then daily through day 24. The net joint diameter is determined by subtracting the value for the contralateral joint. Body weights are also measured daily. Compounds or vehicle are administered by oral gavage on days 20–23. Typically, 8–10 animals are used per group. For each dose, the total daily dose is divided into two equal aliquots which are given at approximately 9 a.m. and 3 p.m.

MMP Assay:

The assay for MMP activity is undertaken essentially by the methods as disclosed by Knight, C. Graham, Willenbrock, Frances and Murphy, Gillian FEBS. 296 (3), 263–266 (1992) with some modifications.

"collagenase (MMP-1): Biogenesis # 5980-0157; 5 nM final concentration substrate: Mca-Pro-Leu-Gly-Leu-Dpa-Ala-Arg-NH$_2$ (BACHEM # M1895); 50 mM final concentration (freeze aliquots of 6.25 mM in DMSO and dilute to 62.5 $\mu$M in assay buffer)

incubation time: 6 hours at room temperature gelatinase-A (MMP-2): Biogenesis # 5980-0257; 2 nM final concentration substrate: Mca-Pro-Leu-Gly-Leu-Dpa-Ala-Arg-NH$_2$ (BACHEM # M1895); 20 $\mu$M final concentration (freeze aliquots of 6.25 mM in DMSO and dilute to 25 $\mu$M in assay buffer)

incubation time: 1 hour at room temperature stromelysin (MMP-3): Biogenesis # 5980-0357; 2 nM final concentration substrate: Mca-Arg-Pro-Lys-Pro-Tyr-Ala-Nva-Trp-Met-Lys(Dnp)-N H$_2$ (BACHEM # M2105); 10 $\mu$M final concentration (freeze aliquots of 1.25 mM in DMSO and dilute to 12.5 $\mu$M in assay buffer)

incubation time: 6 hours at room temperature

Assay buffer: 50 mM HEPES, 10 mM CaCl$_2$, 0.1% BRIJ-35, 0.2% NaN$_3$ at pH 7.0

Enzymes are prepared in assay buffer at a concentration of 11-fold higher than the desired final concentration and are stored in 1 mL aliquots. Activation: 50 mL of trypsin (Sigma # T-1426) per 1 mL aliquot is added (to obtain a 10 nM final concentration) and it is incubated at 37° C. for 30 minutes. 50 $\mu$L of trypsin inhibitor (SIGMA # T-0637) is added; mix and pellet to remove beads. Dilute 10-fold into assay.

| | $\mu$L buffer | $\mu$L compound | $\mu$L enzyme | $\mu$L substrate |
|---|---|---|---|---|
| blank | 40 | 0 | 0 | 160 |
| control | 20 | 0 | 20 | 160 |
| compound | 0 | 20 | 20 | 160 |

Compounds are run at 10 $\mu$M final concentration (diluted DMSO should be added to the controls at the same concentration as in the compound wells).

Activity is measured in a Cytofluor fluorescence plate reader at 340 nm excitation and 400 nm emission.

The present invention may be embodied in other specific forms without departing from the spirit or essential attributes thereof.

What is claimed is:

1. A compound of formula I

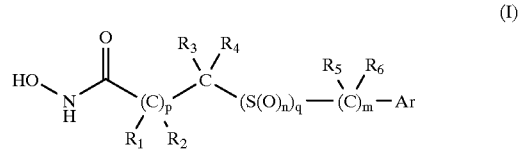

(I)

wherein

R$_1$ is hydrogen, optionally substituted alkyl, optionally substituted alkenyl, optionally substituted cycloalkyl, optionally substituted cycloalkenyl, optionally substituted aryl, optionally substituted heteroaryl, optionally substituted aralkyl, optionally substituted heteroaralkyl, optionally substituted aralkyloxyalkyl, optionally substituted aryloxyalkyl, hydroxy, optionally substituted alkoxy, optionally substituted aryloxy, optionally substituted aralkyloxy, $Y^3Y^4N-$, $Y^1Y^2NCO$-alkyl, aryl-$SO_2Y^1N$-alkyl, arylsultanylalkyl, arylsultinylalkyl, arylsulfonylalkyl, cyclocarbamoylalkyl or imidealkyl;

$R_2$, $R_4$, $R_5$, $R_6$ are independently hydrogen or optionally substituted alkyl, or $R_4$ is optionally substituted aryl or optionally substituted heteroaryl, or $R_2$ and $R_4$ taken together with the carbon atoms through which $R_2$ and $R_4$ are linked form optionally substituted cycloalkyl or optionally substituted cycloalkenyl, or $R_1$ and $R_2$ taken together with the carbon atoms through which $R_1$ and $R_2$ are linked form optionally substituted cycloalkyl;

$R_3$ is optionally substituted alkyl, optionally substituted alkenyl, optionally substituted cycloalkyl, optionally substituted cycloalkenyl, optionally substituted aryl, optionally substituted heteroaryl, optionally substituted aralkyl, optionally substituted aralkenyl, optionally substituted aralkynyl, optionally substituted heteroaralkyl, optionally substituted heteroaralkenyl, optionally substituted heteroaralkynyl, optionally substituted alkyloxyalkyl, optionally substituted aryloxyalkyl, optionally substituted heteroaryloxyalkyl, optionally substituted aryloxyalkenyl, optionally substituted heteroaryloxyalkenyl, optionally substituted aralkyloxyalkyl, optionally substituted aralkyloxyalkenyl, optionally substituted heteroaralkyloxyalkyl, optionally substituted heteroaralkyloxyalkenyl, optionally substituted cycloalkyloxy, optionally substituted cycloalkyloxyalkyl, optionally substituted heterocyclyl, optionally substituted heterocyclyloxyalkyl or optionally substituted heterocyclyloxy, $Y^3Y^4N$alkyl, $Y^1Y^2NCO_2$alkyl, $Y^1Y^2NCO$-alkyl, imidealkyl, or $R_3$ and $R_4$ taken together with the carbon to which $R_3$ and $R_4$ are attached form an optionally substituted cycloalkyl, or one of $R_1$ and $R_2$ and one of $R_3$ and $R_4$ taken together with the carbons through which the one of $R_1$ and $R_2$ and one of $R_3$ and $R_4$ are linked form a bond or optionally substituted cycloalkyl or optionally substituted cycloalkenyl;

Ar is optionally substituted aryl or optionally substituted heteroaryl;

$Y^1$ and $Y^2$ are independently hydrogen, optionally substituted alkyl, optionally substituted aryl or optionally substituted aralkyl, or $Y^1$ and $Y^2$ taken together with the nitrogen atom to which $Y^1$ and $Y^2$ are attached form an optionally substituted heterocyclyl;

$Y^3$ and $Y^4$ are independently $Y^1$ and $Y^2$, or optionally substituted acyl, optionally substituted aroyl, optionally substituted aralkyloxycarbonyl, optionally substituted heteroaralkyloxycarbonyl or optionally substituted alkoxycarbonyl;

n is 0, 1 or 2;

m is 0 or 1;

p is 0 or 1; and q is 0 or 1, or an n-oxide thereof, solvate thereof, hydrate thereof or pharmaceutically acceptable salt thereof;

provided that when p is 1, $R_3$ and $R_4$ are hydrogen, m is 0, Ar is phenyl, and either $R_1$ of $R_2$ is unsubstituted lower alkyl, then q is 1.

2. The compound of claim 1 wherein $R_1$ is hydrogen, optionally substituted alkyl, optionally substituted alkenyl, optionally substituted cycloalkyl, hydroxy, $Y^1Y^2N-$, arylsulfanylalkyl, arylsulfinylalkyl or arylsulfonylalkyl;

$R_2$, $R_4$, $R_5$, $R_6$ are independently hydrogen or optionally substituted alkyl, or $R_2$ and $R_4$ taken together with the carbon atoms through which $R_2$ and $R_4$ are linked form optionally substituted cycloalkyl or optionally substituted cycloalkenyl, or $R_1$ and $R_2$ taken together with the carbon atoms through which $R_1$ and $R_2$ are linked form optionally substituted cycloalkyl;

$R_3$ is optionally substituted alkyl, optionally substituted aryl, optionally substituted heteroaryl, optionally substituted aralkyl, optionally substituted heteroaralkyl, $Y^3Y^4N$alkyl, $Y^1Y^2NCO_2$alkyl, $Y^1Y^2NCO$-alkyl, imidealkyl, or $R_3$ and $R_4$ taken together with the carbon to which $R_3$ and $R_4$ are attached form an optionally substituted cycloalkyl, or one of $R_1$ and $R_2$ and one of $R_3$ and $R_4$ taken together with the carbons through which the one of $R_1$ and $R_2$ and one of $R_3$ and $R_4$ are linked form a bond or optionally substituted cycloalkyl or optionally substituted cycloalkenyl;

Ar is optionally substituted aryl or optionally substituted heteroaryl;

$Y^1$ and $Y^2$ are independently hydrogen, optionally substituted alkyl or optionally substituted aryl, or $Y^1$ and $Y^2$ taken together with the nitrogen atom to which $Y^1$ and $Y^2$ are attached form an optionally substituted heterocyclyl, and $Y^3$ and $Y^4$ are independently $Y^1$ or $Y^2$, or optionally substituted aroyl or optionally substituted aralkyloxycarbonyl.

3. The compound of claim 1 wherein $R_1$ is optionally substituted alkyl, optionally substituted alkenyl, optionally substituted aralkyl or optionally substituted heteroaralkyl.

4. The compound of claim 1 wherein $R_1$ is optionally substituted alkyl.

5. The compound of claim 1 wherein $R_1$ is hydroxy.

6. The compound of claim 1 wherein $R_1$ is optionally substituted alkyl.

7. The compound of claim 1 wherein $R_1$ is $Y^1Y^2N-$ and $Y^1$ or $Y^2$ are hydrogen.

8. The compound of claim 1 wherein $R_2$ is hydrogen.

9. The compound of claim 1 wherein $R_1$ and $R_2$ are optionally substituted alkyl.

10. The compound of claim 1 wherein $R_3$ is optionally substituted aryl, optionally substituted heteroaryl, optionally substituted aralkyl, optionally substituted heteroaralkyl or $Y^3Y^4N$alkyl.

11. The compound of claim 1 wherein $R_3$ is optionally substituted aralkyl.

12. The compound of claim 1 wherein $R_4$ is hydrogen or optionally substituted alkyl.

13. The compound of claim 1 wherein $R_4$ is optionally substituted alkyl.

14. The compound of claim 1 wherein $R_3$ and $R_4$ taken together with the carbon atom to which $R_3$ and $R_4$ are attached form optionally substituted cycloalkyl.

15. The compound of claim 1 wherein Ar is optionally substituted aryl.

16. The compound of claim 15 wherein aryl is 4-methoxyphenyl or 3,4-dimethoxyphenyl.

17. The compound of claim 15 wherein aryl is 4-methoxyphenyl.

18. The compound of claim 15 wherein aryl is 3,4-dimethoxyphenyl.

19. The compound of claim 1 wherein n is 0 or 2.

20. The compound of claim 1 wherein m is 0.

21. The compound of claim 1 wherein q is 1.
22. The compound of claim 1 which is 7-Phenyl-3-phenylsulfonylheptanoic acid hydroxyamide;
7-Phenyl-3-phenylsulfanylheptanoic acid hydroxyamide;
(±)-N-Hydroxy-3-(4-methoxyphenyl)sulfanyl-4-(4-biphenyl)butyaramide;
(±)-N-Hydroxy-3-(4-methoxyphenyl)sulfanyl-4-(4-phenyloxyphelyl)butyramide;
(±)-N-Hydroxy-3-(4-methoxyphenyl)sulfanyl-4-(4-benzyloxyphenyl)butyramide;
(±)-N-Hydroxy-3-(4-methoxyphenyl)sulfanyl-4-(4-n-Butyloxyphenyl)-butyramide;
(±)-N-Hydroxy-3-(4-methoxyphenyl)sulfonyl-4-(4-biphenyl)butyramide;
(±)-N-Hydroxy-3-(4-methoxyphenyl)sulfonyl-4-(4-phenyloxyphenyl)butyramide;
(±)-N-Hydroxy-3-(4-methoxyphenyl)sulfonyl-4-(4-benzyloxyphenyl)butyramide;
(±)-N-Hydroxy-3-(4-methoxyphenyl)sulfonyl-4-(4-n-Butyloxyphenyl)-butyramide;
3-(4-Methoxybenzenesulfonyl)-3-ethyl-7-phenylheptanoic acid hydroxamide;
3-(4-Methoxybenzenesuffonyl)-3,7-diphenylheptanoic acid hydroxamide;
N-Hydroxy-3-(4-methoxybenzenesulfonyl)-3-methylbutyramide;
N-Hydroxy-2-[1-(4-methoxybenzenesulfonyl)cyclopentyl]acetamide;
(2R*,3R*)-2-Amino-3-(4-methoxybenzene)sulfonyl-7-phenylheptanoic acid hydroxy amide;
N-Hydroxy-2-[(3,4-dimethoxyphenyl)sulfonyl]-6-phenylhexanamide;
(E)-N-Hydroxy-3-[(3,4-dimethoxyphenyl)thio]-7-phenyl-2-heptenamide;
(E)-N-Hydroxy-3-[(3,4-dimethoxyphenyl)sulfonyl]-7-phenyl-2-heptenamide;
(Z)-N-Hydroxy-3-[(3,4-dimethoxyphenyl)thio]-7-phenyl-2-heptenamide;
3-(4-Acetoamidophenylsulfonyl)-7-phenylheptanoic acid hydroxyamide;
3-(4-Acetoamidophenylsulfanyl)-7-phenylheptanoic acid hydroxyamide;
3-(2-Naphthalenylsulfonyl)-7-phenylheptanoic acid hydroxyamide;
3-(2-Naphthalenylsulfanyl)-7-phenylheptanoic acid hydroxyamide;
3-(4-Methoxyphenylsulfonyl)-7-phenylheptanoic acid hydroxyamide;
3-(4-Methoxyphenylsulfanyl)-7-phenylheptanoic acid hydroxyamide;
3-(Benzylsulfonyl)-7-phenylheptanoic acid bydroxyamide;
3-(Benzylsulfanyl)-7-phenylheptanoic acid hydroxyamide;
N-Hydroxy-3-(4-methoxybenzenesulfonyl)-4-phenylbutyramide;
N-Hydroxy-3-(4-methoxybenzenesulfanyl)-4-phenylbutyramide;
N-Hydroxy-3-(4-methoxybenzenesulfonyl)-3-phenylpropionamide;
N-Hydroxy-3-(4-methoxybenzenesulfanyl)-3-phenylpropionamide;
3-(4-Methoxybenzenesulfonyl)-5-phenylpentanoic acid hydroxyamide;
3-(4-Methoxybenzenesulfanyl)-5-phenylpentanoic acid hydroxyamide;
3-(4-Methoxybenzenesulfonyl)-6-phenylhexanoic acid hydroxamide;
3-(4-Methoxybenzenesulfanyl)-6-phenylhexanoic acid hydroxamide;
3-(4-Methoxybenzenesulfonyl)-3-methyl-7-phenylheptanoic acid hydroxamide
3-(4-Methoxybenzenesulfanyl)-3-methyl-7-phenylheptanoic acid hydroxamide
N-hydroxy-3-(4-methoxyphenyl)thio-2-(1-propane-3-yl)-7-phenyl-heptanamide;
N-Hydroxy-2-(1-propane-3-yl)-3-(4-methoxyphenyl)sulfonyl-7-phenylheptanamide;
N-Hydroxy-2-{(3,4-dimethoxyphenyl)thio]-3-(3-phenylpropyl-1-yl)-1-cyclopentenecarboxamide;
N-Hydroxy-2-[(3,4-dimethoxyphenyl)sulfonyl]-3-(3-phenylpropyl-1-yl)-1-cyclopentenecarboxamide;
N-Hydroxy-3-(3,4-dimethoxyphenyl-7-phenyl-2-heptenamide;
N-Hydroxy-3-(3,4-dimethoxyphenyl-7-phenylheptanamide;
(−)-(2S,3R)-N-Hydroxy-2-(2-benzenesulfonylethyl)-3-(3,4-dimethoxyphenylsulfonyl)-7-phenylheptanamide;
(+)-(2S,3R)-N-Hydroxy-2-(2-benzenesulfonylethyl)-3-(3,4-dimethoxyphenylsulfonyl)-7-phenylheptanamide;
(−)-N-Hydroxy-2-(2-benzenesulfonylethyl)-3-(3,4-dimethoxyphenylsulfanyl)-7-phenylheptanamide;
(+)-N-Hydroxy-2-(2-benzenesulfonylethyl)-3-(3,4-dimethoxyphenylsulfanyl)-7-phenylheptanamide;
N-Hydroxy-3-(3,4-dimethoxybenzenesulfonyl)-4-phenylbutyramide;
N-Hydroxy-3-(3,4-dimethoxyphenylsulfanyl)-4-phenylbutyramide;
N-Hydroxy-3-(3,4-dimethoxybenzenesulfonyl)-3-phenylproprionamide;
N-Hydroxy-3-(3,4-dimethoxyphenylsulfanyl)-3-phenylpropionamide;
3-(3,4-Dimethoxyphenylsulfanyl)-5-phenylpentanoic acid hydroxamide;
3-(3,4-Dimethoxyphenylsulfonyl)-5-phenylpentanoic acid hydroxamide;
3-(3,4-Dimethoxybenzenesulfonyl)-6-phenylhexanoic acid hydroxamide;
3-(3,4-Dimethoxyphenylsulfanyl)-6-phenylhexanoic acid hydroxamide;
3-(3,4-Dimethoxybenzenesulfonyl)-6-phenylhexanoic acid hydroxamide;
3-(R*)-(3,4-Diimethoxybenzenesulfonyl)-2-(S*)-isopropyl-7-phenylheptanoic acid hydroxamide;
3-(3,4-Dimethoxybenzenesulfanyl)-2-isopropyl-7-phenylheptanoic acid hydroxamide;
(+)-(2R,3R)-3-(3,4-Dimethoxyphenylsulfanyl)-2-methyl-7-phenylheptanoic acid hydroxyamide;
(+)-(2R,3R)-3-(3,4-Dimethoxyphenylsulfonyl)-2-methyl-7-phenylheptanoic acid hydroxyamide;
(+)-(2R,3S)-3-(3,4-Dimethoxyphenylsulfanyl)-2-methyl-7-phenylheptanoic acid hydroxyamide;
(+)-(2R,3S)-3-(3,4-Dimethoxyphenylsulfonyl)-2-methyl-7-phenylheptanoic acid hydroxyamide;

1-[1-(3,4-Dimethoxyphenylsulfonyl)-5-phenylpentyl]
cyclopentane-carboxylic acid hydroxyamide;
1-[1-(3,4-Dimethoxyphenylsulfanyl)-5-phenylpentyl]
cyclopentane-carboxylic acid hydroxyamnide;
3-(3,4-Dimethoxybenzenesulfonyl)-2,2-dimethyl-7-
phenylheptanoic acid hydroxyamide;
3-(4-Methoxybenzenesulfonyl)-2,2-dimethyl-7-
phenylheptanoic acid hydroxyamide;
3-(4-Methoxybenzenesulfinyl)-7-phenylheptanoic acid hydroxamide;
(±)-N-Hydroxy-3-(3,4-Dimethoxyphenyl)sulfonyl-7-phenylheptanamide;
(±)-N-Hydroxy-3-(3,4-methylenedioxyphenyl)sulfonyl-7-phenylheptanamide;
(±)-N-Hydroxy-3-(3,4-dimethoxyphenyl)sulfinyl-7-phenylheptanamide;
(±)-N-Hydroxy-3-(3,4-Dimethoxyphenyl)sulfanyl-7-phenylheptanamide;
(±)-N-hydroxy-3-(3,4-methylenedioxyphenyl)sulfanyl-7-phenylheptanamide;
(−)-N-Hydroxy-3-(3,4-dimethoxyphenyl)sulfonyl-7-phenylheptanamide;
(+)-N-hydroxy-3-(3,4-dimethoxyphenyl)sulfonyl-7-phenylheptananide;
(±)-(2R*,3R*)-3-(4-Methoxybenzenesulfonyl)-7-phenyl-2-(2-phenoxyethyl)heptanoic acid hydroxyamide;
(±)-(2R*,3R*)-3-(4-Methoxybenzenesulfonyl)-7-phenyl-2-(2-phenylsulfanylethyl)heptanoic acid hydroxyamide;
(2R*,3R*)-3-(4-Methoxybenzenesulfonyl)-7-phenyl-2-(2-phenylsulfanyl-ethyl)heptanoic acid hydroxyamide;
(±)-(2R*,3S*)-3-(4-Methoxybenzenesulfonyl)-7-phenyl-2-(benzenesulfonylmethyl)heptanoic acid hydroxyamide;
(±)-(2R*,3S*)-3-(4-methoxybenzenesulfonyl)-7-phenyl-2-(phenylsulfinylmethyl)heptanoic acid hydroxyaride;
(±) 2-Hydroxy-3-(4-methoxybenzenesulfonyl)-2-methyl-7-phenylheptanoic acid hydroxyamide;
(±)-3-(4-Methoxyphenylsulfanyl)-2-methyl-7-phenylheptanoic acid hydroxyamide;
(±)-3-(4-Methoxybenzenesulfonyl)-2-methyl-7-phenylheptanoic acid hydroxyamide;
3-(3,4-Dimethoxybenzenesulfonyl)-5-methylhexanoic acid hydroxyamide;
5-(4-Butoxyphenyl)-3-(3,4-dimethoxybenzenesulfonyl)-pentanoic acid hydroxyamide;
3-(3,4-Dimethoxybenzenesulfonyl)hexanoic acid hydroxyamide;
3-(3,4-Dimethoxybenzenesulfonyl)-4-methylpentanoic acid hydroxyamide;
3-(3,4-Dimethoxybenzenesulfonyl)-5-methylhexanoic acid hydroxyamide;
3-(3-Benzyloxyphenyl)-3-(3,4-dimethoxybenzenesulfonyl)-N-hydroxypropionamide;
3-(2-Benzyloxyphenyl)-3-(3,4-dimethoxybenzenesulfonyl)-N-hydroxypropionamide;
3-(3-Benzyloxy-4-methoxyphenyl)-3-(3,4-dimethoxybenzenesulfonyl)-N-hydroxypropionamide;
3-(3,4-Dimethoxybenzenesulfonyl)-N-hydroxy-3-(3-phenoxyphenyl)propionamide;
3-(3-(4-Chlorophenoxy)phenyl)-3-(3,4-dimethoxybenzenesulfonyl)-N-hydroxyprcpionarmide;
3-(3,4-Dimethoxybenzenesulfonyl)-N-hydroxy-3-(3-(4-methoxyphenoxy)phenyl)propionamide;
N-[2-(3,4-Dimethoxybenzenesulfonyl)-3-hydroxycarbamoyl-propyl]-N methylbenzamide;
N-[2-(3,4-Dimethoxybenzenesulfonyl)-3-hydroxycarbamoyl-butyl]-N methylbenzamide;
Methyl-phenyl-carbaenic acid 3-(3,4-dimethoxybenzonesulfonyl)-4-hydroxycarbamoylbutyl ester;
[3-(3,4-Dimethoxybenzenesulfonyl)-4-hydroxycarbamoylbutyl]methyl-carbamic acid benzyl ester;
3-(3,4-Dimethoxybenzenesulfonyl)hexanedioic acid-1-hydroxyamide-6-(methylphenylanide);
3-(3,4-Dimethoxybenzenesulfonyl)heptanedioic acid-1-hydroxyamide-7-(methylphenylamide);
3-(3,4-Dimethoxybenzenesulonyl)-6-(1,3-dioxo-1,3-dihydroisoindol-2-yl)hexanoic acid hydroxyamide;
7-(3,4-Dihydro-2H-quinolin-1-yl)-3-(3,4-dimethoxybenzenesulfonyl)-7-oxoheptanoic acid hydroxyamide;
7-(3,4-Dihydro-2H-quinolin-1-yl)-3-(3,4-dimethoxybenzenesulfonyl)-6-oxohexanoic acid hydroxyamide;
7-Benzo(1,3)dioxol-5-yl-3-(3,4-dimethoxybenzenesulfonyl)heptanoic acid hydroxyamide;
3-(3,4-Dimethoxybenzenesulfonyl)-3-(thien-3-yl)-N-hydroxypropionamide;
3-(3,4-Dimethoxybenzenesulfonyl)-5-phenylpentanoic acid hydroxyamide;
3-(3,4-Dimethoxybenzenesulfonyl)-5-(3-phenoxyphenyl)pentanoic acid hydroxyamide;
5-(4-Benzyloxyphenyl)-3-(3,4-dimethoxybenzenesulfonyl)pentanoic acid hydroxyamide;
2-{(3,4-Dimethoxybenzenesulfonyl)-[4-(4-fluorobenzyloxyphenyl]methyl}-4-methylpentanoic acid hydroxyamide;
3-(3,4-dimethoxybenzenesulfonyl)-7-phenyl-2-(4-phenylbutyl)heptanoic acid hydroxyamide;
2-[1-(3-(3,4-dimethoxybenzenesulfonyl)-5-phenylpeatyl]-N 1-hydroxy-N 4-methyl-N 4-phenylsuccinamide;
3-(3,4-dimethoxybenzenesulfonyl)-7-phenyl-2-(3-phenylpropyl)heptanoic acid hydroxyamide;
3-(3,4-dimethoxybenzenesulfonyl)-2-isopropyl-7-phenylheptanoic acid hydroxyamide;
3-(3,4-dimethoxybenzenesulfonyl)-2-isobutyl-7-phenylheptanoic acid hydroxyamide;
3-(3,4-dimethoxybenzenesulfonyl)-7-phenyl-2-propylheptanoic acid hydroxyamide;
3-(3,4-dimethoxybenzenesulfonyl)-7-phenyl-2-(4-phenyl-butyl)heptanoic acid hydroxyamide;
3-(3,4-dimethoxybenzenesulfonyl)-2-benzenesulfonylethyl-7-phenylheptanoic acid hydroxyamide;
3-(3,4-dimethoxybenzenesulfonyl)-7-phenyl-2-(5-phenylpentyl)heptanoic acid hydroxyamide;
4-Benzenesulfonyl-2-}(3,4-dimethoxybenzenesulfonyl)-[4-(4-fluorobenzloxy)phenyl]methyl}-N-hydroxy-butyramide;

2-{(3,4-dimethoxybenzenesulfonyl)-[4-(4-fluorobenryloxy)phenyl]methyl}-N-hydroxy-4-phenyl-butyramide;

2-{(3,4-dimethoxybenzenesulfonyl)-[4-(4-fluorobenzyloxy)phenyl]methyl}-N-hydroxybutyramide;

2-{(3,4-dimethoxybenzenesulfonyl)-[4-(4-fluorobenzyloxy)-phenyl]methyl}-pentanoic acid hydroxyamide;

2-{(3,4-dimethoxybenzenesulfonyl)-[4-(4-fluorobenzyloxy)-phenyl]methyl}-4-meffhylpentEtnoic acid hydroxyamnide;

2-{(3,4-dimethoxybenzenesulfonyl)-[4-(4-fluorobenzyloxy)-phenyl]methyl}-N-hydroxy-3-methylbutyramide;

2-{(3,4-dimethoxybenzenesulfonyl)-[4-(4-fluorobenzyloxy)-phenyl]methyl}-7-phenylheptanoic acid hydroxyamide:

2-{(3,4-dimethoxybenzenesulfonyl)-[4-(4-fluorobenzyloxy)phenyl]methyl}-5-phenylpentanoic acid hydroxyamide;

2-{(3,4-dimethoxybenzenesulfonyl)-[4-(4-fluorobenzyloxy)phcayl]-methyl}-N 1-hydroxy-N 4-methyl-N 4-phenyl-succinimide;

2-{(3,4-dimethoxybenzeresulfonyl)-[4-(4-fluorobenzyloxy)phenyl]methyl}-6-phenylhexanoic acid hydroxyamide;

2-[Biphenyl-4-yl-(3,4-dimethoxybenzenesulfonyl) methyl]-4-methylpentanoic acid hydroxyamide;

2-[(3,4-Dimethoxybenzenesulfonyl)-(4-phenoxypblenyl) methyl]-N-hydroxy-butyramide;

4-Benzenesulfonyl-2-[biphenyl-4-yl-(3,4-dimethoxybenzenesulfonyl)methyl]-N-hydroxybutyraride;

2-[Biphenyl-4-yl-(3,4-dimethoxybenzenesulfonyl) methyl]-N-hydroxy-4-phenylbutyramide;

2-[Biphenyl-4-yl-(3,4-dimethoxybenzenesulfonyl) methyl]-N-hydroxybutyramide;

2-[Biphenyl-4-yl-(3,4-dimethoxybenzenesulfonyl) methyl]-4-methylpentanoic acid hydroxyamide;

2-[Biphenyl-4-yl-(3,4-dimethoxybenzenesulfonyl) methyl]-N-hydroxy-3-methylbutyraminde:

2-[Biphenyl-4-yl-(3,4-dimethoxybenzenesulfonyl) methyl]-7-phenylheptanoic acid hydroxyanide;

2-[Biphenyl-4-yl-(3,4-dimethoxybenzenesulfonyl) methyl]-5-phenylpentanoic acid hydroxyamide;

2-[(3,4-Dimethoxybenzenesulfonyl)-(4-phonoxyphenyl) methyl]-N-hydroxy-3-methylbutyrarride;

2-[(3,4-Dimethoxybenzenesulfonyl)-(4-phenoxyphenyl) methyl]-7-phenylheptanoic acid hydroxyamide;

3-(3,4-Dimethoxybenzenesulfonyl)-2-ethylhexanoic acid hydroxyamide;

3-(3,4-Dimethoxybenzenesulfonyl)-2-(3-phenylpropyl) hexanoic acid hydroxyamide;

2-[(3-Benzyloxyphenyl)-(3,4-dimethoxybenzenesulfonyl)methyl]-5-phenylpentanoic acid hydroxyamide;

3-(4-Methoxybenzenesulfonyl)-3-(4-ethoxyphenyl) propionic acid hydroxyanide;

3-(4-Methoxybenzenesulfonyl)-3-(4-biphenyl)propionic acid hydroxy amide);

3-(4-Methoxybenzenesulfonyl)-3-(4-phenoxyphenyl) propionic acid hydroxy amide;

3-(4-Methoxybenzenesulfonyl)-3-(4-benzytoxyphenyl)-propionic acid hydroxy amide, 3-(4-Methoxybenzenesulfonyl)-3-(4-fluorobenzyloxypheuyl)propionic acid hydroxy amide;

3-(4-Methoxybenzenesulfonyl)-3-(4-(3-trifluoromethylphenoxy)phenyl- propionic acid hydroxy amide;

(+)-3-(4-Methoxyphenylsulfonyl)-7-phenylheptanoic acid hydroxamide;

(−)-3-(4-Methoxyphenylsulfonyl)-7-phenylheptanoic acid hydroxamide, (−)-(2S,3S)-3-(3,4-Dimethoxybenzeuesulfanyl)-2-methyl-7-heptanoic acid hydroxyamide;

(−)-(2S,3S)-3-(3,4-Dimethoxybenzeuesulfonyl)-2-methyl-7-heptanoic acid hydroxyamide;

(−)-(2S,3R)-3-(3,4-Dimethoxyphenylsulfanyl)-2-methyl-7-heptanoic acid hydroxyamide; or (−)-(2S,3R)-3-(3,4-Dimethoxybenzenesulfonyl)-2-methyl-7-phenylheptanoic acid hydroxyamide.

23. The compound of claim 22 which is

7-Phenyl-3-phenylsulfonylheptanoic acid hydroxyamide;

7-Phenyl-3-phenylsulfanylheptanoic acid hydroxyamide;

3-(4-Acetoamidophenylsulfonyl)-7-phenylheptanoic acid hydroxyamide;

3-(4-Acetoamidophenylsulfanyl)-7-phenylheptanoic acid hydroxyamide;

3-(2-Naphthalenylsulfonyl)-7-phenylheptanoic acid hydroxyamide;

3-(2-Naphthalenylsulfanyl)-7-phenylheptanoic acid hydroxyamide;

3-(Benzylsulfonyl)-7-phenylheptanoic acid hydroxyamide; or 3-(Benzylsulfanyl)-7-phenylheptanoic acid hydroxyamide.

24. The compound of claim 22 which is
3-(4-Methoxyphenylsulfonyl)-7-phenylheptanoic acid hydroxyamide.

25. The compound of claim 22 which is
3-(4-Methoxyphenylsulfanyl)-7-phenylheptanoic acid hydroxyamide.

26. The compound of claim 22 which is
(±)-N-Hydroxy-3-(4-methoxyphenyl)sulfonyl-4-(4-phenyloxyphenyl)butyramide.

27. The compound of claim 22 which is
(±)-N-Hydroxy-3-(4-methoxyphenyl)sulfonyl-4-(4-benzyloxyphenyl)butyramide.

28. The compound of claim 22 which is
N-Hydroxy-3-(4-methoxybenzenesulfonyl)-3-methylbutyramide.

29. The compound of claim 22 which is
N-Hydroxy-2-[1-(4-methoxybenzenesulfonyl) cyclopentyl]acetamide.

30. The compound of claim 22 which is
N-Hydroxy-2-[1-(4-methoxybenzenesulfonyl)-4-phenylcyclohexyl]acetamide.

31. The compound of claim 22 which is
N-Hydroxy-2-[(3,4-dimethoxyphenyl)sulfonyl]-6-phenylhexanamide.

32. The compound of claim 22 which is
N-Hydroxy-2-[(3,4-dimethoxyphenyl)sulfonyl]-3-(3-phenylpropyl-1-yl)-1-cyclopentenecarboxamide.

33. The compound of claim 22 which is (−)-N-Hydroxy-2-(2-benzenesulfonylethyl)-3-(3,4-dimethoxyphenylsulfanyl)-7-phenylheptanamide.

34. The compound of claim 22 which is
3-(R*)-(3,4-Dimethoxybenzenesulfonyl)-2-(S*)-isopropyl-7-phenylheptanoic acid hydroxamide.

35. The compound of claim 22 which is
(+)-(2R,3R)-3-(3,4-Dimethoxyphenylsulfanyl)-2-methyl-7-phenylheptanoic acid hydroxyamide.

36. The compound of claim 22 which is
(+)-(2R,3R)-3-(3,4-Dimethoxyphenylsulfonyl)-2-methyl-7-phenylheptanoic acid hydroxyamide.

37. The compound of claim 22 which is
(+)-(2R,3S)-3-(3,4-Dimethoxyphenylsulfanyl)-2-methyl-7-phenylheptanoic acid hydroxyamide.

38. The compound of claim 22 which is
(+)-(2R,3S)-3-(3,4-Dimethoxyphenylsulfonyl)-2-methyl-7-phenylheptanoic acid hydroxyamide.

39. The compound of claim 22 which is
3-(3,4-Dimethoxybenzenesulfonyl)-2,2-dimethyl-7-phenylheptanoic acid hydroxyamide.

40. The compound of claim 22 which is
3-(4-Methoxybenzenesulfonyl)-2,2-dimethyl-7-phenylheptanoic acid hydroxyamide.

41. The compound of claim 22 which is
(±)-N-Hydroxy-3-(3,4-Dimethoxyphenyl)sulfonyl-7-phenylheptanamide.

42. The compound of claim 22 which is
(±)-N-Hydroxy-3-(3,4-dimethoxyphenyl)sulfinyl-7-phenylheptanamide.

43. The compound of claim 22 which is
(−)-N-Hydroxy-3-(3,4-dimethoxyphenyl)sulfonyl-7-phenylheptanamide.

44. The compound of claim 22 which is
(+)-N-hydroxy-3-(3,4-dimethoxyphenyl)sulfonyl-7-phenylheptanamide.

45. The compound of claim 22 which is
(±)-(2R*,3S*)-3-(4-Methoxybenzenesulfonyl)-7-phenyl-2-(benzenesulfonylmethyl)heptanoic acid hydroxyamide.

46. The compound of claim 22 which is
7-Benzo(1,3)dioxol-5-yl-3-(3,4-dimethoxybenzenesulfonyl)heptanoic acid hydroxyamide.

47. The compound of claim 22 which is
3-(3,4-dimethoxybenzenesulfonyl)-2-isopropyl-7-phenylheptanoic acid hydroxyamide.

48. The compound of claim 22 which is
3-(3,4-dimethoxybenzenesulfonyl)-2-benzenesulfonylethyl-7-phenylheptanoic acid hydroxyamide.

49. The compound of claim 22 which is
3-(4-methoxybenzenesulfonyl)-3-(4-phenoxyphenyl)propionic acid hydroxy amide.

50. The compound of claim 22 which is
3-(4-methoxybenzenesulfonyl)-3-(4-benzyloxyphenyl)propionic acid hydroxy amide.

51. The compound of claim 22 which is
3-(4-methoxybenzenesulfonyl)-3-(4-fluorobenzyloxyphenyl)propionic acid hydroxy amide.

52. The compound of claim 22 which is
(+)-3-(4-methoxyphenylsulfonyl)-7-phenylheptanoic acid hydroxamide.

53. The compound of claim 22 which is
(−)-3-(4-methoxyphenylsulfonyl)-7-phenylheptanoic acid hydroxamide.

54. The compound of claim 22 which is
(−)-(2S,3S)-3-(3,4-Dimethoxybenzenesulfanyl)-2-methyl-7-phenylheptanoic acid hydroxyamide.

55. The compound of claim 22 which is
(−)-(2S,3S)-3-(3,4-Dimethoxybenzenesulfonyl)-2-methyl-7-phenylheptanoic acid hydroxyamide.

56. The compound of claim 22 which is
(−)-(2S,3R)-3-(3,4-dimethoxyphenylsulfanyl)-2-methyl-7-phenylheptanoic acid hydroxyamide.

57. The compound of claim 22 which is
(−)-(2S,3R)-3-(3,4-dimethoxybenzenesulfonyl)-2-methyl-7-phenylheptanoic acid hydroxyamide.

58. A pharmaceutical composition comprising a pharmaceutically acceptable amount of the compound of claim 1 and a pharmaceutically acceptable carrier.

59. A method for treating a disease state capable of being modulated by inhibiting TNF comprising administering to a patient suffering from said disease state an effective amount of the compound of claim 1.

60. The method of claim 59 wherein the disease state is an inflammatory disease or autoimmune disease.

61. The method of claim 59 wherein the disease state is selected from the group consisting of joint inflammation, arthritis, rheumatoid arthritis, rheumatoid spondylitis and osteoarthritis, sepsis, septic shock, gram negative sepsis, toxic shock syndrome, acute respiratory distress syndrome, asthma, bone resorption diseases, reperfusion injury, graft vs host reaction, allograft rejection malaria, myalgias, HIV, AIDS, cachexia, Crohn's disease, ulcerative colitis, pyresis, systemic lupus erythematosus, multiple sclerosis, type I diabetes mellitus, psoriasis, Bechet's disease, anaphylactoid purpura nephritis, chronic glomerulonephritis, inflammatory bowel disease and leukemia.

62. The method of claim 61 wherein the disease state is joint inflammation.

63. A method for treating a disease state capable of being modulated by inhibiting production of cyclic AMP phosphodiesterase comprising administering to a patient suffering from said disease state an effective amount of the compound of claim 1.

64. The method of claim 62 wherein the disease state is a pathological condition associated with a function of cyclic AMP phosphodiesterase, eosinophil accumulation or a function of the eosinophil.

65. The method of claim 64 wherein the pathological condition is asthma, atopic dermatitis, urticaria, allergic rhinitis, psoriasis, rheumatic arthritis, ulcerative colitis, Crohn's disease, adult respiratory distress syndrome, diabetes insipidus, keratosis, dermatitis, cerebral senility, multi-infarct dementia, senile dementia, memory impairment associated with Parkinson's disease, cardiac arrest, stroke and intermittent claudication.

66. The method of claim 65 wherein the pathological condition is asthma.

67. A method for treating a disease state capable of being modulated by inhibiting a matrix metalloproteinase comprising administering to a patient suffering from said disease state an effective amount of the compound of claim 1.

68. A compound as claimed in claim 1 wherein
$R_1$ is substituted aryl, substituted aralkyl, substituted aralkyloxyalkyl, substituted aryloxyalkyl, substituted arylsulfonylalkyl, substituted aryloxy, substituted aralkloxy, substituted arylsulfanylalkyl, or substituted aryksulfinylalkyl, wherein the aryl moiety is substituted with at least one substituenit selected from aralkoxy, acyl, nitro, alkoxycarbonyl, aryloxycarbonyl, aralkoxycarbonyl, acylarnino, aroylamino, alkylsulfonyl, arylsulfonyl, alkylsulfinyl, arylsulfinyl, alkylthio, aralkylthio, oxyalkylenyloxy, $Y^1Y^2NCO$— or $Y^1Y^2NSO_2$—, wherein $Y^1$ and $Y^2$ are independently hydrogen, optionally substituted alkyl, optionally substituted aryl, optionally substituted aralkyl, or $Y^1$ and $Y^2$ taken together with the nitrogen atom to which $Y^1$ and $Y^2$ are attached form an optionally substituted heterocyclyl, or $Y^1Y^2N$—, wherein $Y^1$ is optionally substituted aryl and $Y^2$ is substituted alkyl, or $Y^1$ hydrogen and $Y^2$ is substituted alkyl, or $Y^1$ is optionally substituted aralkyl and $Y^2$ is optionally substituted alkyl, or $Y^1$ and $Y^2$ are independently optionally substituted aryl or optionally substituted aralkyl, or $Y^1$ and $Y^2$ are independently optionally substituted alkyl, or $Y^1$ and $Y^2$ are hydrogen, or $Y^1$ and $Y^2$ taken together with the nitrogen atom to which $Y^1$ and $Y^2$ are attached form an optionally substituted heterocyclyl; or wherein the alkyl moiety is substituted with at least one substituent selected from hydroxyl, halo, cycloalkyl, cycloalkenyl, or heterocyclyl.

69. A compound as claimed in claim 1 wherein $R_1$ is substituted heteroaryl or substituted heteroaralkyl, wherein the heteroaryl moiety is substituted with at least one substituent selected from aryl, aralkyl, ayoxy, aralkoxy, acyl, nitro, alkoxycarbonyl, aryloxycarbonyl, aralkoxycarbonyl, acylamino, aroylamino, alkylsulfonyl, arylsulfonyl, alkylsulfinyl, arylsulfinyl, alkylthio, arylthio, aralkylthio, oxyalkylenyloxy, cycloalkyl substituted alkyl, hydroxy substituted alkyl, cycloalkenyl substituted alkyl, heterocycl substituted alkyl, or $Y^1Y^2N$—, $Y^1Y^2NCO$—, $Y^1Y^2NSO_2$—; or wherein the alkyl moiety is substituted with at least one substituent selected from hydroxyl, halo, cycloalkyl, cycloalkenyl, or heterocyclyl.

70. A compound as claimed in claim 1 wherein $R_1$ is optionally substituted alkenyl, substituted cycloalkyl, substituted alkoxy, optionally substituted cycloalkenyl, $Y^1Y^2NCO$-alkyl, aryl-$SO_2Y^1N$-alkyl, cyclocarbamoylalkyl, imidealkyl, or alkyl substituted with at least a cycloalkenyl or halo group.

71. A compound as claimed in claim 1 wherein $R_1$ is $Y^3Y^4N$— wherein $Y^4$ is substituted acyl, substituted aroyl, substituted aralkoxycarbonyl, optionally substituted heteroaralkyoxycarbonyl, substituted alkoxycarbonyl, substituted aryl, or substituted aralkyl, wherein the aryl moiety is substituted with at least one substituent selected from aralkoxy, acyl, nitro, alkoxycarbonyl, aryloxycarbonyl, aralkoxycarbonyl, acylamino, aroylamino, alkylsulfonyl, arylsulfonyl, alkylsulfinyl, arylsulfinyl, alkyltio, aralkylthio, oxyalkylenyloxy, $Y^1Y^2NCO$— or $Y^1Y^2NSO_2$—, wherein $Y^1$ and $Y^2$ are independently hydrogen, optionally substituted alkyl, optionally substituted aryl, optionally substituted aralkyl or $Y^1$ and $Y^2$ taken together with the nitrogen atom to which $Y^1$ and $Y^2$ are attached form an optionally substituted heterocyclyl, or $Y^1Y^2N$—, wherein $Y^1$ is optionally substituted aryl and $Y^2$ is substituted alkyl, or $Y^1$ hydrogen and $Y^2$ is substituted alkyl; or $Y^1$ is optionally substituted aralkyl and $Y^2$ is optionally substituted alkyl, or $Y^1$ and $Y^2$ are independently optionally substituted aryl or optionally substituted aralkyl, or $Y^1$ and $Y^2$ are independently optionally substituted alkyl, or $Y^1$ and $Y^2$ are hydrogen, or $Y^1$ and $Y^2$ taken together with the nitrogen atom to which $Y^1$ and $Y^2$ are attached form an optionally substituted heterocyclyl, or wherein the alkyl moiety is substituted with at least one substituent selected from hydroxyl, halo, cycloalkyl, cycloalkenyl, or heterocyclyl.

72. A compound as claimed in claim 1 wherein $R_2$ is substituted alkyl, or $R_2$ and $R_4$ taken together with the carbon atoms through which $R_2$ and $R_4$ are linked form optionally substituted cycloalkyl or optionally substituted cyclalkenyl, or $R_1$ and $R_2$ taken together with the carbon atoms through which $R_1$ and $R_2$ are linked form substituted cycloalkyl.

73. A compound as claimed in claim 1 wherein $R_3$ is optionally substituted alkenyl, substituted cycloalkyl, optionally substituted cycloalkenyl, optionally substituted aralkenyl, optionally substituted aralkynyl, optionally substituted heteroaralkenyl, optionally substituted heteroaralkynyl, optionally substituted aryloxyalkenyl, optionally substituted heteroarytoxyalkenyl, optionally substituted aralkyloxyalklenyl, optionally substituted heteroaralkyloxyalkenyl, optionally substituted heterocyclytoxyalkyl, optionally substituted heterocyclyloxy, $Y^1Y^2NCO_2$alkyl, $Y^1Y^2NCO$-alkyl or imidealkyl, or alkyl substituted with at least a heterocyclyl, cycloalkenyl or halo group, or $R_3$ and $R_4$ taken together with the carbon to which $R_3$ and $R_4$ are attached form a substituted cycloalkyl, or one of $R_1$ and $R_2$ and one of $R_3$ and $R_4$ taken together with the carbons through which the one of $R_1$ and $R_2$ and one of $R_3$ and $R_4$ are linked form a bond or substituted cycloalkyl or optionally substituted cycloalkenyl.

74. A compound as claimed in claim 1 wherein $R_3$ is substituted alkyloxyalkyl, substituted aryl, substituted aralkyl, substituted aryloxyalkyl, or substituted aralkyloxyalkyl, wherein the aryl moiety is substituted with at least one substituent selected from aralkoxy, acyl, nitro, alkoxycarbonyl, aryloxycarbonyl, aralkoxycarbonyl, acylamino, aroylamino, alkylsulfonyl, arylsulfonyl, alkylsulfinyl, arylsulfinyl, alkylthio, aralkylthio, oxyalkylenyloxy, $Y^1Y^2NCO$— or $Y^1Y^2NSO_2$—, wherein $Y^1$ and $Y^2$ are independently hydrogen, optionally substituted alkyl, optionally substituted aryl, optionally substituted aralkyl or $Y^1$ and $Y^2$ taken together with the nitrogen atom to which $Y^1$ and $Y^2$ are attached form an optionally substituted heterocyclyl, or $Y^1Y^2N$—, wherein $Y^1$ is optionally substituted aryl and $Y^2$ is substituted alkyl, or $Y^1$ hydrogen and $Y^2$ is substituted alkyl, or $Y^1$ is optionally substituted aralkyl and $Y^2$ is optionally substituted alkyl, or $Y^1$ and $Y^2$ are independently optionally substituted aryl or optionally substiftuted aralkyl, or $Y^1$ and $Y^2$ are independently optionally substituted alkyl, or $Y^1$ and $Y^2$ are hydrogen, or $Y^1$ and $Y^2$ taken together with the nitrogen atom to which $Y^1$ and $Y^2$ are attached form an optionally substituted heterocyclyl, or wherein the alkyl moiety is substituted with at least one substituent selected from hydroxyl, halo, cycloalkyl, cycloalkenyl or heterocyclyl.

75. A compound as claimed in claim 1 wherein $R_3$ is substituted heteroaryl, substituted heteroaryloxyalkyl, substituted heteroaralkyloxyalkyl, or substituted heteroaralkyl, wherein the heteroaryl moiety is substituted with at least one substituent selected from aryl, aralkyl, aryloxy, aralkoxy, acyl, nitro, alkoxycarbonyl, aryloxycarbonyl, aralkoxycarbonyl, acylamino, aroylamino, alkylsulfonyl, arylsulfonyl, alkylsulfinyl, arylsulfinyl, alkylthio, arylthio, aralkylthio, oxyalkylenyloxy, cycloalkyl substituted alkyl, hydroxy substituted alkyl, cycloalkenyl substituted alkyl, heterocyclyl substituted alkyl, or $Y^1Y^2N$—, $Y^1Y^2NCO$—, $Y^1Y^2NSO_2$—, or wherein the alkyl moiety is substituted with at least one substituent selected from hydroxyl, halo, cycloalkyl, cycloalkenyl or heterocyclyl.

76. A compound as claimed in claim 1 wherein $R_3$ is substituted cycloalkyloxy, substituted cycloalkyloxyalkyl or substituted heterocyclyl.

77. A compound as claimed in claim 1 wherein $R_3$ is $Y^3Y^4N$-alkyl, wherein $Y^4$ is substituted aryl, or substituted aralyl, wherein the aryl moiety is substituted with at least one substituent selected from aralkoxy, acyl, nitro, alkoxycarbonyl, aryloxycarbonyl, aralkoxycarbonyl, acylamino, aroylamino, alkylsulfonyl, arylsulfonyl, alkylsulfinyl, arylsulfinyl, alkylthio, aralkylthio, oxyalkylenyloxy, $Y^1Y^2NCO$— or $Y^1Y^2NSO_2$—, wherein $Y^1$ and $Y^2$ are independently hydrogen, optionally substituted alkyl, optionally substituted aryl, optionally substituted aralkyl or $Y^1$ and $Y^2$ taken together with the nitrogen atom to which $Y^1$ and $Y^2$ are attached form an optionally substituted heterocyclyl, or $Y^1Y^2N$—, wherein $Y^1$ is optionally substituted aryl and $Y^2$ is substituted alkyl, or $Y^1$ hydrogen and $Y^2$ is substituted alkyl, or $Y^1$ is optionally substituted aralkyl and $Y^2$ is optionally substituted alkyl, or $Y^1$ and $Y^2$ are independently optionally substituted aryl or optionally substituted aralkyl, or $Y^1$ and $Y^2$ are independently optionally substituted alkyl, or $Y^1$ and $Y^2$ are hydrogen, or $Y^1$ and $Y^2$ taken together with the nitrogen atoni to which $Y^1$ and $Y^2$ are attached form an optionally substituted heterocyclyl, or wherein the alkyl moiety is substituted with at least one substituent selected from hydroxyl, halo, cycloalkyl, cycloalkeniyl, or heterocyclyl.

78. A compound as claimed in claim 1 wherein $R_3$ is $Y^3Y^4N$-alkyl, wherein $Y^4$ is substituted acyl, substituted alkyl, optionally substituted aroyl, optionally substituted aralkyloxycarbonyl, optionally substituted heteroaralkyloxyearbonyl or optionally substituted alkoxycarbonyl.

79. A compound as claimed in claim 1 wherein $R_4$ is substituted aryl, wherein the aryl moiety is substituted with at least one substituent selected from aralkoxy, acyl, nitro, alkoxycarbonyl, aryloxycarbonyl, aralkoxycarbonyl, acylamino, aroylamino, alkylsulfonyl, arylsulfonyl, alkylsutfinyl, arylsulfinyl, alkylthio, aralkylthio, oxyalkylenyloxry, $Y^1Y^2NCO$— or $Y^1Y^2NSO_2$—, wherein $Y^1$ and $Y^2$ are independently hydrogen, optionally substituted alkyl, optionally substituted aryl, optionally substituted aralkyl or $Y^1$ and $Y^2$ taken together with the nitrogen atom to which $Y^1$ and $Y^2$ are attached form an optionally substituted heterocyclyl, or $Y^1Y^2N$—, wherein $Y^1$ is optionally substituted aryl and $Y^2$ is substituted alkyl, or $Y^1$ hydrogen and $Y^2$ is substituted alkyl, or $Y^1$ is optionally substitited aralkyl and $Y^2$ is optionally substituted alkyl, or $Y^1$ and $Y^2$ are independently optionally substituted aryl or optionally substituted aralkyl, or $Y^1$ and $Y^2$ are independently optionally substituted alkyl, or $Y^1$ and $Y^2$ are hydrogen, or $Y^1$ and $Y^2$ taken together with the nitrogen atom to which $Y^1$ and $Y^2$ are attached form an optionally substituted heterocyclyl.

80. A compound as claimed in claim 1 wherein $R_4$ is alkyl substituted with at least a halo, cycloalkenyl or heterocyclyl group, or substituted heteroaryl, wherein the heteroaryl moiety is substituted with at least one substituent selected from aryl, aralkyl, aryloxy, aralkoxy, acyl, nitro, alkoxycarbonyl, aryloxycarbonyl, aralkoxycarbonyl, acylamino, aroylamino, alkylsulfonyl, arylsulfonyl, alkylsulfinyl, arylsulfinyl, alkylthio, arylthio, aralkylthio, oxyalkylenyloxy, cycloalkyl substituted alkyl, hydroxy substituted alkyl, cycloalkenyl substituted alkyl, heterocyclyl substituted alkyl, $Y^1Y^2N$—, $Y^1Y^2NCO$— or $Y^1Y^2NSO_2$—.

81. A compound as claimed in claim 1 wherein $R_5$ is substituted alkyl.

82. A compound as claimed in claim 1 wherein $R_6$ is substituted alkyl.

83. A compound as claimed in claim 1 wherein

Ar is aryl substituted with at least one substituent selected from aralkoxy, acyl, nitro, alkoxycarbonyl, aryloxycarbonyl, aralkoxycarbonyl, acylamino, aroylamino, alkylsulfonyl, arylsulfonyl, alkylsulfinyl, arylsulfinyl, alkylthio, aralkylthio, oxyalkylenyloxy, $Y^1Y^2NCO$— or $Y^1Y^2NSO_2$—, wherein $Y^1$ and $Y^2$ are independently hydrogen, optionally substituted alkyl, optionally substituted aryl, optionally substituted aralkyl or $Y^1$ and $Y^2$ taken together with the nitrogen atom to which $Y^1$ and $Y^2$ are attached form an optionally substituted heterocyclyl, or $Y^1Y^2N$—, wherein $Y^1$ is optionally substituted aryl and $Y^2$ is substituted alkyl, or $Y^1$ hydrogen and $Y^2$ is substituted alkyl, or $Y^1$ is optionally substituted aralkyl and $Y^2$ is optionally substuted alkyl, or $Y^1$ and $Y^2$ are independently optionally substituted aryl or optionally substituted aralkyl, or $Y^1$ and $Y^2$ are independently optionally substituted alkyl, or $Y^1$ and $Y^2$ are hydrogen, or $Y^1$ and $Y^2$ taken together with the nitrogen atom to which $Y^1$ and $Y^2$ are attached form an optionally substituted heterocyclyl.

84. A compound as claimed in claim 1 wherein

Ar is heteroaryl substituted with at least one substituent selected from aryl, aralkyl, aryloxy, aralkoxy, acyl, nitro, alkoxycarbonyl, aryloxycarbonyl, aralkoxycarbonyl, acylamino, aroylamino, alkylsulfonyl, arylsulfonyl, alkylsulfinyl, arylsulfinyl, alkylthio, arylthio, aralkylthio, oxyalkylenyloxy, cycloalkyl substituted alkyl, hydroxy substituted alkyl, cycloalkenyl substituted alkyl, heterocyclyl substituted alkyl, $Y^1Y^2N$—, $Y^1Y^2NCO$—, $Y^1Y^1NSO_2$—, or allyl substituted with at least a halo, cycloalkenyl or heterocyclyl group.

85. A compound as claimed in claim 1 wherein p and q are independently 0.

86. A compound as claimed in claim 1 wherein

Ar is aryl substituted with one or more alkoxy substituents or heteroaryl substituted with one or more alkoxy substituents.

87. The compound of claim 1 which is (±)-N-Hydroxy-3-(4-methoxyphenyl)sulfanyl-4-(4-benzyloxyphenyl)butarnmide;

(±)-N-Hydroxy-3-(4-methoxyphenyl)sulfonyl-4-(4-benzyloxyphenyl)butyramide;

3-(4-Mothoxybenzenesulfonyl)-3,7-diphenylheptanoic acid hydroxamide,

N-Hydroxy-2-[(3,4-dimethoxyphenyl)sulfonyl]-6-phenylhexanamid;

(E)-N-Hydroxy-3-[(3,4-dimethoxyphenyl)thio]-7-phenyl-2-1-heptenamide;

(E)-N-Hydroxy-3-[(3,4-dimethoxyphenyl)sulfonyl]-7-phenyl-2-heptenamide;

(Z)-N-Hydroxy-3-[(3,4-dimethoxyphenyl)thio]-7-phenyl-2-heptenamide;

N-Hydroxy-2-[(3,4-dimethoxyphenyl)thio]-3-(3-phenylpropyl-1-yl)-1-cyclopentenecarboxamide;

N-Hydroxy-2-[(3,4-dimethoxyphenyl)sulfonyl]-3-(3-phenylpropyl-1-yl)-1-cyclopentenecarboxamide;

N-Hydroxy-3-(3,4-dimethoxyphenyl-7-phenyl-2-heptenamide;

N-Hydroxy-3-(3,4-dimethoxyphenyl-7-phenylheptanamide;

(±)-N-Hydroxy-3-(3,4-methylenedioxyphenyl)sulfonyl-7-phenylheptanamide;

(±)-N-hydroxy-3-(3,4-methylenedioxyphenyl)sulfanyl-7-phenylheptanamide;

3-(3-Benzyloxyphenyl)-3-(3,4-dimethoxybenzenesulfonyl)-N-hydroxypropionamide;

3-(2-Benzyloxyphenyl)-3-(3,4-dimethoxybenzenesulfonyl)-N-hydroxypropionamide;

3-(3-Benzyloxy-4-methoxyphenyl)-3-(3,4-dimethoxybenzenesulfonyl)-N-hydroxypropionamide;

N-[2-(3,4-Dimethoxybenzenesulfonyl)-3-hydroxycarbamoyl-propyl]-N-methylbenzamide;

N-[2-(3,4-Dimethoxybenzenesulfonyl)-3-hydroxycarbamoyl-butyl]-N methylbenzamide;

Methyl-phenyl-carbamic acid 3-(3,4-dimethoxybenzenesulfonyl)-4-hydroxycarbamoylbutyl ester;

[3-(3,4-Dimethoxybenzenesulfonyl)-4-hydroxycarbamoylbutyl]methyl-carbamic acid benzyl ester:, 3-(3,4-Dimethoxybenzenesulfonyl)hexanedioic acid-1-hydroxyamide-6-(methylphentylamide);

3-(3,4-Dimethoxybenzenesulfonyl)heptanedioic acid-1-hydroxyamide-7-(methylphentylamide);

3-(3,4-Dimethoxybenzenesulfonyl)-6-(1,3-dioxo-1,3-dihydroisoindol-2-yl)hexanoic acid hydroxyamide;

7-(3,4-Dihydro-2H-quinolin-1-yl)-3-(3,4-dimethoxybenzenesulfonyl)-7-oxoheptanoic acid hydroxyamide;

7-(3,4-Dihydro-2H-quinolin-1-yl)-3-(3,4-dimethoxybenzenesulfonyl)-6-oxohexanoic acid hydroxyamide;

7-Benzo(1,3)dioxol-5-yl-3-(3,4-dimethoxybenzenesulfonyl)heptanoic acid hydroxyamide;

5-(4-Benzyloxyphenyl)-3-(3,4-dimethoxybenzenesulfonyl)pentanoic acid hydroxyamide;

2-{(3,4-Dimethoxybenzenesulfonyl)-[4-(4-fluorobenzyloxyphenyl]methyl}-4-methylpentanoic acid hydroxyarnide;

2-[1-(3-(3,4-dimethoxybenzenesulfonyl)-5-phenylpentyl]-N 1-hydroxy-N 4-methyl-N 4-phenylsuccinamide;

4-Benzenesulfonyl-2-{(3,4-dimethoxylbenzenesulfonyl)-[4-(4-fluorobenzyloxy)phenyl]methyl}-N-hydroxy-butyramide;

2-{(3,4-dimethoxybenzenesulfonyl)-[4-(4-fluorobenzyloxy)phenyl]methyl}-N-hydroxy-4-phenyl-butyramide;

2-{(3,4-dimithoxybenzenesulfonyl)-[4-(4-fluorobenzyloxy)phenyl]methyl}-N-hydroxybutyramide;

2-{(3,4-dimethoxybenzenesulfonyl)-[4-(4-fluorobenzyloxy)-phenyl]methyl}-pentanoic acid hydroxyamide;

2-{(3,4-dimethoxybenzenesulfonyl)-[4-(4-fluorobenzyloxy)-phenyl]methyl}-4-methylpentanoic acid hydroxyamide;

2-{(3,4-dimethoxybenzenesulfonyl)-[4-(4-fluorobenzyloxy)-phenyl]methyl}-N-hydroxy-3-methylbutyramide;

2-{(3,4-dimethoxybenzenesulfonyl)-[4-(4-fluorobenzyloxy)-phenyl]methyl}-7-phenylheptanoic acid hydroxyamide;

2-{(3,4-dimethoxybenzenesulfonyl)-[4-(4-fluorobenzyloxy)phenyl]methyl}-5-phenylpentanoic acid hydroxyamide;

2-{(3,4-dimethoxybenzenesulfonyl)-[4-(4-fluorobenzyloxy)phenyl]-methyl}-N 1-hydroxy-N 4-methyl-N 4-phenyl-succinimide;

2-{(3,4-dimethoxybenzenesulfonyl)-[4-(4-fluorobenzyloxy)phenyl]methyl}-6-phenylhexanoic acid hydroxyamide;

2-[(3-Benzyloxyphenyl)-(3,4-dimethoxybenzenesulfonyl)methyl]-5-phenylpentanoic acid hydroxyamide;

3-(4-Methaxybenzenesulfonyl)-3-(4-benzyloxyphenyl)-propionic acid hydroxy amide; or 3-(4-Methoxybenzenesulfonyl)-3-(4-fluorobenzyloxyphenyl)propionic acid hydroxy amide.

88. The compound of claim 1 which is

N-Hydroxy--2-[(3,4-dimethoxyphenyl)sulfonyl]-6-phenylhexanamide;

(E)-N-Hydroxy-3-[(3,4-dimethoxyphenyl)thio]-7-phenyl-2-heptenamide;

(E)-N-Hydroxy-3-[(3,4-dimethoxyphenyl)sulfonyl]-7-phenyl-2-heptenamide;

(Z)-N-Hydroxy-3-[(3,4-dimethoxyphenyl)thio-7-phenyl-2-heptenamide;

N-Hydroxy-2-[(3,4-dimethoxyphenyl)thiol-3-(3-phenylpropyl-1-yl)-1-cyclopentenecarboxamide;

N-Hydroxy-2-[(3,4-dimethoxyphenyl)sulfonyl]-3-(3-phenylpropyl-1-yl)-1-cyclopentenecarboxamide;

N-Hydroxy-3-(3,4-dimethoxyphenyl-7-phenyl-2-heptenamide;

N-Hydroxy-3-(3,4-dimethoxyphenyl-7-phenylheptanamide;

(−)-(2S,3R)-N-Hydroxy-2-(2-benzenesulfonylethyl)-3-(3,4-dimethoxyphenylsulfonyl)-7-phenylheptanamide;

(+)-(2S,3R)-N-Hydroxy-2-(2-benzenesulfonylethyl)-3-(3,4-dimethoxyphenylsulfonyl)-7-phenylheptanamide;

(−)-N-Hydroxy-2-(2-benzenesulfonylethyl)-3-(3,4-dimethoxyphenylsulfanyl)-7-phenylheptanamide;

(+)-N-Hydroxy-2-(2-benzenesulfonylethyl)-3-(3,4-dimethoxyphenylsulfanyl)-7-phenylheptanamide;

N-Hydroxy-3-(3,4-dimethoxybenzenesulfonyl)-4-phenylbutyramide;

N-Hydroxy-3-(3,4-dimethoxyphenylsulfanyl)-4-phenylbutyramide;

N-Hydroxy-3-(3,4-dimethoxybenzenesulfonyl)-3-phenylprionamide;

N-Hydroxy-3-(3,4-dimetioxyphenylsulfanyl)-3-phenylpropionamide;

3-(3,4-Dimethoxyphenylsulfanyl)-5-phenylpentanoic acid hydroxamide;

3-(3,4-Dimethoxyphenylsulfonyl)-5-phenylpentanoic acid hydroxamide;

3-(3,4-Dimethoxybenzenesulfonyl)-6-phenylhexanoic acid hydroxamide;

3-(3,4-Dimethoxyphenylsulfanyl)-6-phenylhexanoic acid hydroxamide;

3-(3,4-Dimethoxybenzenesulfonyl)-6-phenylhexanoic acid hydroxamide;

3-(R*)-(3,4-Dimethoxybenzenesulfonyl)-2-(S*)-isopropyl-7-phenylheptanoic acid hydroxamide;

3-(3,4-Dimethoxybezenesulanyl)-2-isopropyl-7-phenylheptanoic acid hydroxamide;

(+)-(2R,3R)-3-(3,4-Dimethoxyphenylsulfanyl)-2-methyl-7-phenylheptanoic acid hydroxyamide;

(+)-(2R,3R)-3-(3,4-Dimethoxyphenylsulfonyl)-2-methyl-7-phenylheptanoic acid hydroxyamide;

(+)-(2R,3S)-3-(3,4-Dimethoxyphenylsulfanyl)-2-methyl-7-phenylheptanoic acid hydroxyamide;

(+)-(2R,3S)-3-(3,4-Dimethoxyphenylsulfonyl)-2-methyl-7-phenylheptanoic acid hydroxyamide;

1-[1-(3,4-Dimethoxyphenylsulfonyl)-5-phenylpentyl]cyclopentane-carboxylic acid hydroxyamide;

1-[1-(3,4-Dimethoxyphenylsulfanyl)-5-phenylpentyl]cyclopentane-carboxylic acid hydroxyamide;

3-(3,4-Dimethoxybenzenesulfonyl)-2,2-dimethyl-7-phenylheptanoic acid hydroxyamide;

(±)-N-Hydroxy-3-(3,4-Dimethoxyphenyl)sulfonyl-7-phenylheptanamide;

(±)-N-Hydroxy-3-(3,4-methylenedioxyphenyl)sulfonyl-7-phenylheptanamide;

(±)-N-Hydroxy-3-(3,4-dimethoxyphenyl)sulfinyl-7-phenylheptanamide;

(±)-N-Hydroxy-3-(3,4-Dimethoxyphenyl)sulfanyl-7-phenylheptanamide;

(−)-N-Hydroxy-3-(3,4-dimethoxyphenyl)sulfonyl-7-phenylheptanamide;

(+)-N-hydroxy-3-(3,4diinethoxyphenyl)sulfonyl-7-phenylheptanamide;

3-(3,4-Dimethoxybenzenesulfonyl)-5-methylhexanoic acid hydroxyamide;

5-(4-Butoxyphenyl)-3-(3,4-dimethoxybenzenesulfonryl)-pentanoic acid bydroxyamide;

3-(3,4-Dimethoxybenzenesulfonyl)hexanoic acid hydroxyamide;

3-(3,4-Dimethoxybenzenesulfonyl)-4-methylpentanoic acid hydroxyamide;

3-(3,4-Dimethoxybenzenesulfanyl)-5-metlhylhexanoic acid hydroxyamide;

3-(3-Benzyloxyphenyl)-3-(3,4-dimethoxybenzenesulfonyl)-N-hydroxypropionamide;

3-(2-Benzyloxyphenyl)-3-(3,4-dimethoxybenzenesulfonyl)-N-hydroxypropionamide;

3-(3-Benzyloxy-4-methoxyphenyl)-3-(3,4-dimethoxybenzenesulfonyl)-N-hydroxypropionamide;

3-(3,4-Dimethoxybenzenesulfonyl)-N-hydroxy-3-(3-phenoxyphenyl)propionamide;

3-(3-(4-Chlorophenoxy)phenyl)-3-(3,4-dimethoxybenzenesulfonyl)-N-hydroxypropionarmide;

3-(3,4-Dimethoxybenzenesulfonyl)-N-hydroxy-3-(3-(4-methoxyphenoxy)phenyl)propionamide;

N-[2-(3,4-Dimethoxybenzenesulfonyl)-3-hydroxycarbamoyl-propyl]-N methylbenzamide;

N-[2-(3,4-Dimethoxybenzenesulfonyl)-3-hydroxycarbamoyl-butyl]-N methylbenzamide;

Methyl-phenyl-carbamic acid 3-(3,4-dimethoxybenzenesulfonyl)-4-hydroxycarbamoylbutyl ester;

[3-(3,4-Dimethoxybenzenesulfonyl)-4-hydroxycarbamoylbutyl]methyl-carbamic acid benzyl ester;

3-(3,4-Dimethoxybenzenesulfonyl)hexanedioic acid-1-hydroxyamide-6-(methylphenylamide);

3-(3,4-Dimethoxybenzenesulfonyl)heptanedioic acid-1-hydroxyamide-7-(methylphenylamide);

3-(3,4-Dimethoxybenzenesulfonyl)-6-(1,3-dioxo-1,3-dihydroisoindol-2-yl)hexanoic acid hydroxyamide;

7-(3,4-Dihydro-2H-quinolin-1-yl)-3-(3,4-dimethoxybenzenesulfonyl)-7-oxoheptanoic acid hydroxyamide;

7-(3,4-Dihydro-2H-quinolin-1-yl)-3-(3,4-dimethoxybenzenesulfonyl)-6-oxohexanoic acid hydroxyamnide;

7-Benzo(1,3)dioxol-5-yl-3-(3,4-dimethoxybenzenesulfonyl)heptanoic acid hydroxyamide;

3-(3,4-Dimethoxybenzenesulfonyl)-3-(thien-3-yl)-N-hydroxypropionamide;

3-(3,4-Dimethoxybenzenesulfonyl)-5-phenylpentanoic acid hydroxyamide;

3-(3,4Dimethoxybenzenesulfonyl)-5-(3-phenoxyphenyl)pentanoic acid hydroxyamide;

5-(4-Benzyloxyphenyl)-3-(3,4-dimethoxybenzenesulfonyl)pentanoic acid hydroxyamide;

2-{(3,4-Dimethoxybenzenesulfonyl)-[4-(4-fluorobenzyloxyphenyl]methyl}-4-methylpentanoic acid hydroxyamide;

3-(3,4-dimethoxybenzenesufonyl)-7-phenyl-2-(4-phenylbutyl)heptanoic acid hydroxyamide;

2-[1-(3-(3,4-dimethoxybenzenesulfonyl)-5-phenylpentyl]-N 1-hydroxy-N 4-methyl-N 4-phenylsuccinamide;

3-(3,4-dimethoxybenzenesulfonyl)-7-phenyl-2-(3-phenylpropyl)heptanoic acid hydroxyamide;

3-(3,4-dimethoxybenzenesulfonyl)-2-isopropyl-7-phenylheptanoic acid hydroxyamide;

3-(3,4-dimethoxybenzenesulfonyl)-2-isobutyl-7-phenylheptanoic acid hydroxyamide;

3-(3,4-dimethoxybenzonesulfonyl)-7-phenyl-2-propylheptanoic acid hydroxyamide;

3-(3,4-dimethoxybenzenesulfonyl)-7-phenyl-2-(4-phenyl-butyl)heptanoic acid hydroxyamide;

3-(3,4-dimethoxybenzenesulfonyl)-2-benzenesulfonylethyl-7-phenylheptanoic acid hydroxyamide;

3-(3,4-dimethoxybenzenesulfonyl)-7-phenyl-2-(5-phenylpentyl)heptanoic acid hydroxyamide;

4-Benzenesulfonyl-2-{(3,4-dimethoxybenzenesulfonyl)-[4-(4-fluorobenzyloxy)phenyl]methyl}-N-bydroxy-butyramide;

2-{(3,4-dimethoxybenzenesulfonyl)-[4-(4-fluorobenzyloxy)phenyl]methyl}-N-hydroxy-4-phenyl-butyramide;

2-{(3,4-dimethoxybenzenesulfonyl)-[4-(4-fluorobenzyloxy)phenyl]methyl}-N-hydroxybutyramide;

2-{(3,4-dimethoxybenzenesulfonyl)-[4-(4-fluorobenzyloxy)-phenyl]methyl}-pentanoic acid hydronyamide;

2-{(3,4-dimethoxybenzenesulfonyl)-[4-(4-fluorobenzyloxy)-phenyl]methyl}-4-methylpentanoic acid hydroxyamide;

2-{(3,4-dimethoxybenzenesulfonyl)-[4-(4-fluorobenzyloxy)-phenyl]methyl}-N-hydroxy-3-methylbutyramide;

2-{(3,4-dimethoxybenzenesulfonyl)-[4-(4-fluorobenzyloxy)-phenyl]methyl}-7-phenylheptanoic acid hydroxyamide;

2-{(3,4-dimethoxybenzenesulfonyl)-[4-(4-fluorobenzyloxy)phenyl]methyl}-5-phenylpentanoic acid hydroxyamide;

2-{(3,4-dimethoxybenzenesulfonyl)-[4-(4-fluorobenyloxy)phenyl]-methyl}-N 1-hydroxy-N 4-methyl-N 4-phenyl-succinimide;

2-{(3,4-dimethoxybenzenesulfonyl)-[4-(4-fluorobenzyioxy)phenylmethyl}-6-phenylhexanoic acid hydroxyamide;

2-[Biphenyl-4-yl-(3,4-dimethoxybenzenesulfonyl)methyl]-4-methylpentanoic acid hydroxyamide;

2-[(3,4-Dimethoxybenzenesulfonyl)-(4-phenoxyphenyl)methyl]-N-hydroxy-butyramide;

4-Benzenesulfonyl-2-[biphenyl-4-yl-(3,4-dilethoxybenzenesulfonyl)methyl]-N-hydroxybutyramide;

2-[Biphenyl-4-yl-(3,4-dimethoxybenzenesulfonyl)methyl]-N-hydroxy-4-phenylbutyramide;

2-[Biphenyl-4-yl-(3,4-dimethoxybenzenesulfonyl)methyl]-N-hydroxybutyramide;

2-[Biphenyl-4-yl-(3,4-dimethoxybenzenesulfonyl)methyl]-4-methylpentanoic acid hydroxyamide;

2-[Biphenyl-4-yl-(3,4-dimethoxybenzenesulfanyl)methyl]-N-hydroxy-3-methylbutyramide;

2-[Biphenyl-4-yl-(3,4-dimethoxybenzenesulfonyl)methyl]-7-phenylheptanoic acid hydroxyamide;

2-[Bipheayl-4-yl-(3,4-dimethoxybenzenesulfonyl)methyl]-5-phenylpentanoic acid hydroxyamide;

2-[(3,4-Dimethoxybenzenesulfonyl)-(4-phenoxyphenyl)methyl]-N-hydroxy-3-methylbutyramide;

2-[(3,4-Dimethoxybenzenesulfonyl)-(4-phenoxyphenyl)methyl]-7-phenylheptanoic acid hydroxyamide;

3-(3,4-Dimethoxybenzenesulfonyl)-2-ethylhexanoic acid hydroxyamide;

3-(3,4-Dimetioxybenzenesulfonyl)-2-(3-phenylpropyl)hexanoic acid hydroxyamide;

2-[(3-Benzyloxyphenyl)-(3,4-dimethoxybenzenesulfonyl)methyl]-5-phenylpentanoic acid hydroxyamide;

(−)-(2S,3S)-3-(3,4-Dimethoxybenzenesulfanyl)-2-methyl-7-heptanoic acid hydroxyamide;

(−)-(2S,3S)-3-(3,4-Dimethoxybenzenesulfonyl)-2-methyl-7-heptanoic acid hydroxyamide;

(−)-(2S,3R)-3-(3,4-Dimethoxyphenylsulfanyl)-2-methyl-7-heptanoic acid hydroxyamide;

(±)-N-hydroxy-3-(3,4-methylenedioxyphenyl)sulfanyl-7-phenylheptanamide;

(±)-N-hydroxy-3-(3,4-methylenedioxyphenyl)sulfanyl-7-heptanamide; or (−)-(2S,3R)-3-(3,4-Dimetoxybenzenesulfonyl)-2-methyl-7-phenylheptanoic acid hydroxyamide.

89. A compound which is selected from

N-Hydroxy-2-[1-(4-methoxybenzenesulfonyl)-4-phenylcyclohexyl]-acetamide;

2-[(3,4-Dimethoxybenzenesulfonyl)-(4-phenoxyphenyl)methyl]-N-hydroxy-4-(2-methoxyethoxy)butyramide;

2-[Biphenyl-4-yl-(3,4-dimethoxybenzenesulfonyl)methyl]-N-hydroxy-4-(2-methoxyethoxy)butyramide;

3-(3,4-dimethoxybenzenesulfonyl)-2-[2-(2-methoxyethoxy)ethyl]-7-phenylheptanoic acid hydroxyamide; or 2-{(3,4-dimethoxyberzenesulfonyl)-(4-(4-fluorobenzyloxy)-phenyl]methyl}-N-hydroxy-4-(2-methoxyethoxy)butyramide.

90. The compound of claim 22, which is 3-(4-Methoxyphenylsulfonyl)-7-phenylheptanoic acid hydroxyamide;

3-(4-Methoxyphenylsulfanyl)-7-phenylheptanoic acid hydroxyamide;

N-hydroxy-3-(4-methoxybenzenesulfonyl)-4-phenylbutyramide;

N-hydroxy-3-(4-methoxybenzenesulfanyl)-4-phenylbutyramide;

N-hydroxy-3-(4-methoxybenzenesulfonyl)-3-phenylpropionamide;

N-hydroxy-3-(4-methoxybenzenesulfanyl)-3-phenylpropionamide;

3-(4-Methoxybenzenesulfonyl)-5-phenylpentanoic acid hydroxyamide;

3-(4-Methoxybenzenesulfanyl)-5-phenylpentanoic acid hydroxyamide;

3-(4-Methoxybenzenesulfonyl)-6-phenylhexanoic acid hydroxamide;

3-(4-Methoxybenzenesulfanyl)-6-phenylhexanoic acid hydroxamide;

3-(4-Methoxybenzenesulfonyl)-3-methyl-7-phenylheptanoic acid hydroxamide 3-(4-Methoxybenzenesulfanyl)-3-methyl-7-phenylheptanoic acid hydroxamide (±)-N-Hydroxy-3-(4-methoxyphenyl)sulfanyl-4-(4-biphenyl)butyramide;

(±)-N-Hydroxy-3-(4-methoxyphenyl)sulfanyl-4-(4-phenyloxyphenyl)butyramide;

(±)-N-Hydroxy-3-(4-methoxyphenyl)sulfanyl-4-(4-benzyloxyphenyl)butyramide;

(±)-N-Hydroxy-3-(4-methoxyphenyl)sulfanyl-4-(4-n-butyloxyphenyl)butyramide;

(±)-N-Hydroxy-3-(4-methoxyphenyl)sulfonyl-4-(4-biphenyl)butyramide;

(±)-N-Hydroxy-3-(4-methoxyphenyl)sulfonyl-4-(4-phenyloxyphenyl)butyramide;

(±)-N-Hydroxy-3-(4-methoxyphenyl)sulfonyl-4-(4-benzyloxyphenyl)butyramide;

(±)-N-Hydroxy-3-(4-methoxyphenyl)sulfonyl-4-(4-n-butyloxyphenyl)butyramide;

3-(4-Methoxybenzenesulfonyl)-3-ethyl-7-phenylheptanoic acid hydroxamide;

3-(4-Methoxybenzenesulfonyl)-3,7-diphenylheptanoic acid hydroxamide;

N-Hydroxy-3-(4-methoxybenzenesulfonyl)-3-methylbutyramide;

N-Hydroxy-2-[1-(4-methoxybenzenesulfonyl)cyclopentyl]acetamide;

(2R*,3R*)-2-Amino-3-(4-methoxybenzene)sulfonyl-7-phenylheptanoic acid hydroxy amide, N-hydroxy-3-(4-methoxyphenyl)thio-2-(1-propane-3-yl)-7-phenyl-heptanamide;

N-Hydroxy-2-(1-propane-3-yl)-3-(4-methoxyphenyl)sulfonyl-7-phenylheptanamide;

3-(4-Methoxybenzenesulfonyl)-2,2-dimethyl-7-phenylheptanoic acid hydroxyamide;

3-(4-Methoxybenzenesulfinyl)-7-phenylheptanoic acid hydroxyamide;

(±)-(2R*,3R*)-3-(4-Methoxybenzenesulfonyl)-7-phenyl-2-(2-phenoxyethyl)heptanoic acid hydroxyamide;

(±)-(2R*,3R*)-3-(4-Methoxybenzenesulfonyl)-7-phenyl-2-(2-phenylsulfanylethyl)heptanoic acid hydroxyamide;

(2R*,3R*)-3-(4-Methoxybenzenesulfonyl)-7-phenyl-2-(2-phenylsulfanyl-ethyl)heptanoic acid hydroxyamide;

(±)-(2R*,3R*)-3-(4-Methoxybenzenesulfonyl)-7-phenyl-2-(benzenesulfonylmethyl)heptanoic acid hydroxyamide;

(±)-(2R*,3R*)-3-(4-methoxybenzenesulfonyl)-7-phenyl-2-(phenylsulfanylmethyl)heptanoic acid hydroxyamide;

(±) 2-Hydroxy-3-(4-methoxybenzenesulfonyl)-2-methyl-7-phenylheptanoic acid hydroxyamide;

(±)-3-(4-Methoxyphenylsulfanyl)-2-methyl-7-phenylheptanoic acid hydroxyamide;

(±)-3-(4-Methoxybenzenesulfonyl)-2-methyl-7-phenylheptanoic acid hydroxyamide;

3-(4-Methoxybenzenesulfonyl)-3-(4-ethoxyphenyl)propionic acid hydroxyamide;

3-(4-methoxybenzenesulfonyl)-3-(4-biphenyl)propionic acid hydroxy;

3-(4-methoxybenzenesulfonyl)-3-(4-phenoxyphenyl)propionic acid hydroxy amide;

3-(4-methoxybenzenesulfonyl)-3-(4-benzyloxyphenyl)propionic acid hydroxy amide;

3-(4-methoxybenzenesulfonyl)-3-(4-fluorobenzyloxyphenyl)-propionic acid hydroxy amide;

3-(4-methoxybenzenesulfonyl)-3-(4-(3-trifluoromethylphenoxy)-phenyl-propionic acid hydroxy amide;

(+)-3-(4-methoxyphenylsulfonyl)-7-phenylheptanoic acid hydroxamide, or (−)-3-(4-methoxyphenylsulfonyl)-7-phenylheptanoic acid hydroxamide.

91. The compound of claim 22 which is

N-Hydroxy-2-[(3,4-dimethoxyphenyl)sulfonyl]-6-phenylhexanamide;

(E)-N-Hydroxy-3-[(3,4-dimethoxyphenyl)thio]-7-phenyl-2-heptenamide;

(E)-N-Hydroxy-3-[(3,4-dimethoxyphenyl)sultonyl]-7-phenyl-2-heptenamide;

(Z)-N-Hydroxy-3-[(3,4-dimethioxyphenyl)thio]-7-phenyl-2-heptenamide;

N-Hydroxy-2-[(3,4-dimethoxyphenyl)thio-3-(3-phenylpropyl-1-yl)-1-cyclopentenecarboxamide;

N-Hydroxy-2-[(3,4-dimethoxyphenyl)sulfonyl]-3-(3-phenylpropyl-1-yl)-1-cyclopentenecarboxamide;

N-Hydroxy-3-(3,4-dimethoxyphenyl-7-phenyl-2-heptenamide;

N-Hydroxy-3-(3,4-dimethoxyphenyl-7-phenylheptanamide;

(−)-(2S,3R)-N-Hydroxy-2-(2-benzenesulfonylethyl)-3-(3,4-oxyphenylsulfonyl)-7-phenylheptanamide;

(+)-(2S,3R)-N-Hydroxy-2-(2-benzenesulfonylethyl)-3-(3,4-oxyphenylsulfonyl)-7-phenylheptanamide;

(−)-N-Hydroxy-2-(2-benzenesulfonylethyl)-3-(3,4-oxyphenylsulfanyl)-7-phenylheptanamide;

(+)-N-Hydroxy-2-(2-benzenesulfonylethyl)-3-(3,4-oxyphenylsulfanyl)-7-phenylheptanamide;

N-Hydroxy-3-(3,4-dimethoxybenzenesulfonyl)-4-phenylbutyramide;

N-Hydroxy-3-(3,4-dimethoxyphenylsulfanyl)-4-phenylbutyramide;

N-Hydroxy-3-(3,4-dimethoxybenzenesulfonyl)-3-phenylproprionamide;

N-Hydroxy-3-(3,4-dimethoxyphenylsulfanyl)-3-phenylpropionanide;

3-(3,4-Dimethoxyphenylsulfanyl)-5-phenylpentanoic acid hydroxamide;

3-(3,4-Dimethoxyphenylsulfonyl)-5-phenylpentanoic acid hydroxamide;

3-(3,4-Dimethoxybenzenesulfonyl)-6-phenylhexanoic acid hydroxamide;

3-(3,4-Dimethoxyphenylsulfanyl)-6-phenylhexanoic acid hydroxamide;

3-(3,4-Dimethoxybenzenesulfonyl)-6-phenylhexanoic acid hydroxamide;

3-(R*)-(3,4-Dimethoxybenzenesulfonyl)-2-(S*)-isopropyl-7-phenylheptanoic acid hydroxamide;

3-(3,4-Dimethoxybenzenesulfanyl)-2-isopropyl-7-pheryllheptanoic acid hydroxamide;

(+)-(2R,3R)-3-(3,4-Dimethoxyphenylsulfanyl)-2-methyl-7-phenylheptanoic acid hydroxyamide;

(+)-(2R,3R)-3-(3,4-Dimethoxyphenylsulfonyl)-2-methyl-7-phenylheptanoic acid hydroxyamide;

(+)-(2R,3S)-3-(3,4-Dimethoxyphenylsulfanyl)-2-methyl-7-phenylheptanoic acid hydroxyamide;

(+)-(2R,3S)-3-(3,4-Dimethoxyphenylsulfonyl)-2-methyl-7-phenylheptanoic acid hydroxyamide;

1-[1-(3,4-Dimethoxyphenylsulfonyl)-5-phenylpentyl]cyclopentane-carboxylic acid hydroxyamide;

1-[1-(3,4-Dimethoxyphenylsulfanyl)-5-phenylpentyl]cyclopentane-carboxylic acid hydroxyamide;

3-(3,4-Dimethoxybenzenesulfonyl)-2,2-dimethyl-7-phenylheptanoic acid hydroxyamide;

(±)-N-Hydroxy-3-(3,4-Dimethoxyphenyl)sulfonyl-7-phenylheptanamide;

(±)-N-Hydroxy-3-(3,4-methylenedioxyphenyl)sulfonyl-7-phenylheptanamide;

(±)-N-Hydroxy-3-(3,4-dimethoxyphenyl)sulfinyl-7-phenylheptanamide;

(±)-N-Hydroxy-3-(3,4-Dimethoxyphenyl)sulfanyl-7-phenylheptanamide;

(±)-N-hydroxy-3-(3,4-methylenedioxyphenyl)sulfanyl-7-heptanamide;

(−)-N-Hydroxy-3-(3,4-dimethoxyphenyl)sulfonyl-7-phenylheptanamide;

(+)-N-hydroxy-3-(3,4-dimethoxyphenyl)sulfonyl-7-phenylheptanamide;

3-(3,4-Dimethoxybenzenesuifonyl)-5-methythexanoic acid hydroxyamide;

5-(4-Butoxyphenyl)-3-(3,4-dimethoxybenzenesulfonyl)-pentanoic acid hydroxyamide;
3-(3,4-Dimethoxybenzenesulfonyl)hexanoic acid hydroxyamide;
3-(3,4-Dimethoxybenzenesulfonyl)-4-methylpentanoic acid hydroxyamide;
3-(3,4-Dimethoxybenzenesulfonyl)-5-methylhexanoic acid hydroxyamide;
3-(3-Benzyloxyphenyl)-3-(3,4-dimethoxybenzenesulfonyl)-N-hydroxypropionamide;
3-(2-Benzyloxyphenyl)-3-(3,4-dimethoxybenzenesulfonyl)-N-hydroxypropionamide;
3-(3-Benzyloxyphenyl)-3-(3,4-dimethoxybenzenesulfonyl)-N-hydroxypropionamide;
3-(3,4-Dimethoxybenzenesulfonyl)-N-hydroxy-3-(3-phenoxyphenyl)propionamide;
3-(3-(4-Chlorophenoxy)phenyl)-3-(3,4-diinethoxybenzenesulfonyl)-N-hydroxypropionamide;
3-(3,4-Dimethoxybenzenesulfonyl)-N-hydroxy-3-(3-(4-methoxyphenoxy)phenyl)propionamide,
N-[2-(3,4-Dimethoxybenzenesulfonyl)-3-hydroxycarbamoyl-propyl]-N methylbenzamide;
N-[2-(3,4-Dimethoxybenzenesulfonyl)-3-hydroxycarbamoyl-butyl]-N methylbenzamide;
Methyl-phenyl-carbamic acid 3-(3,4-dimethoxybenzenesalfonyl)-4-hydroxycarbamoyl-butyl ester;
[3-(3,4-Dimethoxybenzensulfonyl)-4-hydroxycarbamoylbutyl]methyl-cafhamic acid benzyl ester;
3-(3,4-Dimethoxybenzenesulfonyl)hexanedioic acid-1-hydroxyamide-6-(methylphenylamide);
3-(3,4-Dimethoxybenzenesulfonyl)heptanedioic acid-1-hydroxyamide-7-(methylphenylamide);
3-(3,4-Dimethoxybenzenesulfonyl)-6-(1,3-dioxo-1,3-dihydroisoindol-2-yl)hexanoic acid hydroxyamide;
7-(3,4-Dihydro-2H-quinolin-1-yl)-3-(3,4-dimethoxybenzenesulfonyl)-7-oxoheptanoic acid hydroxyamide;
7-(3,4-Dihydro-2H-quinolin-1-yl)-3-(3,4-dimethoxybenzenesulfonyl)-6-oxohexanoic acid hydroxyamide;
7-Benzo(1,3)dioxol-5-yl-3-(3,4-dimethoxybenzenesulfonyl)heptanoic acid hydroxyamide;
3-(3,4-Dimethoxybenzenesulfonyl)-3-(thien-3-yl)-N-hydroxypropionamide;
3-(3,4-Dimethoxybenzenesulfonyl)-5-phenylpentanoic acid hydroxyamide;
3-(3,4-Dimethoxybenzenesulfonyl)-5-(3-phenoxyphenyl)pentanoic acid hydroxyamide;
5-(4-Benzyloxyphenyl)-3-(3,4-dimethoxybenzenesulfonyl)pentanoic acid hydroxyamide;
2-{(3,4-Dimethoxybeuzenesulfonyl)-[4-(4-fluorobenzyloxyphenyl]methyl}-4-methylpentanoic acid hydroxyamide;
3-(3,4-dimethoxybenzenesulfonyl)-7-phenyl-2-(4-phenylbutyl)heptanoic acid hydroxyamide;
2-[1-(3-(3,4-dimethoxyberzenesulfonyl)-5-phenylpentyl]-N 1-hydroxy-N 4-methyl-N 4-phenylsuccinamide;
3-(3,4-dimethoxybenzenesulfonyl)-7-phenyl-2-(3-phenylpropyl)heptanoic acid hydroxyamide;
3-(3,4-dimethoxybenzenesulfonyl)-2-isopropyl-7-phenylheptanoic acid hydroxyamide;
3-(3,4-dimethoxybenzenesulfonyl)-2-isobutyl-7-phenylheptanoic acid hydroxyamide;
3-(3,4-dimethoxybenzenesulfonyl)-7-phenyl-2-propylheptanoic acid hydroxyamide;
3-(3,4-dimethoxybenzenesulfonyl)-7-phenyl-2-(4-phenyl-butyl)heptanoic acid hydroxyamide;
3-(3,4-dimethoxybenzenesulfonyl)-2-benzenesulfonylethyl-7-phenylheptanoic acid hydroxyamide;
3-(3,4-dimethoxybenzenesulfonyl)-7-phenyl-2-(5-phenypentyl)heptanoic acid hydroxyamide;
4-Benzenesulfonyl-2-{(3,4-dimethoxybenzenesulfonyl)-[4-(4-fluorobenzyloxy)phenyl]methyl}-N-hydroxy-butyramide;
2-{(3,4-dimethoxybenzenesulfonyl)-[4-(4-fluorobenzyloxy)phenyl]methyl}-N-hydroxy-4-phenyl-butyramide;
2-{(3,4-dimethoxybenzenesulfonyl)-[4-(4-fluorobenzyloxy)phenyl]methyl}-N-hydroxybutyramide;
2-{(3,4-dimethoxybenzenesulfonyl)-[4-(4-fluorobenzyloxy)-phenyl]methyl}-pentanoic acid hydroxyamide;
2-{(3,4-dimethoxybenzenesulfonyl)-[4-(4-fluorobenzyloxy)-phenyl]methyl}-4-methylpentanoic acid hydroxyamide;
2-{(3,4-dimethoxybenzenesulfonyl)-[4-(4-fluorobenzyloxy)-phenyl]methyl}-N-hydroxy-3-methylbultyramide;
2-{(3,4-dimethoxybenzenesulfonyl)-[4-(4-fluorobenzyloxy)-phenyl]methyl}-7-phenylheptanoic acid hydroxyamide;
2-{(3,4-dimethoxybenzenesulfonyl)-[4-(4-fluorobenzyloxy)phenyl]methyl}-5-phenylpentanoic acid hydroxyamide;
2-{(3,4-dimethoxybenzenesulfonyl)-[4-(4-fluorobenzyloxy)phenyl]-methyl}-N 1-hydroxy-N 4-methyl-N 4-phenyl-succinimide;
2-{(3,4-dimethoxybenzenesulfonyl)-[-(4-fluorobenzyloxy)phenyl]methyl}-6-phenylhexanoic acid hydroxyamide;
2-[Biphenyl-4-yl-(3,4-dimethoxybenzenesulfonyl)methyl]-4-methlpentanoic acid hydroxyamide;
2-[(3,4-Dimethoxybenzetiesulfonyl)-(4-phenoxyphenyl)methyl]-N-hydroxy-butyramide;
4-Benzenesulfonyl-2-[biphenyl-4-yl-(3,4-dimethoxybenzenesulfonyl)methyl]-N-hydroxybutyramide;
2-[Biphenyl-4-yl-(3,4-dimethoxybenzenesulfonyl)methyl]-N-hydroxy-4-phenylbutyramide;
2-[Biphenyl-4-yl-(3,4-dimethoxybenzenesulfonyl)methyl]-N-hydroxybutyramide;
2-[Biphenyl-4-yl-(3,4-dimethoxybenzenesulfonyl)methyl]-4-methylpentanoic acid hydroxyamide;
2-[Biphenyl-4-yl-(3,4-dimethoxybenzenesulfonyl)methyl]-N-hydroxy-3-methylbutyramide;
2-[Biphenyl-4-yl-(3,4-dimethoxybenzenesulfonyl)methyl]-7-phenylheptanoic acid hydroxyamide;
2-[Biphenyl-4-yl-(3,4-dimethoxybenzenesulfonyl)methyl]-5-phenylpentanoic acid hydroxyanide;

2-[(3,4-Dimethoxybenzenesulfonyl)-(4-phenoxyphenyl)
methyl]-N-hydroxy-3-methylbutyramide;

2-[(3,4-Dimethoxybenzenesulfonyl)-(4-phenoxyphenyl)
methyl]-7-phenylheptanoic acid hydroxyamide;

3-(3,4-Dimethoxybenzenesulfonyl)-2-ethylhexanoic acid
hydroxyamide;

3-(3,4-Dimethoxybenzenesulfonyl)-2-(3-phenylpropyl)
hexanoic acid hydroxyamide;

2-[(3-Benzyloxyphenyl)-(3,4-dimethoxybenzenesulfonyl)methyl]-5-phenylpentanoic acid hydroxyamide;

(−)-(2S,3S)-3-(3,4-Dimethoxybenzenesulfanyl)-2-methyl-7-heptanoic acid hydroxyamide;

(−)-(2S,3S)-3-(3,4-Dimethoxybenzenesulfonyl)-2-methyl-7-heptanoic acid hydroxyamide;

(−)-(2S,3R)-3-(3,4-Dimethoxyphenylsulfanyl)-2-methyl-7-heptanoic acid hydroxyamide; or (−)-(2S,3R)-3-(3,4-Dimethoxybenzenesulfonyl)-2-methyl-7-phenylheptanoic acid hydroxyamide.

92. A compound as claimed in claim 1 wherein

Ar is di-alkoxy substituted aryl or di-alkoxy substituted heteroaryl.

93. A compound as claimed in claim 92 wherein the di-alkoxy substituted aryl is 3,4-dimethoxy phenyl.

* * * * *